(12) United States Patent
Kuroiwa et al.

(10) Patent No.: US 9,902,970 B2
(45) Date of Patent: Feb. 27, 2018

(54) COMPLEX CHROMOSOME ENGINEERING FOR PRODUCTION OF HUMAN ANTIBODIES IN TRANSGENIC ANIMALS

(71) Applicant: SAB, LLC, Sioux Falls, SD (US)

(72) Inventors: Yoshimi Kuroiwa, La Jolla, CA (US); Hiroaki Matsushita, Sioux Falls, SD (US); Akiko Sano, Kanagawa pref (JP)

(73) Assignee: SAB, LLC, Sioux Falls, SD (US)

( * ) Notice: Subject to any disclaimer, the term of this patent is extended or adjusted under 35 U.S.C. 154(b) by 2 days.

(21) Appl. No.: 14/416,870

(22) PCT Filed: Aug. 5, 2013

(86) PCT No.: PCT/US2013/053618
§ 371 (c)(1),
(2) Date: Jan. 23, 2015

(87) PCT Pub. No.: WO2014/022853
PCT Pub. Date: Feb. 6, 2014

(65) Prior Publication Data
US 2015/0211020 A1    Jul. 30, 2015

Related U.S. Application Data

(60) Provisional application No. 61/679,288, filed on Aug. 3, 2012.

(51) Int. Cl.
| | |
|---|---|
| C12N 15/85 | (2006.01) |
| C07H 21/02 | (2006.01) |
| C12P 21/00 | (2006.01) |
| A01K 67/027 | (2006.01) |
| C07K 16/12 | (2006.01) |
| C07K 16/00 | (2006.01) |
| C07K 16/46 | (2006.01) |

(52) U.S. Cl.
CPC ...... C12N 15/8509 (2013.01); A01K 67/0278 (2013.01); C07K 16/00 (2013.01); C07K 16/462 (2013.01); *A01K 2207/15* (2013.01); *A01K 2217/072* (2013.01); *A01K 2217/075* (2013.01); *A01K 2227/101* (2013.01); *A01K 2267/01* (2013.01); *C12N 2015/8518* (2013.01); *C12N 2800/208* (2013.01)

(58) Field of Classification Search
None
See application file for complete search history.

(56) References Cited

U.S. PATENT DOCUMENTS

| | | | |
|---|---|---|---|
| 5,625,126 A | 4/1997 | Lonberg et al. | |
| 7,402,729 B2* | 7/2008 | Kuroiwa | A01K 67/0275 800/13 |
| 7,803,981 B2 | 9/2010 | Robl et al. | |
| 2011/0236378 A1* | 9/2011 | Green | A01K 67/0278 424/133.1 |
| 2012/0167237 A1 | 6/2012 | Bradley et al. | |
| 2012/0222140 A1* | 8/2012 | Kuroiwa | C07K 16/00 800/6 |
| 2013/0318643 A1* | 11/2013 | Bradley | C07K 16/00 800/4 |
| 2015/0018225 A1* | 1/2015 | Morishita | C07K 16/28 506/9 |

FOREIGN PATENT DOCUMENTS

| | | |
|---|---|---|
| CA | 2780945 A1 | 5/2011 |
| WO | WO 00/76310 A1 | 12/2000 |
| WO | WO 02/070648 | 9/2002 |
| WO | WO 2005/007696 | 1/2005 |
| WO | WO 2010/03990 | * 8/2010 |
| WO | WO 2011062207 | * 5/2011 |

OTHER PUBLICATIONS

Matsushita et al., Species-Specific Chromosome Engineering Greatly Improves Fully Human Polyclonal Antibody Production Profile in Cattle PLOS ONE 2015; pp. 1-30.*
Ren et al. Silencing of the immunoglobulin heavy chain locus by removal of alleight constant-region genes in a 200-kb regionGenomics 84 (2004) 686-695.*
Wuerffel et al., S-S Synapsis during Class Switch Recombination Is Promoted by Distantly Located Transcriptional Elements and Activation-Induced Deaminase Immunity vol. 27, Issue 5, Nov. 26, 2007, pp. 711-722.*
Kouprina et al., A new generation of human artificial chromosomes for functional genomics and gene therapy. Cell Mol Life Sci. Apr. 2013; 70(7): 1135-1148.*
Kuroiwa, Y. et al. Manipulation of human minichromosomes to carry greater than megabase-sized chromosome inserts. Nat Biotechnol 18, 1086-1090 (2000).
Kuroiwa, Y. et al. Cloned transchromosomic calves producing human immunoglobulin. Nat Biotechnol. 20, 889-894 (2002).
Lemieux, R., Bazin, R. and Neron, S. Therapeutic intravenous immunoglobulins. Mol Immunol. 42, 839-848 (2005).
Jolles, S., Sewell, W.A.C. and Misbah, S.A. Clinical uses of intravenous immunoglobulin. Clini Exp Immunol. 142, 1-11 (2005).
Newcombe, C. and Newcombe, A.R. Antibody production: polyclonal-derived biotherapeutics. J Chromatogr B Analyt Technol Biomed Life Sci. 848, 2-7 (2007).
Farrugia, A. & Poulis, P. Intravenous immunoglobulin: regulatory perspectives on use and supply. Transfus. Med. 11, 63-74 (2001).
Kuroiwa, Y. et al. Antigen-specific human polyclonal antibodies from hyperimmunized cattle. Nat Biotechnol. 27, 173-181 (2009).

(Continued)

Primary Examiner — Maria Leavitt
(74) Attorney, Agent, or Firm — McDonnell Boehnen Hulbert & Berghoff LLP

(57) ABSTRACT

The invention relates to large-scale production of human antibodies by transgenic animals with high production of fully human IgG up to >10 g/L in sera with human IgG1 subclass dominancy. This invention also supports a feasibility of complex chromosome engineering for complicated genetic studies in non-murine mammalian species.

22 Claims, 83 Drawing Sheets

(56) References Cited

OTHER PUBLICATIONS

Echelard, Y. Year of the ox. Nat Biotechnol. 27, 146-147 (2009).
Aitken, R. et al. Structure and diversification of the bovine immunoglobulin repertoire. Veterinary Immunol. Immunopathol. 72, 21-29 (1999).
Chen, L. et al. Characterization of the bovine immunoglobulin lambda light chain constant IGLC genes. Veterinary Immunol. Immunopathol. 124, 284-294 (2008).
Ekman, A., Niku, M., Liljavirta, J. & Iivanainen, A. Bos taurus genome sequence reveals the assortment of immunoglobulin and surrogate light chain genes in domestic cattle. BMC Immunol. 10:22, (2009).
Hosseini, A., Campbell, G., Prorocic, M. and Aitken, R. Duplicated copies of the bovine JH locus contribute to the Ig repertoire. Intern. Immunol. 16, 843-852 (2004).
Kitamura, D., Roes, J., Kuhn, R. & Rajewsky, K. A B cell-deficient mouse by targeted disruption of the membrane exon of the immunoglobulin chain gene. Nature 350, 423-426 (1991).
Kuroiwa, et al. "Sequential targeting of the genes encoding immunoglobluin-u and prion protein in cattle," Nat Genet, 36, 775-780 (2004).
Tomizuka, K. et al. Double trans-chromosomic mice: Maintenance of two individual human chromosome fragments containing Ig heavy and k loci and expression of fully human antibodies. Proc. Natl. Acad. Sci. USA 97, 722-727 (2000).
Yel, L et al. Mutations in the mu heavy chain gene in patients with agammaglobulinemia. New Engl J Med 335, 1486-1493 (1996).
Kitamura, D. et al. A critical role of gamma-5 protein in B cell development. Cell 69, 823-831 (1992).
Mundt, C., Licence, S., Shimizu, T., Melchers, F. & Martensson, I-L. Loss of Precursor B Cell Expansion but Not Allelic Exclusion in VpreB1/VpreB2 double-deficient mice. J Exp Med 193, 435-445 (2001).
Zou, X. et al. Block in development at the pre-B-II to immature B cell stage in mice iithout Igk and Iglambda light chain. J Immunol 170, 1354-1361 (2003).
Pelanda, R., Braun, U., Hobeika, E., Nussenzweig, M. C. & Reth, M. B cell progenitors are arrested in maturation but have intact VDJ recombination in the absence of Ig-alpha and Ig-beta. J Immunol 169, 865-872 (2002).
Lonberg, N. Human antibodies from transgenic animals. Nat Biotechnol. 23, 1117-1125 (2005).
Chaudhuri, J. & Alt, F. W. Class switch recombination: interplay of transcription, DNA deamination and DNA repair. Nat Review Immunol 4, 541-552 (2004).
Kues, et al. "Advances in farm animal transgenesis" Preventative Veterinary Medicine, 102(2): 146-156. Apr. 2011.
Stoop, J. W., Zegers, B. J. M., Sander, P. C. and Ballieux, R. E. Serum immunoglobulin levels in healthy children and adults. Clin Exp Immunol. 4, 101-112 (1969).
Kaisho, T., Schwenk, F. & Rajewsky, K. The roles of gamma1 heavy chain membrane expression and cytoplasmic tail in IgG1 responses. Science 276, 412-415 (1997).
Wilson, M. D. et al. Species-specific transcription in mice carrying human chromosome 21. Science 322, 434-438 (2008).
Flajnik, M.F. Comparative analyses of immunoglobulin genes: surprises and portents. Nat Rev Immunol 2, 688-698 (2002).
Kawano, Y., Yoshikawa, S., Minegishi, Y. & Karasuyama, H. Pre-B Cell receptor assesses the quality of IgH chains and tunes the Pre-B cell repertoire by delivering differential signals. J Immunol 177, 2242-2249 (2006).
Casola, S. et al. B cell receptor signal strength determines B cell fate. Nat Immunol 5, 317-327 (2004).
Keenan, R. A. et al. Censoring of autoreactive B cell development by the pre-B cell receptor. Science 321, 696-699 (2008).
Martin, F. & Keamey, J.F. Marginal-zone B cells. Nat Review Immunol 2, 323-335 (2002).
Siber,G. R. et al. Correlation between serum IgG2 concentrations and the antibody response to bacterial polysaccharide antigens. New Engl J Med 303,178 (1990).
Shackelford, P. G. et al. Correlation of serum immunoglobulin subclass concentrations with antibody responses of children to immunization with Haemophilus influenzae type b polysaccharide-pertussis vaccine. J Clin Immunol 5, 390-395 (1985).
International Search Report and Written Opinion for PCT/US2013/053618, dated Oct. 24, 2013.
Duteau, et al. "Characterization of the human Ig guest locus in HAC transgenic cattle." Dissertation University of Massachusetts Amherst, May 2005.
Choi, et al. "Fully human antigen-specific polyclonal antibody response induced in cloned human artificial chromosome transchromosomic cattle." Dissertation University of Massachusetts Amherst, Feb. 2005.
Zhao, et al. "Physical mapping of the bovine immunoglobulin heavy chain constant region gene locus," Journal of Biological Chemistry, 278(37): 35024-35032, Jun. 2003.

\* cited by examiner

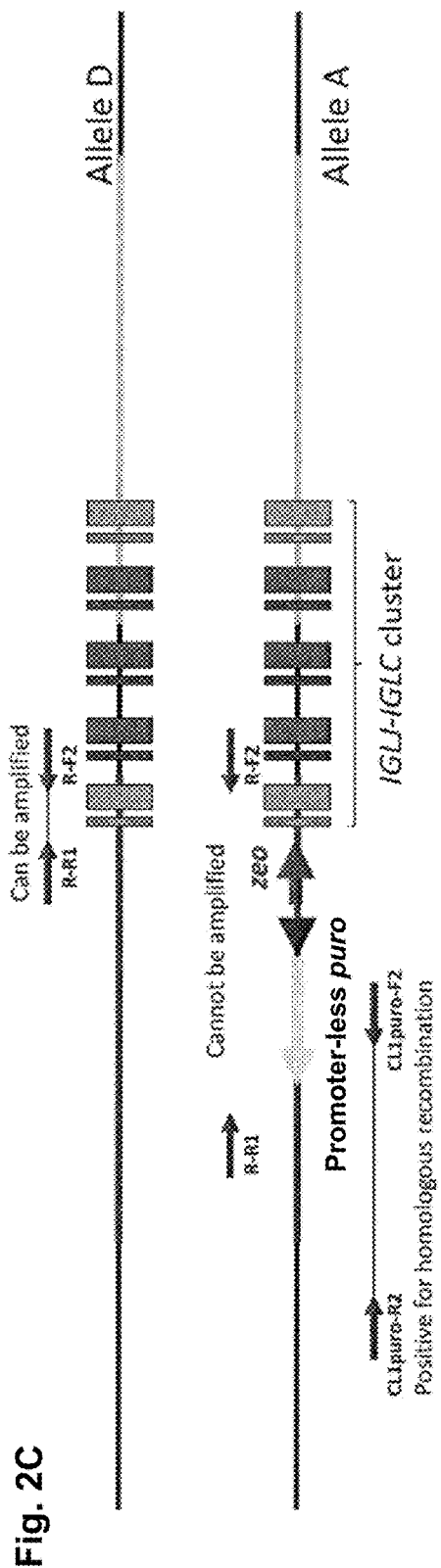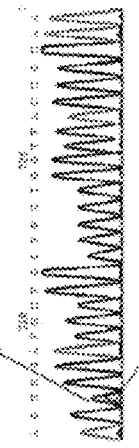
Fig. 2C

Fig. 2E

Fig. 3A
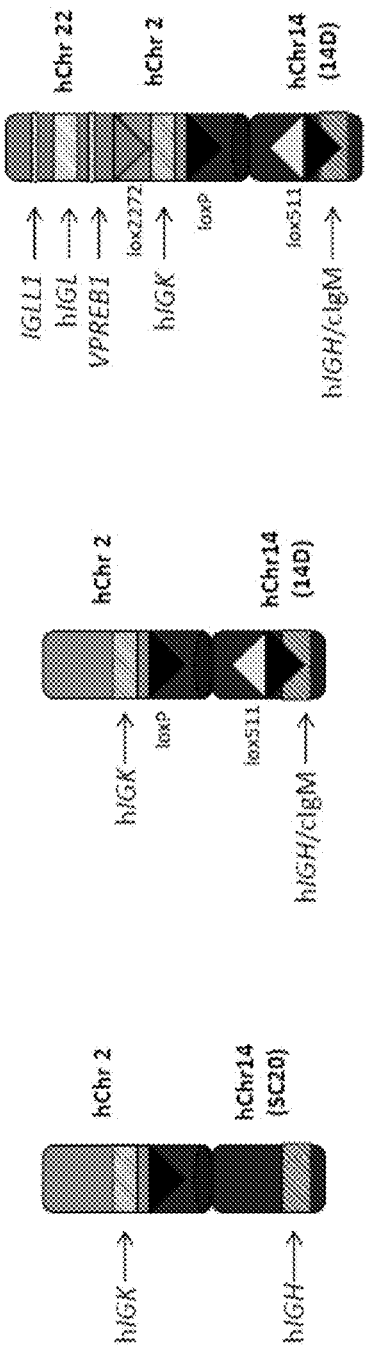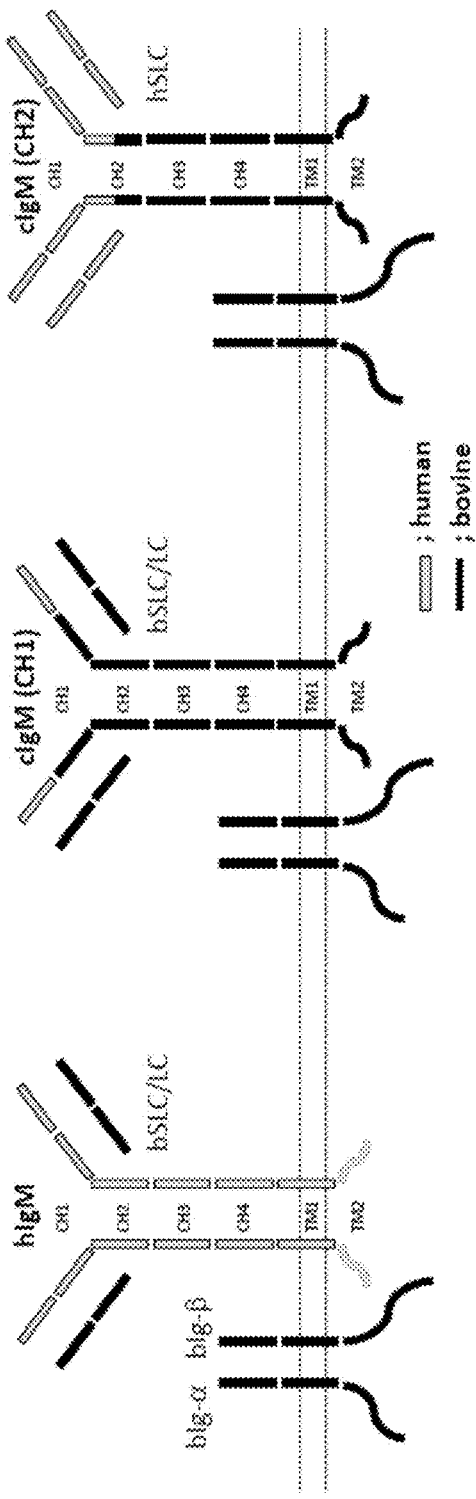

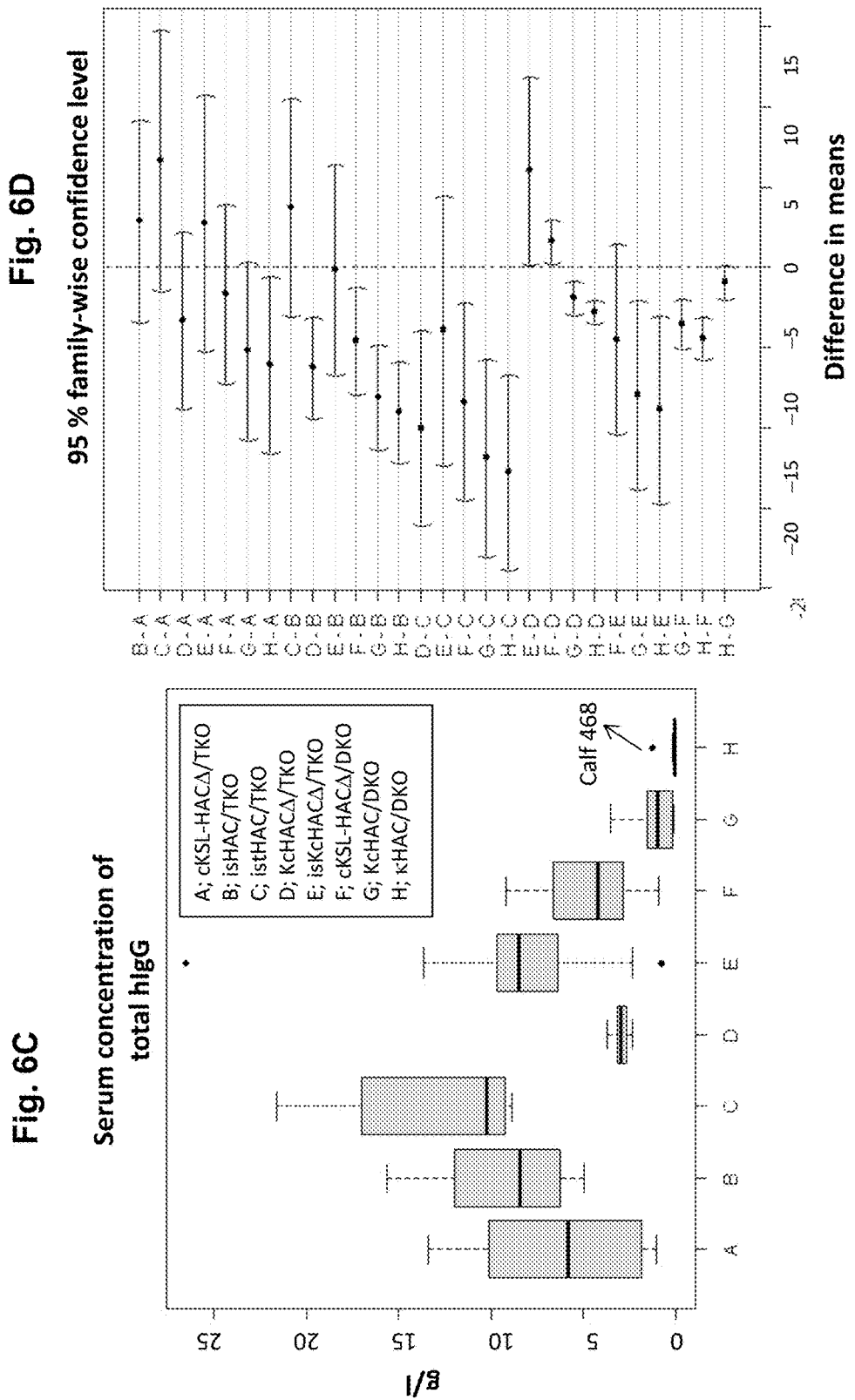

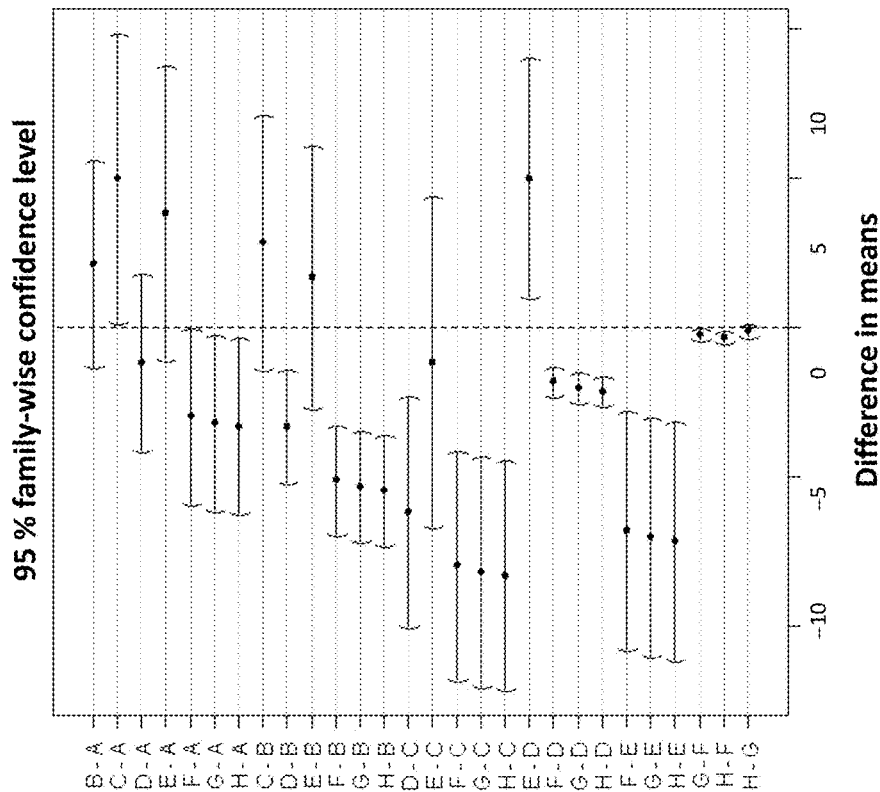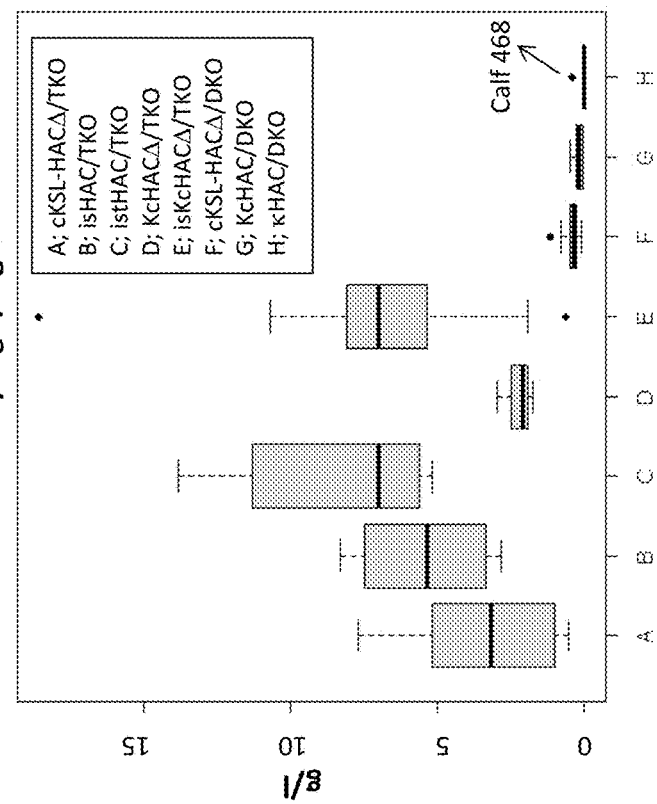

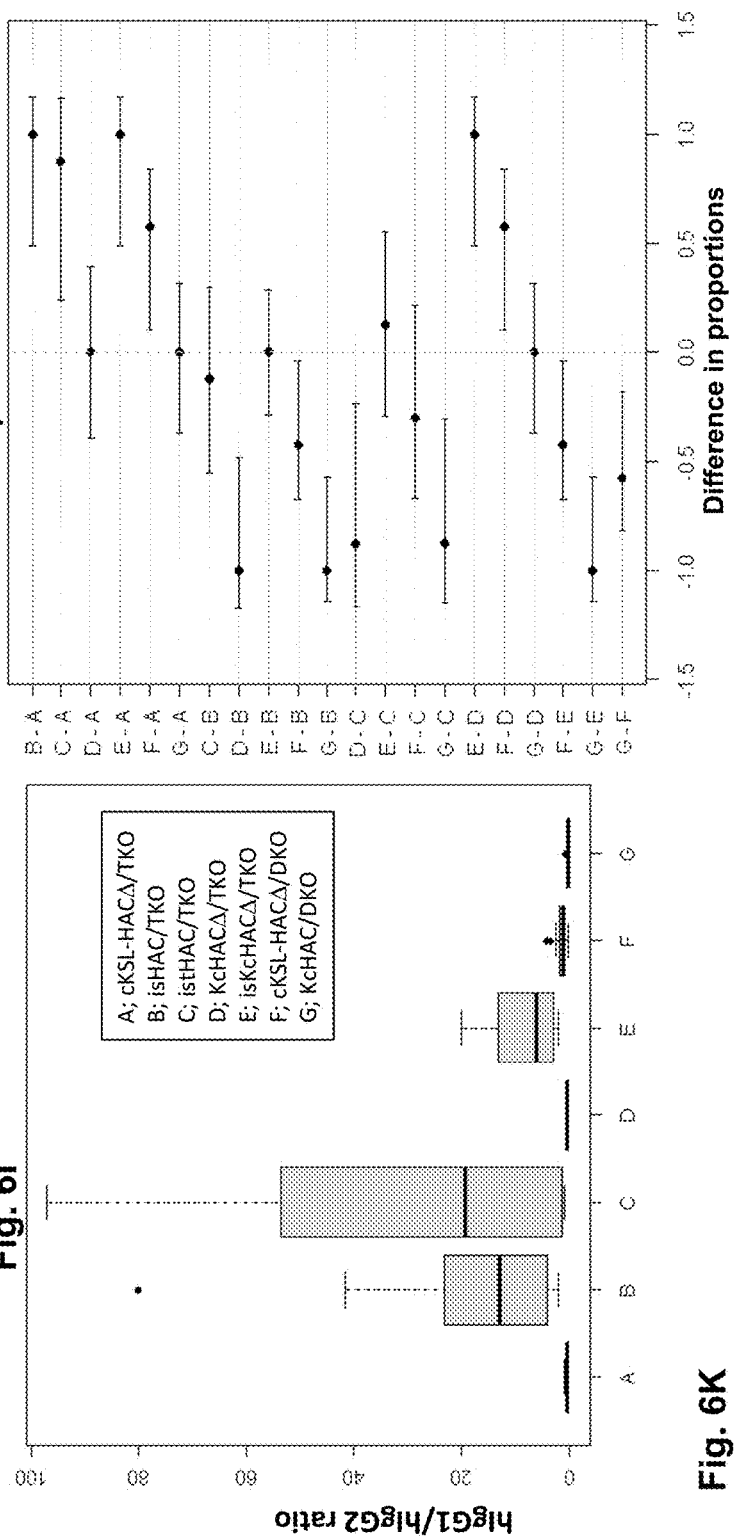
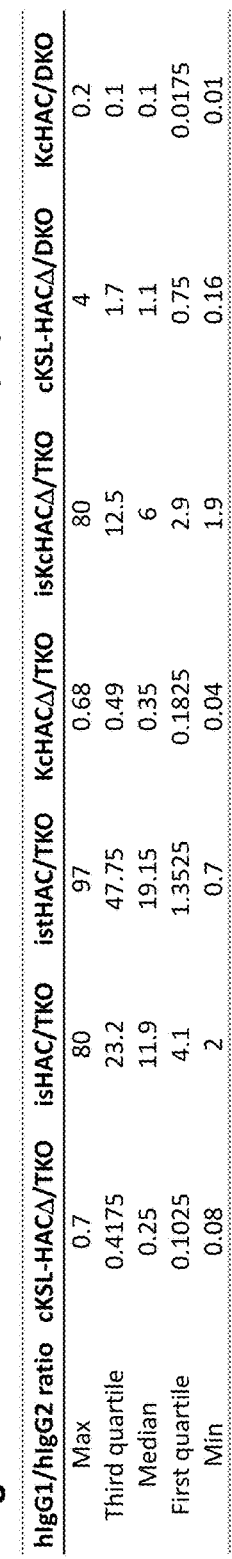
Fig. 6I
Fig. 6J
Fig. 6K

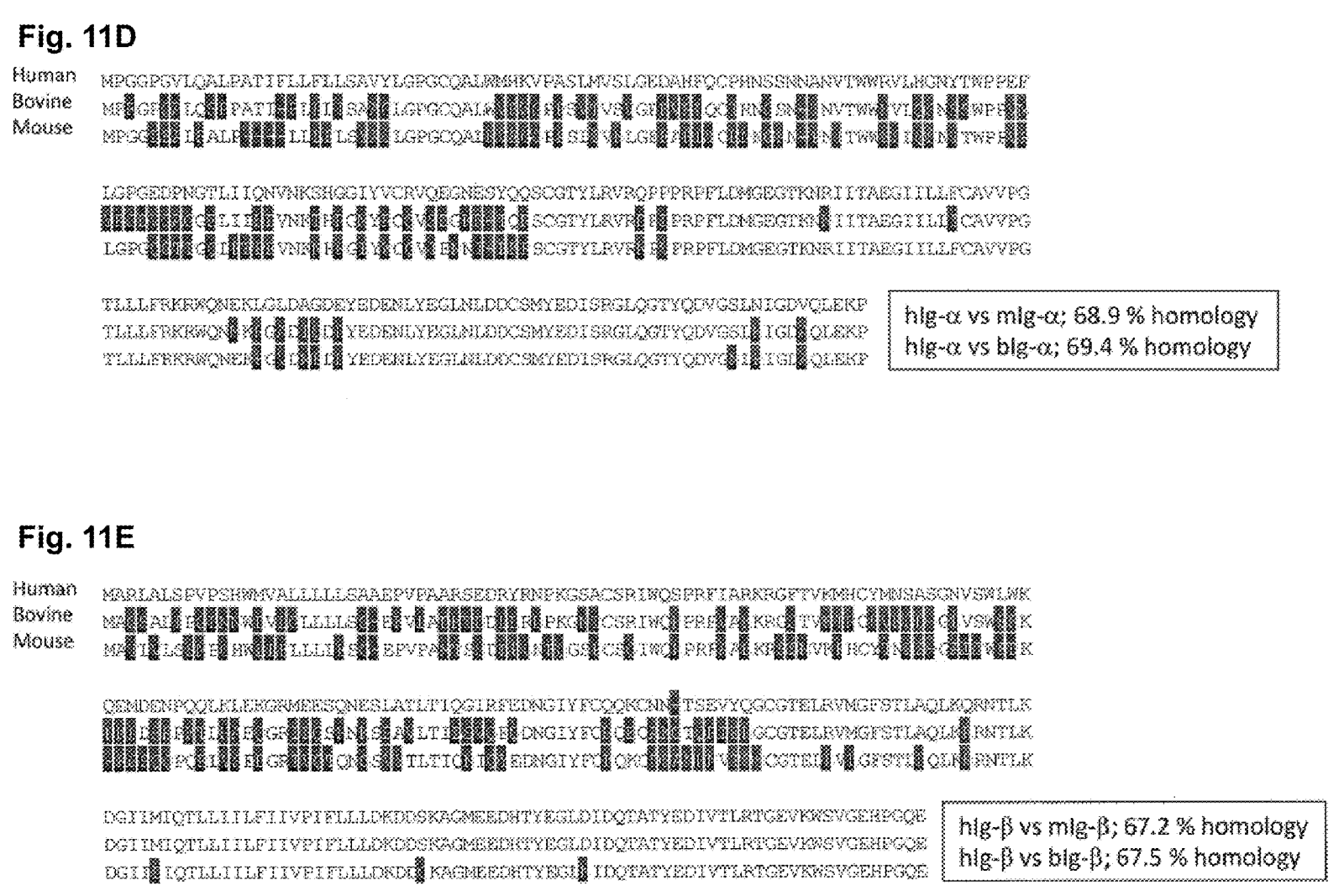

Human
Bovine
Mouse hIg-α vs mIg-α; 68.9 % homology
hIg-α vs bIg-α; 69.4 % homology

Fig. 11E

Human
Bovine
Mouse hIg-β vs mIg-β; 67.2 % homology
hIg-β vs bIg-β; 67.5 % homology

Fig. 13C

Human       LQLEESCAEAQDGELDGLWTTITIFITLFLLSVCYSATVTFFKVKWIFSSVVDLKQTIPPDYRNMIGQGA
Bovine      L....EE.CA..AQQGELDGLWTTI.IFTTLFLLSVCYSATVI.FK/KWIFSSVV.LH..TI..PDYRNMIGQGA

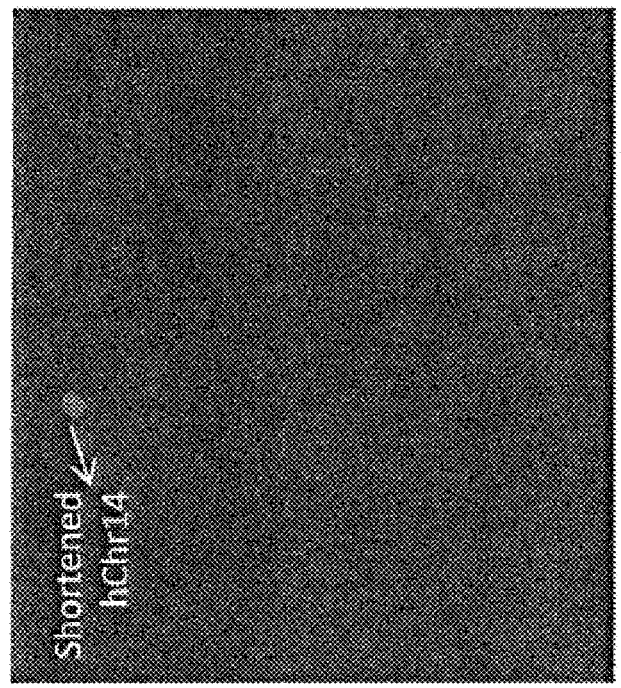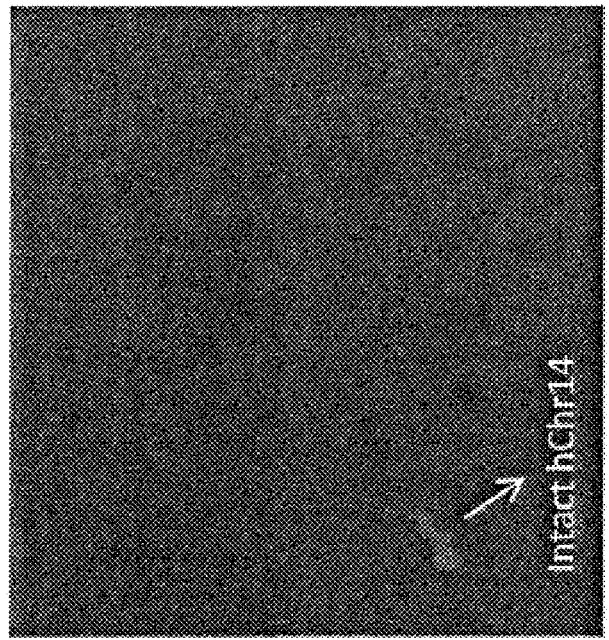
Fig. 17E

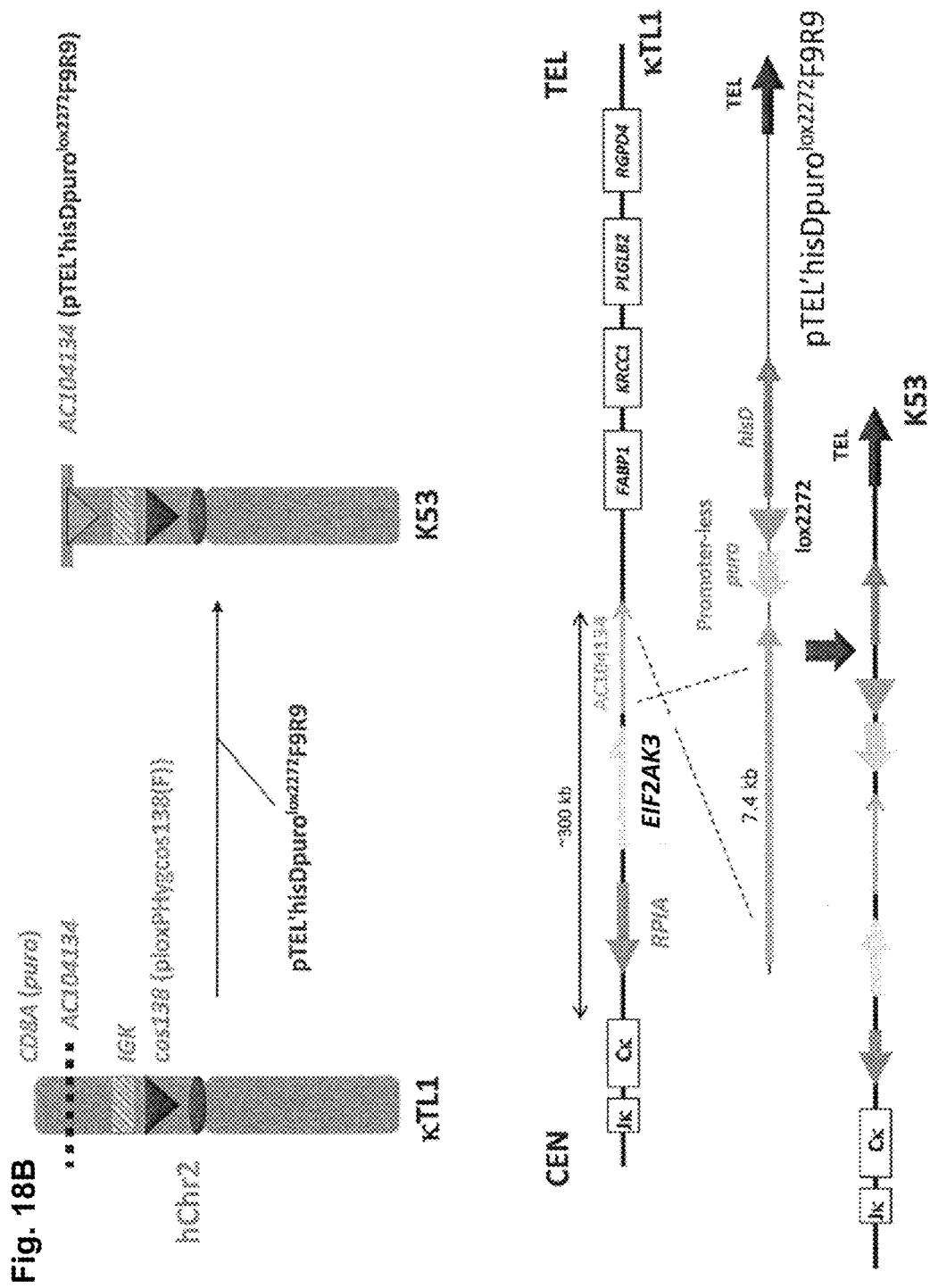

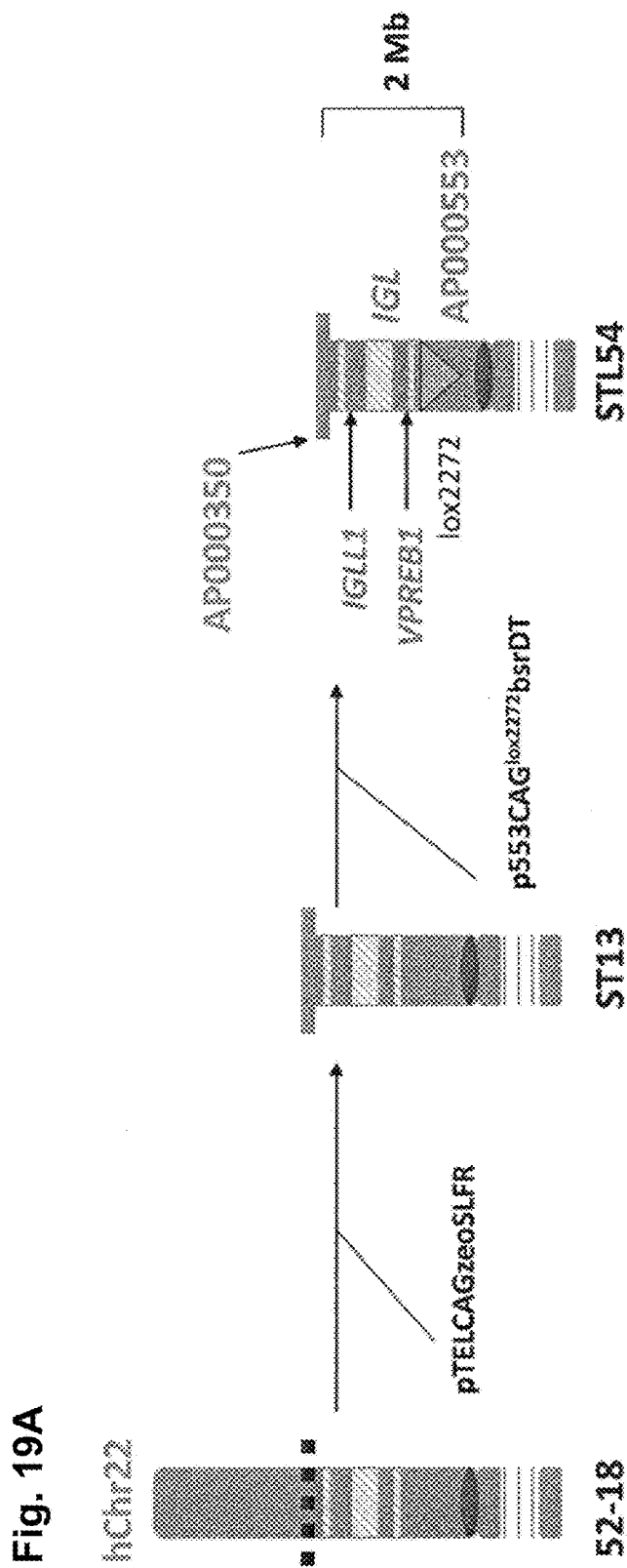

Fig. 27A

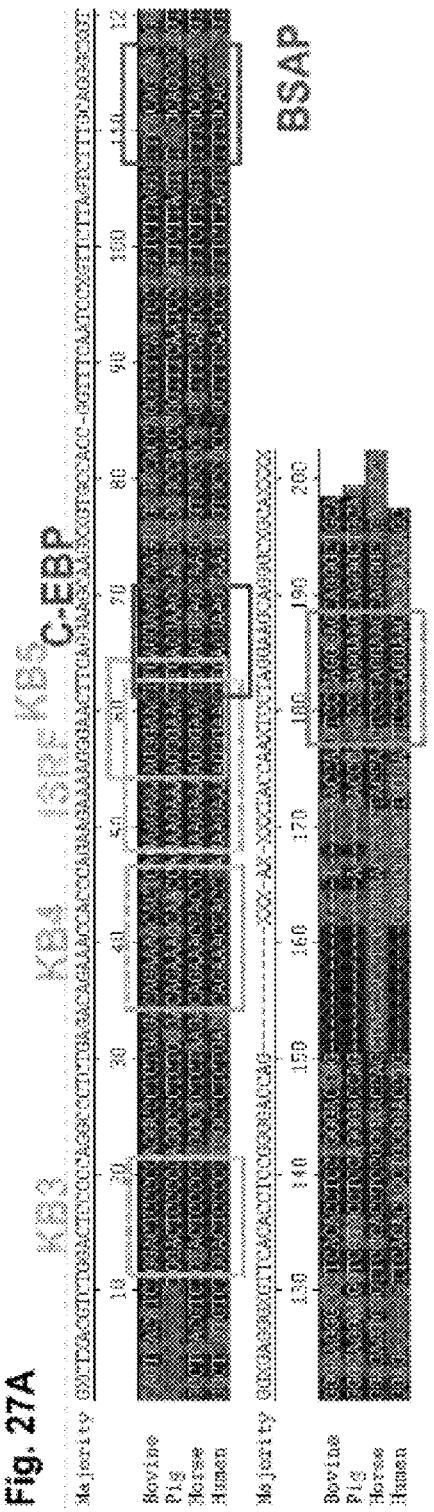

Decoration 'Decoration #1': Shade (with solid deep red) residues that differ from the Consensus.

Decoration 'Decoration #2': Shade (with solid bright cobalt) residues that match the Consensus exactly.

Fig. 27B

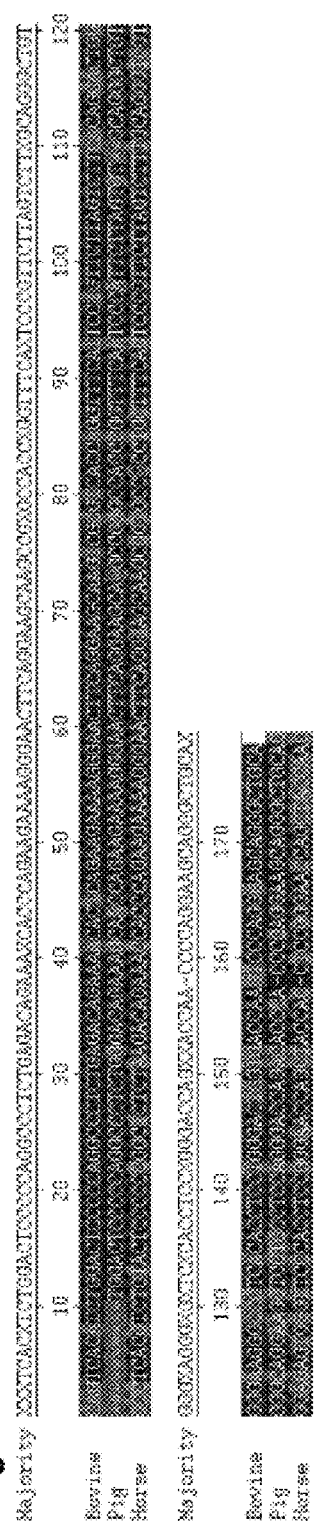

Decoration 'Decoration #1': Shade (with solid deep red) residues that differ from the Consensus.

Decoration 'Decoration #2': Shade (with solid bright cobalt) residues that match the Consensus exactly.

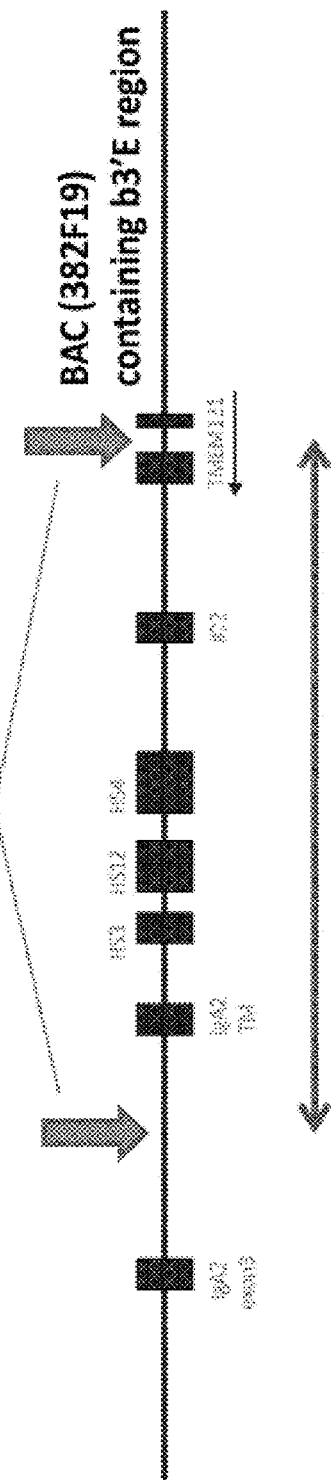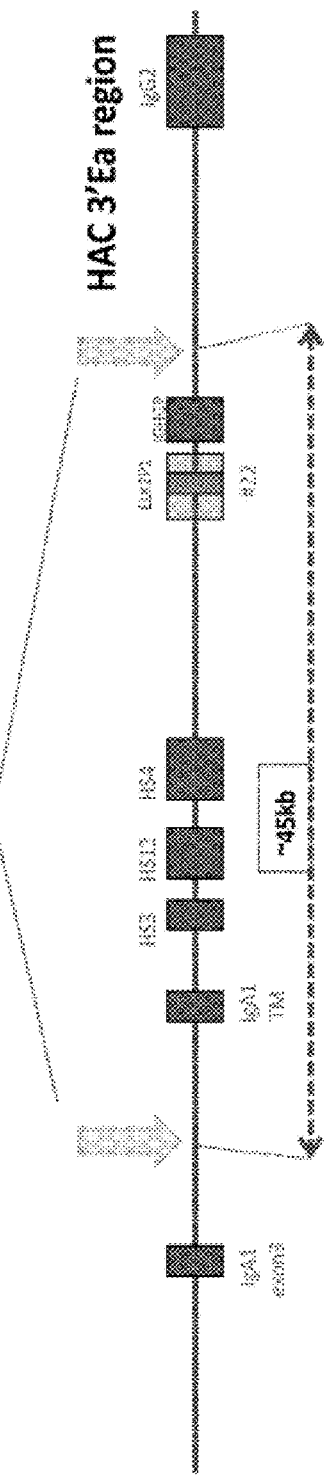
Fig. 29C

COMPLEX CHROMOSOME ENGINEERING FOR PRODUCTION OF HUMAN ANTIBODIES IN TRANSGENIC ANIMALS

RELATED APPLICATIONS

This application is a U.S. national phase of International Application No. PCT/US2013/053618 filed on Aug. 5, 2013, which claims benefit of U.S. Provisional Application No. 61/679,288 filed Aug. 3, 2012, both of which are incorporated by reference herein in their entirety.

BACKGROUND OF THE INVENTION

Human antibodies, also known as intravenous immunoglobulin (IVIG), obtained from donated human plasma with or without immunization of specific antigens, have been used therapeutically for many years. However, human plasma-derived IVIG has also entailed substantial challenges and restrictions, mainly due to the voluntary nature of donation from uncontrollable human populations. In particular, it is difficult to robustly generate human plasma-derived IVIG against human-origin antigens, such as cancer cells, due to immune tolerance in humans. Thus, improved systems for obtaining human antibodies are needed.

SUMMARY OF THE INVENTION

In a first aspect, the invention provides a human artificial chromosome (HAC) vector comprising genes encoding:
(a) one or more human antibody heavy chains, wherein each gene encoding an antibody heavy chain is operatively linked to a class switch regulatory element;
(b) one or more human antibody light chains; and
(c) one or more human antibody surrogate light chains, and/or an ungulate-derived IgM heavy chain constant region;
wherein at least one class switch regulatory element of the genes encoding the one or more human antibody heavy chains is replaced with an ungulate-derived class switch regulatory element.

In one embodiment, the one or more human antibody heavy chains comprise a human IgG antibody heavy chain. In another embodiment, the IgG heavy chain comprises an IgG1 antibody heavy chain. In a further embodiment, the one or more human antibody heavy chains comprise a human IgA antibody heavy chain. In another embodiment, the one or more human antibody heavy chains comprise a human IgM antibody heavy chain. In a still further embodiment, the one or more human antibody heavy chains comprise IgG1, IgG2, IgG3, IgG4, IgA1, IgA2, IgE and IgD human antibody heavy chains.

In one embodiment, the HAC vector comprises a gene encoding an ungulate-derived IgM heavy chain constant region, wherein the ungulate-derived IgM heavy chain constant region is expressed as a chimera with a human IgM heavy chain variable region. In another embodiment, the ungulate-derived IgM heavy chain constant region is a bovine-derived IgM heavy chain constant region.

In a further embodiment, the one or more human antibody heavy chains comprise a human IgG antibody heavy chain, wherein a transmembrane domain and an intracellular domain of a constant region of the human IgG heavy antibody chain are replaced with a transmembrane domain and an intracellular domain of an ungulate-derived IgG antibody heavy chain constant region. In another embodiment, the human IgG antibody heavy chain comprises a human IgG1 antibody heavy chain. In a further embodiment, the ungulate-derived IgG antibody heavy chain constant region comprise a bovine-derived IgG antibody heavy chain constant region.

In one embodiment, the ungulate-derived class switch regulatory element comprises an Iγ-Sγ class switch regulatory element. In another embodiment, the Iγ-Sγ class switch regulatory element comprises $I\gamma_1$-$S\gamma_1$. In a still further embodiment, each class switch regulatory element of the genes encoding the one or more human antibody heavy chains is replaced with an ungulate-derived class switch regulatory element. In another embodiment, the ungulate-derived class switch regulatory element(s) are bovine-derived class switch regulatory elements.

In one embodiment, the HAC vector comprises one or more genes encoding a human antibody surrogate light chain selected from the group consisting of VpreB1, VpreB3 and λ5 human antibody surrogate light chains.

In another embodiment, the HAC further comprises an ungulate-derived enhancer operatively linked to one or more genes encoding the one or more human antibody heavy chains. In one embodiment, the enhancer comprises a 3'Eα enhancer.

In a second aspect, the present invention provides a transgenic ungulate comprising a HAC vector according to any embodiment or combination of embodiments of the first aspect of the invention. In one embodiment, the transgenic ungulate is a transgenic bovine.

In a third aspect, the present invention provides transgenic ungulates comprising genes integrated into its genome encoding:
(a) one or more human antibody heavy chains, wherein each gene encoding an antibody heavy chain is operatively linked to a class switch regulatory element;
(b) one or more human antibody light chains; and
(c) one or more human antibody surrogate light chains, and/or an ungulate-derived IgM heavy chain constant region;
wherein at least one class switch regulatory element of the genes encoding the one or more human antibody heavy chains is replaced with an ungulate-derived class switch regulatory element.

The transgenic ungulates of this third aspect of the invention may comprise any embodiment or combination of embodiments of genes, class switch regulatory elements, and/or enhancers as described for the HACs of the first aspect of the invention, but where the genes, class switch regulatory elements, and/or enhancers are integrated into its genome.

In a fourth aspect, the present invention provides methods of producing a human antibody, comprising:
(a) administering a target antigen to the transgenic ungulate of any embodiment or combination of embodiments of the second and third aspects of the invention to produce and accumulate human antibody specific to the target antigen in the serum or plasma of the ungulate; and
(b) recovering the human antibody specific to the target antigen from the serum or plasma of the ungulate.

In one embodiment, the recovering comprises:
(i) isolating lymphocytes from the transgenic ungulate;
(ii) generating a human monoclonal antibody producing hybridoma from the lymphocytes; and
(iii) recovering human monoclonal antibody specific to the target antigen from the hybridoma.

In a further embodiment, the lymphocytes from the transgenic ungulate are isolated from lymph nodes of the transgenic ungulate. In a further embodiment, the transgenic ungulate is hyperimmunized with the target antigen.

In a fifth aspect, the invention provides compositions comprising a human antibody produced by the methods of any embodiment or combination of embodiments of the fourth aspect of the invention.

BRIEF DESCRIPTION OF THE DRAWINGS

FIG. 8 shows DNA sequence alignment between the bovine IGLJ2-IGLC2 and IGLJ3-IGLC3 genes. (A) Intron DNA sequence alignment between the bovine IGLJ2-IGLC2 and IGLJ3-IGLC3 genes. "JL2-CL2" (SEQ ID NO: 147) and "JL3-CL3" (SEQ ID NO: 148) corresponds to intronic sequence of the IGLJ2-IGLC2 and IGLJ3-IGLC3 genes, respectively. (B) 3'UTR DNA sequence alignment between the bovine IGLC2 and IGLC3 genes. "bCL2" (SEQ ID NO: 149) and "bCL3" (SEQ ID NO: 150) corresponds to 3'UTR sequence of the IGLC2 and IGLC3 genes, respectively.

FIG. 27 shows that ECS of the Iγ1 region is well conserved. (A) Multiple sequence alignment of ECS of Iγ1 in human (SEQ ID NO: 166), bovine (SEQ ID NO: 187), pig (SEQ ID NO: 189) and horse (SEQ ID NO: 188). (B) Multiple sequence alignment of ECS of Iγ1 in ungulates.

DETAILED DESCRIPTION OF THE INVENTION

Figure 1A:
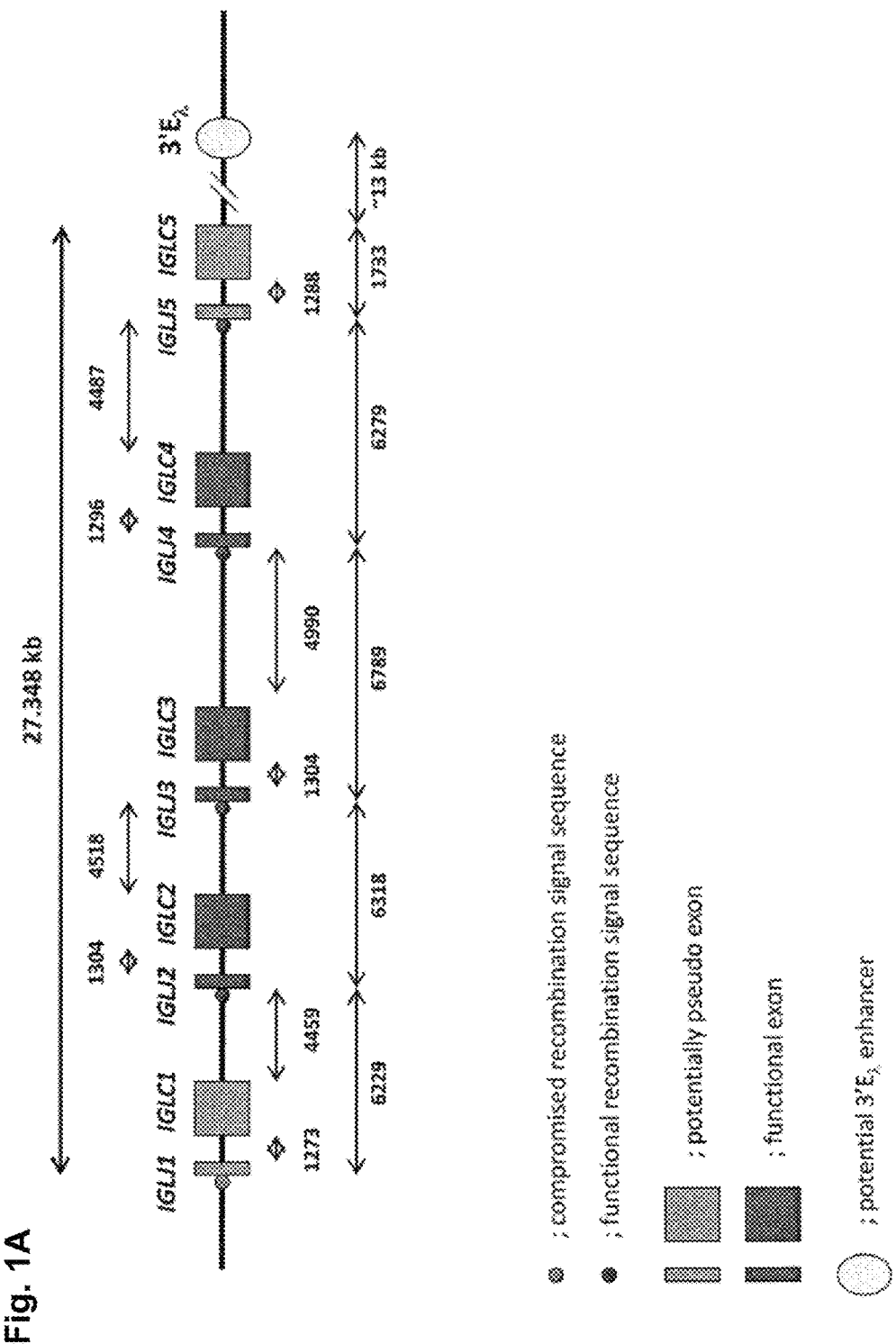
FIG. 1 shows the structure of the bovine IGLJ-IGLC gene cluster and its cluster deletion strategy. (A) Genomic organization of the bovine IGLJ-IGLC gene cluster. (B) Structure of targeting vectors and a strategy for the cluster deletion. The plasmid $pC_{\lambda 1}CAGzeoPuro^{loxP}DT$ was a first knockout (KO) vector to place a loxP site 5' outside of the IGLJ1 gene, composed of 9.9 kb and 3.1 kb genomic DNA as a long and short arm, respectively, a loxP sequence, the CAG promoter-driven zeocin-resistant gene (zeo), DT-A and promoter-less puromycin-resistant gene (puro). The plasmid $pC_{\lambda 5}CAG^{loxP}neoDT$ was a second KO vector to place another loxP site 3' outside of the IGLC5 gene, composed of 8.7 kb and 1.5 kb genomic DNA as a long and short arm, respectively, a loxP sequence, the chicken β-actin promoter-driven neomycin-resistant gene (neo), DT-A, SV40 polyA and CAG promoter. The second KO vector was co-transfected with a Cre-expression plasmid to bring about the cluster deletion, which reconstitutes the CAG promoter-driven puro gene.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," "below," and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides a human artificial chromosome (HAC) vector comprising genes encoding:

(a) one or more human antibody heavy chains, wherein each gene encoding an antibody heavy chain is operatively linked to a class switch regulatory element;

(b) one or more human antibody light chains; and (c) one or more human antibody surrogate light chains, and/or an ungulate-derived IgM heavy chain constant region;

wherein at least one class switch regulatory element of the genes encoding the one or more human antibody heavy chains is replaced with an ungulate-derived class switch regulatory element.

The HAC vectors of the invention can be used, for example, for large-scale production of fully human antibodies by transgenic animals, as described for the methods of the invention. As shown in the examples that follow, the HAC vectors can be used to produce unexpectedly high levels of antigen-specific polyclonal antibodies in ungulates, relative to previous HACs.

In the present invention, the term "HAC vector" means a vector which comprises at least a human chromosome-derived centromere sequence, a telomere sequence, and a replication origin, and may contain any other sequences as desired for a given application. When present in a host cell, the HAC vector exists independently from a host cell chromosome the nucleus. Any suitable methods can be used to prepare HAC vectors and to insert nucleic acids of interest into the HAC, including but not limited to those described in the examples that follow. The HAC vector is a double stranded DNA vector, as is known to those of skill in the art.

The HAC vector of the present invention comprises one or more genes encoding a human antibody heavy chain. Any human antibody heavy chain or combinations of human antibody heavy chains in combination may be encoded by one or more nucleic acids on the HAC. In various embodiments, 1, 2, 3, 4, 5, 6, 7, 8, or all 9 of human antibody heavy chains IgM, IgG1, IgG2, IgG3, IgG4, IgA1, IgA2, IgE and IgD may be encoded on the HAC in one or more copies. In one embodiment, the HAC comprises a human IgM antibody heavy chain encoding gene, alone or in combinations with 1, 2, 3, 4, 5, 6, 7, or the other 8 human antibody chain encoding genes. In one preferred embodiment, the HAC comprises a gene encoding at least a human IgG1 antibody heavy chain; in this embodiment, it is further preferred that the HAC comprises a gene encoding a human IgM antibody heavy chain or a gene encoding a human IgM antibody heavy chain that has been chimerized to encode an ungulate-derived IgM heavy chain constant region (such as a bovine heavy chain constant region). In another embodiment, the HAC comprises a gene encoding at least a human IgA antibody heavy chain; in this embodiment, it is further preferred that the HAC comprises a gene encoding a human IgM antibody heavy chain or a gene encoding a human IgM antibody heavy chain that has been chimerized to encode an ungulate-derived IgM heavy chain constant region (such as a bovine heavy chain constant region). In another preferred embodiment, the HAC comprises genes encoding all 9 antibody heavy chains, and more preferably where the gene encoding a human IgM antibody heavy chain has been chimerized to encode an ungulate-derived IgM heavy chain constant region. In another embodiment, the HAC may comprise a portion of human chromosome 14 that encodes the human antibody heavy chains. The variable region genes and the constant region genes of the human antibody heavy chain form a cluster and the human heavy chain locus is positioned at 14q32 on human chromosome 14. In one embodiment, the region of human chromosome 14 inserted in the HAC comprises the variable region and the constant region of the human antibody heavy chains from the 14q32 region of human chromosome 14.

In the HAC vectors of the present invention, at least one class switch regulatory element of the human antibody heavy chain encoding nucleic acid is replaced with an ungulate-derived class switch regulatory element. The class switch regulatory element refers to nucleic acid which is 5' to an antibody heavy chain constant region. Each heavy chain constant region gene is operatively linked with (i.e.: under control of) its own switch region, which is also associated with its own I-exons. Class switch regulatory elements regulate class switch recombination and determine Ig heavy chain isotype. Germline transcription of each heavy chain isotype is driven by the promoter/enhancer elements located just 5' of the I-exons and those elements are cytokine or other activator-responsive. In a simple model of class switch, the specific activators and/or cytokines induce each heavy chain isotype germline transcription from its class switch regulatory element (i.e., activator/cytokine-responsive promoter and/or enhancer). Class switch is preceded by transcription of I-exons from each Ig heavy (IGH) locus-associated switch region. As each heavy chain constant region gene is linked with its own switch region.

Any suitable ungulate-derived class switch regulatory element can be used. As used herein, "ungulates" may be any suitable ungulate, including but not limited to bovine, pig, horse, donkey, zebra, deer, oxen, goats, sheep, and antelope. For example, the human heavy chain gene isotypes listed below has the following class switch regulatory elements:

IgM: I$\mu$-S$\mu$,
IgG1: I$\gamma$1-S$\gamma$1,
IgG2: I$\gamma$2-S$\gamma$2,
IgG3: I$\gamma$3-S$\gamma$3,
IgG4: I$\gamma$4-S$\gamma$4,
IgA1: I$\alpha$1-S$\alpha$1,
IgA2: I$\alpha$2-S$\alpha$2, and
IgE: I$\epsilon$-S$\epsilon$.

In various embodiments, 1, more than 1, or all of the human antibody heavy chain genes on the HAC have their class switch regulatory element replaced with an ungulate-derived class switch regulatory element, including but not limited to ungulate I$\mu$-S$\mu$, I$\gamma$-S$\gamma$, I$\alpha$-S$\alpha$, or I$\epsilon$-S$\epsilon$, class switch regulatory elements. In one embodiment, an I$\gamma$1-S$\gamma$1 human class switch regulatory element for human IgG1 heavy chain encoding nucleic acid on the HAC (such as that in SEQ ID NO: 183) is replaced with an ungulate I$\gamma$1-S$\gamma$1 class switch regulatory element. Exemplary ungulate I$\gamma$1-S$\gamma$1 class regulatory switch elements include a bovine IgG1 I$\gamma$1-S$\gamma$1 class switch regulatory element (SEQ ID NO: 182), a horse I$\gamma$1-S$\gamma$1 class switch regulatory element (SEQ ID NO: 185), and a pig I$\gamma$1-S$\gamma$1 class switch regulatory element (SEQ ID: 186). However, it is not necessary to replace the human class switch regulatory element with an ungulate class switch regulatory element from the corresponding heavy chain isotype. Thus, for example, an I$\gamma$3-S$_\gamma$3 human class switch regulatory element for human IgG3 heavy chain encoding nucleic acid on the HAC can be replaced with an ungulate I$\gamma$1-S$\gamma$1 class switch regulatory element. As will be apparent to those of skill in the art based on the teachings herein, any such combination can be used in the HACs of the invention.

In another embodiment, the HAC comprises at least one ungulate enhancer element to replace an enhancer element associated with one or more human antibody heavy chain constant region encoding nucleic acids on the HAC. There are two 3' enhancer regions (Alpha 1 and Alpha 2) associated with human antibody heavy chain genes. Enhancer elements are 3' to the heavy chain constant region and also help regulate class switch. Any suitable ungulate enhancer can be used, including but not limited to 3'Eα enhancers. Non-limiting examples of 3' Eα enhancers that can be used include 3'Eα, 3'Eα1, and 3'Eα2. Exemplary 3'Eα enhancer elements from bovine that can be used in the HACs and replace the human enhancer include, but are not limited to bovine HS3 enhancer (SEQ ID NO: 190), bovine HS12 enhancer (SEQ ID NO: 191), and bovine enhancer HS4. This embodiment is particularly preferred in embodiments wherein the HAC comprises the variable region and the constant region of the human antibody heavy chains from the 14q32 region of human chromosome 14.

The HAC vectors of the present invention may comprise one or more genes encoding a human antibody light chain. Any suitable human antibody light chain-encoding genes can be used in the HAC vectors of the invention. The human antibody light chain includes two types of genes, i.e., the kappa/K chain gene and the lambda/chain gene. In one embodiment, the HAC comprises genes encoding both kappa and lambda, in one or more copies. The variable region and constant region of the kappa chain are positioned at 2p11.2-2p12 of the human chromosome 2, and the lambda chain forms a cluster positioned at 22q11.2 of the human chromosome 22. Therefore, in one embodiment, the HAC vectors of the invention comprise a human chromosome 2 fragment containing the kappa chain gene cluster of the 2p11.2-2p12 region. In another embodiment, the HAC vectors of the present invention comprise a human chromosome 22 fragment containing the lambda chain gene cluster of the 22q11.2 region.

In another embodiment, the HAC vector comprises at least one gene encoding a human antibody surrogate light chain. The gene encoding a human antibody surrogate light chain refers to a gene encoding an imaginary antibody light chain which is associated with an antibody heavy chain produced by a gene reconstitution in the human pro-B cell to constitute the pre-B cell receptor (preBCR). Any suitable human antibody surrogate light chain encoding gene can be used, including but not limited to the VpreB1 (SEQ ID NO: 154), VpreB3 (SEQ ID NO: 178) and λ5 (also known as IgLL1, SEQ ID NO: 157) human antibody surrogate light chains, and combinations thereof. The VpreB gene and the λ5 gene are positioned within the human antibody lambda chain gene locus at 22q11.2 of the human chromosome 22. Therefore, in one embodiment the HAC may comprise the 22q11.2 region of human chromosome 22 containing the VpreB gene and the λ5 gene. The human VpreB gene of the present invention provides either or both of the VpreB1 gene (SEQ ID NO: 154) and the VpreB3 (SEQ ID NO: 178) gene and in one embodiment provides both of the VpreB1 gene and the VpreB3 gene.

In yet another embodiment, the HAC vector comprises a gene encoding an ungulate-derived IgM heavy chain constant region. In this embodiment, the IgM heavy chain constant region is expressed as a chimera with the human IgM antibody heavy chain variable region. Any suitable ungulate IgM heavy chain antibody constant region encoding nucleic acid can be used, including but not limited to bovine IgM, (SEQ ID NO: 152), horse IgM, (SEQ ID NO: 176), sheep IgM, (SEQ ID NO: 174), and pig IgM, (SEQ ID NO: 175). In one embodiment, the chimeric IgM comprises the sequence in SEQ ID NO: 200. Pre-BCR/BCR signaling through the IgM heavy chain molecule promotes proliferation and development of the B cell by interacting with the B cell membrane molecule Ig-alpha/Ig-beta to cause a signal transduction in cells. Transmembrane region and/or other constant region of IgM are considered to have important roles in the interaction with Ig-alpha/Ig-beta for signal transduction. Examples of the IgM heavy chain constant regions include nucleic acids encoding constant region domains such as CH1, CH2, CH3, and CH4, and the B-cell transmembrane and cytoplasmic domains such as TM1 and TM2. The nucleic acid encoding an ungulate-derived IgM heavy chain constant region which is comprised in the human artificial chromosome vector of the invention is not particularly limited so long as the region is in a range which may sufficiently induce the signal of the B-cell receptor or B-cell proliferation/development in the above-described IgM heavy chain constant region. In one embodiment, the nucleic acid encoding an ungulate-derived IgM heavy chain constant region provides a transmembrane and cytoplasmic TM1 domain and TM2 domain derived from an ungulate, and in other embodiments encodes the ungulate-derived CH2 domain, CH3 domain, CH4 domain, TM1 domain, and TM2 domain or the ungulate-derived CH1 domain, CH2 domain, CH3 domain, CH4 domain, TM1 domain, and TM2 domain.

In one embodiment, the gene encoding the IgM heavy chain constant region of the bovine is a gene encoding a bovine IgM heavy chain constant region which is included in an IGHM region at which a bovine endogenous IgM heavy chain gene is positioned (derived from IGHM) or a gene encoding a bovine IgM heavy chain constant region in an IGHML1 region (derived from IGHML1). In another embodiment, the gene encoding a bovine IgM heavy chain constant region is included in the IGHM region.

In a further embodiment, the HAC comprises a gene encoding a human antibody heavy chain comprises a gene encoding a human heavy chain (for example, a human IgG heavy chain, such as an IgG1 heavy chain), and wherein a transmembrane domain and an intracellular domain of a constant region of the human heavy chain gene are replaced with a transmembrane domain and an intracellular domain of an ungulate-derived heavy chain (for example, an ungulate IgG heavy chain, such as an IgG1 heavy chain), constant region gene. In one embodiment, gene encoding the transmembrane domain and the intracellular domain of an ungulate-derived (such as bovine) IgG (such as IgG1) heavy chain constant region are used to replace the corresponding regions of the human IgG heavy chain gene. In another embodiment, the gene encoding the TM1 and TM2 domains of an ungulate-derived (such as bovine) IgG (such as IgG1) heavy chain constant region are used to replace the corresponding regions of the human IgG heavy chain gene. In another embodiment, the gene encoding the one or more of the CH1-CH4 domains and/or the TM1 and TM2 domains of an ungulate-derived (such as bovine) IgG (such as IgG1) heavy chain constant region are used to replace the corresponding regions of the human IgG heavy chain gene.

In a second aspect, the invention provides transgenic ungulates comprising a HAC vector according to any embodiment or combination of embodiments of the first aspect of the invention. The transgenic ungulate comprising the HAC vector of the present invention refers to an animal into which the human artificial chromosome vector of the present invention is introduced. The transgenic ungulate having the HAC of the present invention is not particularly limited so long as the animal is a transgenic ungulate in which the human artificial chromosome fragment may be introduced into a cell thereof, and any non-human animals, for example, ungulates such as cows, horses, goats, sheep, and pigs; and the like may be used. In one aspect, the transgenic ungulate is a bovine. A transgenic ungulate having the HAC vector of the present invention may be constructed, for example, by introducing the HAC vector of the present invention into an oocyte of a host animal using any suitable technique, such as those described herein. The HAC vector of the present invention may, for example, be introduced into a somatic cell derived from a host ungulate by a microcell fusion method. Thereafter, the animal having the HAC vector may be constructed by transplanting a nucleus or chromatin agglomerate of the cell into an oocyte and transplanting the oocyte or an embryo to be formed from the oocyte into the uterus of a host animal to give birth. It may be confirmed by a method of Kuroiwa et al. (Kuroiwa et al., Nature Biotechnology, 18, 1086-1090, 2000 and Kuroiwa et al., Nature Biotechnology, 20, 889-894) whether an animal constructed by the above method has the human artificial chromosome vector of the present invention.

In a third aspect, the invention provides transgenic ungulates comprising genes integrated into its genome encoding:
(a) one or more human antibody heavy chains, wherein each gene encoding an antibody heavy chain is operatively linked to a class switch regulatory element;
(b) one or more human antibody light chains; and
(c) one or more human antibody surrogate light chains, and/or an ungulate-derived IgM heavy chain constant region;
wherein at least one class switch regulatory element of the genes encoding the one or more human antibody heavy chains is replaced with an ungulate-derived class switch regulatory element.

In this third aspect, the transgenic ungulate may comprise any embodiment or combination of embodiments of the nucleic acids as described herein for the HAC, but rather than being present in a HAC, they are integrated into a chromosome of the ungulate.

In a fourth aspect, the invention provides a method of producing a human antibody, comprising: (a) administering a target antigen to the transgenic ungulate of any embodiment or combination of embodiments of the invention to produce and accumulate human antibody specific to the target antigen in the serum or plasma of the ungulate; and (b) recovering the human antibody specific to the target antigen from the serum or plasma of the ungulate. In one embodiment, recovering the antibody comprises: (i) isolating lymphocytes from the transgenic ungulate; (ii) generating a human monoclonal antibody producing hybridoma from the lymphocytes; and (iii) recovering human monoclonal antibody specific to the target antigen from the hybridoma. In another embodiment, the lymphocytes from the transgenic ungulate are isolated from lymph nodes of the transgenic ungulate. In a further embodiment the transgenic ungulate is hyperimmunized with the target antigen.

A target antigen-specific human antibody may be produced by immunizing the transgenic ungulate having the HAC vector of the present invention with a desired target antigen to produce the target antigen-specific human antibody in the serum of the transgenic ungulate and recovering the target antigen-specific human antibody from the serum of the transgenic ungulate. The target antigens for immunizing the transgenic ungulate having the HAC vector of the present invention are not particularly limited and examples include a tumor-associated antigen, an antigen associated with allergy or inflammation, an antigen associated with cardiovascular disease, an antigen associated with autoimmune disease, an antigen associated with neurodegenerative disease, and an antigen associated with viral or bacterial infections.

Examples of tumor-associated antigens include CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD55, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, cc-chemokine receptor (CCR) 4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth facter receptor (EGFR), EGFRvIII, EGFR2 (HER2), EGFR3 (HERS), EGFR4 (HER4), endoglin, epithelial cell adhesion molecule (Ep-CAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR)3, FGFR4, FLT1, FLT3, folate receptor, Frizzled homologue 10 (FZD10), frizzled receptor 4 (FZD-4), G250, G-CSF receptor, ganglioside (GD2, GD3, GM2, GM3, and the like), globo H, gp75, gp88, GPR-9-6, heparanase I, hepatocyte growth factor (HGF), HGF receptor, HLA antigen (HLA-DR, and the like), HM1.24, human milk fat globule (HMFG), hRS7, heat shock protein 90 (hsp90), idiotype epitope, insulin-like growth factor (IGF), IGF receptor (IGFR), interleukin (IL-6, IL-15, and the like), interleukin receptor (IL-6R, IL-15R, and the like), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Nec1-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (DR4, DR5, and the like), system ASC amino acid transporter 2 (ASCT2), trkC, TROP-2, TWEAK receptor Fn14, type IV collagenase, urokinase receptor, vascular endothelial growth factor (VEGF), VEGF receptor (VEGFR1, VEGFR2, VEGFR3, and the like), vimentin, VLA-4, and the like.

Examples of antigens associated with allergy or flare include IL-6, IL-6R, IL-5, IL-5R, IL-4, IL-4R, TNF, TNF receptor, CCR4, chemokine, chemokine receptor, and the like. Examples of antigens associated with cardiovascular disease include GPIIb/IIIa, PDGF, PDGF receptor, blood coagulation factor, IgE, and the like. Examples of antigens associated with viral or bacterial infections include gp120, CD4, CCR5, a verotoxin, an anthrax protective antigen, a methicillin-resistant *Staphylococcus aureus* (MRSA) antigen, a hepatitis type B virus (HBV) antigen, a cytomegalovirus (CMV) antigen, a Rabies antigen, a Varicella zoster antigen, and the like. Other examples thereof include a T cell surface membrane protein mixtures, a Rh (D) antigen, crotalid venom, digoxin, and the like.

The immunization is carried out by administering the target antigen with, for example, a complete Freund's adjuvant or an appropriate adjuvant such as an aluminum hydroxide gel, and pertussis bacteria vaccine, subcutaneously, intravenously, or intraperitoneally into a transgenic ungulate. In one embodiment, the immunization comprises hyper-immunization, which refers to immunization that goes beyond just giving the animals protective titers to an antigen. For example, if a protective titer is 1:120, we may hyper-immunize an animal to 1:10,240 so that these titers may be diluted in the production of a biotherapeutic in order to give protective titers in a passive transfer of immunity. Examples of the form of administering the target antigen into an transgenic ungulate having the HAC vector of the present invention include peptides, protein, bacteria, viruses, cells, biological tissue pieces, and the like. When the target antigen is a partial peptide, a conjugate is produced with a carrier protein such as bovine serum albumin (BSA), keyhole Limpet hemocyanin (KLH) or the like, and is used as the immunogen. The target antigen is administered once to 10 times every 1 to 4 weeks after the first administration. After 1 to 14 days from each administration, blood is collected from the animal to measure the antibody value of the serum.

Examples of the method for detecting and measuring the target antigen-specific human antibody included in the serum include a binding assay by an enzyme-linked immunosorbent assay, and the like. The binding amount of a human antibody in the serum may be measured by incubating the serum comprising the human antibody with antigen expressing cells, and then using an antibody specifically recognizing a human antibody.

Further, in addition to these methods, the antibody may be selected by identifying a target antigen of the antibody according to a method known in the art. Examples of the method for recovering human antibodies from the serum include a method of purifying by adsorbing the human antibody on a protein A carrier, a protein G carrier, or a carrier on which the human immunoglobulin specific antibody is supported. Methods used in purification of proteins, such as gel filtration, ion exchange chromatography, and ultrafiltration, may be combined.

A human antibody produced by the above method may be a polyclonal antibody or a monoclonal antibody. Methods of preparing and utilizing various types of antibodies are well-known to those of skill in the art and would be suitable in practicing the present invention (see, for example, Harlow, et al. Antibodies: A Laboratory Manual, Cold Spring Harbor Laboratory, 1988; Kohler and Milstein, Nature, 256:495 (1975)). An example of a preparation method for hybridomas comprises the following steps of: (1) immunizing a transgenic ungulate with a target antigen; (2) collecting antibody-producing cells from the transgenic ungulate (i.e. from lymph nodes); (3) fusing the antibody-producing cells with myeloma cells; (4) selecting hybridomas that produce a monoclonal antibody reacting target antigen from the fused cells obtained in the above step; and (5) selecting a hybridoma that produces a monoclonal antibody reacting with target antigen from the selected hybridomas.

EXAMPLES

Methods

All animal procedures were performed in compliance with Hematech's guidelines, and protocols were approved by the Institutional Animal Care and Use Committee.

Genomic Library.

Genomic DNA was extracted either from CHO cells containing the κHAC vector (κC1-1) or the bovine fibroblast cell lines, 6939 and 3427, to construct the κHAC or bovine genomic libraries, respectively. Each λ phage-based genomic library was constructed using λFIX II vector through a custom library construction service (Lofstrand Labs Ltd.). Library screening and λ phage DNA extraction/purification was done as described previously[5]. The bovine genomic BAC library (CHORI-240) was purchased from Children's Hospital Oakland Research Institute and screening was performed, according to their instruction.

Construction of Targeting Vectors.

Each vector construction was performed as previously described[5, 12, 20, 21] with some modification as described below. pTEL'hisDpuro$^{lox2272}$F9R9; a genomic DNA fragment for a homologous arm was amplified by using a PCR primer pair, kD-F9 and kD-R9, in 40 cycles of 98° C. for 10 s and 68° C. for 9 min. This PCR product was subcloned into Bam HI site of a plasmid pTEL'hisDpuro$^{lox2272}$, which was constructed as follows. The modified lox2272-containing oligo DNAs (Oligo DNA pair 1; see Table 1 below) were, after annealing, cloned into Hin dIII site of a plasmid pPUR (BD Bioscience Clontech), generating a plasmid pPUR$^{lox2272}$. On the other hand, another plasmid pTEL'hisDPm was constructed by modifying the previous plasmid pTELpuro, where the puro gene was replaced with hisD gene, Eco RI site was replaced with Srf I and Spe I site was converted to Pme I site. The Bam HI fragment from the pPUR$^{lox2272}$ was then cloned, after blunting, to Pme I site of the pTEL'hisDPm, which generated pTEL'hisDpuro$^{lox2272}$F9R9.

pTELCAGzeoSLF2R2;

the plasmid pTELpuro was further modified by converting the Eco RI site to Srf I and then to Pme I and by replacing the puro gene to CAGzeo gene {pTELCAGzeo(Sr)Pm}. On the other hand, a genomic DNA fragment for a homologous arm was amplified by using a PCR primer pair, SL-F2 and SL-R2, in 40 cycles of 98° C. for 10 s and 68° C. for 9 min. This PCR product was subcloned into Bam HI site of the plasmid pTELCAGzeo(Sr)Pm, which generated pTELCAGzeoSLF2R2.

p553CAG$^{lox2272}$BsrDT;

The previous targeting vector pHCF2loxPHyg was modified where the homology arm sequence of the HCF2 gene was replaced with that of the AP000553, which was amplified by using a PCR primer pair, 553-F3 and 553-R3, in 40 cycles of 98° C. for 10 seconds and 68° C. for 15 min, generating p553loxPHyg(F). This plasmid was Not I-digested and self-ligated, followed by cloning of DT-A fragment into Srf I site. On the other hand, pDRIVE-CAG (InvivoGen) was modified as below. The lacZ fragment (Bsr GI-Eco RI) was replaced with the loxP-containing oligo DNAs (Oligo DNA pair 2; see Table 1 below) after annealing and then Sda I-Swa I fragment was cloned into Pst I/Sma I-digested pBluescript SK—(Stratagene), generating pCAG$^{loxP}$. The loxP sequence was further replaced with the lox2272-containing sequence that was generated after annealing two oligo DNAs (Oligo DNA pair 3; see Table 1 below). And then, the bsr gene was added to Spe I site, generating pcAG$^{loxP2272}$bsr. Finally, the Not I-Kpn I fragment (CAG-lox2272-polyA-bsr) was cloned into the Not I site to complete p553CAG$^{lox2272}$BsrDT.

pSC355CAG$^{lox511}$hisDDT; a genomic DNA fragment for a homologous arm was amplified by using a PCR primer pair, SC355-F3 and SC355-R3, in 40 cycles of 98° C. for 10 seconds and 68° C. for 15 min. This PCR product was subcloned into Spe I site of a plasmid pBluescript where the Kpn I site was converted to Srf I site, generating pSC355F3R3. The pCAG$^{loxP}$ plasmid was similarly modified where the loxP sequence was further replaced with the lox511-containing sequence that was generated after annealing two oligo DNAs (Oligo DNA pair 4; see Table 1 below). And then, the hisD gene was added to Spe I site, generating pCAG$^{lox511}$hisD. The Not I-Kpn I fragment (CAG-lox511-polyA-hisD) was cloned into the Eco RV site of pSC355F3R3. Finally, the DT-A cassette was subcloned into Not I to complete pSC355CAG$^{lox511}$hisDDT.

p14CEN(FR)hygpuro$^{lox511}$DT;

a genomic DNA fragment for a homologous arm was amplified by using a PCR primer pair, 14CEN-F and 14CEN-R, in 40 cycles of 98° C. for 10 seconds and 68° C. for 15 min. This PCR product was subcloned into Bam HI site of a plasmid pBluescript where the Kpn I site was converted to Pme I site, generating p14CEN(FR). The modified lox511-containing oligoDNAs (Oligo DNA pair 5; see Table 1 below) were, after annealing, cloned into Hind III site of a plasmid pPUR (BD Bioscience Clontech), generating a plasmid pPUR$^{lox511}$. The Bam HI fragment from the pPUR$^{lox511}$ was cloned to Bam HI site of pBluescript SK (Stratagene), followed by cloning of the hyg gene to Eco RV, generating pHygPuro$^{lox511}$. The Not I-Kpn I fragment (puro-lox511-hyg) was cloned into the Hpa I site of p14CEN(FR). Finally, the DT-A cassette was subcloned into Pme I to complete p14CEN(FR)hygpuro$^{lox511}$DT.

pRNR2$^{loxP}$bsrDT;

the previous vector pRNR2$^{loxP}$bsr (Ref 20) was modified to construct the pRNR2$^{loxP}$bsrDT by simply adding the DT-A cassette.

pCH1CAGzeo(R)DT(F);

a genomic λ phage library was constructed from CHO cells containing the κHAC using λ FIX II vector through a custom library construction service (Lofstrand). The genomic library was screened for hIGHM constant region by using a probe that was a PCR product by amplified a PCR pair, hCμ-FR, and then clones #1, #4 and #7 were isolated. From the clone #4, 1.7 kb of Pml I fragment was subcloned into Sma I site of pBluescript, generating pCH1S (F). 1 kb of Sac I-Pml I fragment from the plasmid pBCμAY37-95 where Sal I-bovine IGHM genomic fragment was cloned into pBluescript was subcloned into Pst I site of the pCH1S (F), generating pCH1SSP (F). 7.4 kb of the Sma I-Eco RI fragment from the above clone #1 was cloned into Eco RV/Eco RI-digested pCH1SSP (F), generating pCH1SL. On the other hand, from the plasmid pBCμAY37-95, 3.5 kb of Sac I fragment was subcloned into pBluescript and then the Xho I fragment of floxed CAGzeo {CAGzeo fragment was subcloned into Eco RV site of pBS246 (Gibco)} was cloned into Van91 I site, generating pmAYSazeo (F). The Sac I fragment from the pmAYSazeo (F) was further subcloned into blunted Eco RI site of pCH1SL, generating pCH1zeo (F). As a final step, the DT-A cassette was subcloned into Not I site of the pCH1zeo (F) to complete the pCH1CAGzeo (R)DT(F).

pCH2CAGzeoDT;

an annealed oligo DNA pair, SeSp, was cloned into blunted Pst I site of pBluescript. From the pBCμAY37-95, 2 kb of Sph I-Bam HI fragment was subcloned into Sph I-Bam HI site, generating pmAYSpB. Similarly, 2 kb of Bam HI-Pml I fragment from the pBCμAY37-95 was subcloned into Bam HI-Pme I site (converting the original Spe I site), generating pmAYSpBPml. 0.6 kb of Eco RI-Sex AI fragment from the above clone #1 was subcloned into Eco RI-Sex AI site of the pmAYSpBPml, generating pRISe. Then, the floxed CAGzeo was subcloned into Van91 I site of the pRISe, generating pRISeCAGzeo (R), of which Not I site was converted to Eco RI site, generating pRISeCAGzeoE. Meanwhile, 1.7 kb of Pml I fragment from the above clone #4 was subcloned into Sma I site of pBluescript of which Eco RV site was converted to Mlu I site, generating pCH2S (F). 6.6 kb of Mlu I-Eco RI fragment from the above clone #1 was cloned into Mlu I-Eco RI of the pCH2S (F), generating pCH2LS. Then, the Eco RI fragment from the pRISeCAGzeoE was subcloned into Eco RI site of the pCH2LS, generating pCH2CAGzeo (F). As a final step, the DT-A cassette was subcloned into Not I site of the pCH2CAGzeo (F) to complete the pCH2CAGzeoDT.

pCC1BAC-isHAC;

the genomic λ phage library constructed from CHO cells containing the κHAC was screened to isolate genomic DNA fragments covering the human $I_{\gamma1}$-$S_{\gamma1}$ region followed by the hIGHG1 constant region by using a probe that was a PCR product by amplified with a PCR pair, g1(g2)-FR, and then we identified clones #h10 and #h18/h20. From the clone #h10, 2 kb of Afe I-Bam HI fragment was rescued to be used as a short arm while 10.5 kb of Apa I-Hpa I fragment was obtained from the clone #h18/h20 for a long arm. On the other hand, a bovine genomic λ phage library was screened to isolate genomic DNA fragments covering the bovine $I_{\gamma1}$-$S_{\gamma1}$ region followed by the bIGHG1 constant region by using a probe that was a PCR product by amplified with a PCR pair, bIgG1-FR, and then we identified a clone #b42, from which a 9.7 kb fragment (5' end through Bsu36 I) was assembled to replace a 6.8 kb of the human $I_{\gamma1}$-$S_{\gamma1}$ region. A Bsu36 I-Apa I linker was used to join 3' end of the bovine $I_{\gamma1}$-$S_{\gamma1}$ region and 5' end of the hIGHG1 constant region. The neo gene flanked by FRT and DT-A gene were inserted as shown in FIG. 22B. All the above assembles were done on a BAC-based backbone vector pCC1BAC (EPICENTRE).

phI$_{\gamma1}$FRTCAGattPhisDDT;

11.4 kb of Kpn I-Not I genomic fragment from clone h10 was isolated from the clone #h10 and subcloned into pBluescript SK(−) vector. Then, the FRT-CAG promoter-attP-polyA-hisD cassette was inserted into the 5' Bam HI site which is 1.8 kb downstream from the Kpn I site. Finally, DT-A gene was cloned into Not I site.

ph$_{\gamma1}$TMNoeattPDT;

7.5 kb of Sac II genomic fragment from clone h20 was subcloned into pBluescript SK (−) vector. Next, the neo-attP cassette was inserted into Hin dIII site, followed by cloning of DT-A gene into Not I site.

pBAC-istHAC;

7.3 kb of Bmg BI-Sph I bovine genomic fragment containing the bovine TM1/TM2 domain was obtained from the clone #b66, of which 5' part was joined with 3' part of the 9.5 kb of the bovine $I_{\gamma1}$-$S_{\gamma1}$ fragment (from #b42) and 1.6 kb of hIGHG1 gene (from #h10) from the isHAC by a linker, pNsiI-bG1-hG1-BmgBI. The attB-DsRed-FRT cassette was inserted at 5' side of the 9.5 kb of the bovine $I_{\gamma1}$-$S_{\gamma1}$ fragment (from #b42) and another attB sequence was placed at 3' side of 7.3 kb of Bmg BI-Sph I bovine genomic fragment containing the bovine TM1/TM2 domain that was obtained from the clone #b66. All the above assembles were done on a BAC-based backbone vector pCC1BAC (EPICENTRE).

pC$_{\lambda1}$CAGzeoPuro$^{loxP}$DT;

a probe amplified by a primer pair, bCLR-FR, identified several λ phage clones covering the 5' side of the IGLJ1-IGLC1 gene. The 13 kb Nde I-Hin dIII genomic fragment was subcloned into pBluescript SK(-) vector and the CAG-zeo/loxP/promoter-less puro cassette was inserted at Afe I site present in the genomic fragment. Finally, DT-A gene was inserted at Not I site. This vector was constructed from the alleles A and B.

pC$_{\lambda5}$CAG$^{loxP}$neoDT;

a probe amplified by a primer pair, bCLL-FR, identified several λ phage clones covering the 3' side of the IGLJ5-IGLC5 gene. The 10 kb Sac II-Nsi I genomic fragment was subcloned into pBluescript SK(-) vector and the CAG promoter/loxP/poly A/neo cassette was inserted at Hin dIII site present in the genomic fragment. Finally, DT-A gene was inserted at Not I site. This vector was constructed from the alleles A and B.

Modification of the Human Chromosome 14 Fragments in Chicken DT40 Cells.

Figure 17A:
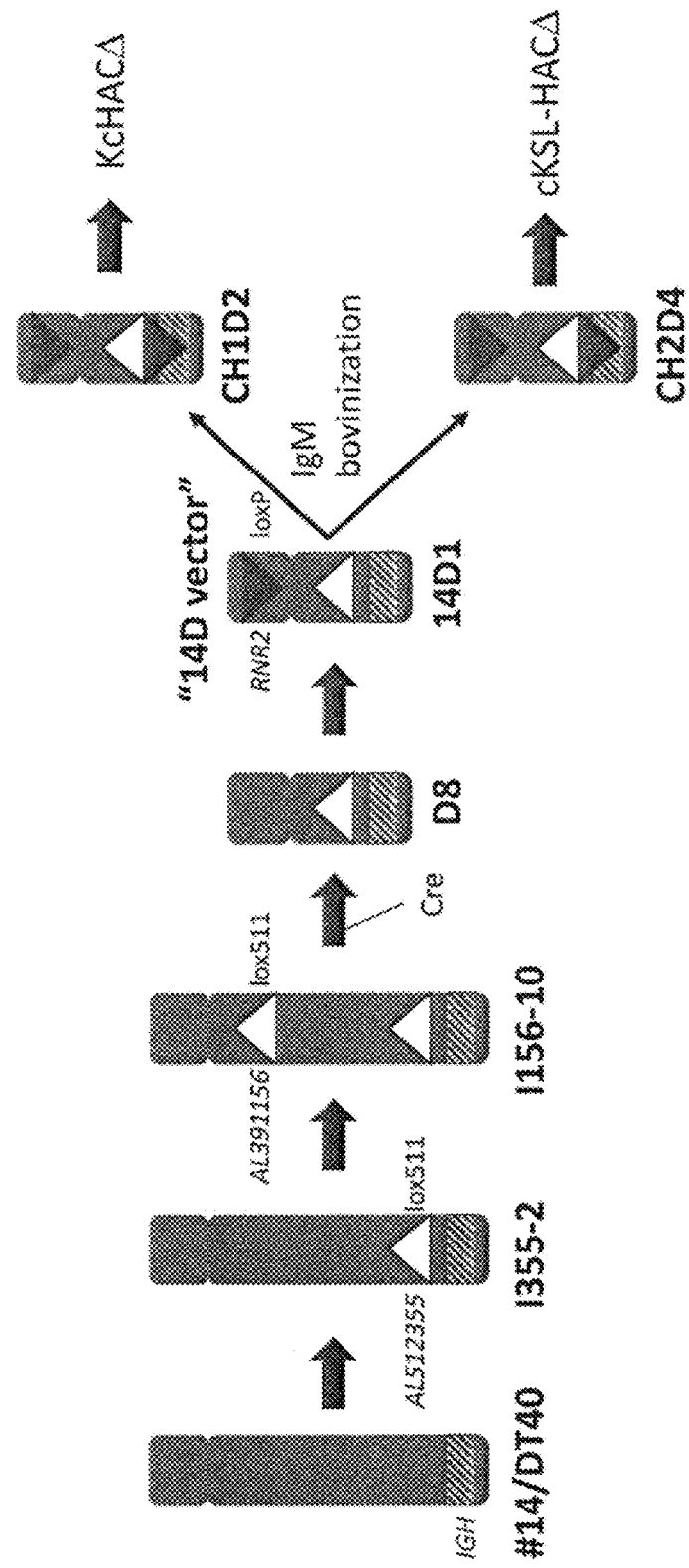
FIG. 17 shows construction of 14D vector. (A) A flow of the 14D vector construction. The first lox511 was integrated at the AL512355 on the intact hChr14 to generate I355-2. Then, the second lox511 was placed at the AL391156 to generate I156-10. Cre introduction brought about a big DNA deletion on the chromosome to generate D8. 14D1 was built by integrating the loxP at RNR2 locus. Subsequently, the cIgM (CH1) or cIgM (CH2) bovinization generated CH1D2 or CH2D4, which was used for the KcHACΔ or cKSL-HACΔ vector construction, respectively. (B) Detailed strategy of the 14D vector construction. The targeting vector pSC355CAG$^{lox511}$hisDDT consists of 8.2 kb and 2.0 kb genomic DNA as a long and short arm, respectively, CAG promoter, lox511, SV40 polyA signal, the chicken β-actin promoter-driven hisD gene and DT-A gene, which was used to integrate the lox511 sequence at the AL512355, ~300 kb centromeric to the IGHA2 locus. Another targeting vector p14CEN(FR)hygpuro$^{lox511}$DT is composed of 8.2 kb and 1.8 kb genomic DNA as a long and short arm, respectively, the promoter-less puro gene, lox511, chicken β-actin promoter-driven hyg gene and DT-A gene, which was used to integrate the lox511 sequence at the AL391156. Cre introduction induced the big DNA deletion (~85 Mb) between the two lox511 sites to generate the 14D. As a result of the big deletion, the CAG promoter-driven puro gene was reconstituted and selected by puromycin. Puromycin-resistant cells were subjected to genomic PCR, CAGpuro-F3R3, to confirm the deletion at molecular level. The cells were also sensitive to hygromycin B or histidinol due to the deletion. (C) The IgM bovinization for the CH1D and CH2D. The bovinization vector pCH1CAGzeo(R)DT(F) comprises 7.4 kb and 1.7 kb human genomic DNA as a long and short arm, respectively, 6 kb of the bovine IGHM constant region genomic DNA covering the CH1 through TM2 domains where the floxed, CAG promoter-driven zeo gene cassette was integrated between the CH4 and TM1 intron, and DT-A gene. After the homologous recombination, part of the hIGHM constant region, the CH1 through TM2 domains, was bovinized on the CH1D. Another bovinization vector pCH2CAGzeoDT(F) contains 7.2 kb and 1.7 kb human genomic DNA as a long and short arm, respectively, 5.4 kb of the bovine IGHM constant region genomic DNA covering the CH2 through TM2 domains where the floxed, CAG promoter-driven zeo gene cassette was integrated between the CH4 and TM1 intron, and DT-A gene. After the homologous recombination, part of hIGHM constant region, the CH2 through TM2 domains, was bovinized on the CH2D. (D) Genotyping of each targeting event. At the AL512355, SC355KO-F2R2 was used as a positive PCR specific to the homologous recombination along with the negative PCR, 355N-FR, which was prohibited by the presence of KO cassette. At the AL391156, 14CENKO-F3R3 was used as a positive PCR specific to the homologous recombination along with the negative PCR, 14CEN(N)-F2R2, which was prohibited by the presence of KO cassette. For the CH1D modification {e.g., cIgM (CH1) bovinization}, cHAC-F3F3 was used as a positive PCR specific to the homologous recombination along with CH1 5'-FR and cHAC 3'-FR to check the junction sequences between the human and bovine sequence. Similarly, for the CH2D modification {e.g., cIgM (CH2) bovinization}, cHAC-F3F3 was used as a positive PCR specific to the homologous recombination along with CH2 5'-FR and cHAC 3'-FR to check the junction sequences between the human and bovine sequence. (E) Human COT-1 FISH between the intact hChr14 and the shortened hChr14 fragment.
Figure 17B:
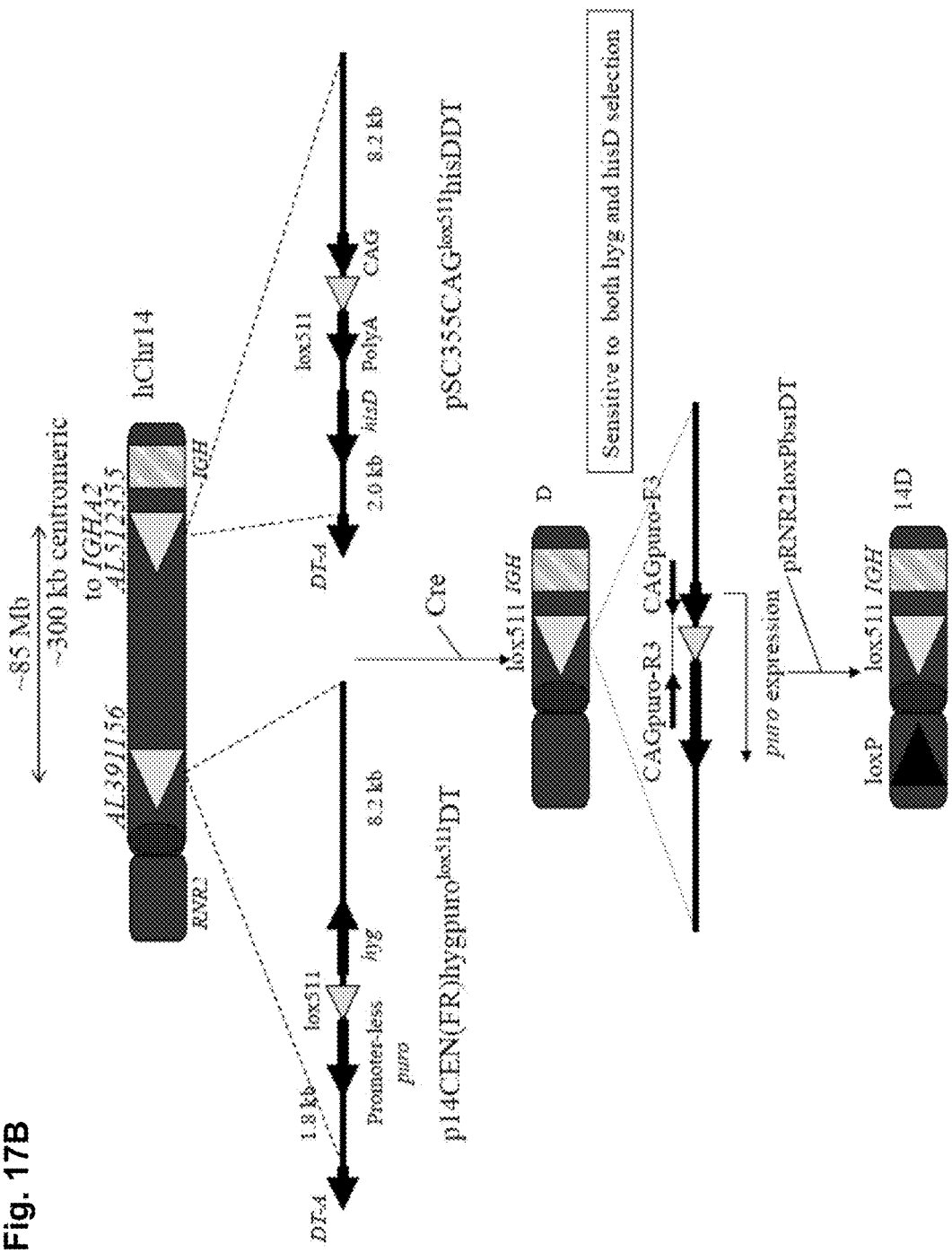
Figure 17C:
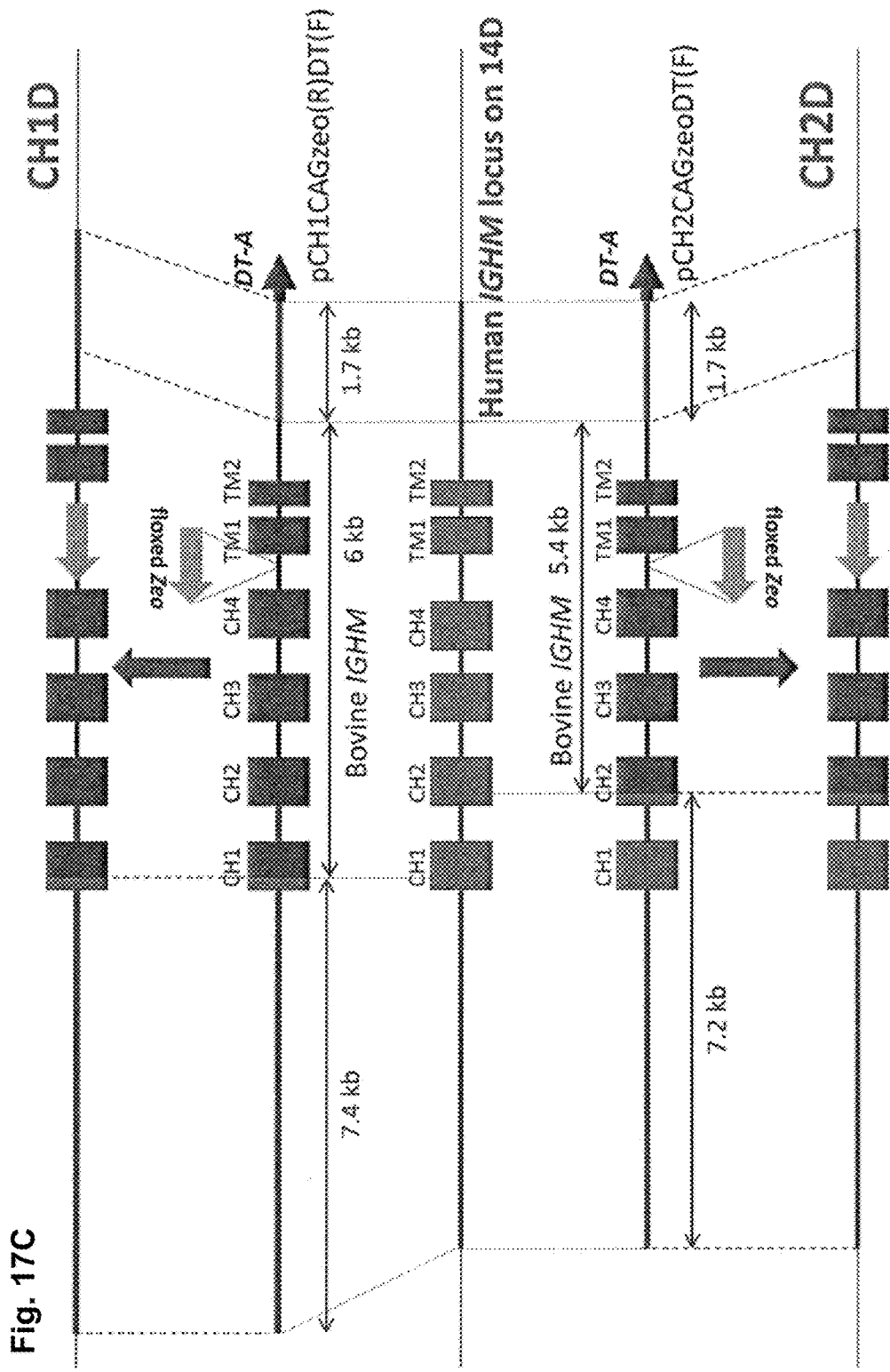
Figure 17D:
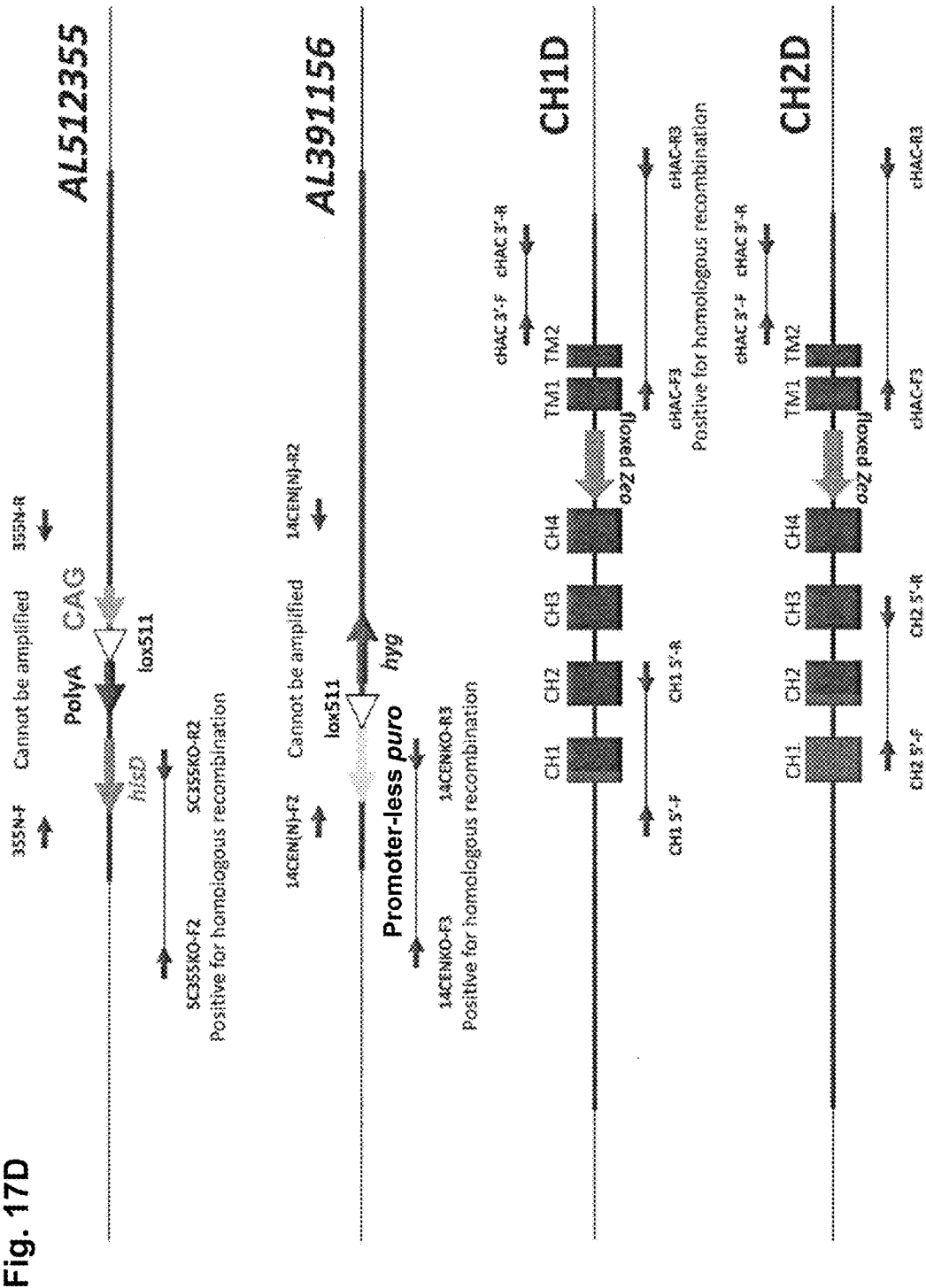

For the purpose of using structure-defined hChr14 vector and of removing as many irrelevant human genes as possible, the intact hChr14 was modified, followed by the IgM bovinization (FIG. 17A). Chicken DT40 cells retaining the intact hChr14 was electroporated with the targeting vector pSC355CAG$^{lox511}$hisDDT to integrate the lox511 and the CAG promoter at the locus AL512355, which is about 300 kb centromeric to the hIGH locus. Colonies were selected with histidinol and subjected to genomic PCR screening to confirm the occurrence of the homologous recombination with primers, SC355KO-F2/R2, as a positive PCR and also with primers, 355N-F/R, as a negative PCR (FIG. 17D). Clone I355-2 was identified as a successfully targeted clone.

I355-2 was further transfected with the targeting vector p14CEN(FR)hygpuro$^{lox511}$DT to integrate another lox511 and the promoter-less puro gene at the locus AL391156, which is about the 85 Mb centromeric to the AL512355. Colonies were selected with hygromycin B and subjected to PCR screening to confirm the occurrence of the homologous recombination with primers, 14CENKO-F3/R3(see Table 1 below), as a positive PCR and also with primers, 14CEN (N)-F2/R2 (see Table 1 below), as a negative PCR (FIG. 17D). Clone I156-10 was identified as a successfully targeted clone.

I156-10 was transfected with the Cre expression plasmid to mediate site-specific recombination between the two lox511 sites, one on the locus AL512355 and another on the AL391156, to delete about 85 Mb of sequence between them to shorten the hChr14 from 106 Mb down to about 21 Mb. Cells where the big deletion took place were selected with puromycin as puromycin resistance is conferred by the CAG promoter-lox511-puro cassette reconstituted at the recombination site. This cassette reconstitution was confirmed by PCR with primers, CAGpuro-F3/R3 (see Table 1 below), as described in the bIGL cluster deletion section. Also, histidinol and hygromycin B sensitivity was confirmed as both hisD and hyg cassettes are to be removed as a result of this 85 Mb deletion (FIG. 17B). Finally, fluorescent in-situ hybridization (FISH) with human COT-1 DNA as a probe confirmed the shortening of the hChr14 (FIG. 17E). Clone D8 was identified as a successfully shortened clone. Clone D8 was sequentially modified with the targeting vector pRNR2loxPbsrDT to integrate the loxP sequence and the GFP gene at the RNR2 locus, as described previously[20, 21]. Clones 14D1 was selected for the final IgM bovinization step (CH1D and CH2D).

Clone 14D1 was finally bovinized with the targeting vector pCH1CAGzeo(R)DT(F) to replace the CH1 domain through the TM2 domain of the hIGHM gene with that of bovine to generate the cIgM (CH1) protein. Colonies were selected with zeocin and subjected to genomic PCR screening to confirm the occurrence of the homologous recombination with primers (see Table 1 below), cHAC-F3/R3, as a positive PCR and also with primers, CH1 5'-F/R and cHAC 3'-F/R, to make sure that the junction sequences between human and bovine are accurate (FIG. 17D). Clone CH1D2 was identified as a positive clone retaining the CH1D fragment for the KcHACΔ construction. Similarly, clone 14D1 was bovinized with the targeting vector pCH2CAGzeoDT(F) to replace the CH2 domain through the TM2 domain of the hIGHM gene with that of bovine to generate the cIgM (CH2) protein and then clone CH2D4 was selected for the cKSL-HACΔ construction.

Figure 18A:
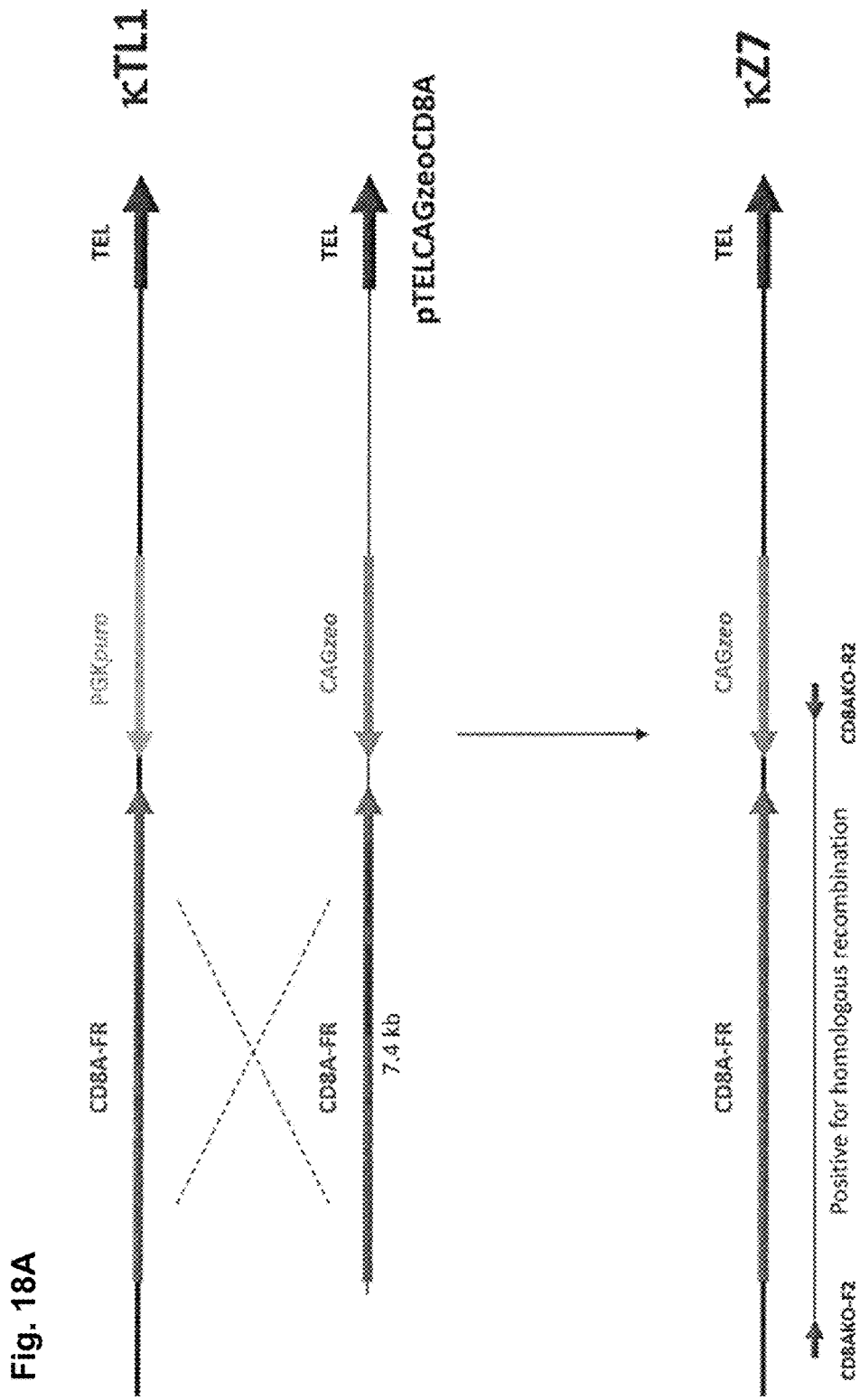
FIG. 18 shows modification of the hChr2 fragment. (A) Generation of clone κZ7. The clone κTL1 was transfected with the targeting vector pTELCAGzeoCD8A to replace the puro cassette with zeo cassette. The targeted event was confirmed by genomic PCR, CD8AKO-F2R2. (B) Truncation of the hChr2 fragment to generate clone K53. The clone κTL1 was transfected with the targeting vector pTEL'hisDpuro$^{lox2272}$F9R9, composed of 7.4 kb of genomic DNA as a homologous arm, promoter-less puro gene, lox2272, the chicken β-actin promoter-driven hisD gene and human telomeric repeat sequence (TEL), to truncate the hChr2 fragment and to integrate the lox2272 at the AC104134.

Modification of the Human Chromosome 2 Fragments in Chicken DT40 Cells.

κTL1 is a DT40 clone containing the hChr2 fragment covering the hIGK locus. This cell line was transfected with the vector pTELCAGzeoCD8A to simply replace the PGK-puro cassette with the CAGzeo because zeocin selection usually works better in bovine fibroblasts at later steps. After zeocin selection, genomic PCR, CD8AKO-F2R2 (FIG. 18A) specific to the homologous recombination, identified clone κZ7, for which puromycin sensitivity was confirmed, and then used for the KcHACΔ construction with the CH1D2.

On the other hand, the κTL1 was also electroporated with the targeting vector pTEL'hisDpuro$^{lox2272}$F9R9 to both truncate the hChr2 fragment and integrate the lox2272 and the promoter-less puro gene at the locus AC104134, which is about 300 kb telomeric to the hIGK constant region Cκ gene, IGKC. Colonies were selected with histidinol, and then puromycin sensitivity was confirmed since the successful truncation results in the loss of the puro cassette at the CD8A locus. Genomic DNA was extracted from puromycin sensitive colonies and subjected to PCR screening with primers, FABP1-F, which amplifies the FABP1 locus present in κTL1 but absent in the targeted clones (FIG. 18B). Clone K53 was identified and used for the cKSL-HACΔ construction.

Modification of the Human Chromosome 22 Fragment in Chicken DT40 Cells.

Figure 19B:
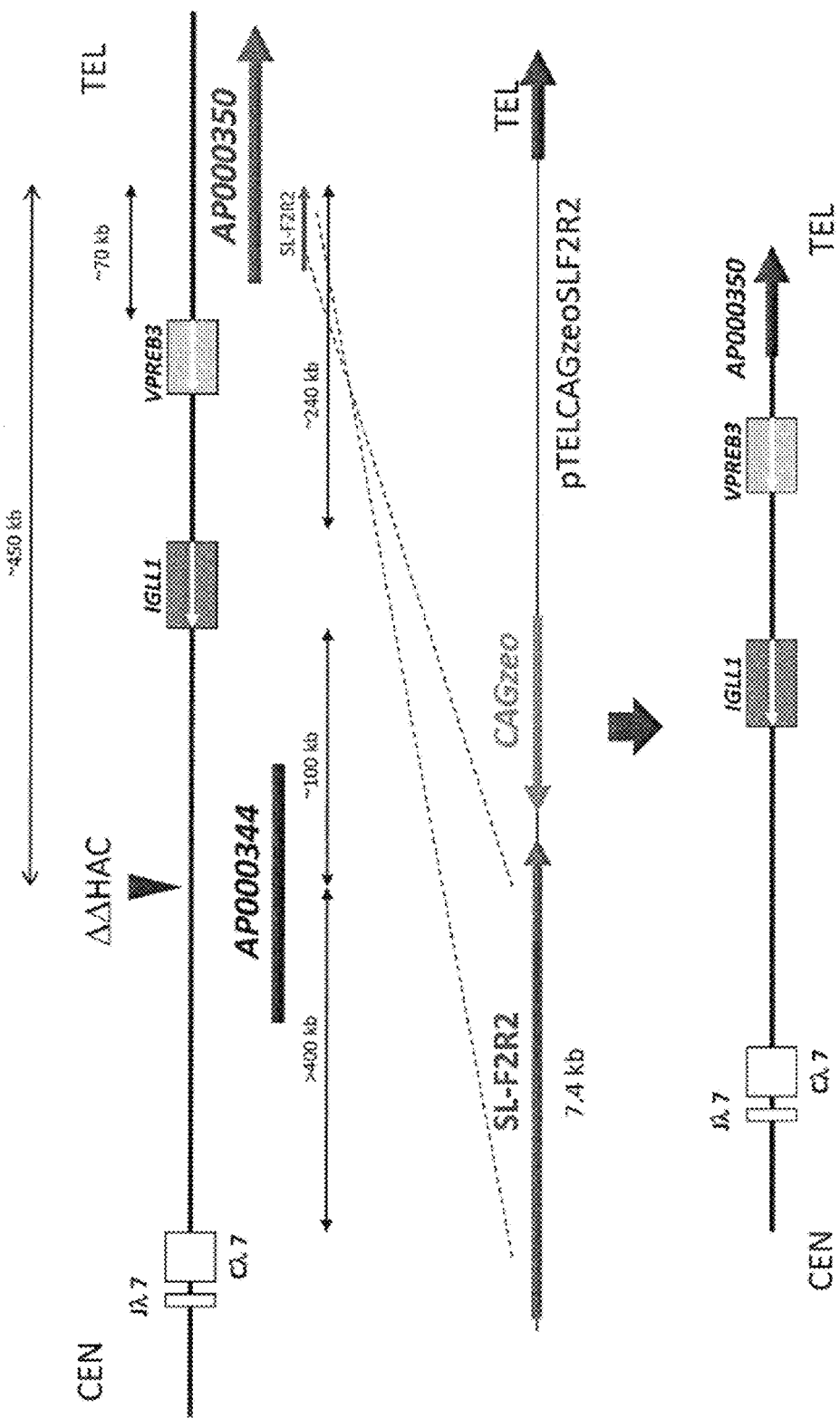
FIG. 19 shows modification of the hChr22 fragment. (A) Generation of clone STL54. The intact hChr22 retained in a clone 52-18 was truncated at the AP000350 by the targeted truncating vector pTELCAGzeoSLFR to generate ST13. Subsequently, the lox2272 sequence was integrated at the AP000553 by the targeting vector p553CAG$^{lox2272}$bsrDT to generate STL54. (B) Truncation of the hChr22 at the AP000350. The locus AP000350 is located ~70 kb telomeric to the hVPREB3 locus. The truncating vector pTELCAG-zeoSLFR consists of 7.4 kb genomic DNA as a homologous arm, the CAG promoter-driven zeo gene and human telomeric repeat sequence (TEL). After the homologous recombination, the hChr22 was truncated at the AP000350. (C) Integration of the lox2272 site at the AP000553. The targeting vector p553CAG$^{lox2272}$bsrDT comprises 6.9 kb and 2.8 kb genomic DNA as a long and short arm, CAG promoter, lox2272, SV40 polyA signal, the chicken β-actin promoter-driven bsr gene and DT-A gene. 553KO-F3R3 was used as a positive PCR specific to the homologous recombination along with the negative PCR, 553-F4R4, which was prohibited by the presence of KO cassette.

The outline is depicted in FIG. 19A. 52-18, a DT40 cell line retaining the intact hChr22, was electroporated with the targeting vector pTELCAGzeoSLFR to truncate the hChr22 at the AP000350 locus, which is about 450 kb telomeric to the AP000344 locus at which the hChr22 was truncated for the ΔΔHAC vector (FIG. 19B). Colonies were selected with zeocin and their genomic DNA was subjected to PCR screening with primers (see Table 1 below), 350T-FR, which amplifies the AP000350 locus present in 52-18 but absent in the targeted clones. Clone ST13 was identified as a successfully truncated clone.

Figure 19C:
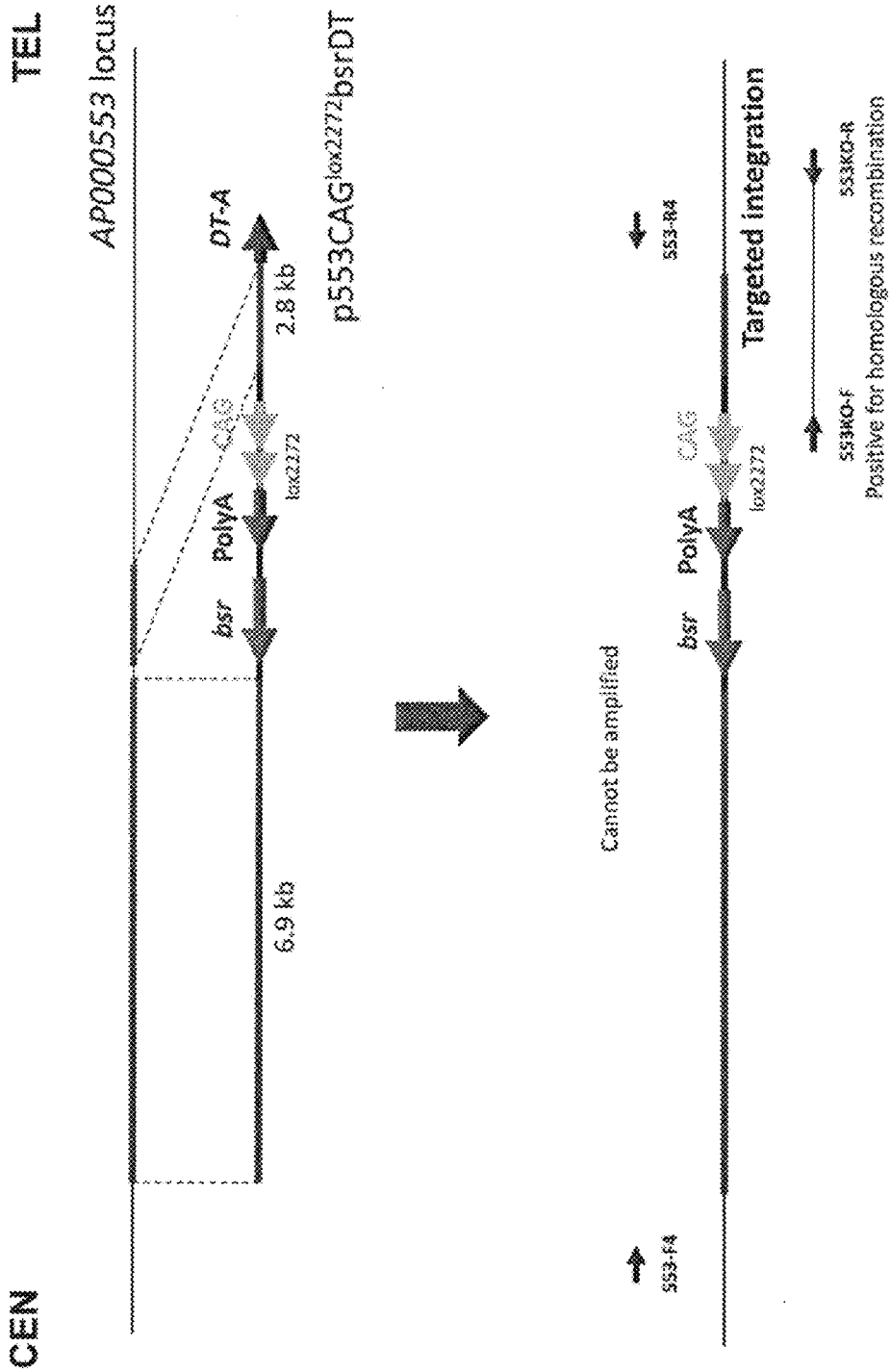

ST13 was modified with the targeting vector p553CAG$^{lox2272}$bsrDT to integrate the lox2272 and the CAG promoter at the locus AP000553. Colonies were selected with blasticidin S and subjected to PCR screening to confirm the occurrence of homologous recombination with primers, 553KO-FR, as a positive PCR and also with primers, 553-F4R4, as a negative PCR (FIG. 19C). Clone STL54 was identified as a successfully targeted clone.

Translocation of the Human Chromosome 22 Fragment to the Human Chromosome 2 Fragment to Generate the SLKH Fragment in Chicken DT40 Cells.

Figure 20A:
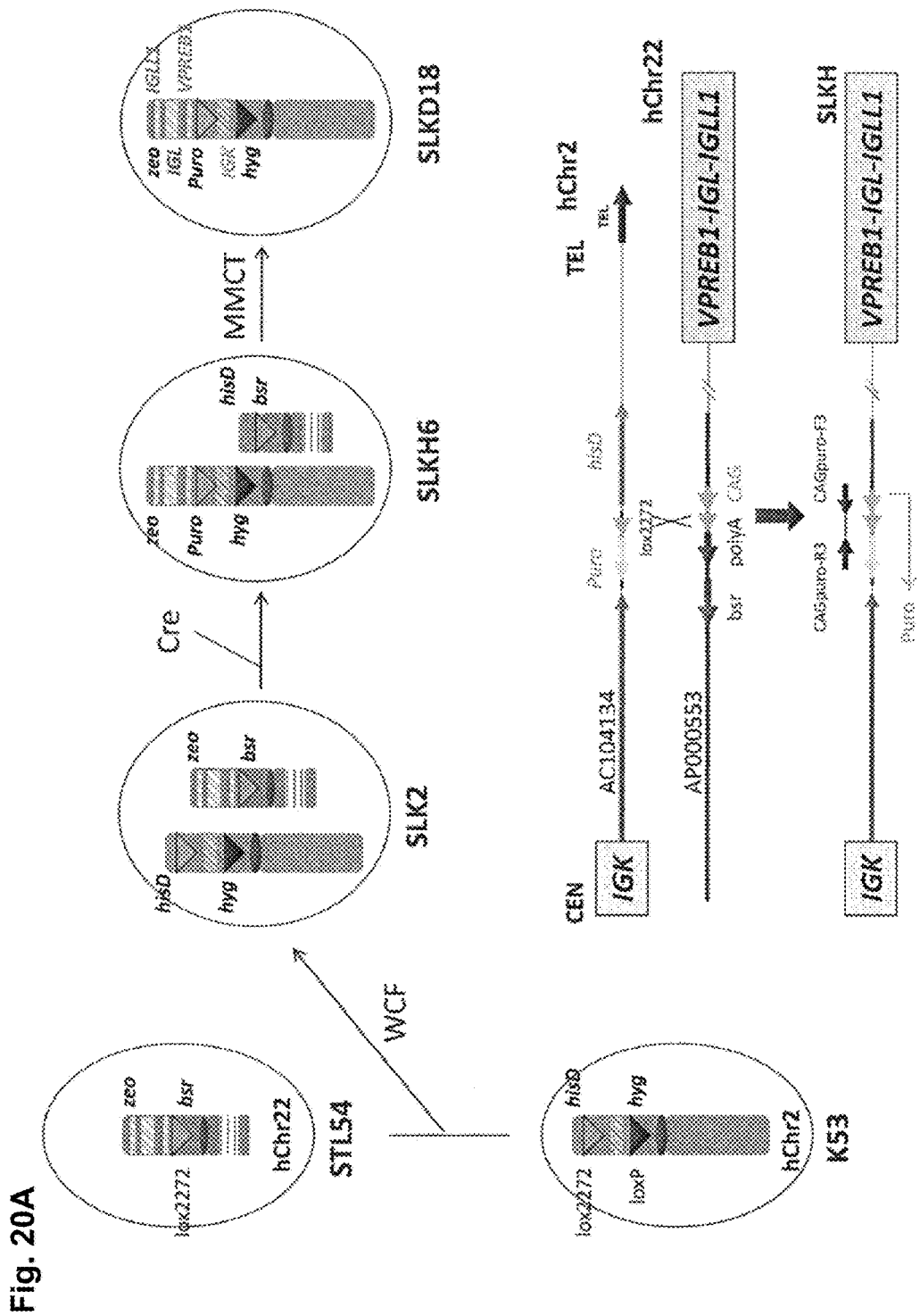
FIG. 20 shows construction of the SLKH fragment. (A) A flow of generation of the SLKH fragment. The two DT40 clones K53 and STL54 were subjected to whole cell fusion to generate a DT40 hybrid clone SLK2. Then, the Cre recombinase was introduced to induce the chromosome translocation between the two hChr fragments that built the SLKH fragment. As a result of the chromosome translocation, the CAG promoter-driven puro gene was reconstituted and selected by puromycin. Furthermore, the occurrence of translocation was confirmed by genomic PCR, CAGpuro-F3R3. From the DT40 hybrid clone SLKH6, the SLKH fragment was transferred to a plane DT40 cell by MMCT to generate SLKD18. (B) Multi-color FISH on the SLK2, SLKH6 and SLKD18. The SLK2 was simply stained with human COT-1 probe, confirming the presence of the longer hChr2 fragment and shorter hChr22 fragment. For the SLKH6 and SLKD18, two-color FISH was implemented. In the SLKH6, the two reciprocally translocated hChr fragments were seen; the longer one was the SLKH fragment. In the SLKD18, just the single SLKH fragment was present.
Figure 20B:
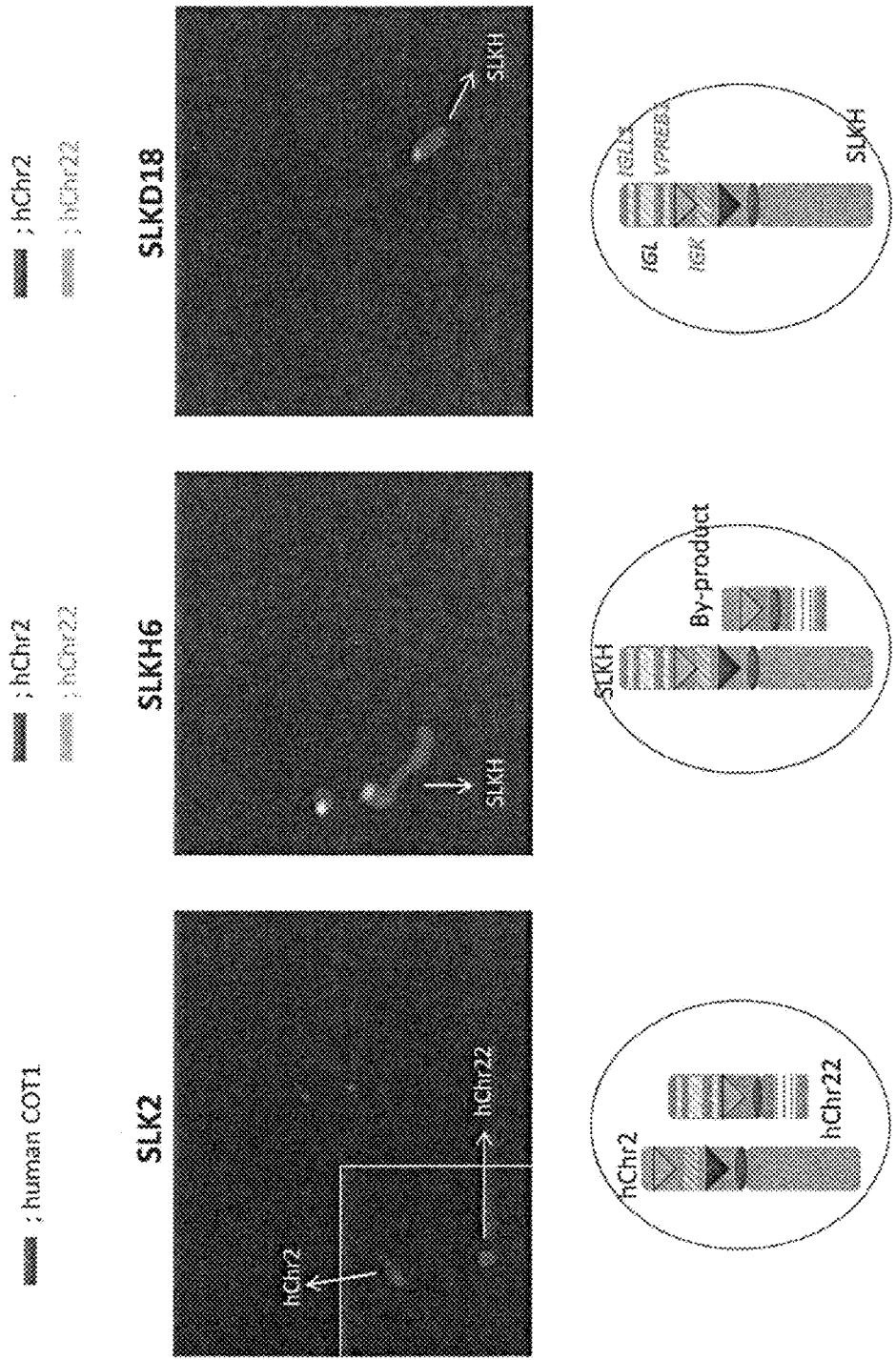

The SLKH fragment was constructed in DT40 hybrid cells using the chromosome cloning system (FIG. 20A). Clone K53 retaining the hChr2 fragment with the hyg cassette and clone STL54 retaining the hChr22 fragment with the bsr cassette were fused (whole cell fusion, WCF) to generate DT40 hybrid cells. Colonies were maintained in hygromycin B and blasticidin S to select for cells retaining both hChr fragments, which was confirmed by genomic PCR with the following primers (see Table 1 below), IGKC-F/R, IGKV-F/R, RPIA-F/R, EIF2AK3-F/R and cos138KO-F/R for the hChr2 fragment, and another set of primers, 553P-F/R, hVpreB1-F/R, hVpreB3-F/R, IgL-F/R, 344-F/R, hL5-F/R, 350P-F/R and 553KO-F/R for the hChr22 fragment. FISH using Human COT-1 DNA as a probe confirmed the presence of the two human chromosome fragments (FIG. 20B). Clone SLK2 was identified as a positive clone. SLK2 was transfected with the Cre expression plasmid to mediate site-specific recombination between the two lox2272 sites, one at the locus AC104134 on the hChr2 fragment and another at the locus AP000553 on the hChr22 fragment. Recombinants were selected by puromycin as puromycin resistance is conferred by reconstitution of the CAG promoter-lox2272-puro cassette at the translocation site. This was also confirmed by the genomic PCR, CAGpuro-F3R3, followed by direct sequencing of the PCR product. SLKH6 was identified as a successfully translocated clone retaining the SLKH fragment (FIG. 20A, 20B).

The SLKH fragment was transferred from DT40 hybrid cell line SLKH6 to plain DT40 cells by MMCT. Selection was done with puromycin and then colonies were investigated for blasticidin S sensitivity as the successful transfer of the SLKH fragment into DT40 cells should result in the loss of the bsr cassette (FIG. 20A). Genomic DNA from blasticidin S-sensitive and puromycin-resistant colonies was extracted and the SLKH fragment retention was confirmed by PCR primers (see Table 1 below), IGKC-F/R, IGKV-F/R, RPIA-F/R, EIF2AK3-F/R, cos138KO-F/R, CAGpuro-F3/R3, 553P-F/R, hVpreB1-F/R, hVpreB3-F/R, IgL-F/R, 344-F/R, hL5-F/R, 350P-F/R, and 553KO-F/R. Two-color FISH using the hChr2 painting probe directly labeled with Rhodamine and the hChr22 painting probe directly labeled with Fluorescein confirmed the presence of the SLKH fragment (FIG. 20B). SLKD18 was identified as a positive clone.

Construction of cKSL-HACΔ and KcHACΔ Vectors in Chicken DT40 Cells.

Figure 3B:
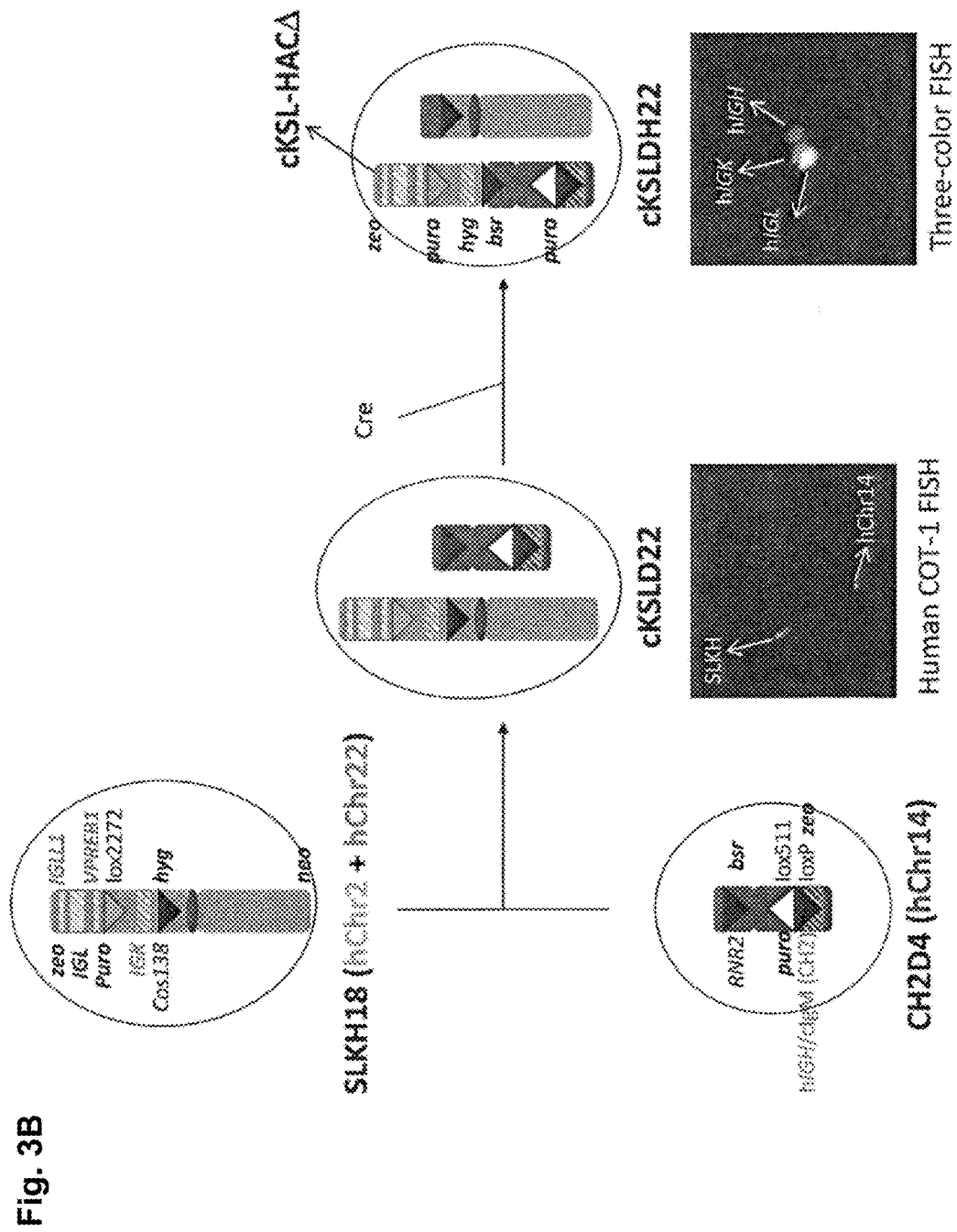
FIG. 3 shows the concept and construction of the KcHACΔ and cKSL-HACΔ vectors. (A) Structure of the KcHACΔ and cKSL-HACΔ vectors. The KcHACΔ vector is a derivative of the original κHAC where part of the hIGHM gene constant region, the CH1 through TM domains, is bovinized with the bovine-origin sequence. Because of this modification, the KcHACΔ vector expresses the bovinized, chimeric IgM {cIgM (CH1)} protein on pre-BB cell surface. Through the bovinized CH1 domain, the cIgM (CH1) better pair with bovine surrogate light chain (bSLC)/light chain (bLC). Furthermore, the bovinized TM1-TM2 domains more efficiently interact with bovine Ig-α/β complex (bIg-α/β) for better pre-BCR/BCR signaling. The cKSL-HACΔ vector is composed of the three different human chromosome (hChr) fragments, hChr14 (14D), hChr2 and hChr22 containing the entire human IGL and surrogate light chain (hVPREB1 and hIGLL1) loci. In this vector, part of the hIGHM gene constant region, the CH2 through TM domains, is bovinized to express the cIgM (CH2) protein. At pre-B cell stage, this cIgM (CH2) may preferentially pair with human surrogate light chain (hSLC, hVPREB1/hIGLL1) to mimic human pre-BCR but with the bovinized TM1-TM2 domain interacting better with bIg-α/β for pre-BCR signal transduction. (B) Construction of the cKSL-HACΔ vector in chicken DT40 cells. The DT40 clone, SLKH18, containing the SLKH fragment where the hChr22 fragment was translocated to the hChr2 fragment, was fused with another DT40 clone, CH2D4, retaining the cIgM (CH2)-bovinized 14D vector to generate the DT40 hybrid clone cKSLD22. The presence of the two hChr fragments was confirmed by human COT1 DNA fluorescent in-situ hybridization (FISH). By introducing a Cre-expression plasmid, chromosome translocation between the two hChr fragments was induced to generate the cKSL-HACΔ vector. Three color-FISH indicates the presence of the hIGH, hIGK and hIGL loci on the cKSL-HACΔ vector. (C) Construction of the KcHACΔ vector in chicken DT40 cells.
Figure 12A:
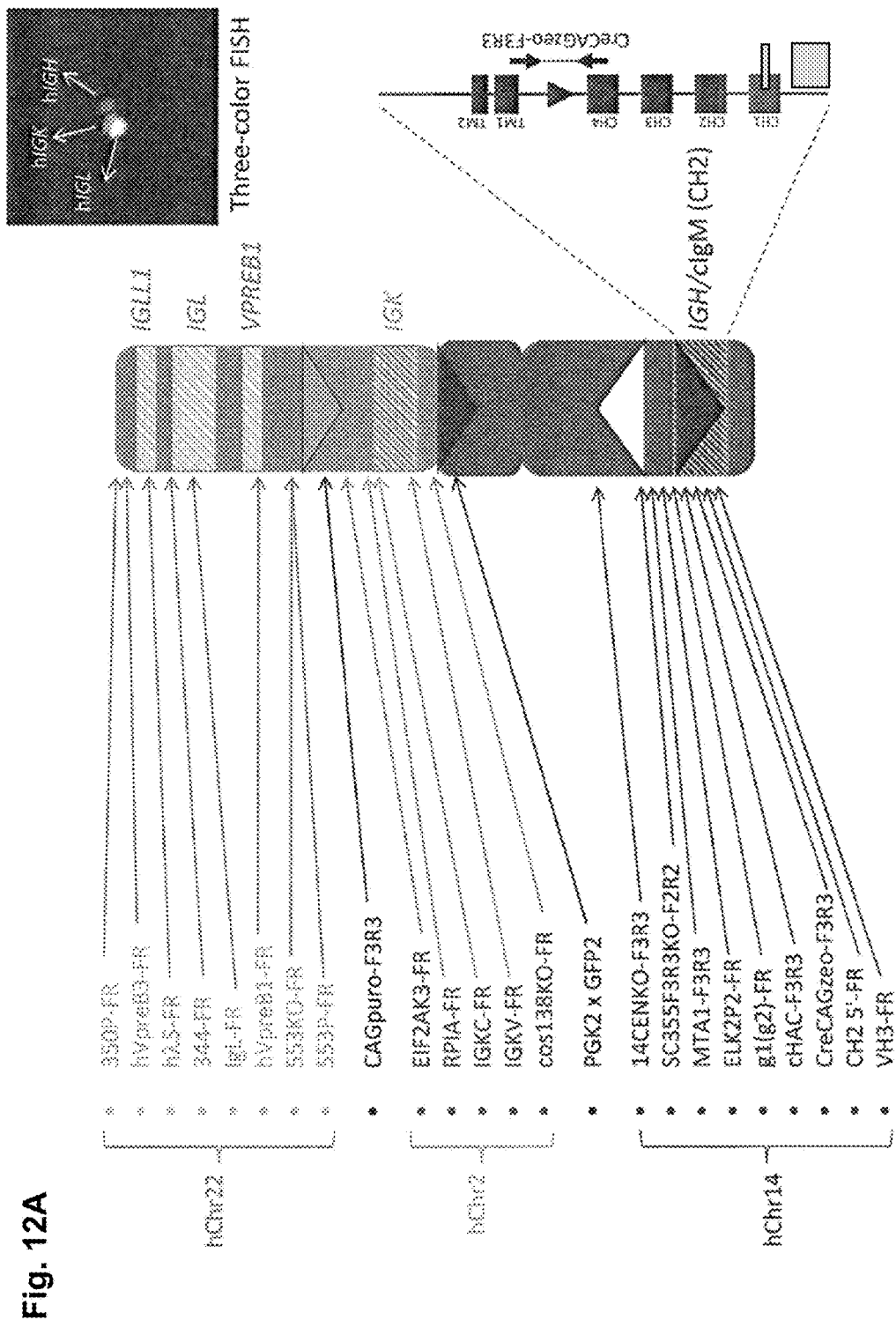
FIG. 12 shows genotyping of the cKSL-HACΔ and KcHACΔ vector, and characterization of the cKSL-HACΔ/DKO calves. (A) Extensive genomic PCR for genotyping of the cKSL-HACΔ vector. Location of each genomic PCR primer pair is depicted in relation to the cKSL-HACΔ vector structure. (B) Extensive genomic PCR for genotyping of the KcHACΔ vector. Location of each genomic PCR primer pair is depicted in relation to the KcHACΔ vector structure. (C) CGH analysis on the CHO clones containing either the cKSL-HACΔ, KcHACΔ or KcHAC vector. In the upper panel, the cKSL-HACΔ containing CHO clones (cKSLDC6, 15, 23) were compared with the κC1-1 containing the κHAC and the KCF4 containing the KcHAC vector. There was no apparent structural difference among all the HACs, except for potential some amplification of DNA around the 3'$E_{a2}$ region (dashed circled) unique to the SC20-based HACs, κHAC and KcHAC. DNA from cKSLDC15 was used as a reference. The lower panel shows CGH pattern among three different CHO clones containing the KcHACΔ vector, where DNA from KCDC1 was used as a reference. There was no apparent structural difference of the KcHACΔ among the three cell lines. (D) Transcription of the human IGL, VPREB1 and IGLL1 genes in the cKSL-HACΔ/DKO calves. PBMCs from three cKSL-HACΔ/DKO calves (Calf 1-3) at newborn stage were subjected to RT-PCR to confirm expression of the human IGL, VPREB1 and IGLL1 genes. N, negative control; P, positive control.
Figure 12B:
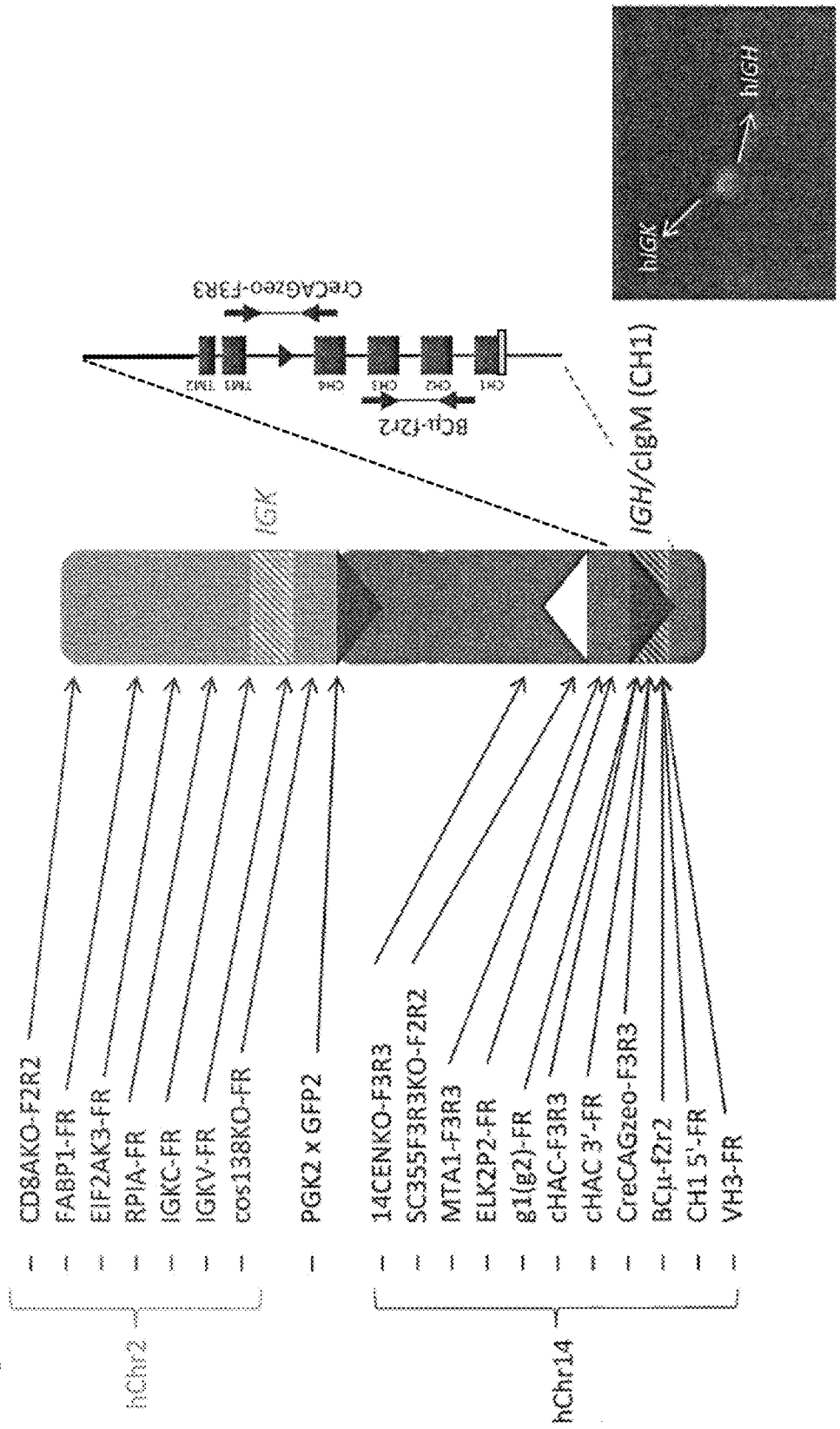
Figure 21:
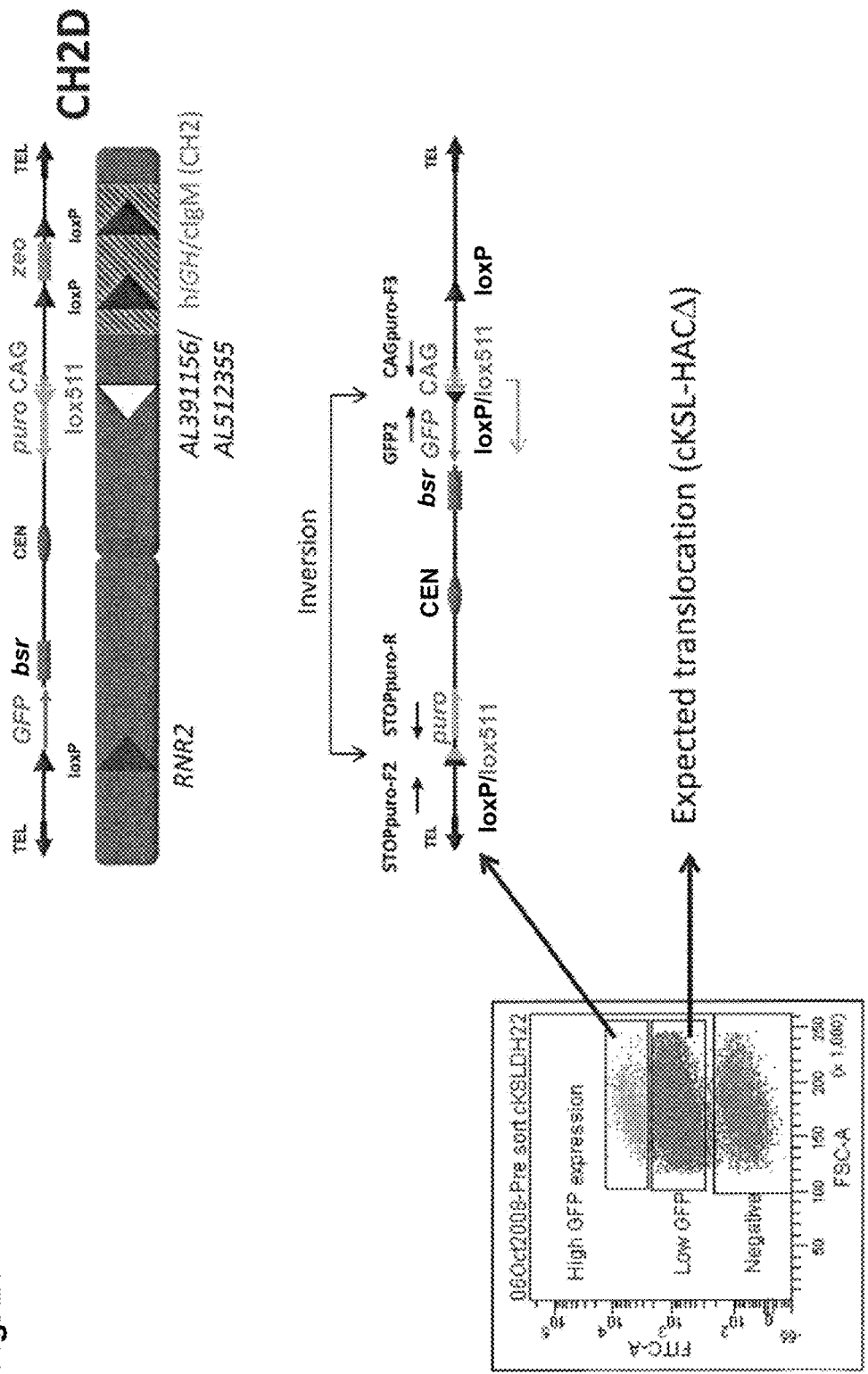
FIG. 21 shows occurrence of the chromosome inversion on the CH2D. A leaky recombination between the loxP at the RNR2 locus and the lox511 at the deletion junction site AP391156/AP512355 caused the inversion that also reconstituted the CAG promoter-driven GFP gene, leading to the higher GFP expression than the PGK promoter-driven GFP gene from the cKSL-HACΔ vector. The inversion was confirmed by genomic PCR, STOPpuro-F2R2 and GFP2× CAGpuro-F3.

The cKSL-HACΔ vector was constructed in DT40 hybrid cells as outlined in FIG. 3B, using the chromosome cloning system. SLKD18 which contains the hChr2 fragment translocated with the hChr22 fragment, bearing the hyg cassette, and CH2D4 which contains the hChr14 fragment (14D) with the bsr cassette and the cIgM (CH2)-bovinized hIGH locus, were fused to generate DT40 hybrid clone cKSLD22, selected by hygromycin B and blasticidin S. Extensive genomic PCR was done with a first set of PCR primers (see Table 1 below) for the hChr22, 553P-F/R, hVpreB1-F/R, hVpreB3-F/R, IgL-F/R, 344-F/R, hL5-F/R, 350P-F/R, and 553KO-F/R, a second set of primers for the hChr2, IGKC-F/R, IGKV-F/R, RPIA-F/R, EIF2AK3-F/R, cos138KO-F/R, CAGpuro-F3/R3 (junction between the hChr2 and hChr22), and a third set of primers (see Table 1 below) for the hChr14, RNR2-1×STOP-3, VH3-F/R, g1(g2)-F/R, 14CENKO-F3/R3, CH2 5'-F/R, cHAC-F3/R3 and SC355F3R3KO-F/2R2. Furthermore, FISH using Human COT-1 DNA also confirmed the presence of the two human chromosome fragments.

cKSLD22 was electroporated with the Cre expression plasmid to mediate site-specific recombination between the two loxP sites, one at the cos138 locus on the SLKH fragment and another at the RNR2 locus on the CH2D fragment, and also to delete the floxed CAG promoter-zeo cassette within the cIgM (CH2) domain. Recombinants were enriched by sorting of GFP positive cells as GFP expression is conferred by reconstitution of the PGK promoter-loxP-GFP cassette at the translocation site. Sorting was conducted twice which resulted in two distinct GFP positive populations with different expression levels. The lower GFP population contained the successfully translocated cKSL-HACΔ determined by PCR primers (see Table 1 below), PGK2× GFP2, and PCR primers, CreCAGzeo-F3/R3, confirmed the CAG promoter-zeo cassette deletion in the cIgM (CH2) site. The higher GFP population contained an inverted CH2D fragment between the loxP at the RNR2 locus and the lox511 at the locus AL512355/AL391156 by a leaky Cre-mediated recombination which was confirmed by PCR primers (see Table 1 below), CAGpuro-F3×GFP2 and STOPpuro-F2× STOPpuro-R, followed by direct sequencing (FIG. 21). cKSLDH22 (2L) was finally identified as a DT40 hybrid cell line retaining the cKSL-HACΔ, subjected to extensive genomic PCR and three color-FISH (FIG. 12A). The KcHACΔ vector was similarly constructed in DT40 cells as outlined in FIG. 3C. The clone KCDH1 was subjected to extensive genomic PCR and two color-FISH (FIG. 12B). Likewise, we also constructed the KcHAC where the hChr2 fragment (KTL1) was translocated to the SC20 fragment bearing the bovinized cIgM (CH1).

Construction of the isHAC and isKcHACΔ Vectors in Chicken DT40 Cells.

Figure 22A:
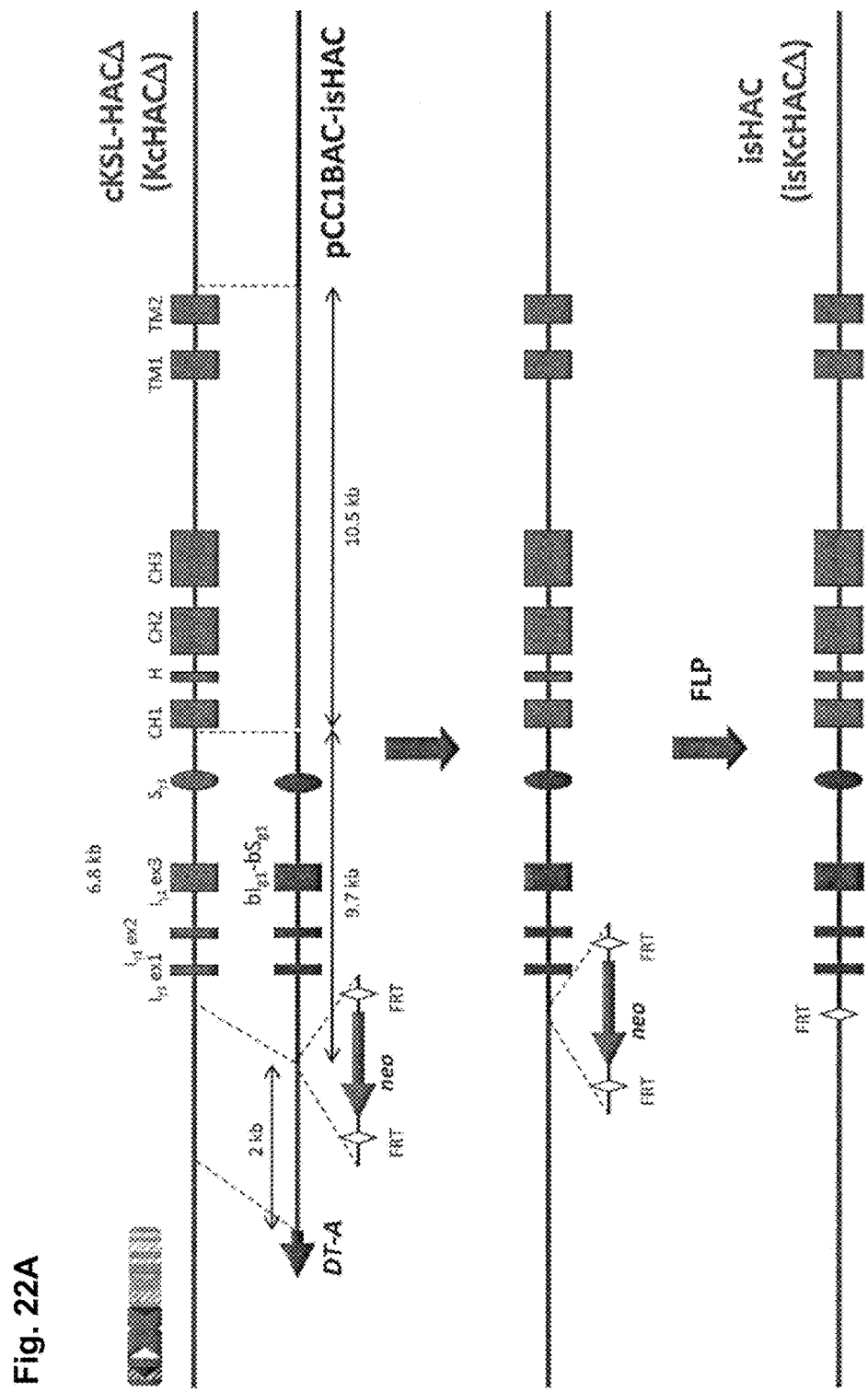
FIG. 22 shows construction of the isHAC and isKcHACΔ vectors. (A) A flow of the isHAC and isKcHACΔ vector construction. The bovinizing vector pCC1BAC-isHAC is a BAC-based one (backbone is pCC1BAC vector), consisting of 10.5 kb and 2 kb of genomic DNA as a long and short arm, respectively, 9.7 kb of the bovine genomic DNA covering the bovine $I_{\gamma 1}$-$S_{\gamma 1}$ and its surrounding region to replace the human corresponding 6.8 kb of $I_{\gamma 1}$-$S_{\gamma 1}$ region, the chicken β-actin promoter-driven neo gene flanked by FRT sequence and DT-A gene. After the targeted bovinization, the neo cassette is removed by FLP introduction. (B) Detailed information of the targeting vector pCC1BAC-isHAC. The 2 kb of Afe I-Bam HI fragment and 10.5 kb of Apa I-Hpa I fragment for a short arm and long arm were obtained from clone h10 and clone h18/h20, respectively, derived from λ, phage genomic library constructed from CHO cells containing the κHAC by screening using a probe around the human $I_{\gamma 1}$-$S_{\gamma 1}$ region. The 9.7 kb fragment (5' end through Bsu36 I) was obtained from clone b42 derived from the λ phage bovine genomic library. (C) Genotyping of the bovinized $I_{\gamma 1}$-$S_{\gamma 1}$ region. Basically, five sets of genomic PCR were implemented, as indicated. iscont1-F1/R1 is a positive PCR specific to the homologous recombination. iscont1-F1×hIgG1-R10 is a negative PCR that is prohibited by the presence of the neo cassette. isHAC-Sw-dig-F5/R3 and isHAC-TM-dig-F3/R2 are for structural integrity check of their corresponding region, digested by Bam HI+Pvu II and Age I, Sma I or Pvu II, respectively. bNeo 5'-R×bIgG1-5'-seq-R6 is to confirm the presence of FRT sequence. (D) Genotyping after the FLP-FRT deletion of the neo cassette. (E) Extensive genomic PCR for genotyping of the isHAC vector. Location of each genomic PCR primer pair is depicted in relation to the isHAC vector structure. (F) CGH analysis among three different CHO clones containing the isHAC vector. DNA from isC1-133 was used as a reference. There was no apparent structural difference of the isHAC among the three cell lines. (G) Extensive genomic PCR for genotyping of the isKcHACΔ vector. Location of each genomic PCR primer pair is depicted in relation to the isKcHACΔ vector structure. (H) CGH analysis among three different CHO clones containing the isKcHACΔ vector. DNA from isKCDC15-8 was used as a reference. There was no apparent structural difference of the isKcHACΔ among the three cell lines.
Figure 22B:
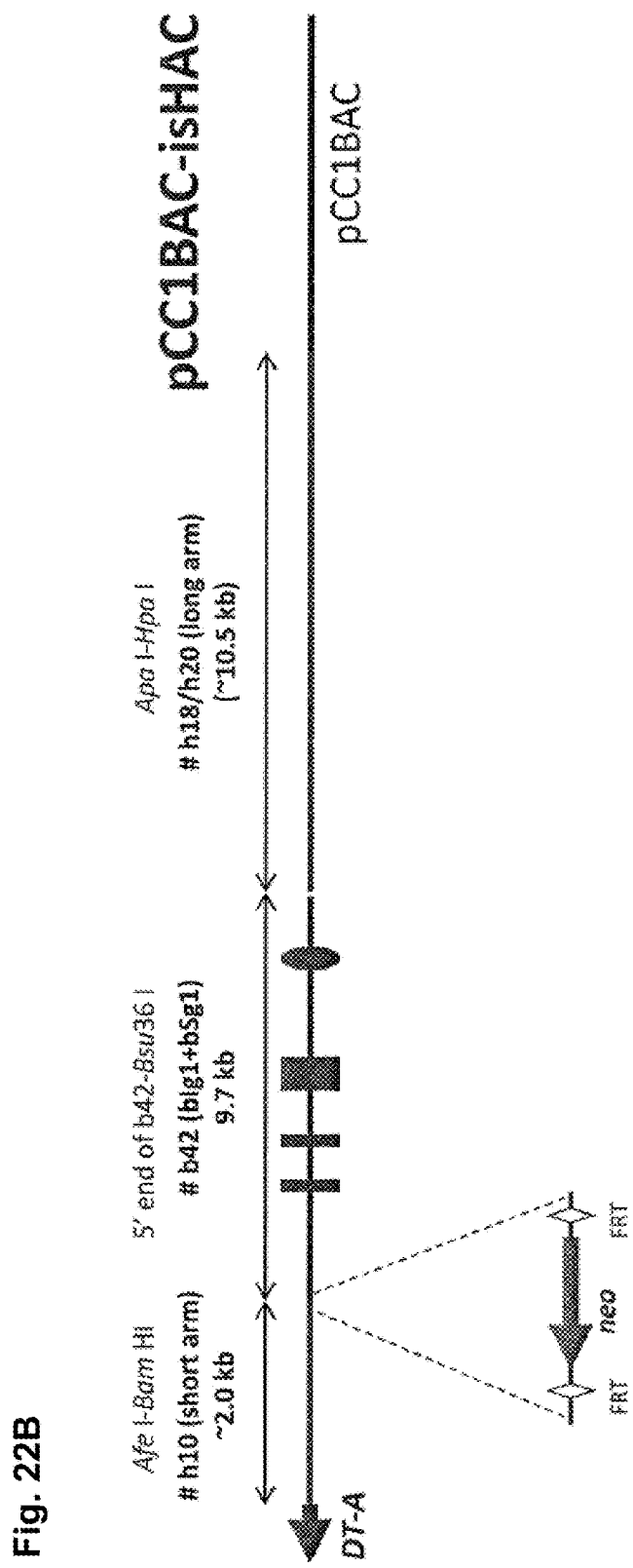
Figure 22C:
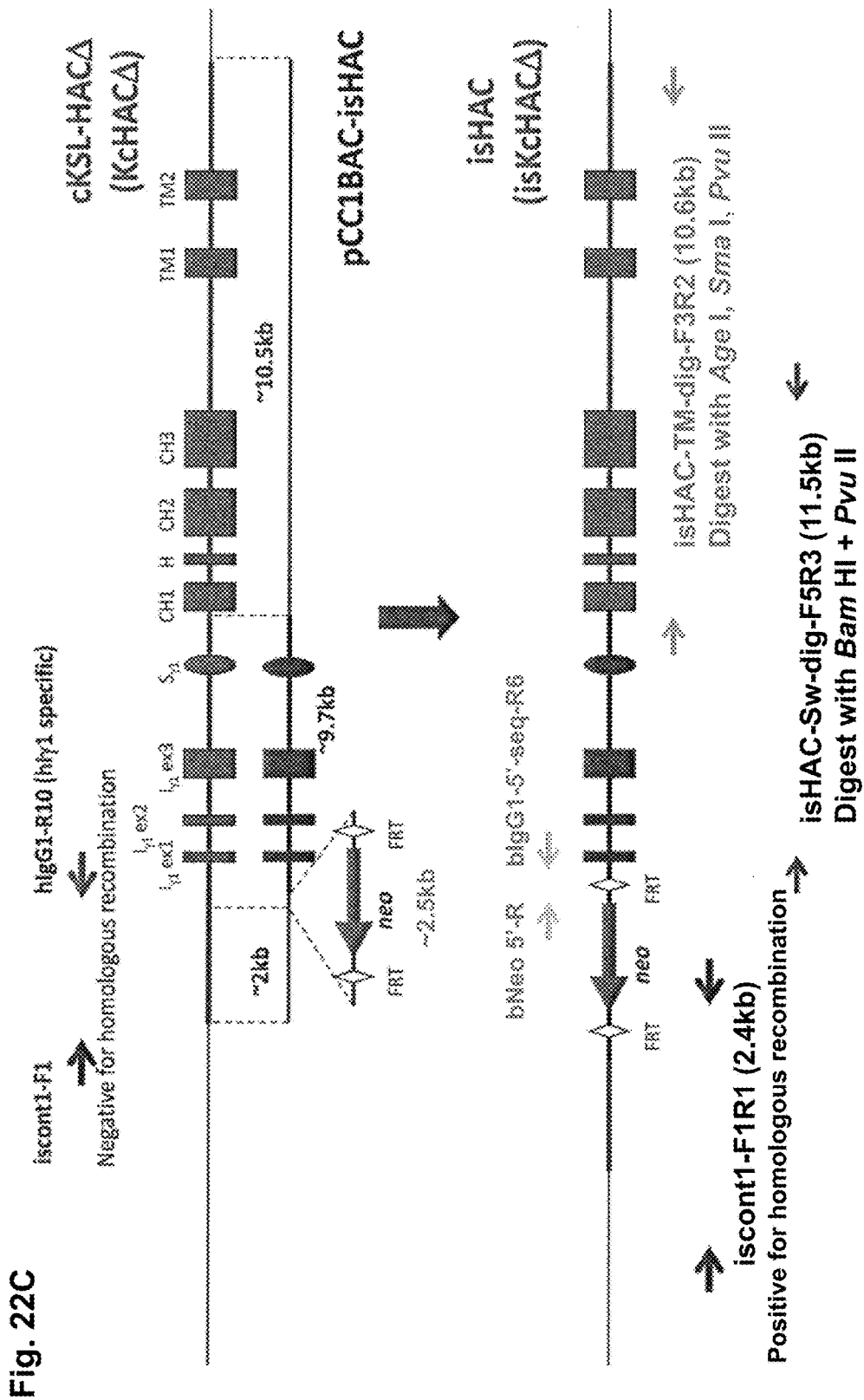
Figure 22D:
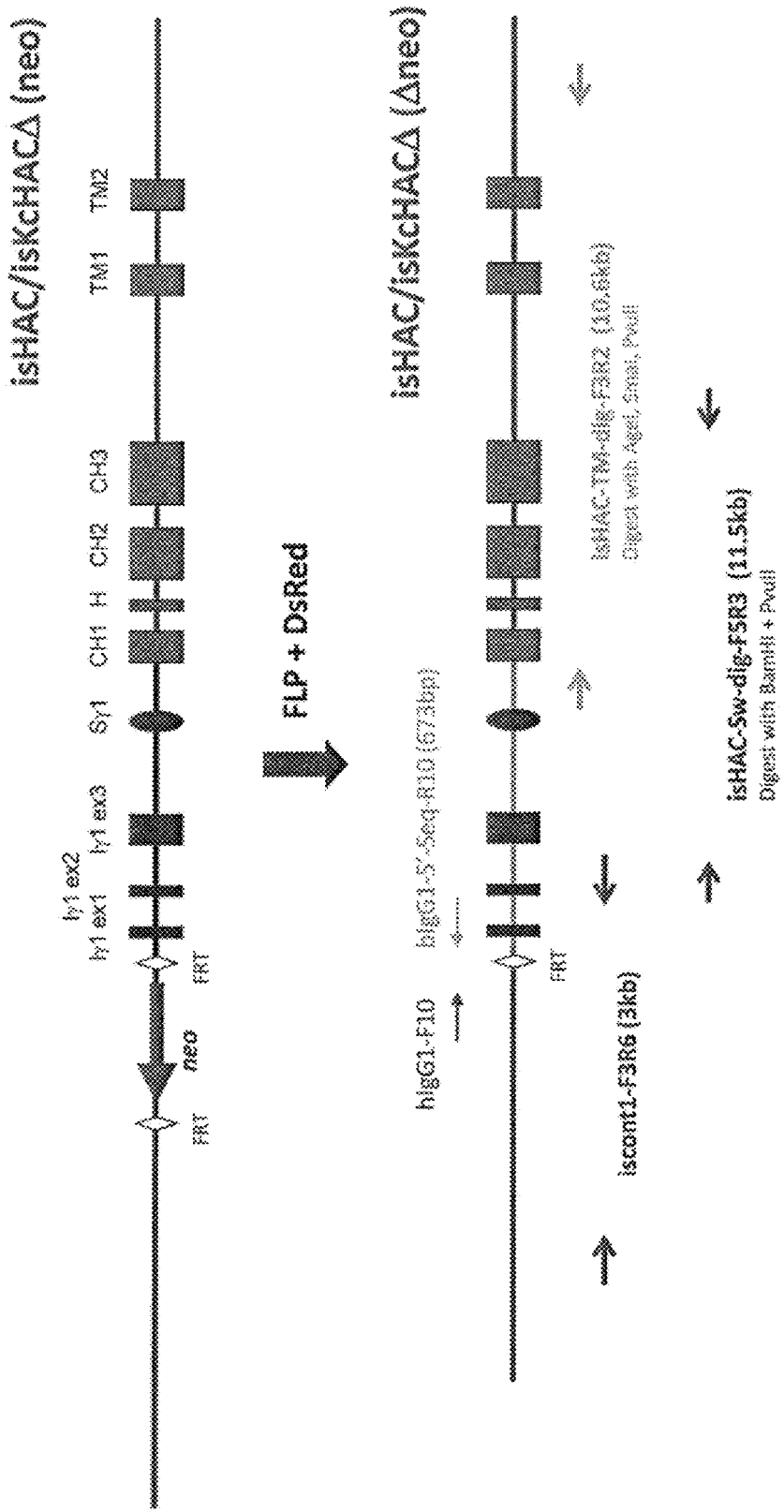
Figure 22E:
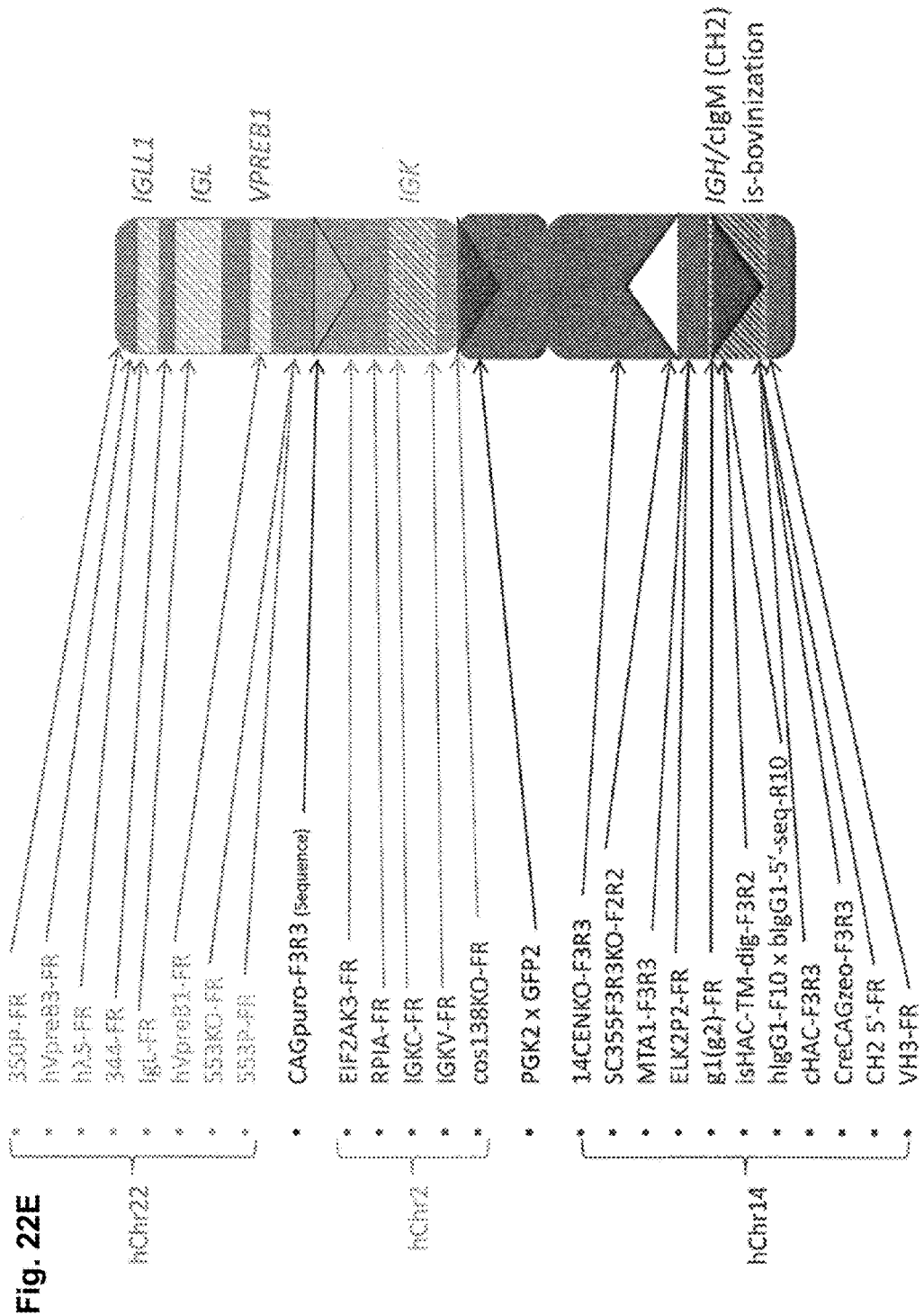
Figure 22F:
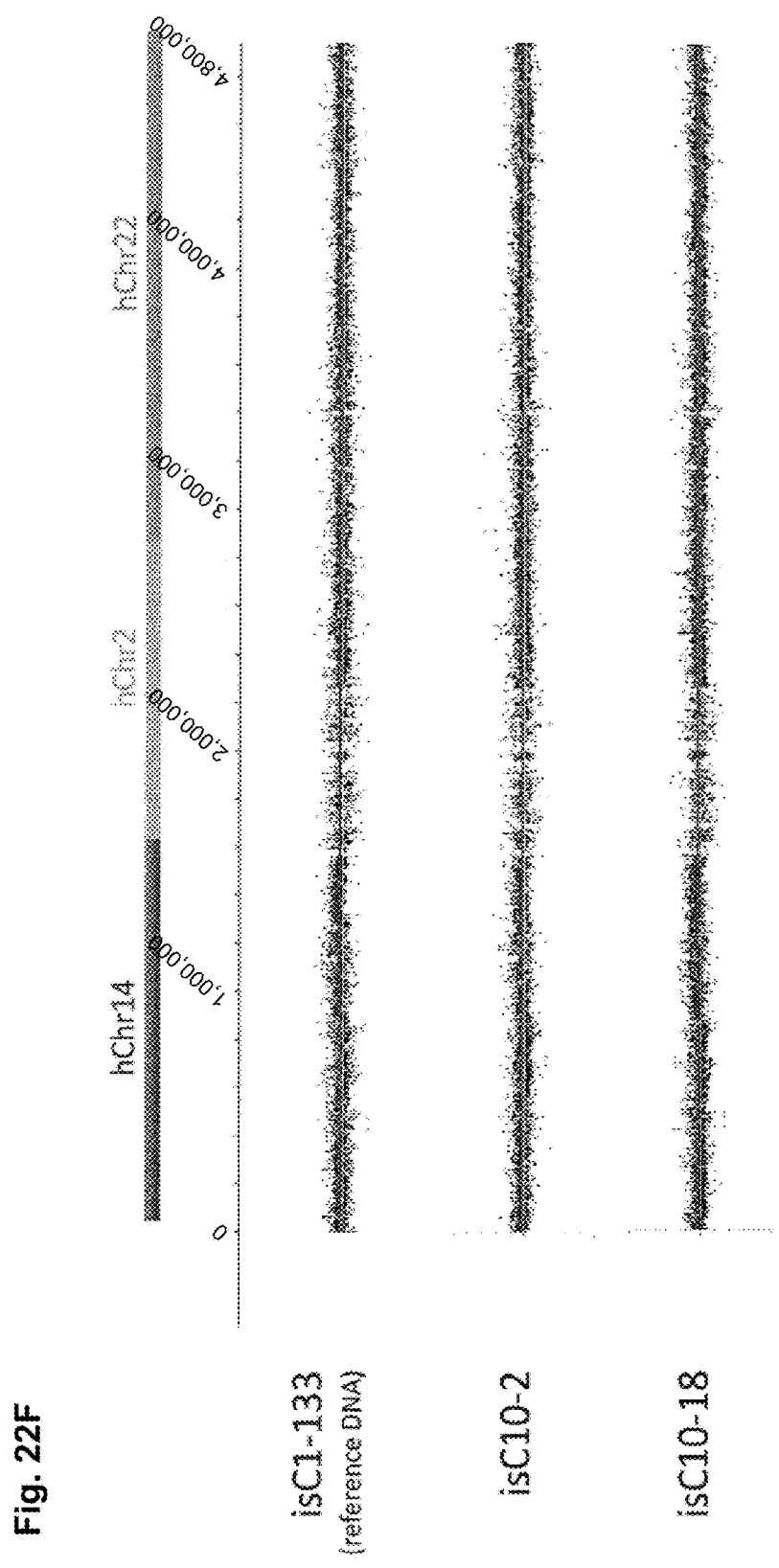
Figure 22G:
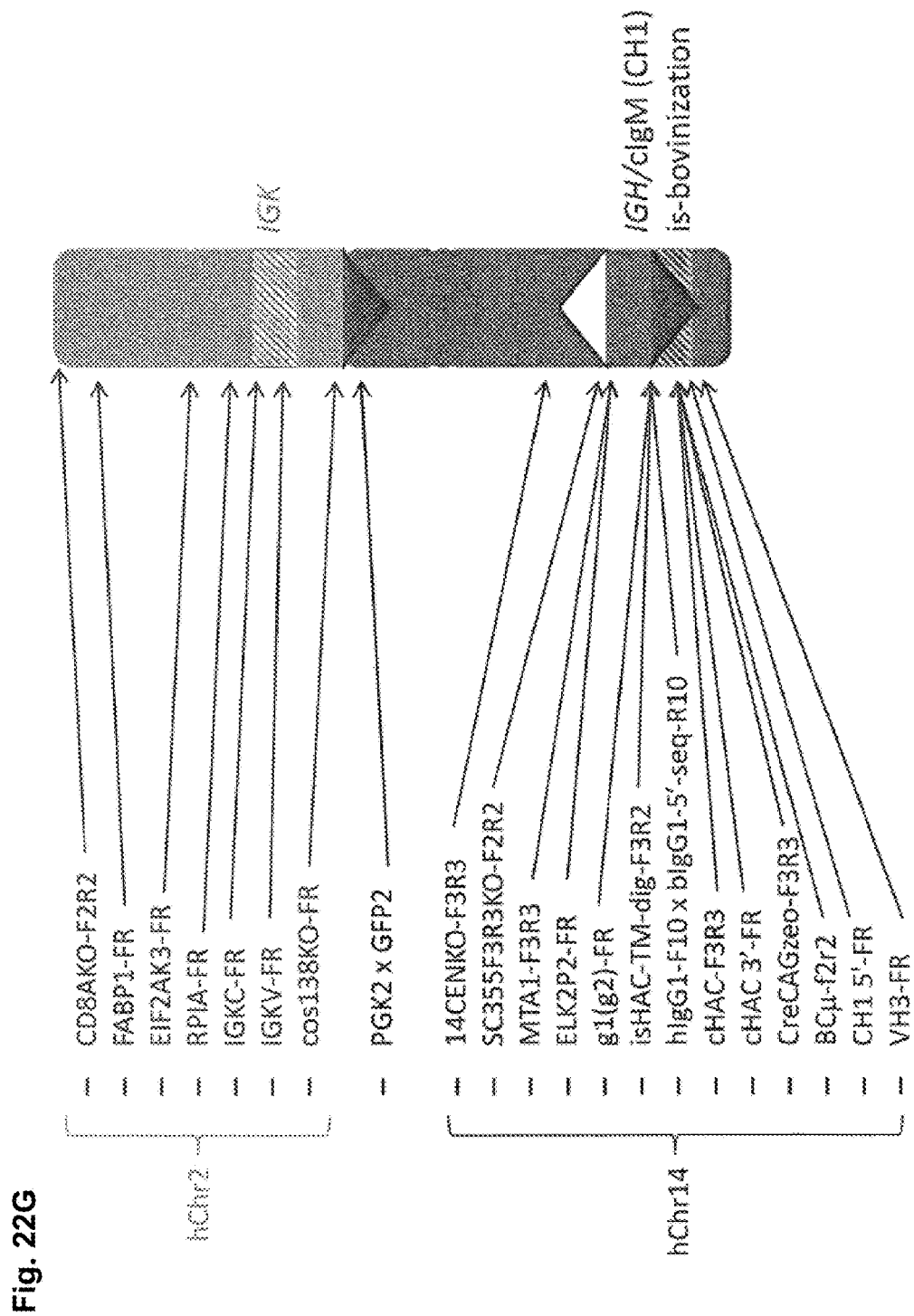
Figure 22H:
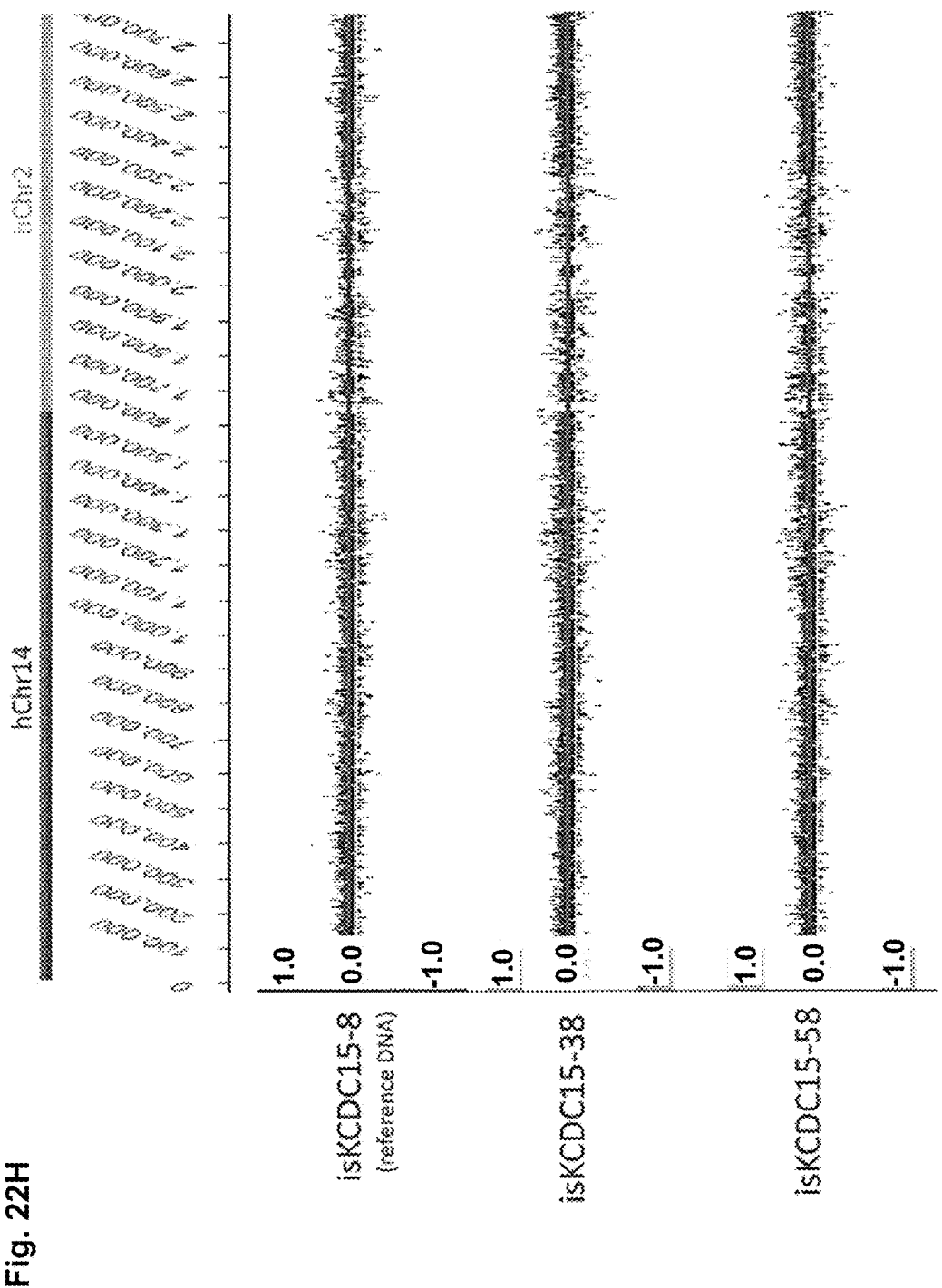

Outline of the isHAC (isKcHACΔ) construction is depicted in FIG. 22A. The targeting vector pCC1BAC-isHAC was constructed (FIG. 22B) and used to bovinize the $I_{\gamma 1}$-$S_{\gamma 1}$ region on the cKSL-HACΔ or KcHACΔ. Clone cKSLDD1, a chicken DT40 cell line retaining the cKSL-HACΔ obtained by MMCT from cKSLDH22 (2L), was electroporated with the targeting vector pCC1BAC-isHAC. Colonies were selected with G418 and their genomic DNA was subjected to PCR screening with primers, iscont1-F1R1, to identify the occurrence of the homologous recombination. Furthermore, additional diagnostic PCRs were also performed to check structural integrity (FIG. 22C). One clone is 1-11 was selected for the subsequent neo cassette deletion by introduction of the FLP-expression plasmid. The is 1-11 was co-transfected with the FLP-expressing plasmid and the DsRed-expressing plasmid. DsRed-positive cells were sorted and subjected to single colony isolation. G418-sensitive colonies where the neo cassette was deleted by the FRT-FLP recombination were tested for the genomic PCRs including iscont1-F3/R6 (see Table 1 below) (FIG. 22D). Finally, we selected isH11-S2 and isH9-3, and then they were transferred to CHO cells to establish master cell banks, isC1-133, isC10-2 and isC10-18, respectively, for which the extensive genomic PCR and CGH were performed to check structural integrity (FIG. 22E, 22F). The isKcHACΔ was constructed in DT40 cells, similarly to the isHAC, and two clones, isKCDH17, isKCDH30, were selected and then were transferred to CHO cells to establish master cell banks, isKCDC8 and isKCDC38, respectively, for which the extensive genomic PCR and CGH were performed to check structural integrity (FIG. 22G, 22H).

Construction of the istHAC Vector in Chicken DT40 Cells.

Figure 23A:
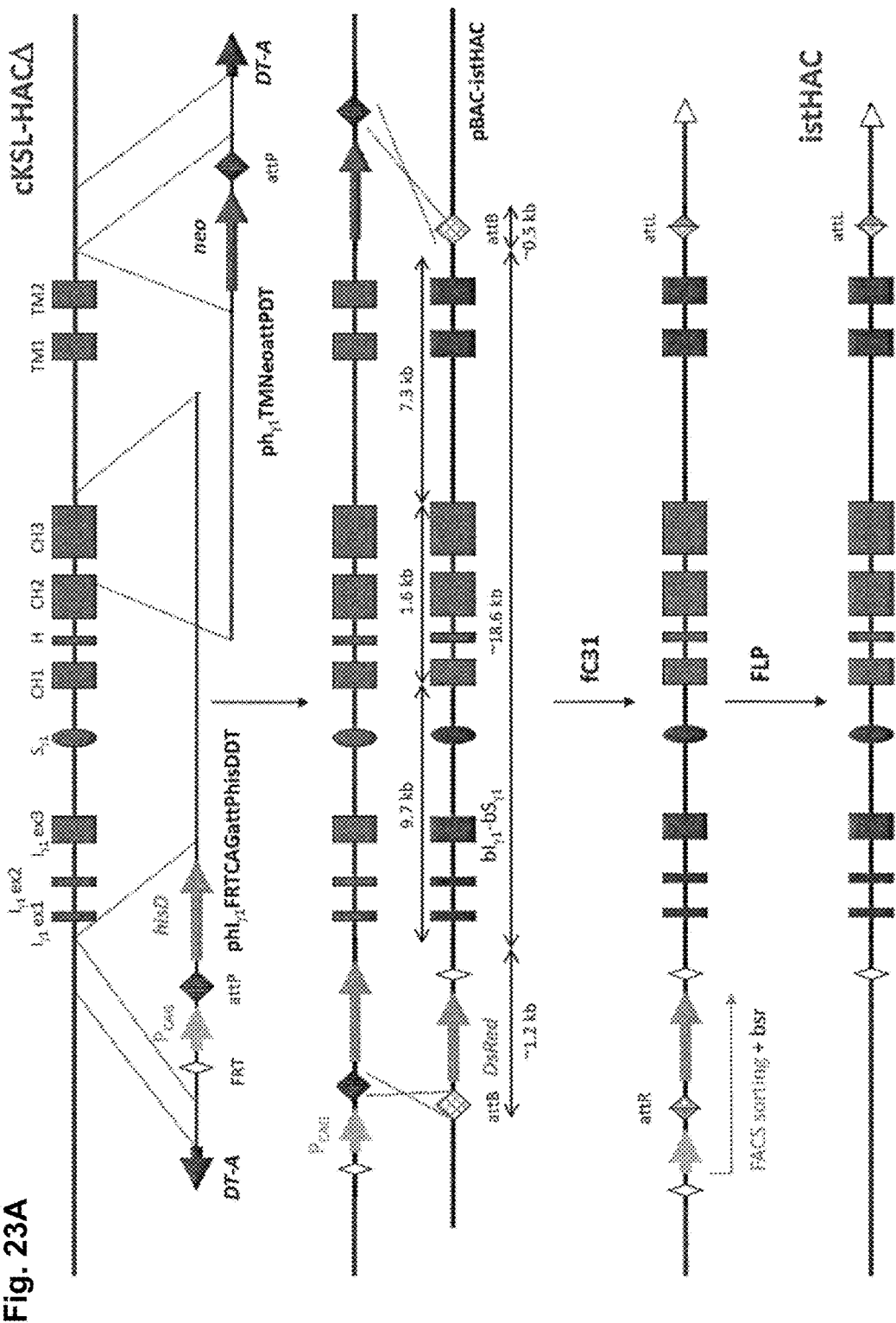
FIG. 23 shows construction of the istHAC vector. (A) A flow of the istHAC vector construction. The attP sequence is integrated at 5' side of the $hI_{\gamma 1}$ exon 1 and 3' side of the hIGHG1 TM2 by the targeting vectors $phI_{\gamma 1}$FRTCAGattPhisDDT and $ph_{\gamma 1}$TMNeoattPDT, respectively. Then, the replacement vector pBAC-istHAC is introduced with the φC31 recombinase to bring about the attP/attB recombination to replace the flanked region. The successful replacement causes the CAG promoter-driven DsRed gene to be reconstituted to provide red fluorescence for sorting. Finally, the DsRed cassette is removed by the FLP expression. (B) Integration of the attP sequence at 3' side of the hIGHG1 TM2. The targeting vector $ph_{\gamma 1}$TMNeoattPDT consists of 6.3 kb and 1.2 kb of genomic DNA as a long and short arm, the chicken β-actin promoter-driven neo gene, attP and DT-A gene. hg1TMneoattP-F1/R1 was used as a positive PCR specific to the homologous recombination along with the negative PCRs, hIgG1-F25/R23 and hg1TMneg-F3/R3, which were prohibited by the presence of KO cassette. hIgG1TM-dig-F1/R2, followed by Sma I or Age I digestion, was employed to check structural integrity of the corresponding region. (C) Integration of the attP sequence at 5' side of the hI$_{γ1}$ exon 1. The targeting vector phI$_{γ1}$FRTCAGattPhisDDT comprises 9.6 kb and 1.8 kb of genomic DNA as a long and short arm, the chicken β-actin promoter-driven hisD gene, attP, CAG promoter, FRT and DT-A gene. hg1FRTCAGattPhisD-F1/R1 was used as a positive PCR specific to the homologous recombination along with the negative PCR, iscont1-F1×hIgG1-R10, which was prohibited by the presence of KO cassette. (D) The big DNA replacement mediated by attP-attB recombination. The replacement vector pBACistHAC is made of 18.1 kb of the chimeric genomic DNA (the bI$_{γ1}$-bS$_{γ1}$+the hIGHG1 CH1 through CH3+bIGHG1 TM1-TM2), the promoter-less DsRed, FRT and two flanking attB sequences. The DNA replacement by the φC31 expression was confirmed by DsRed expression and genomic PCR, CAGDsRed-F2/R2 and bIgG1-3'-SeqF3×hIgG1-R15, to check generation of the attR and attL, respectively. (E) Genotyping after the FLP-FRT deletion of the DsRed cassette. (F) Extensive genomic PCR for genotyping of the istHAC vector. Location of each genomic PCR primer pair is depicted in relation to the istHAC vector structure. (G) CGH analysis among three different CHO clones containing the istHAC vector. DNA from istC1-6 was used as a reference. There was no apparent structural difference of the istHAC among the three cell lines.
Figure 23B:
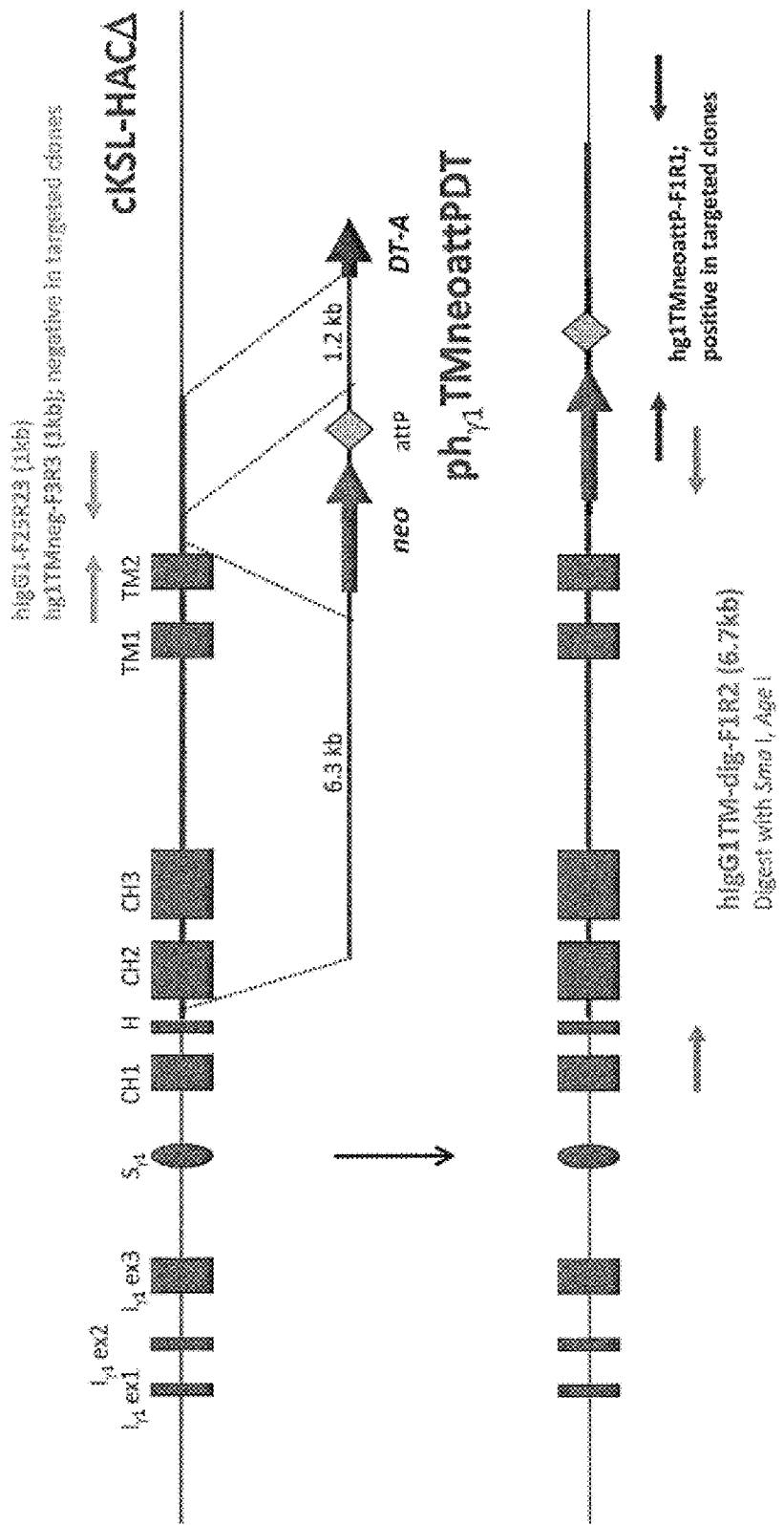
Figure 23C:
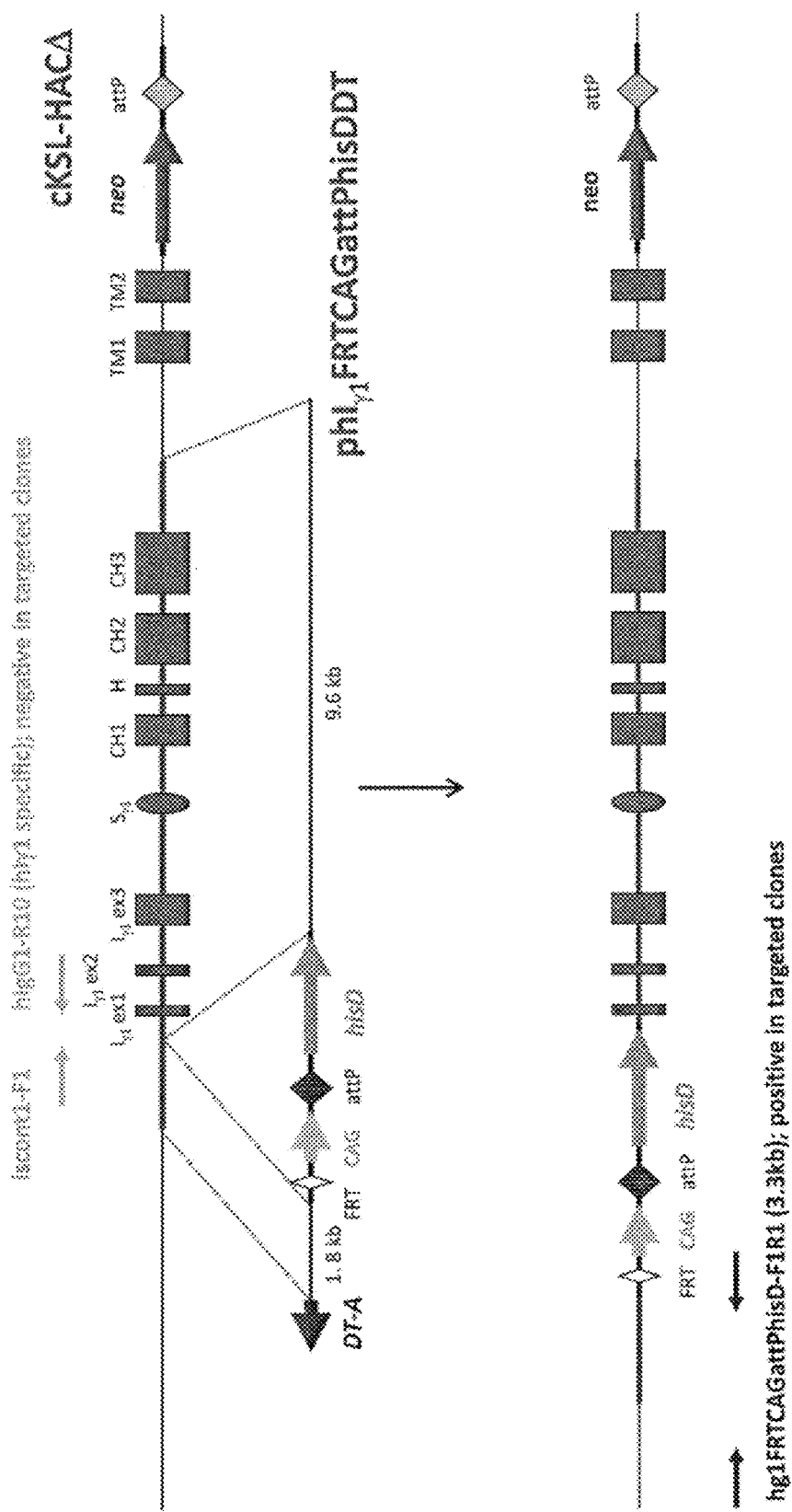
Figure 23D:
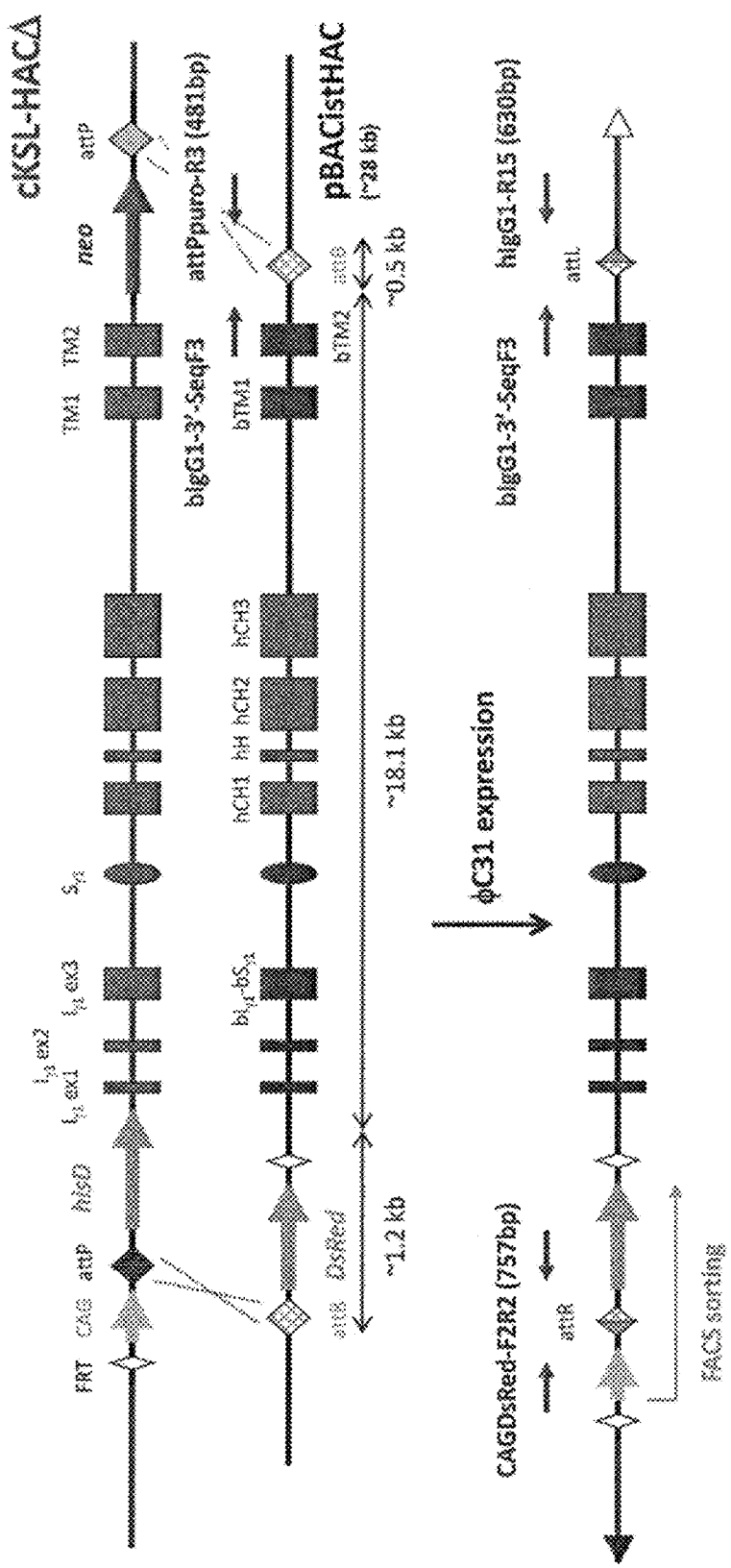

A scheme of construction of the istHAC is depicted in FIG. 23A. Clone cKSLDD1 was sequentially targeted with the two targeting vectors $ph_{\gamma 1}$TMNeoattPDT (FIG. 23B) and $phI_{\gamma 1}$FRTCAGattPhisDDT (FIG. 23C) to integrate the attP sequence at 3' side of the hIGHG1 TM2 domain and at 5' side of the human $I_{\gamma 1}$ region, respectively, which generated two clones ist1-5 and ist1-21. They were co-electroporated with the pBAC-istHAC and φC31-expression vectors together to bring about the big DNA replacement. As shown in FIG. 23D, the expected recombination between the attP and attB should result in reconstitution of the CAG promoter-DsRed gene expression, which can be detected by flow cytometry. DsRed-positive cells were accordingly sorted. This sorting process was repeated 2-3 times until purity of DsRed-positive cells reached >95%. And then, cells were subjected to single colony isolation and examined by three diagnostic genomic PCRs (see Table 1 below), CAGDsRed-F2/R2 (positive), bIgG1-3'-SeqF3×hIgG1-R15 (positive) and bIgG1-3'-SeqF3×attPPuro-R3 (negative). As a result, istH5-S16 from ist1-5 and istH21H-S10 from ist1-21 were selected.

Figure 23E:
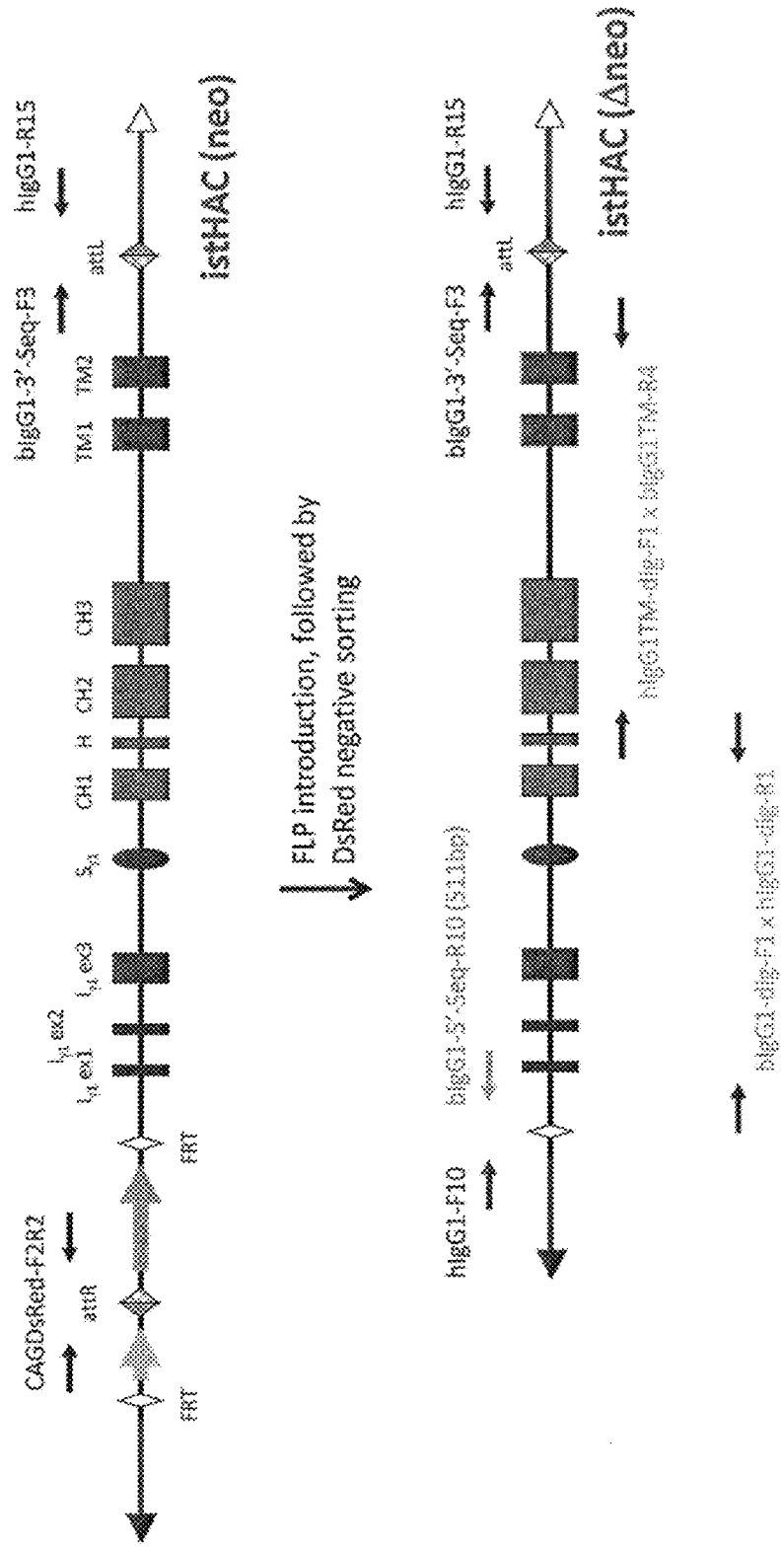
Figure 23F:
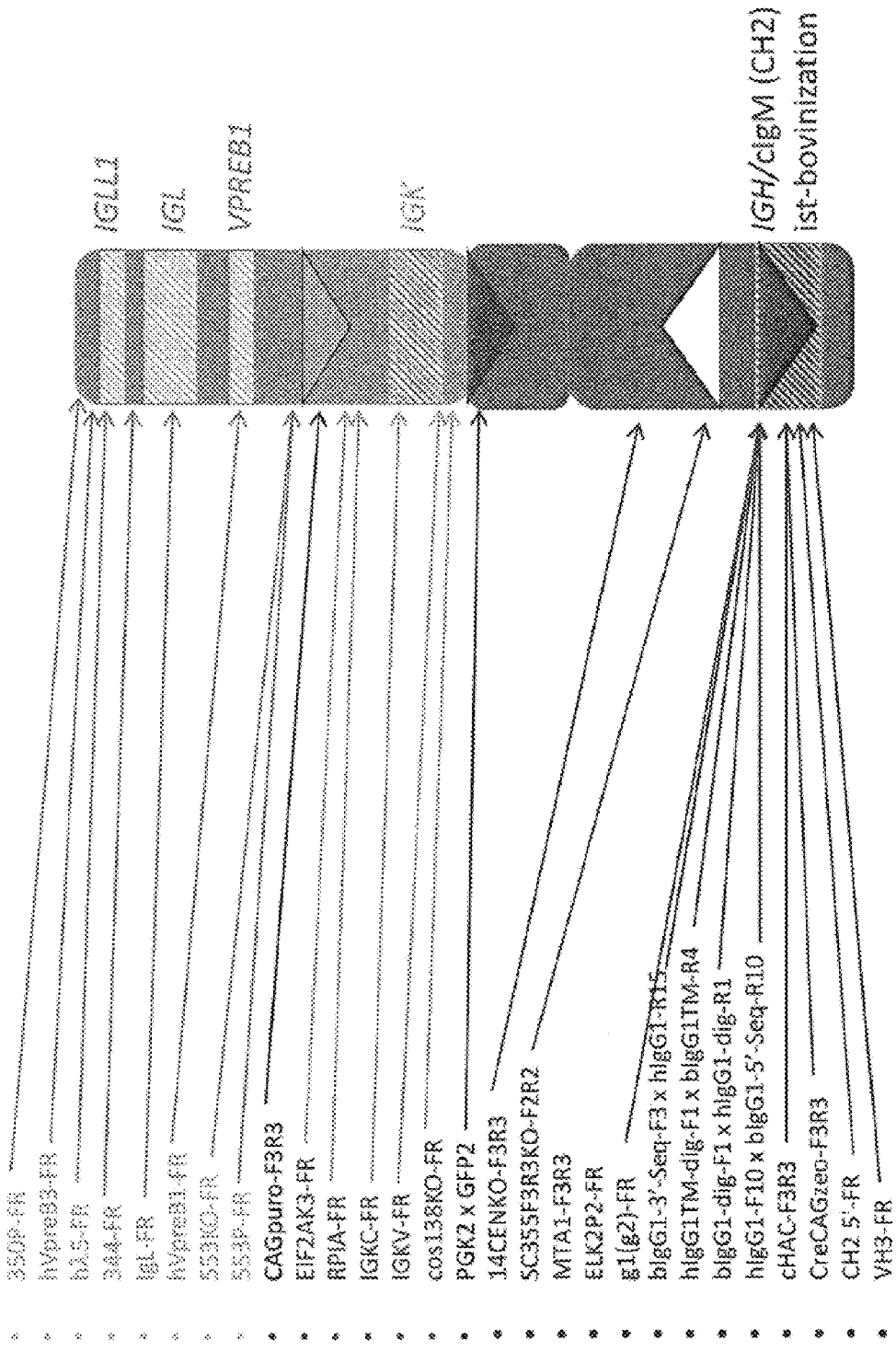
Figure 23G:
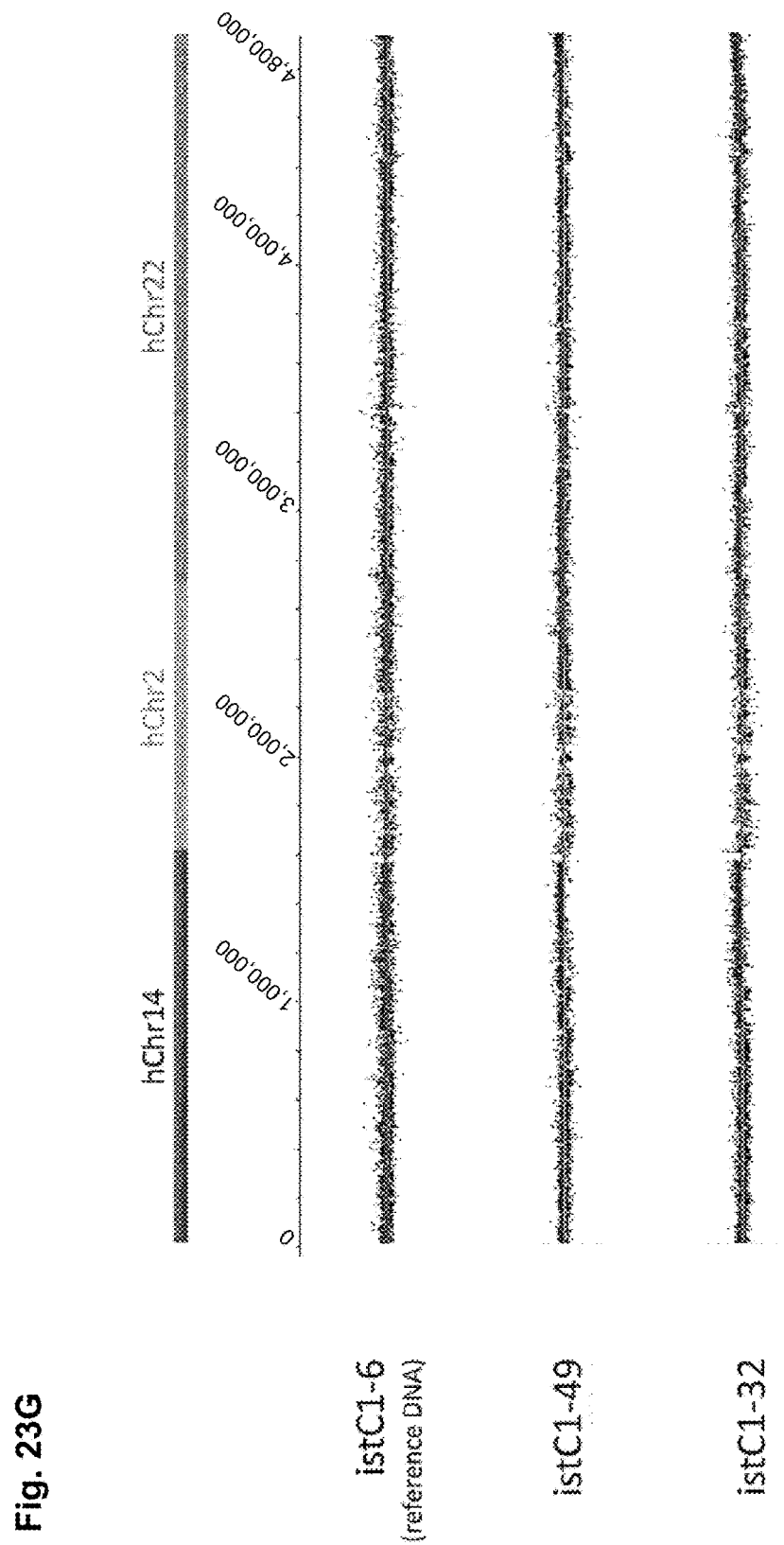

The two clones, istH5-S16 and istH21H-S10, were finally transfected with the FLP-expression vector. As shown in FIG. 23E, FLP expression should cause the removal of the CAG-DsRed gene expression, which can be detected by flow cytometry. DsRed-negative cells were accordingly sorted, resulting in >95% purity of DsRed-negative cells. And then, cells were subjected to single colony isolation and examined by three diagnostic genomic PCRs (see Table 1 below), CAGDsRed-F2/R2 (negative), bIgG1-3'-SeqF3×hIgG1-R15 (positive) and hIgG1-F10×bIgG1-5'-Seq-R10 (positive). Consequently, istHD16L from istH5-S16 and istHD10L from istH21H-S10 were selected and then were transferred to CHO cells to establish master cell banks, istC1-49 and istC1-6, respectively, for which the extensive genomic PCR and CGH were performed to check structural integrity (FIG. 23F, 23G).

Transfection of Chicken DT40 Cells for HAC Vector Construction.

HAC vector construction was carried out as previously described[5, 20, 21]. Briefly, DT40 cells containing each hChr fragment were electroporated (550 V, 25 μF) with ~25 μg of each targeting vector. Colonies were selected by each drug; G418 (2 mg/ml), puromycin (0.5 μg/ml), hygromycin B (1.5 mg/ml), blasticidin S (15 μg/ml), histidinol (0.5 mg/ml) or zeocin (1 mg/ml) for two weeks and their DNAs were subjected to PCR screening as indicated.

Transfection of Bovine Fibroblasts for the Bovine IGLJ-IGLC Gene Cluster Deletion and Microcell-Mediated Chromosome Transfer (MMCT).

Bovine fetal fibroblasts were cultured and transfected as previously described[5, 12, 21]. Briefly, fibroblasts were electroporated with 30 pg of each targeting vector at 550 V and 50 μF. After 48 hours, the cells were selected under an appropriate drug; zeocin (0.4 mg/ml) or puromycin (1 μg/ml) for two weeks and resistant colonies were picked up and transferred to replica plates; one was for genomic DNA extraction and the other was for embryonic cloning. MMCT was done with each HAC vector as described previously[5, 20, 21].

Genomic PCR and RT-PCR Analyses.

These analyses were implemented as previously described[5, 12, 20, 21]. All the PCR products were run on 0.8% agarose gels. Primer sequences are available in Table 1 below.

TABLE 1

Primer sequences.

| Name of oligo DNA | Sequence (5' → 3') | SEQ ID NO |
|---|---|---|
| kD-F9 | TCGAGGATCCGCCAGGGAGACAGATGCCAAGTACGGTTTAG | 1 |
| kD-R9 | TCGAGGATCCAGGATCTTTGGGGGACTGAATGGGGTGTGCT | 2 |
| Oligo DNA pair 1-F | AGCTTGGATCCATAACTTCGTATAGGATACTTTATACGAAGTTATA | 3 |
| Oligo DNA pair 1-R | AGCTTATAACTTCGTATAAAGTATCCTATACGAAGTTATGGATCCA | 4 |
| SL-F2 | TCGAGGATCCGGCCTCCCAAAGGATTATAGACGTGAGCCACTGT | 5 |
| SL-R2 | TCGAGGATCCAAAGAAGGGGCCCGCCTCTGCCTCTAAATCCTGAC | 6 |
| 553-F3 | TGTAGCTGACTTTAGCCACCCACAAGTAC | 7 |
| 553-R3 | CTTGCTGATTATACCTCATCTCCTTCCCTC | 8 |
| Oligo DNA pair 2-F | GTACAATAACTTCGTATAGCATACATTATACGAAGTTATAGATCTG | 9 |
| Oligo DNA pair 2-R | AATTCAGATCTATAACTTCGTATAATGTATGCTATACGAAGTTATT | 10 |
| Oligo DNA pair 3-F | GATCTATAACTTCGTATAGGATACTTTATACGAAGTTATG | 11 |
| Oligo DNA pair 3-R | CTAGCATAACTTCGTATAAAGTATCCTATACGAAGTTATA | 12 |
| SC355-F3 | GTACAATCTTGGATCACTACAACCTCTGCCTACCA | 13 |

TABLE 1-continued

Primer sequences.

| Name of oligo DNA | Sequence (5' → 3') | SEQ ID NO |
|---|---|---|
| SC355-R3 | TGCTGTGTCTAATCAGGTGTTGAACCCATCTACTA | 14 |
| Oligo DNA pair 4-F | GATCTATAACTTCGTATAGTATACATTATACGAAGTTATG | 15 |
| Oligo DNA pair 4-R | CTAGCATAACTTCGTATAATGTATACTATACGAAGTTATA | 16 |
| 14CEN-F | TCGAGGATCCTTCGCCACCCCAAAGATGATTACAGATTAC | 17 |
| 14CEN-R | TCGAGGATCCTACACTAGAAGCACAAACCCCACCATTACACAT | 18 |
| Oligo DNA pair 5-F | AGCTTGGATCCATAACTTCGTATAGTATACATTATACGAAGTTATA | 19 |
| Oligo DNA pair 5-R | AGCTTATAACTTCGTATAATGTATACTATACGAAGTTATGGATCCA | 20 |
| hCm-F | CAGTCCCCGGCAGATTCAGGTGTCC | 21 |
| hCm-R | GAAAGTGGCATTGGGGTGGCTCTCG | 22 |
| SeSp-F | GGACCAGGTGGAGACTGTGCAGTCCTCACCCATAACTTTCAGGGCCTACAGCATGCTG | 23 |
| SeSp-R | CAGCATGCTGTAGGCCCTGAAAGTTATGGGTGAGGACTGCACAGTCTCCACCTGGTCC | 24 |
| g1(g2)-F | ACCCCAAAGGCCAAACTCTCCACTC | 25 |
| g1(g2)-R | CACTTGTACTCCTTGCCATTCAGC | 26 |
| bIgG1-F | TCAACAGCACCTACCGCGTGGTCAG | 27 |
| bIgG1-R | GCGGGTCGTGCCGTACTTGTCCTC | 28 |
| pNsiI-bG1-hG1-BmgBI-F | ATGCATGAGGCTCTGCACAACCACTACACACAGAAGAGCCTCTCCCTGTCTCCGGGTAAATGAGCCTCACGTC | 29 |
| pNsiI-bG1-hG1-BmgBI-R | GACGTGAGGCTCATTTACCCGGAGACAGGGAGAGGCTCTTCTGTGTGTAGTGGTTGTGCAGAGCCTCATGCAT | 30 |
| bCLR-F | TCTGTCTGTCCAACAGTGGC | 31 |
| bCLR-R | ATTATGGGATGAGTCCAGGC | 32 |
| bCLL-F | TTAACTGCGGTACAAGGTGC | 33 |
| bCLL-R | CAACCTCTCCAGGATTCTGG | 34 |
| R-F2 | GACAAGCGTGCTAGGGTCATG | 35 |
| R-R1 | GGGATGGGACCTTGTTAGACTTG | 36 |
| CL1puro-F2 | CGCGCATGGCCGAGTTGAGCGGTTCC | 37 |
| CL1puro-R2 | CAGGCTCCCGGCTGGCGCTGGTAAGTCC | 38 |
| CL5CAG-F2 | GCCCGGCCCCAGATGGAACCCGAGACAGG | 39 |
| CL5CAG-R2 | ATGCCAGGCGGGCCATTTACCGTCATTGA | 40 |
| CAGpuro-F3 | GCGGCGCCGGCAGGAAGGAAATG | 41 |
| CAGpuro-R3 | CGAGGCGCACCGTGGGCTTGTA | 42 |
| L001-F1 | ACCCTCGGTCACCCTGTT | 43 |
| L002-R2 | TGAGAAGGTCTTTATTCAGGAG | 44 |
| BCm-f2 | TCTCTGGTGACGGCAATAG | 45 |
| BCm-r2 | CTTCGTGAGGAAGATGTCGG | 46 |
| BCmKO-F14 | CCACAAAGGAAAAAGCTGCACTGCTATAC | 47 |

TABLE 1-continued

Primer sequences.

| Name of oligo DNA | Sequence (5' → 3') | SEQ ID NO |
|---|---|---|
| BCmKO-R14 | TGTGGGATCAGGAGGTCAGATAGACATC | 48 |
| bIgL-Ld-F1 | GTGGGGCCACAGAAGGCAGGAC | 49 |
| bIgL-C-R | ACCCGGGTAGAAGTCGCTGATGAGA | 50 |
| L003-F2 | CCCTCGGTCACCCTGTTCCC | 51 |
| L004-R2 | CTGGTGTGAGGCGACCTGGG | 52 |
| bIgk-F | CAGCTCCTGGGGCTCCTCCTG | 53 |
| bIgk-R | TGCAATAGGGGTTGATCTGTGGACA | 54 |
| 335N-F | GGGCAACATAGCAAGACACCATTC | 55 |
| 335N-R | TCCTCTCACCTCAGCCTCCATAGTA | 56 |
| SC335KO-F2 | ACGGCG TGAGGACCAAGGAGCGAAACC | 57 |
| SC335KO-R2 | TGAGCGACGAATTAAAAC AGGCGATGAC | 58 |
| 14CEN(N)-F2 | AACAGTTGAATTTATGGGGAGTC | 59 |
| 14CEN(N)-R2 | TCAGGCTTTAAACACAGTATCACAG | 60 |
| 14CENKO-F3 | ACTGAAATATTTTAAATGTTTGCCCTTCCCACTCC | 61 |
| 14CENKO-R3 | AGACCTCCGCGCCCCGCAACCTCCCCTTCTAC | 62 |
| cHAC 3'-F | CAAGCATGGAGCCCGCAGTAATAG | 63 |
| cHAC 3'-R | AAGGTGACCCGGGCAGTTGTAGG | 64 |
| CH1 5'-F | CCGACAGGCAGGGCACGAGGAG | 65 |
| CH1 5'-R | TGCGAGGCGGGACAAAGACAC | 66 |
| cHAC-F3 | TGCAGGTGAAGTGACGGCCAGCCAAGAACA | 67 |
| cHAC-R3 | TGGCAGCAGGGTGACAGGGAAGGCAGGAAAAG | 68 |
| CH2 5'-F | CAGCACCCCAACGGCAACAAAGAAA | 69 |
| CH2 5'-R | CCCCAGGGCTGCACTCACCAACAT | 70 |
| CD8AKO-F2 | AAGGCCCCCAAGCTGATTTCCGTGAGACTAAG | 71 |
| CD8AKO-R2 | GCCTGGACGAGCTGTACGCCGAGTGGT | 72 |
| 553-F4 | GCTAAGGCACTTCGGTTCTCTTTGTGTTC | 73 |
| 553-R4 | GGTTGTCTTTAAAAGCAGGGATAAGGATG | 74 |
| 553KO-F | GTCAGCCAGGCGGGCCATTTACCGTAAGTTATGTA | 75 |
| 553KO-R | AGGGCTGGGTTAGATGGCACCAAATGAAAGGAGAA | 76 |
| STOPpuro-F2 | ACTCCACACAGGCATAGAGTGTC | 77 |
| STOPpuro-R | GTGGGCTTGTACTCGGTCAT | 78 |
| GFP2 | TGAAGGTAGTGACCAGTGTTGG | 79 |
| 350P-F | ACCAGCGCGTCATCATCAAG | 80 |
| 350P-R | ATCGCCAGCCTCACCATTTC | 81 |
| hVpreB3-F | CACTGCCTGCCCGCTGCTGGTA | 82 |
| hVpreB3-R | GGGCGGGGAAGTGGGGGAGAG | 83 |
| h15-F | AGCCCCAAGAACCCAGCCGATGTGA | 84 |

TABLE 1-continued

Primer sequences.

| Name of oligo DNA | Sequence (5' → 3') | SEQ ID NO |
|---|---|---|
| h15-R | GGCAGAGGGAGTGTGGGTGTTGTG | 85 |
| 344-F | ATCATCTGCTCGCTCTCTCC | 86 |
| 344-R | CACATCTGTAGTGGCTGTGG | 87 |
| IgL-F | GGAGACCACCAAACCCTCCAAA | 88 |
| IgL-R | GAGAGTTGCAGAAGGGGTGACT | 89 |
| hVpreB1-F | TGTCCTGGGCTCCTGTCCTGCTCAT | 90 |
| hVpreB1-R | GGCGGCGGCTCCACCCTCTT | 91 |
| 553P-F | AGATCTCTTGAGCCCAGCAGTTTGA | 92 |
| 553P-R | TGAAGTTAGCCGGGGATACAGACG | 93 |
| FABP1-F | TATCAAGGGGGTGTCGGAAATCGTG | 94 |
| FABP1-R | ACTGGGCCTGGGAGAACCTGAGACT | 95 |
| EIF2AK3-F | AGGTGCTGCTGGGTGGTCAAGT | 96 |
| EIF2AK3-R | GCTCCTGCAAATGTCTCCTGTCA | 97 |
| RPIA-F | CTTACCCAGGCTCCAGGCTCTATT | 98 |
| RPIA-R | CTCTACCTCCCTACCCCATCATCAC | 99 |
| IGKC-F | TGGAAGGTGGATAACGCCCT | 100 |
| IGKC-R | TCATTCTCCTCCAACATTAGCA | 101 |
| IGKV-F | AGTCAGGGCATTAGCAGTGC | 102 |
| IGKV-R | GCTGCTGATGGTGAGAGTGA | 103 |
| cos138KO-F | TCTTTCTCTCACCTAATTGTCCTGGC | 104 |
| cos138KO-R | AGGACTGGCACTCTTGTCGATACC | 105 |
| SC355F3R3KO-F2 | GCCATTGTCGAGCAGGTAGT | 106 |
| SC355F3R3KO-R2 | TCCCTCATCAGCCATCCTAA | 107 |
| MTA1-F3 | AGCACTTTACGCATCCCAGCATGT | 108 |
| MTA1-R3 | CCAAGAGAGTAGTCGTGCCCCTCA | 109 |
| ELK2P2-F | CCCACTTTACCGTGCTCATT | 110 |
| ELK2P2-R | ATGAAGGTCCGTGACTTTGG | 111 |
| CreCAGzeo-F3 | GCCCTCACCTTGCAGACCACCTCCATCAT | 112 |
| CreCAGzeo-R3 | CCTCTCCTGCTCAGTCCCCTTCCTTCCATC | 113 |
| VH3-F | AGTGAGATAAGCAGTGGATG | 114 |
| VH3-R | CTTGTGCTACTCCCATCACT | 115 |
| iscont1-F1 | TTGCAAAGGGGCCTGGTGGAATA | 116 |
| hIgG1-R10 | GCAGGGAACGGGATGAGGATAGAGG | 117 |
| bNeo 5'-R | GGGAGAGTGAAGCAGAACGT | 118 |
| bIgG1-5'-seq-R6 | TTGCTGACAAAGGTCCGTCTA | 119 |
| iscont1-R1 | GCTTGGCGGCGAATGGGCTGAC | 120 |

TABLE 1-continued

Primer sequences.

| Name of oligo DNA | Sequence (5' → 3') | SEQ ID NO |
|---|---|---|
| isHAC-TM-dig-F3 | AGAGAAGATGGGGCCCAAGAGCGCAGCTGTCCAGA | 121 |
| isHAC-TM-dig-R2 | GTTCACGCTGTTCTCCTGCCGCACTCCCCGTATGG | 122 |
| isHAC-Sw-dig-F5 | TTTCTCAGGAGGCAGTTAATGTGGTCTGGTATTCC | 123 |
| isHAC-Sw-dig-R3 | GCAGGGCTGCCAGGGGTTAGTGCCGTGGGGGTAGAT | 124 |
| hIgG1-F10 | CCAGGGCCACAGTTAACGGATACGA | 125 |
| bIgG1-5'-Seq-R10 | GGGTCACTTTCTCGGTCCTGGTCT | 126 |
| iscont1-F3 | GGCCCCTCCATTTGTACTTTCTAT | 127 |
| iscont1-R6 | GGGGCAGGAGGAGAAGGGGACGAC | 128 |
| hIgG1-F25 | CCTGGTCCTCACATGGCCATACCTC | 129 |
| hIgG1-R23 | GGTCCGGGCTCTGGGGATTTCAT | 130 |
| hg1TMneg-F3 | CCTCCCTGGTCCTCACATGGCCATA | 131 |
| hg1TMneg-R3 | CATGGCACGGCAGGGTCCGGGC | 132 |
| hIgG1TM-dig-F1 | CTCTGCAGAGCCCAAATCTTGTGACAAAACTCA | 133 |
| hIgG1TM-dig-R2 | CCCCCGGGCTGCAGGAATTCGATATCAAGCTTAGGAC | 134 |
| hg1TMneoattP-F1 | AAGCGGGAAGGGACTGGCTGCTATTGGGCGAAGTG | 135 |
| hg1TMneoattP-R1 | GGAGCCCGGCACCGTCCTGGGTTTCCTTTCCTTAT | 136 |
| hg1FRTCAGattP hisD-F1 | ATGGACGGGATGACCTGGGAGATCGTGGCAAGTTT | 137 |
| hg1FRTCAGattP hisD-R1 | GGGGGCCCGGTACCGAAGTTCCTATTCCGAAGTTC | 138 |
| bIgG1-3'-SeqF3 | CACTGGTCAGTGAGAAGGAC | 139 |
| attPpuro-R3 | CACCCCAGGCTTTACACTTTATGCTTCC | 140 |
| hIgG1-R15 | GCTCCCCCTACCACCTCCCTTTAC | 141 |
| CAGDsRed-F2 | GGCGGGGTTCGGCTTCTGGCGTGTGAC | 142 |
| CAGDsRed-R2 | CTTGGCCATGTAGATTGACTTGAACTCC | 143 |
| bIgG1-dig-F1 | GGCGCCGCTTAAACCACCCCACCAACCCACAA | 144 |
| hIgG1-dig-R1 | ACCTGGGCACGGTGGGCATGTGTGAGTTTTGTC | 145 |
| bIgG1TM-R4 | AGACAGCAAAGAGAAAGAACAGGCCCCCACATTAG | 146 |

CGH Analysis.

Figure 24:
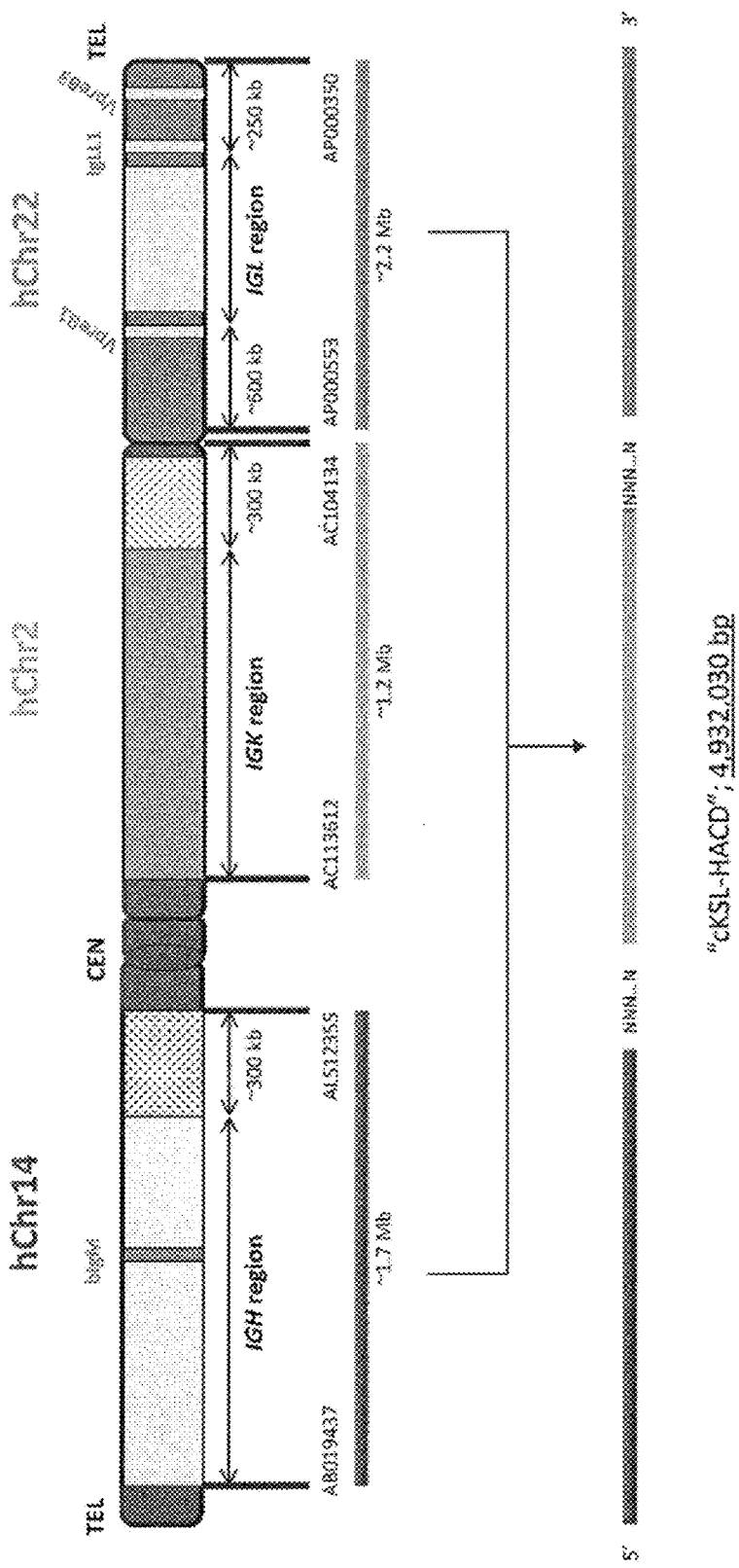
FIG. 24 shows probe design for CGH, based on the deduced cKSL-HACΔ vector sequence. For the hChr14, hChr2 and hChr22 fragment sequence, the AB019437 to AL512355, the AC113612 to AC104134, and the AP000553 to AP000350, respectively, were assembled and linked with artificial "NNN . . . N" to create the 4,932,030 by DNA sequence as the deduced cKSL-HACΔ vector sequence.
Figure 25:
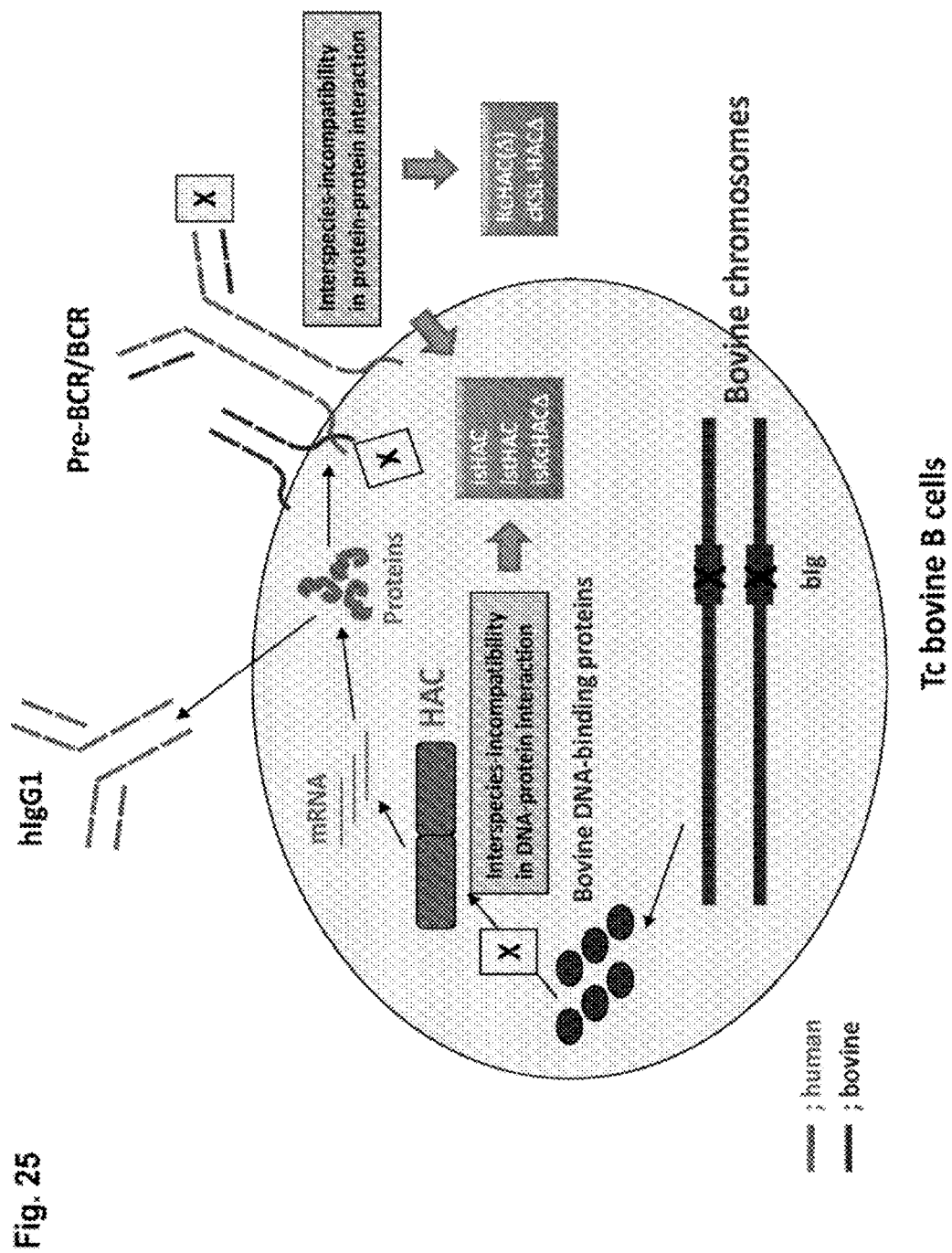
FIG. 25 shows model of interspecies-incompatibilities at two levels in Tc bovine B cells. One is at protein-protein interaction, such as pre-BCR/BCR structure (e.g. pairing between human IgM and bovine surrogate/orthodox light chain, interaction between human IgM/IgG1 and bovine Ig-α/β). Another one is at DNA-protein interaction, such as between human Iγ1-Sγ1 DNA sequence and bovine cytokine/activator-induced bovine DNA binding proteins. The former is addressed by KcHAC(Δ) and cKSL-HACΔ (also by isHAC, istHAC and isKcHACΔ). The latter is addressed by isHAC, istHAC and isKcHACΔ.
Figure 26A:
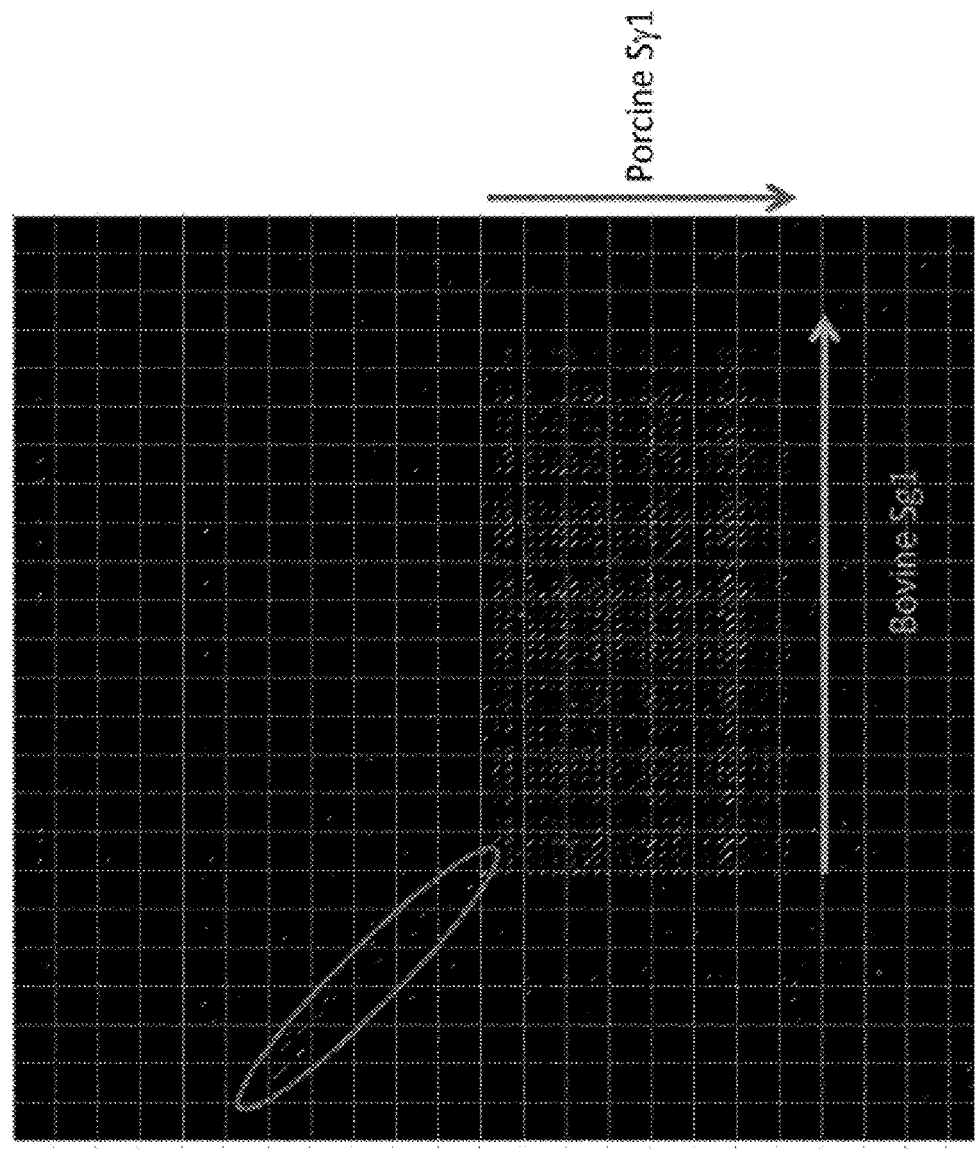
FIG. 26 shows an analysis of Iγ1-Sγ1 region of bovine (SEQ ID NO: 182), horse (SEQ ID NO: 185) and porcine (SEQ ID NO: 186). (A) Comparison between bovine and porcine Iγ1-Sγ1 indicates some homology between bovine and porcine Iγ1 regions (oval), with a potential ECS circled in (B). (C) Comparison between bovine and horse Iγ1-Sγ1 indicates some homology between bovine and horse Iγ1 regions (oval). (D) Comparison between horse and porcine Iγ1-Sγ1 indicates some homology between horse and porcine Iγ1 regions (oval).
Figure 26B:
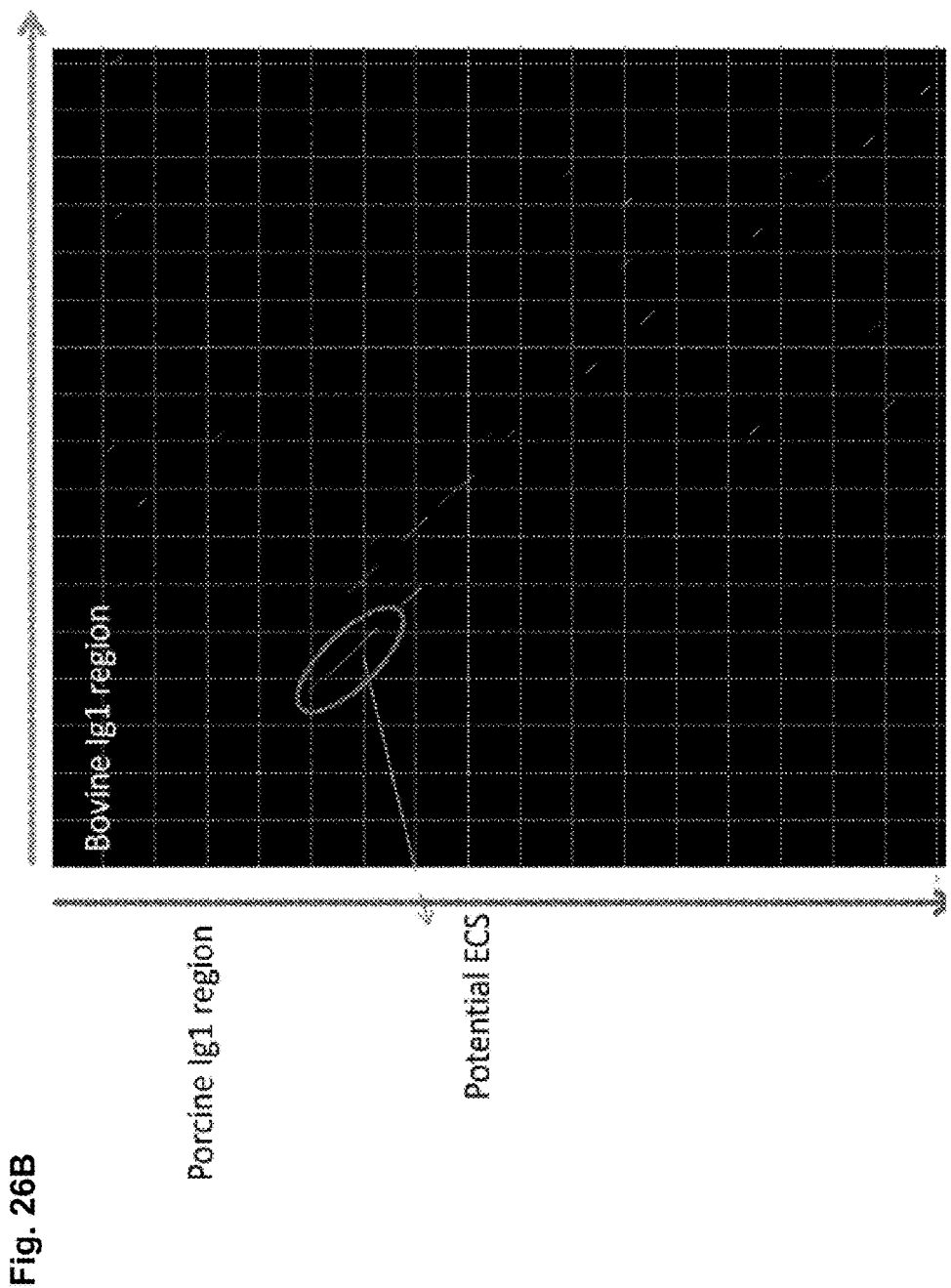
Figure 26C:
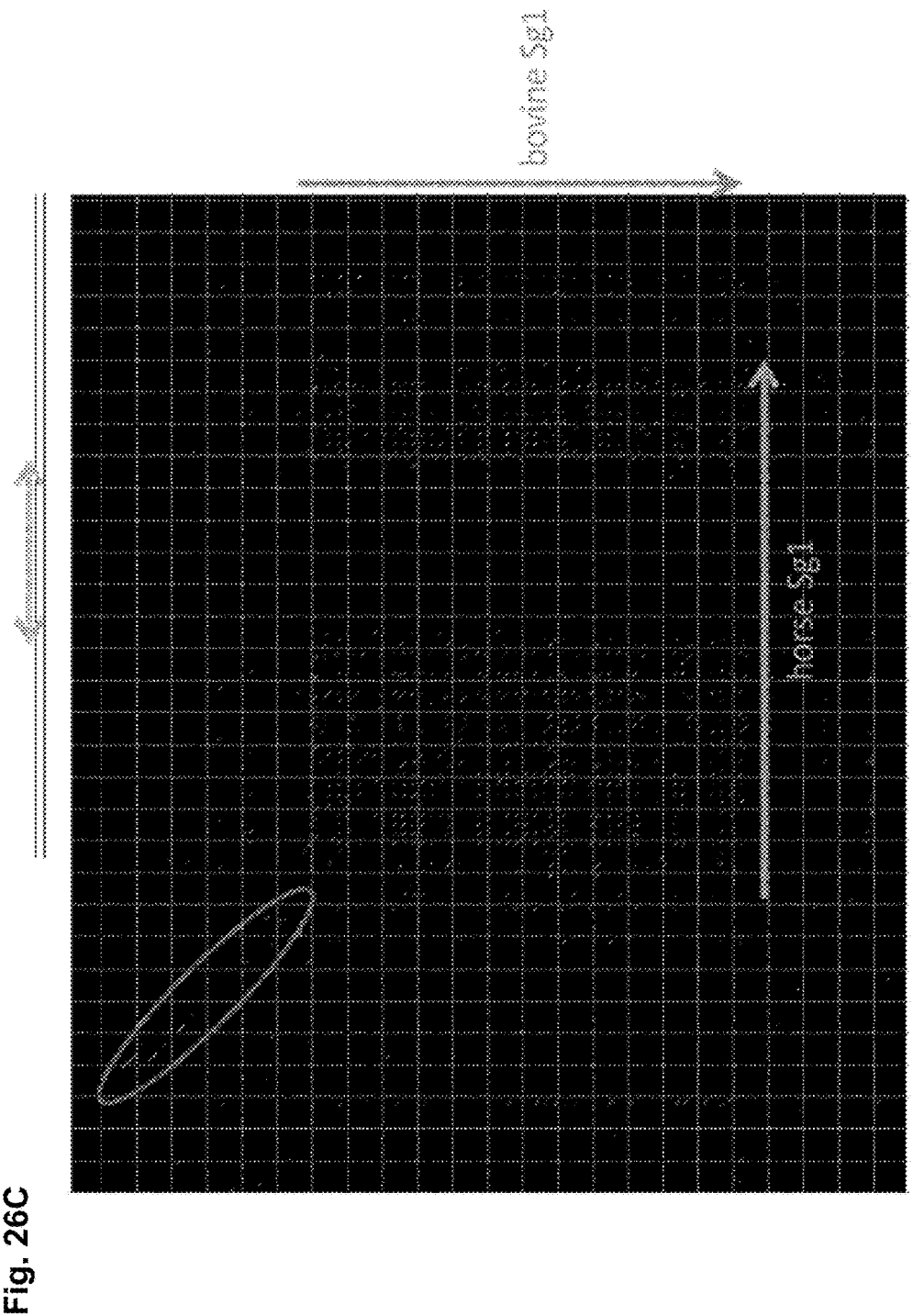
Figure 26D:
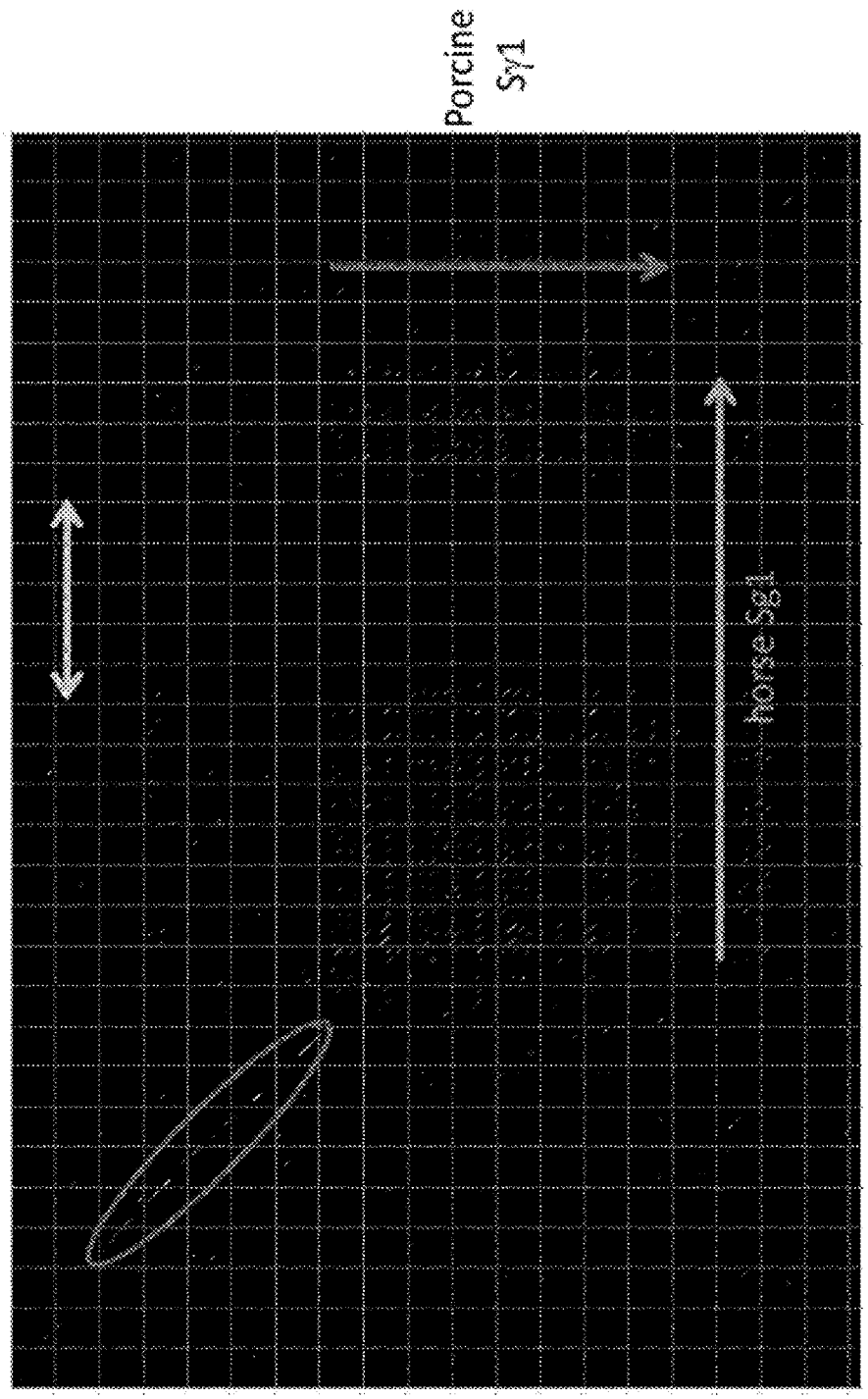
Figure 28:
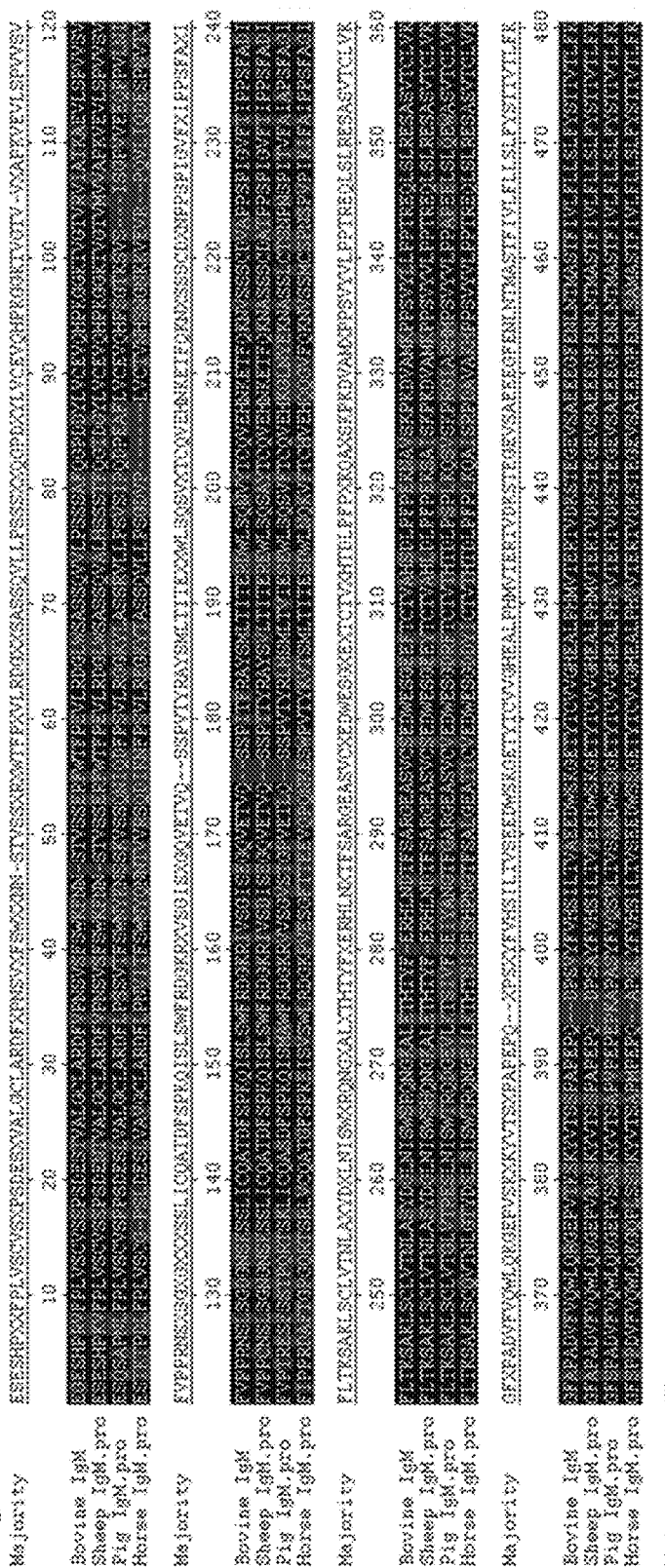
FIG. 28 shows a multiple sequence alignment of IgM in ungulates. Sheep (SEQ ID NO: 174), bovine (SEQ ID NO: 152), pig (SEQ ID NO: 175) and horse (SEQ ID NO: 176).
Figure 29A:
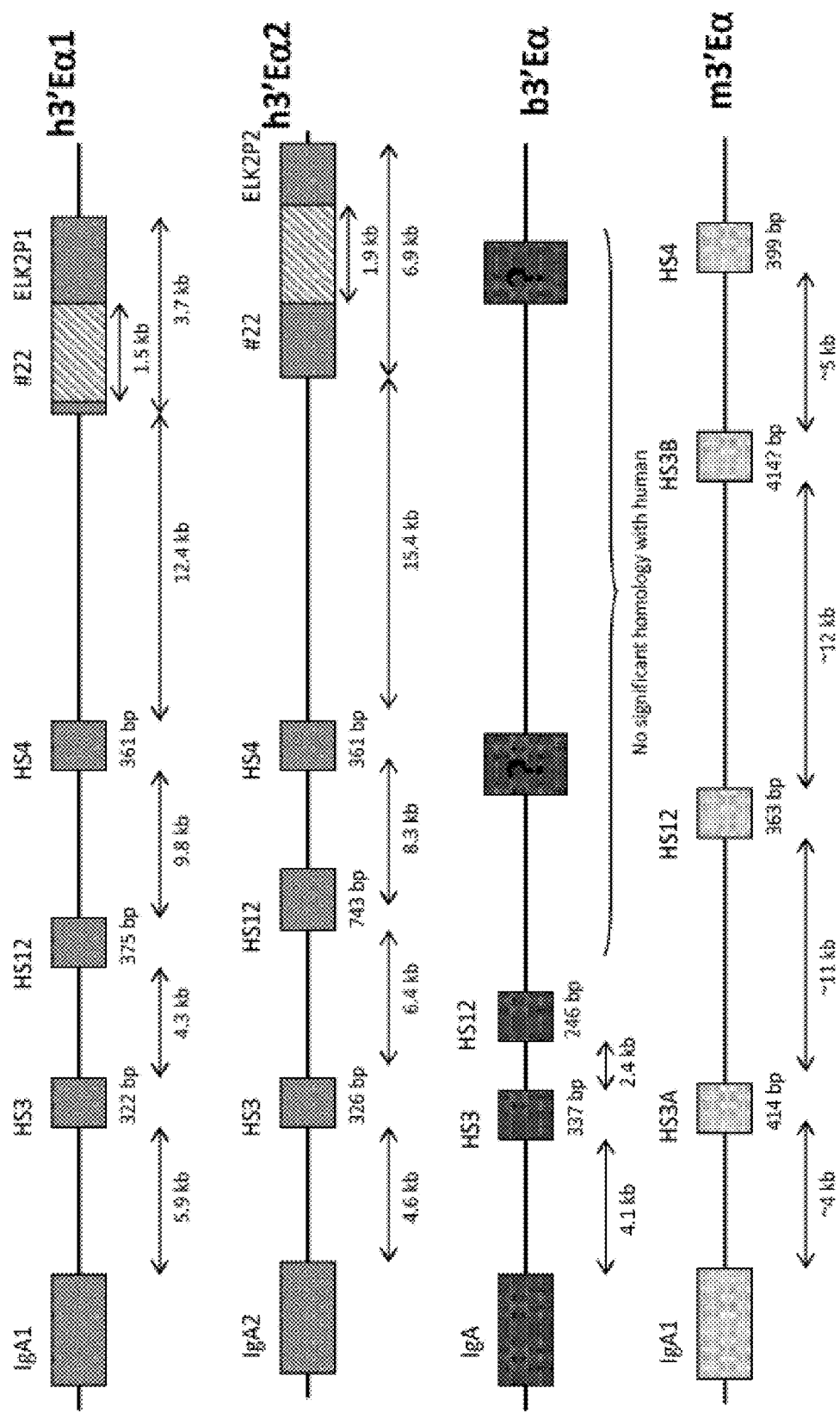
FIG. 29 shows the bovinization of HAC with bovine Ig heavy chain 3' enhancer. (A) Conservation of structure among human, bovine and mouse 3' E-alpha enhancers. (B) Indicates region containing bovine 3'E that was used for bovinization of 3'Ealpha1 on HAC. (C) Bovine genomic fragment used for bovinization of 3'alpha1 on HAC. (D) Demonstrates the construction of mu-HAC. (E) Structural integrity of HAC was confirmed after attP/attB recombination.
Figure 29B:
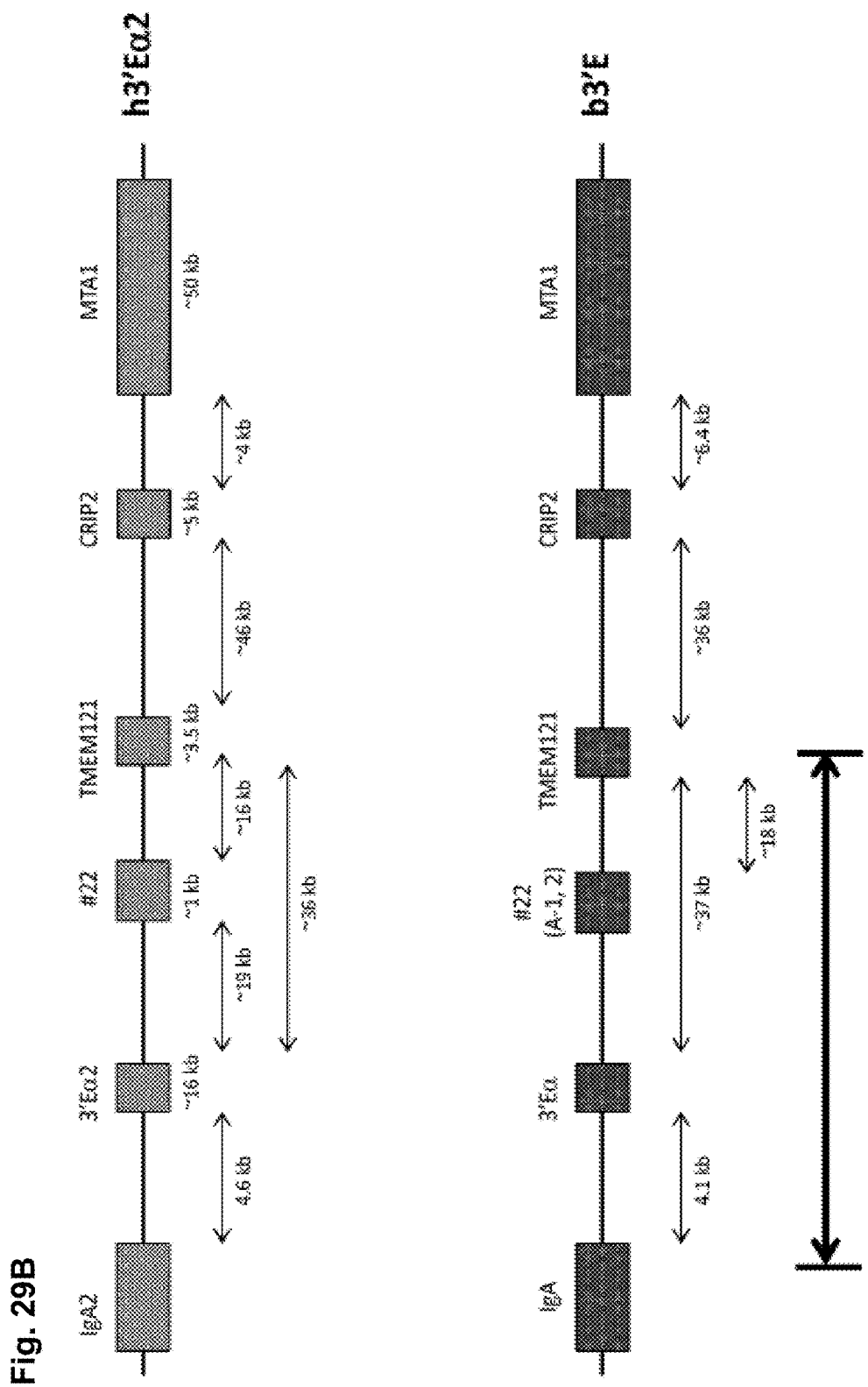
Figure 29D:
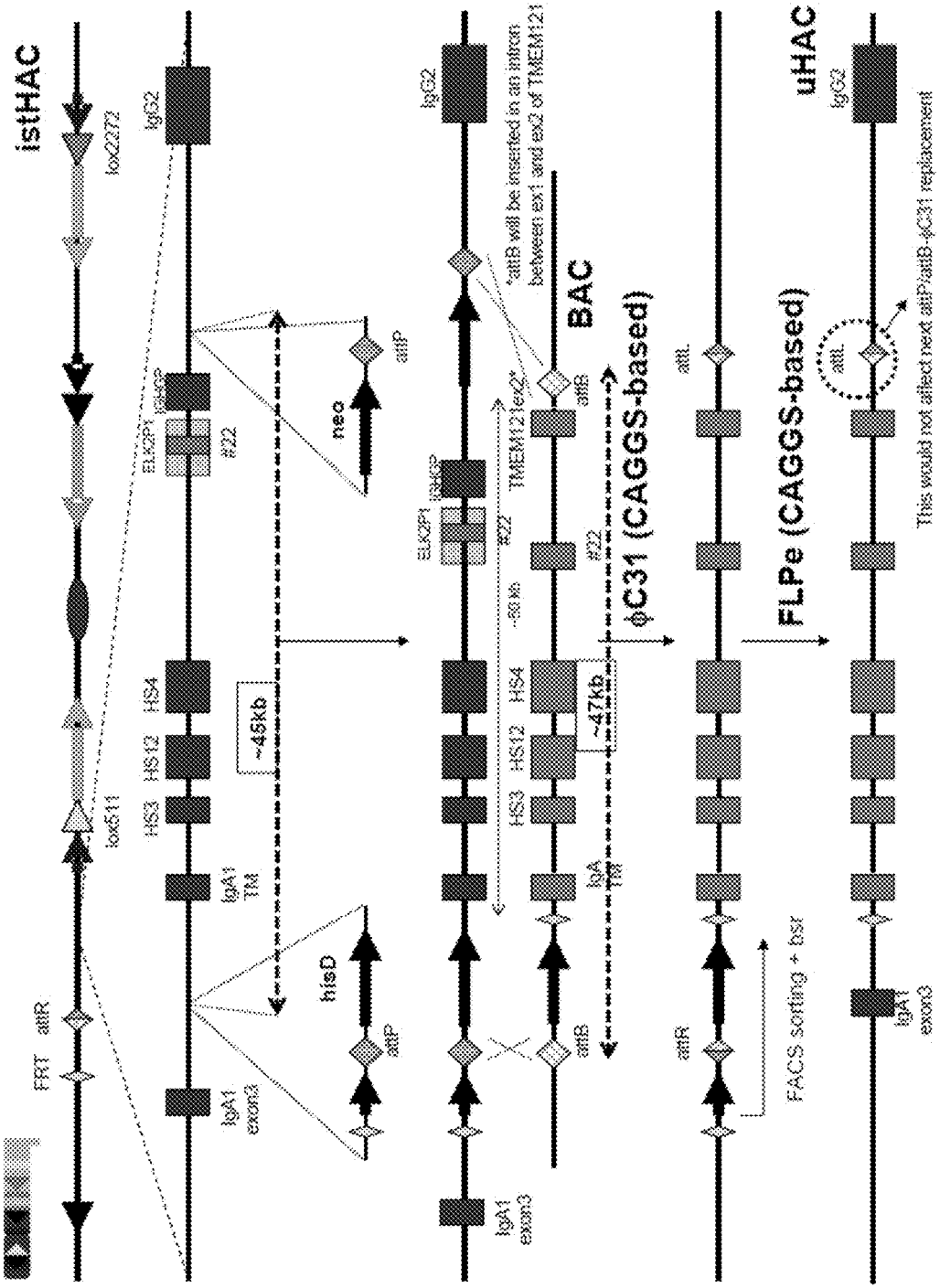
Figure 29E:
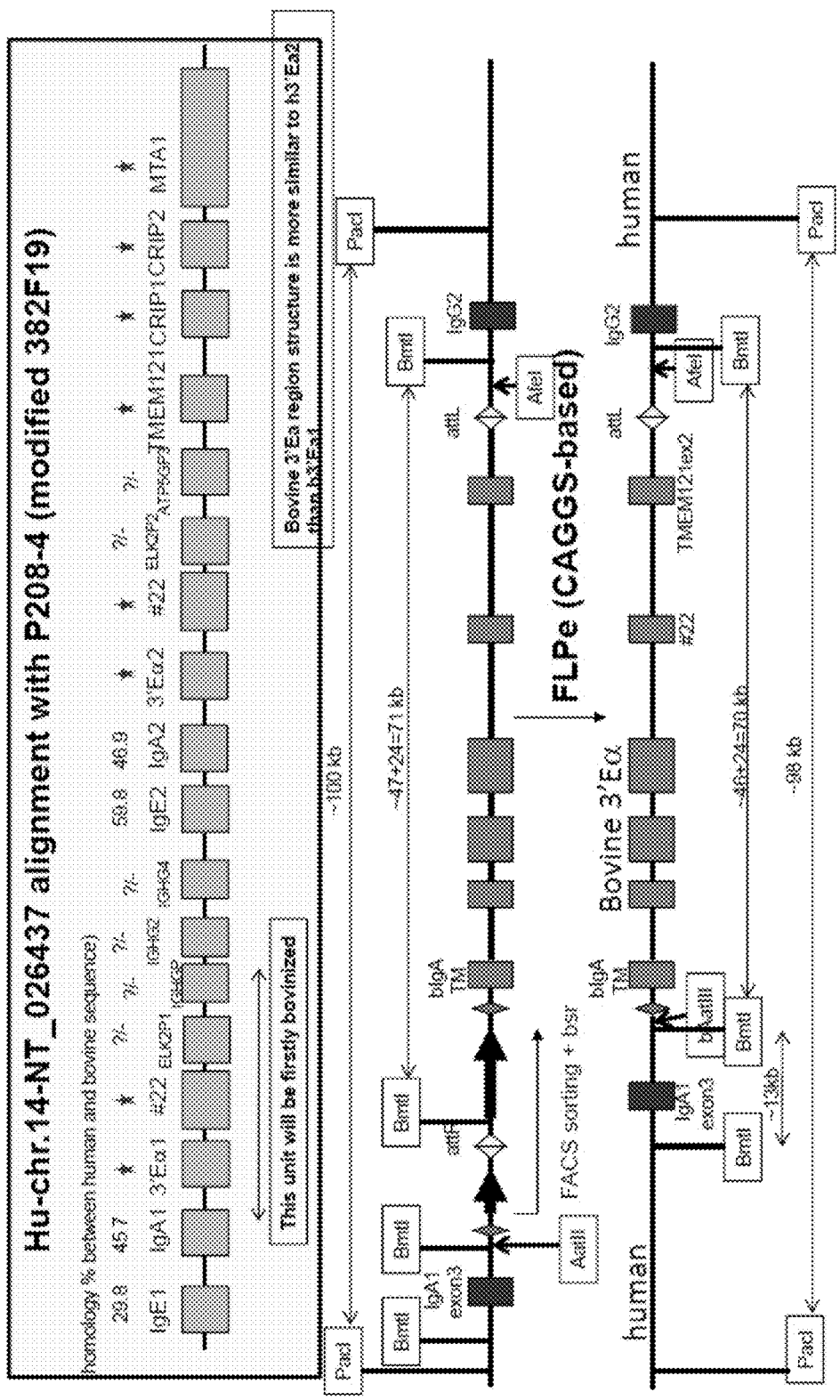
Figure 30:
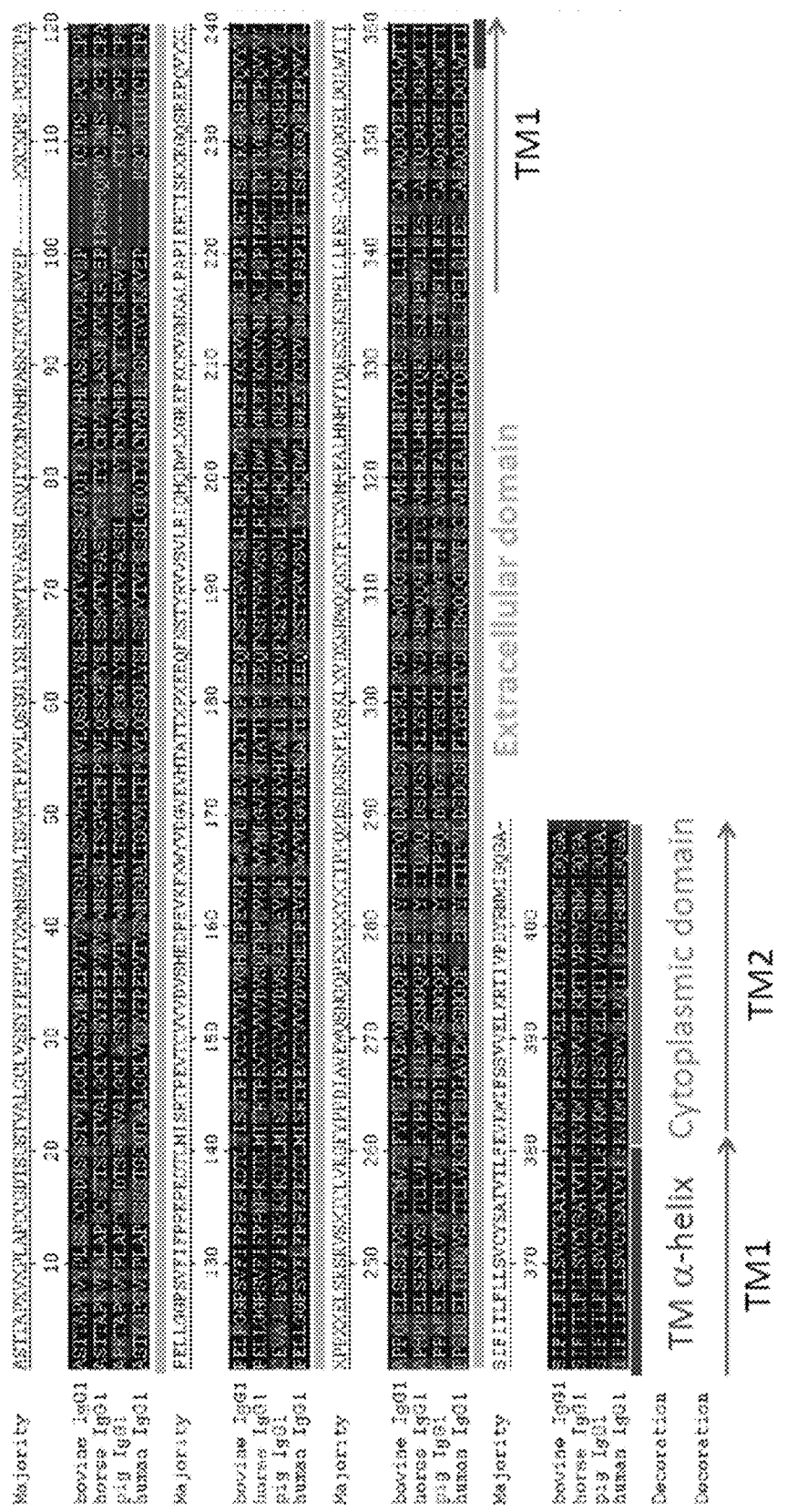
FIG. 30 shows a multiple sequence alignment of IgG1 amino acid sequences in ungulates and human. Bovine (SEQ ID NO: 196), horse (SEQ ID NO: 197), pig (SEQ ID NO: 198) and human (SEQ ID NO: 199).
Figure 31:
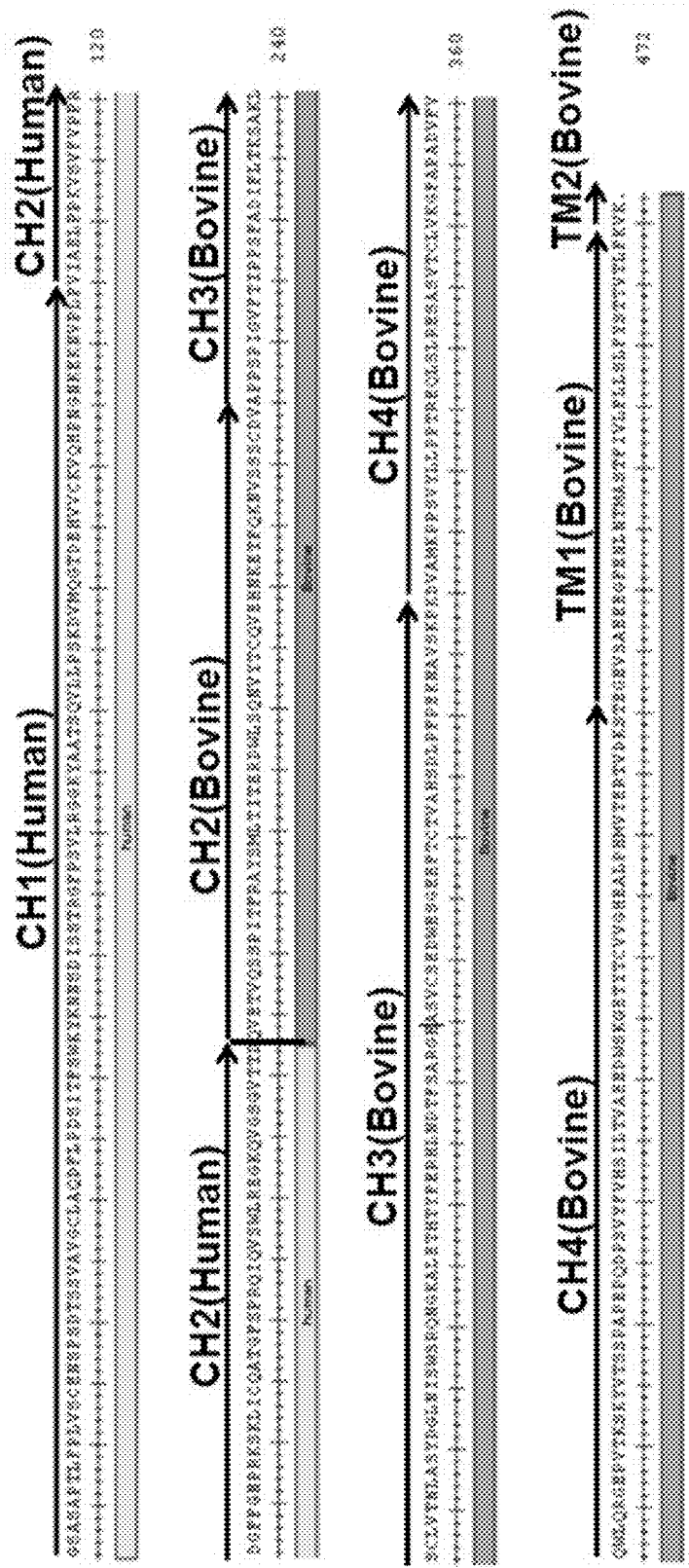
FIG. 31 shows the human-bovine chimeric IgM (CH2-TM2 bovinized IgM)-cIgM(CH2) sequence (SEQ ID NO: 200).

Array probes for CGH analysis were designed by Roche NimbleGen, based on estimated sequence of the cKSL-HACΔ vector (see FIG. 24). Experiments and data analysis were performed by Roche NIMBLEGEN™.

FISH Analysis.

Human COT-1 FISH and hChr-specific multi-color FISH were performed as previously described[5,20,21]. To specifically stain the hIGH, hIGK and hIGL loci, probes were synthesized from DNA derived from BAC clones RP11-417P24, RP11-316G9 and RP11-22M5, respectively.

Flow Cytometry Analysis.

Flow cytometry analysis on B cell development in newborn transgenic (Tc) calves were performed as previously described[5] with the following modifications. To detect surface hIgG on Tc bovine B cells, goat anti-hIgG (Life Technologies) directly labeled with AF 488 was used. To label surface hIgκ or hIgλ on Tc bovine B cells, mouse anti-hIgκ antibody directly labeled with PE (Biolegend) or mouse anti-hIgλ antibody directly labeled with PE (Southern Biotech) was used. To label surface bIgλ or bIgκ on the B cells, mouse monoclonal anti-bIg (in-house clone 132D7)

or mouse monoclonal anti-bIgκ (in-house clone 132B10) followed by Zenon mouse IgG1PE labeling (Life Technologies) were used. Staining was done by a standard protocol and then analyzed by FACSARIA™ flow cytometer (BD Biosciences).

ELISA.

Total hIgG ELISA assay was performed as previously described[5]. For fully hIgG/hIgκ or hIgG/hIgλ detection, goat anti-hIgκ affinity-purified or goat anti-hIgλ affinity-purified (Bethyl) as a capture and goat anti-hIgG Fc-HRP (Bethyl) as a detection antibody were used. For hIgG/bIgκ detection, mouse monoclonal anti-bIgκ (in-house clone 132B10) as a capture and mouse anti-hIgG Fcγ-HRP (Jackson) as a detection antibody were used. For detection of hIgG1 or hIgG2, mouse anti-hIgG1 Fc or mouse anti-hIgG2 Fc (Hybridoma Reagent Laboratory) as a capture and mouse anti-hIgG HRP (Southern Biotech) as a detection antibody were used.

Immunization of Human Oral Squamous Cell Carcinoma to the HAC/TKO and HAC/DKO Calves.

The HAC/TKO and HAC/DKO calves were immunized with X-ray-irradiated human oral squamous cell carcinoma (DSMZ) antigen at $2 \times 10^8$ cells/dose formulated with Montanide ISA 25 adjuvant (Seppic) as water-in-oil emulsion plus Quil A (Accurate Chemical & Scientific Corp) as immune stimulant. The Tc calves were immunized two times at 3-week intervals (primary immunization followed by the booster after 3 weeks). Vaccine was administered by intramuscular injection in the neck region. Serum samples were collected as previously described[5] before each immunization (V1 and V2) and 10 days and 14 days after each immunization for antibody titer analysis. Anti-human oral squamous cell carcinoma antibody titers were determined by flow cytometry analysis.

Measurement of Anti-Human Carcinoma Cell hIgG/hIgκ Titer in Tc Animal Sera by Flow Cytometry.

Sera collected from Tc calves immunized with human carcinoma cells were used as the primary antibody to stain the human carcinoma cells. Pre-immune Tc calf serum (V1D0) was used as the negative controls. AF488-conjugated goat anti-hIgG Fc (Invitrogen) at 1:80 dilution and PE-conjugated mouse anti-hIgκ (BioLegend) at 1:8 dilution were used to detect bound hIgG/hIgκ antibody. The assay was performed in PBS supplemented with 4% horse serum, 0.1% sodium azide and 2 mM EDTA. The results were expressed as % of the human carcinoma cells stained and mean fluorescence intensity (MFI) as measured by FACSARIA™ flow cytometer (BD Biosciences).

Somatic Cell Nuclear Transfer.

Cloned fetuses and calves were produced using chromatin transfer procedure as described previously[5, 12, 20, 21].

Results

Example 1. Bovine IGL Gene Cluster Deletion

Figure 8A:
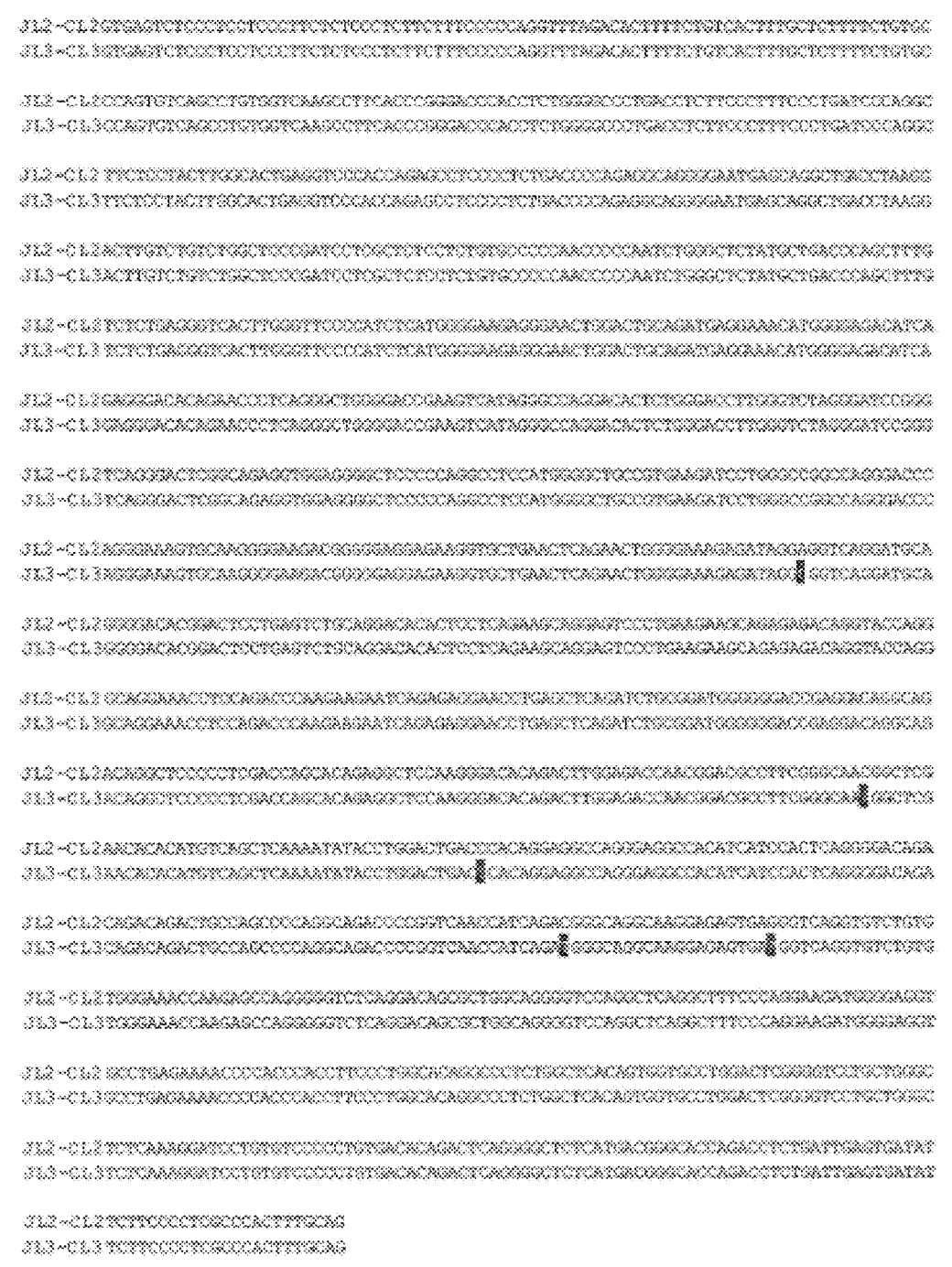
Figure 8B:
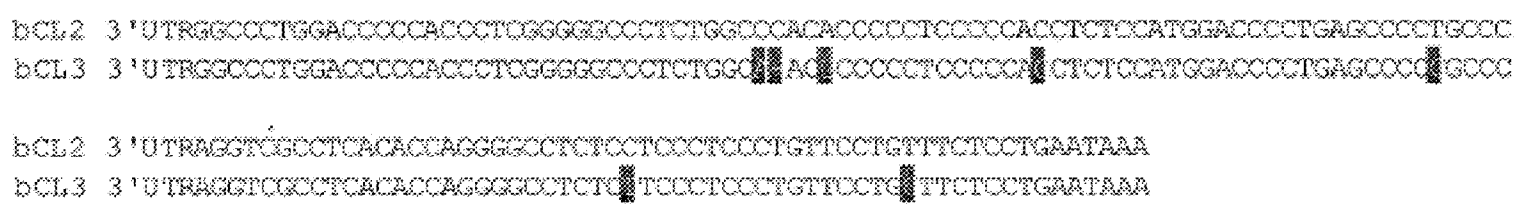

One hypothesis is that inactivation of the bovine Ig light chain, in addition to the bIgH disruption, would support high productivity of fully human IgG in cattle. Because, unlike the human and mouse, cattle predominantly express Igλ light chain over Igκ, the bIGL gene was inactivated. However, there was little information published about the bIGL gene structure in the bovine genome when the inventors started this study, thus the bIGL gene sequence including its surrounding region was determined. For that purpose, a bovine BAC (bacterial artificial chromosome) genomic library was screened and then one BAC clone was subjected to full sequencing by a shotgun approach. A gene cluster composed of the five IGLJ-IGLC genes (IGLJ1-IGLC1 through IGLJ5-IGLC5) was identified, three of which (IGLJ2-IGLC2 through IGLJ4-IGLC4) appeared to be functional, judged from its deduced amino acid sequence (FIG. 1A). Both the IGLJ1-IGLC1 and IGLJ5-IGLC5 genes contain immature stop codon mutations, indicating possible pseudo genes. Around 13 kb downstream of the IGLJ5-IGLC5 gene, a potential enhancer element was found, 3'E$_\lambda$, which showed 60% DNA sequence homology with the human 3'E$_\lambda$ (HSS-3) enhancer sequence. Chen, L et al., reported that four IGLJ-IGLC genes were identified in the bovine. In the inventors' analysis, the IGLJ2-IGLC2 and IGLJ3-IGLC3 exon sequences were identical, however their surrounding sequences, such as intron and 3' untranslated region (UTR), were slightly but different, which led to the conclusion that the IGLJ2-IGLC2 and IGLJ3-IGLC3 are distinct genes (FIG. 8A, 8B).

Figure 1B:
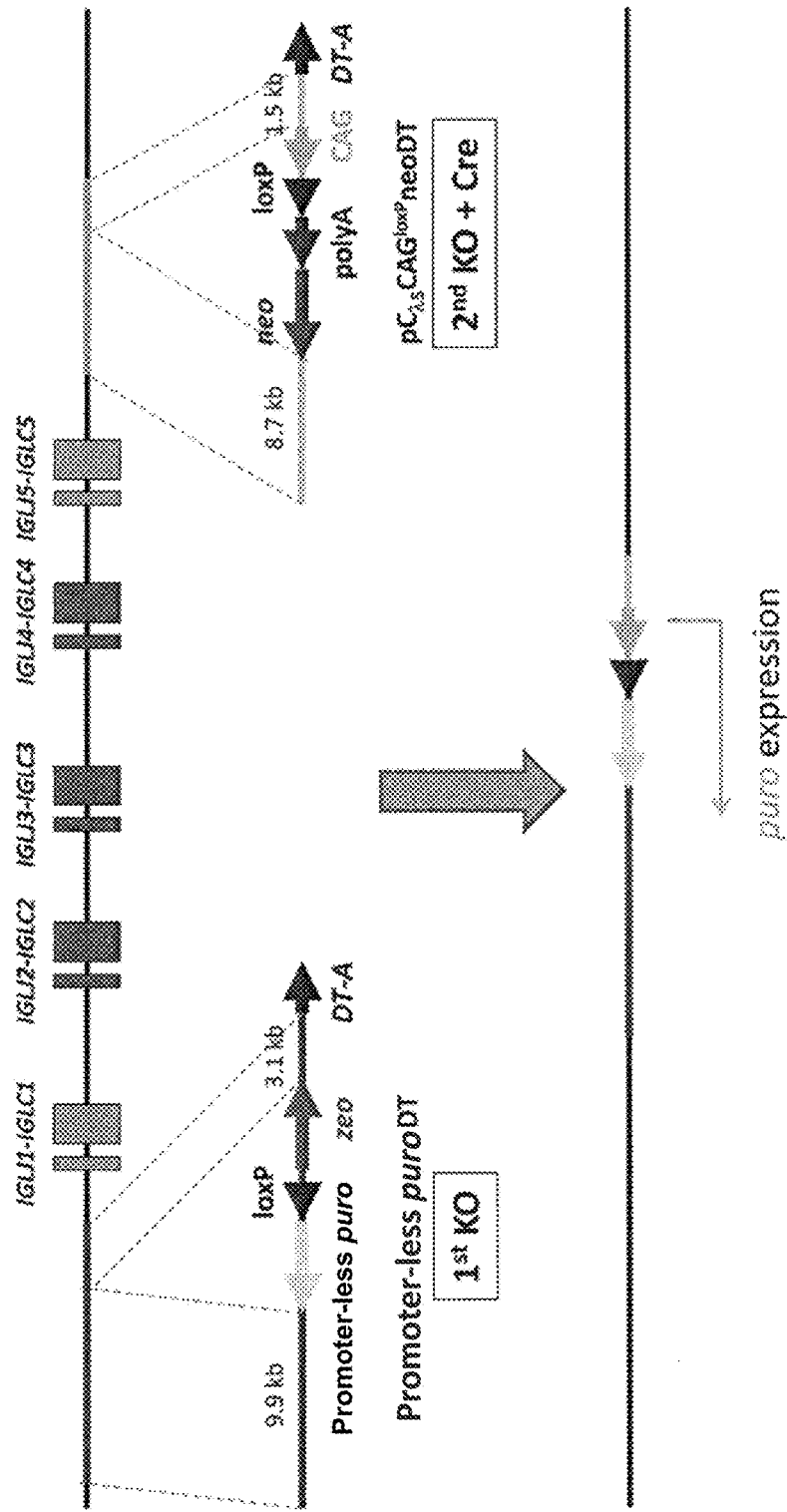

Since the bIGL gene forms the gene cluster, instead of a single gene structure, the strategy was to develop a novel system in somatic cells for deleting the entire IGLJ-IGLC gene cluster by using Cre/loxP-mediated site-specific recombination (FIG. 1b). By means of homologous recombination, each loxP sequence was integrated 5' outside of the IGLJ1 gene by a targeting vector pC$_{\lambda 1}$CAGzeoPuro$^{loxP}$DT and 3' outside of the IGLC5 gene by another targeting vector pC$_{\lambda 5}$CAG$^{loxP}$neoDT, respectively, followed by Cre introduction. This step required three rounds of transfection and somatic cell nuclear transfer (SCNT) just for the hemizygous cluster deletion, which could compromise animal development due to accumulated epigenetic errors. Thus, the strategy was to reduce the number of transfection and SCNT by implementing co-transfection of the Cre expression and second knockout (KO) vectors together; two rounds of transfections ($1^{st}$ KO and then $2^{nd}$ KO+Cre) could complete the cluster deletion. To the inventors' knowledge, such a big DNA deletion (27 kb deletion in length) had never been achieved in somatic cells, and its feasibility was uncertain. Therefore, a powerful positive selection for the deletion was used in such a way that the puromycin-resistant gene (puro) can be reconstituted only when the cluster deletion takes place, which could allow for selection under the presence of puromycin in cell culture. This cluster deletion can take place at two steps at a practical efficiency; twenty-one colonies out of $5 \times 10^6$ somatic cells transfected, all of which showed the expected deletion, indicating, unexpectedly, a high efficiency of Cre/loxP-mediated big DNA deletion (27 kb in this work) together with the second event of homologous recombination (the $2^{nd}$ KO) in bovine fibroblasts. Importantly, the implementation of the two-step big DNA deletion in somatic cells supported the ability of the cells to give rise to healthy cloned animals that are fertile. To the inventors' knowledge, this is the first report of a site-specific big DNA deletion of multiple genes in somatic cells without using ES cells, therefore, it supports a feasibility of more dynamic genome engineering, than just one-to-one single gene modification, in non-murine species where somatic fibroblast cells are available.

Figure 2A:
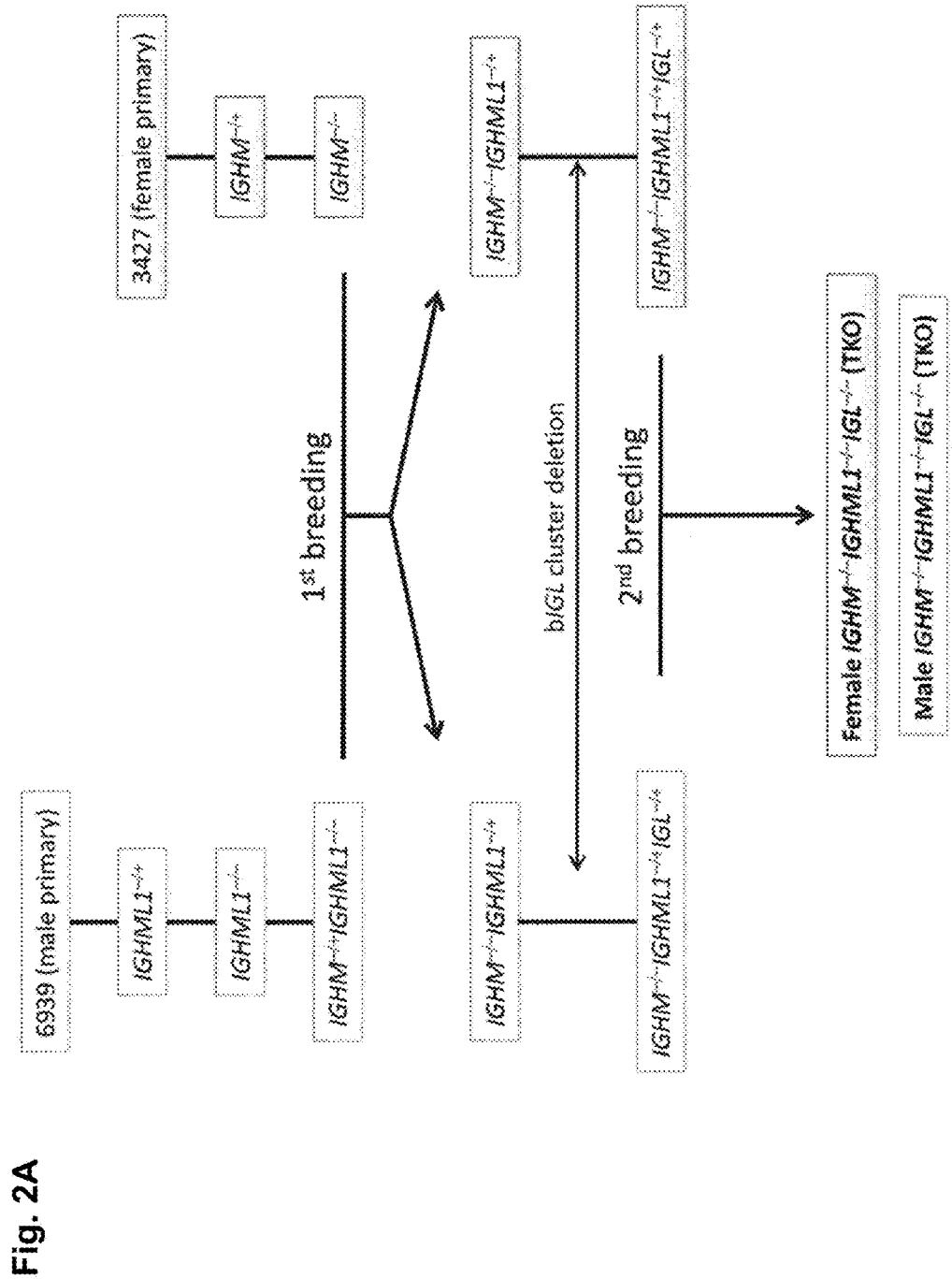
FIG. 2 shows the generation of male and female bovine IGTINF$^{-/-}$IGHML1$^{-/-}$IGL$^{-/-}$ (triple knock out, "TKO") cell lines. (A) Breeding pedigree to establish the TKO cell lines. The male cell line 6939 and female cell line 3427 were sequentially targeted to obtain IGHM$^{-/+}$IGHML1$^{-/-}$ and IGHM$^{-/-}$ animals, respectively, for the first round of breeding, which generated both male and female IGHM$^{-/-}$IGHML1$^{-/+}$ cell lines. These cell lines were subjected to the cluster deletion to generate IGHM$^{-/-}$IGHML1$^{-/+}$IGL$^{-/+}$ animals for the second round of breeding, which led to the establishment of the male and female TKO cell lines. (B) Generation of male and female IGHM$^{-/-}$IGHML1$^{-/+}$ cell lines. In the male cell line IGHM$^{-/+}$IGHML1$^{-/-}$ originated from the cell line 6939, the two IGHML1 alleles, U and u, and the one IGHM allele, AY, were knocked out by the targeting vectors pBCμΔNKOneo, pBCμΔKOpuro and pbCμAYKObsr, respectively. In the female cell line IGHM$^{-/-}$ originated from the cell line 3427, the two IGHM alleles, 10AY and 7AYJ, were knocked out by the targeting vectors pbCμAYKObsr and pbCμ7AYJKOhyg, respectively. After breeding between the male IGHM$^{-/+}$IGHML1$^{-/-}$ and female IGHM$^{-/-}$ animals, each fetus was subjected to genomic PCR (AYKObsr-F2R2, ayKOhyg-F2R2, Neo-F2R2 or Puro-F2R2) to identify the genotype IGHM$^{-/-}$IGHML1$^{-/+}$, leading to establishment of the male and female cell lines, J481 and H412, respectively. In the genomic PCR with AYKObsr-F2R2 for H412, sequence analysis was done to confirm that both the alleles AY and 10AY were disrupted. (C) Integration of the loxP sequence 5' outside of the IGLJ1 gene by the targeting vector $pC_{\lambda 1}CAGzeoPuro^{loxP}DT$ in the cell line J481. The occurrence of the homologous recombination was confirmed by the genomic PCR, CL1puro-F2F2, as a positive PCR. Furthermore, the negative PCR, R-F2×R-R1, was done to double check the homologous recombination because it can be only amplified from the wild type allele; J481 amplified it both from the alleles A and D, showing the double peaks (T for the allele A and G for the allele D). Colony 27 showed only "G", demonstrating that the allele A was specifically knocked out while Colony 22 showed only "T", demonstrating that the allele D was specifically knocked out. From colony 27, the fetal cell line, K655-1, was established, which was positive with the CL1puro-F2R2. (D) Integration of the loxP sequence 3' outside of the IGLC5 gene by the targeting vector $pC_{\lambda 5}(A)CAG^{loxP}neoDT$ in the cell line K655-1. The occurrence of the homologous recombination was confirmed by the genomic PCR, CL5CAG-F2F2, as positive PCR. Moreover, the reconstitution of the CAG promoter-driven puro gene caused by the cluster deletion was also confirmed by the genomic PCR, CAGpuro-F3R3. The cell line G054 was used to generate calves for breeding. (E) Generation of the male and female IGHM$^{-/-}$IGHML1$^{-/-}$IGL$^{-/-}$ (TKO) cell lines. The male and female IGHM$^{-/-}$IGHML1$^{-/+}$IGL$^{-/+}$ animals were subjected to the second round of breeding. Each fetus was examined by a series of genomic PCR, L001-F1×L002×R2 (to amplify the IGLC genes), BCμ-f2r2 (to amplify the IGHM or IGHML1 constant region gene), the cluster deletion-specific CAGpuro-F3R3 and BCμKO-F14R14 (to amplify the targeted IGHM or IGHML1 gene). The five fetal cell lines, E024A-2, A596A-1, A332A, C970 and A114A, were genotyped as shown in the table, proving to be the IGHM$^{-/-}$IGHML1$^{-/-}$IGL$^{-/-}$.

Example 2. Establishment of Male and Female Bovine IGHM$^{-/-}$IGHML1$^{-/-}$IGL$^{-/-}$ Cell Lines Multiple rounds of genetic modifications followed by SCNT in somatic cells could compromise animal development due to potentially accumulated, irreversible epigenetic errors. In order to reduce the round number of SCNT, sequential gene targeting was combined with animal breeding, as summarized in FIG. 2A.

Figure 2B:
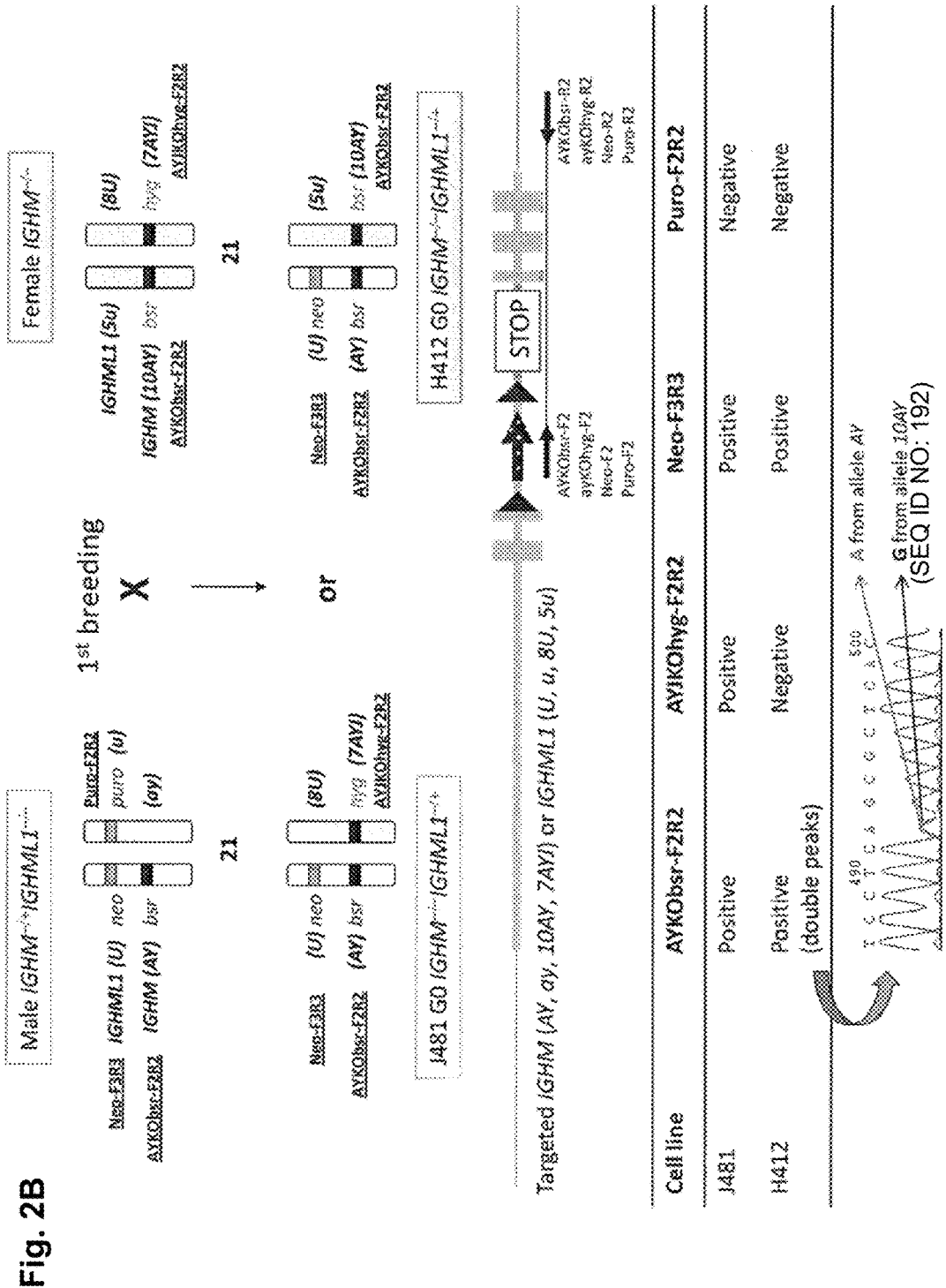
Figure 9:
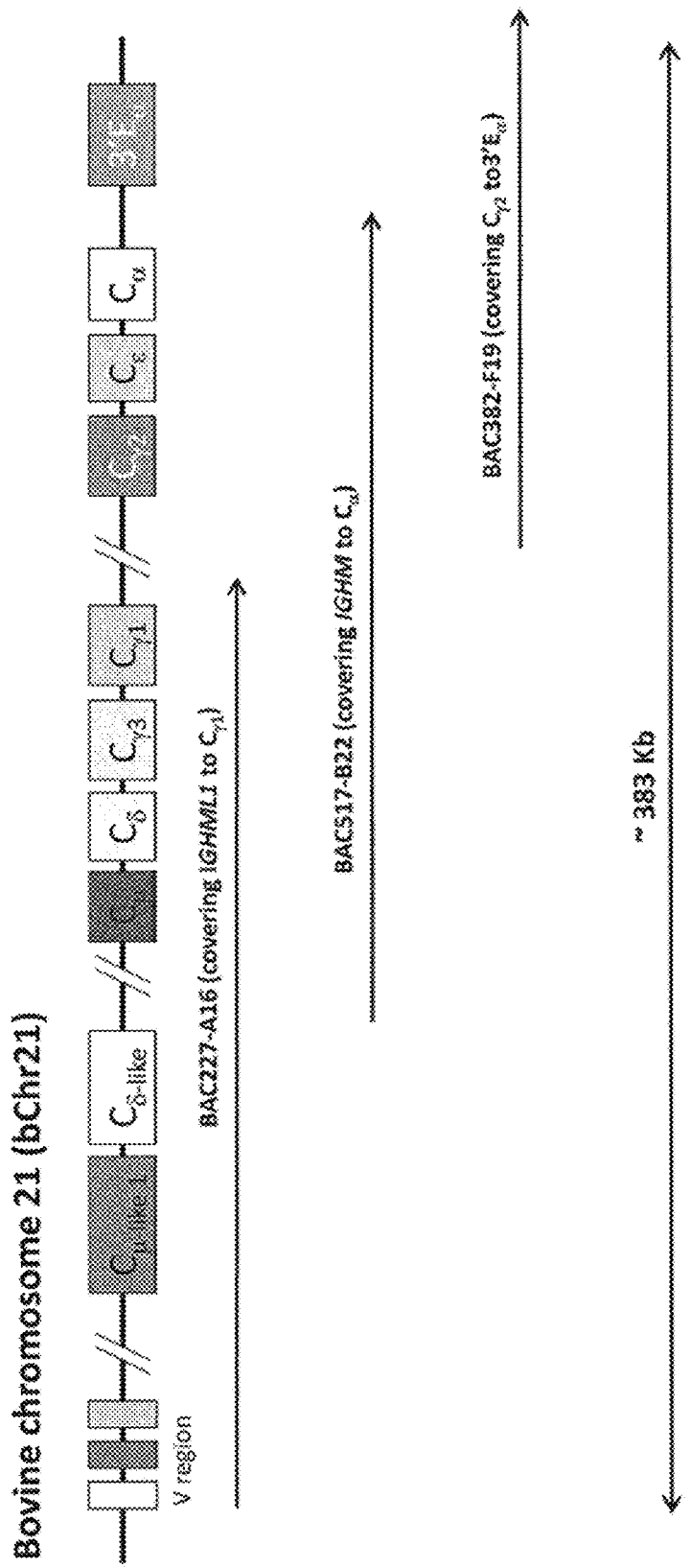
FIG. 9 shows the deduced structure of the bovine IGH gene cluster on the bChr21. A BAC clone 227-A16 seemed to contain part of the IGH variable region and the IGHML1 through the $C_{\gamma 1}$ region. A BAC clone 517-B22 appeared to cover the IGHM through the $C_\alpha$ region. A BAC clone 382-F19 is likely to include the $C_{\gamma 2}$ through the 3'$E_\alpha$ region. The size of the three BAC clones contig is estimated to be around 380 kb in length.

It was previously reported that the IGHML1 locus mapped to the bChr11, the data here indicated that both the IGHM and IGHML1 loci are unexpectedly located on the bovine Chr21 (FIG. 9). So, this study was implemented on the basis of this new and surprising indication. Starting with the male primary Holstein fibroblast line 6939 for which the IGHM and IGHML1 alleles are designated as AY/ay and U/u, respectively (FIG. 2B), IGHM and IGHML1 loci were sequentially knocked out in an allele-specific manner to establish IGHM$^{-/+}$IGHML1$^{-/-}$ cell lines by using the targeting vectors, pBCμΔNKOneo, pBCμΔKOpuro and pbCμAYKObsr, for the alleles U, u and AY, respectively. A female primary Holstein×Jersey cross-breed (HoJo) fibroblast line 3427, for which the IGHM and IGHML1 alleles are designated as 10AY/7AYJ and 8U/5u, respectively (FIG. 2B), was used to generate IGHM$^{-/-}$ cell lines by using the targeting vectors, pbCμAYKObsr and pbCμ7AYJKOhyg, for the alleles 10AY and 7AYJ, respectively. From each of the male IGHM$^{-/+}$IGHML1$^{-/-}$ and female IGHM$^{--}$ cell lines, cloned bovines were generated and then they were bred each other around 18-20 months of age. Around 40 days of gestation, 18 fetuses were collected and genotyped. Seven fetuses (39%) were of the IGHM$^{-/-}$IGHML1$^{-/+}$ genotype. In all the seven fetuses, the neo KO cassette at U and the bsr one at AY were always linked, supporting that data that both the IGHM and IGHML1 loci are unexpectedly located on the bovine Chr21. One male and female cell line, J481 and H412, respectively, were selected for the bIGL gene cluster deletion (FIG. 2B).

The male cell line J481 (IGHM$^{-/-}$IGHML1$^{-/+}$), in which the inventors designated the bIGL alleles as A and D, was transfected with the pC$_{\lambda 1}$(A)CAGzeoPuro$^{loxP}$DT vector specific to the allele A, selected under zeocin and then screened for the occurrence of homologous recombination by a genomic PCR using a primer pair, CL1puro-F2R2, as shown in FIG. 2C. Positive colonies (18%) were identified by sequencing the PCR product, some of which were further subjected to another genomic PCR using a PCR pair, R-R1× R-F2, followed by sequencing (FIG. 2C). The cell line J481 contains the alleles A and D for the bIGL locus and this PCR amplifies one polymorphic site between the two alleles; T for the allele A and G for the allele D. For example, in colony 27, only G was detected, demonstrating that the allele A was disrupted due to the insertion of the CAGzeo/loxP/promoterless puro cassette between the R-R1 and R-F2 primer annealing sites. Colony 27 was used for SCNT to generate 40 day fetuses from which a cell line K655-1 IGHM$^{-/-}$IGHML1$^{-/+}$IGL1$^{-/+}$ was established.

Figure 2D:
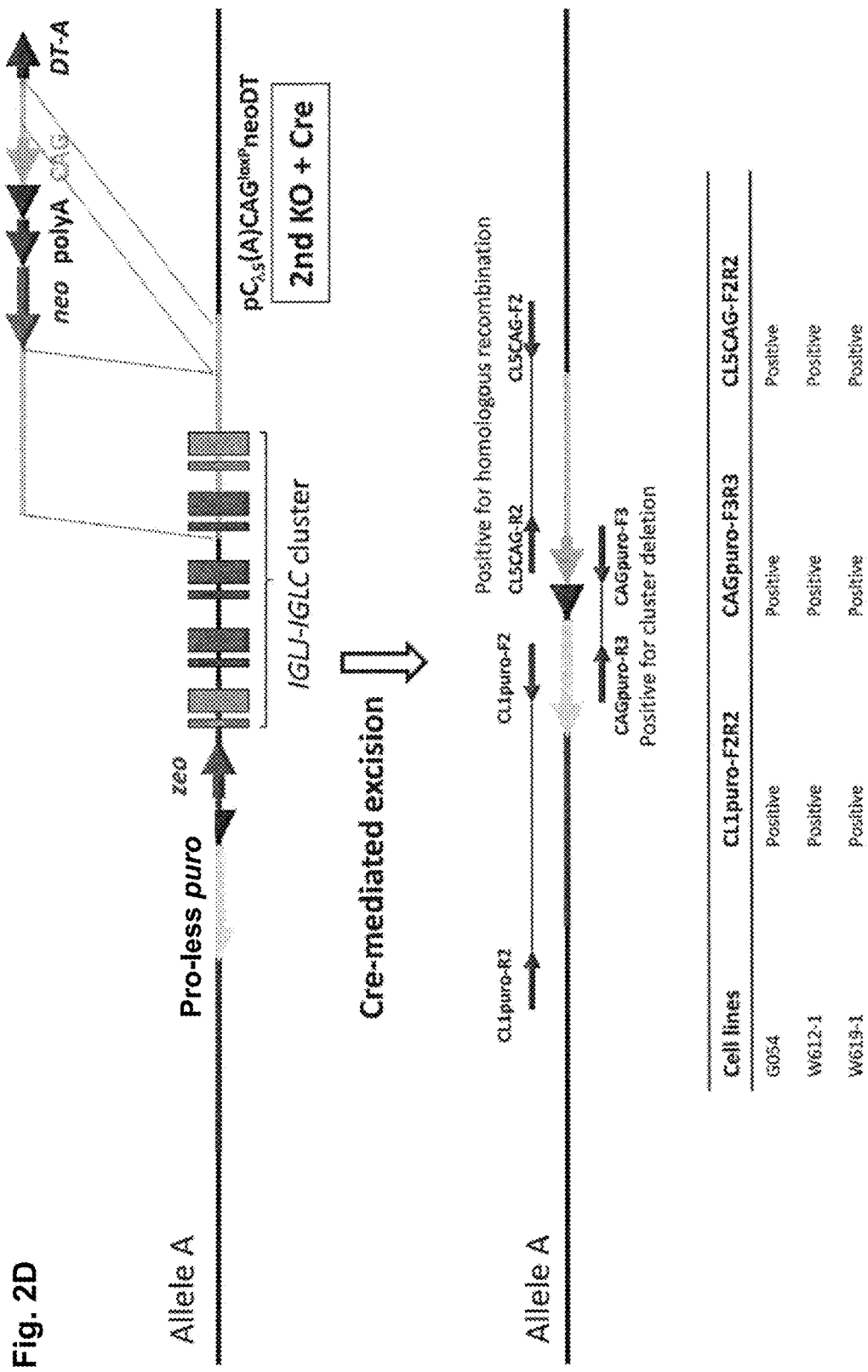
Figure 2E:
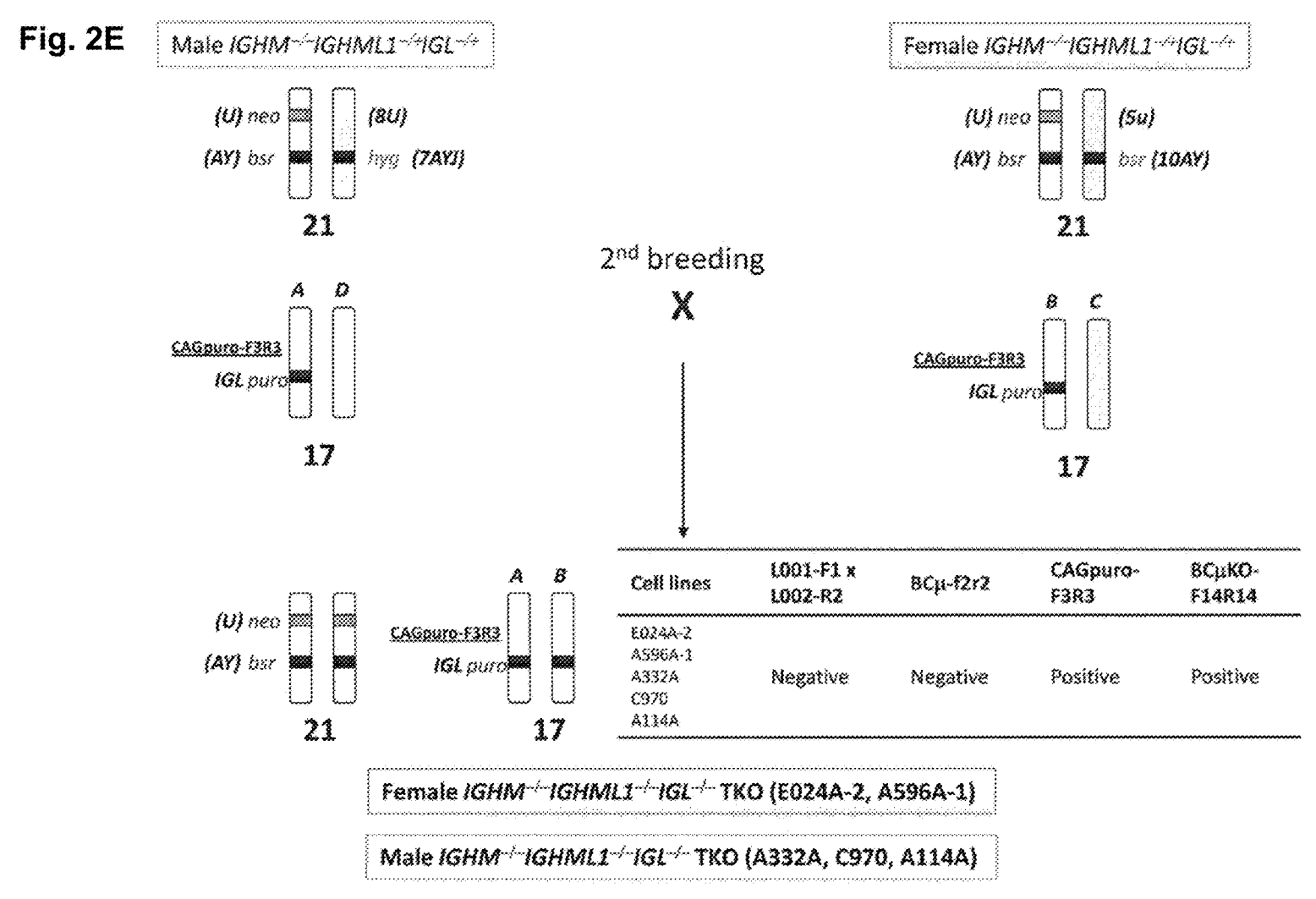
Figure 10:
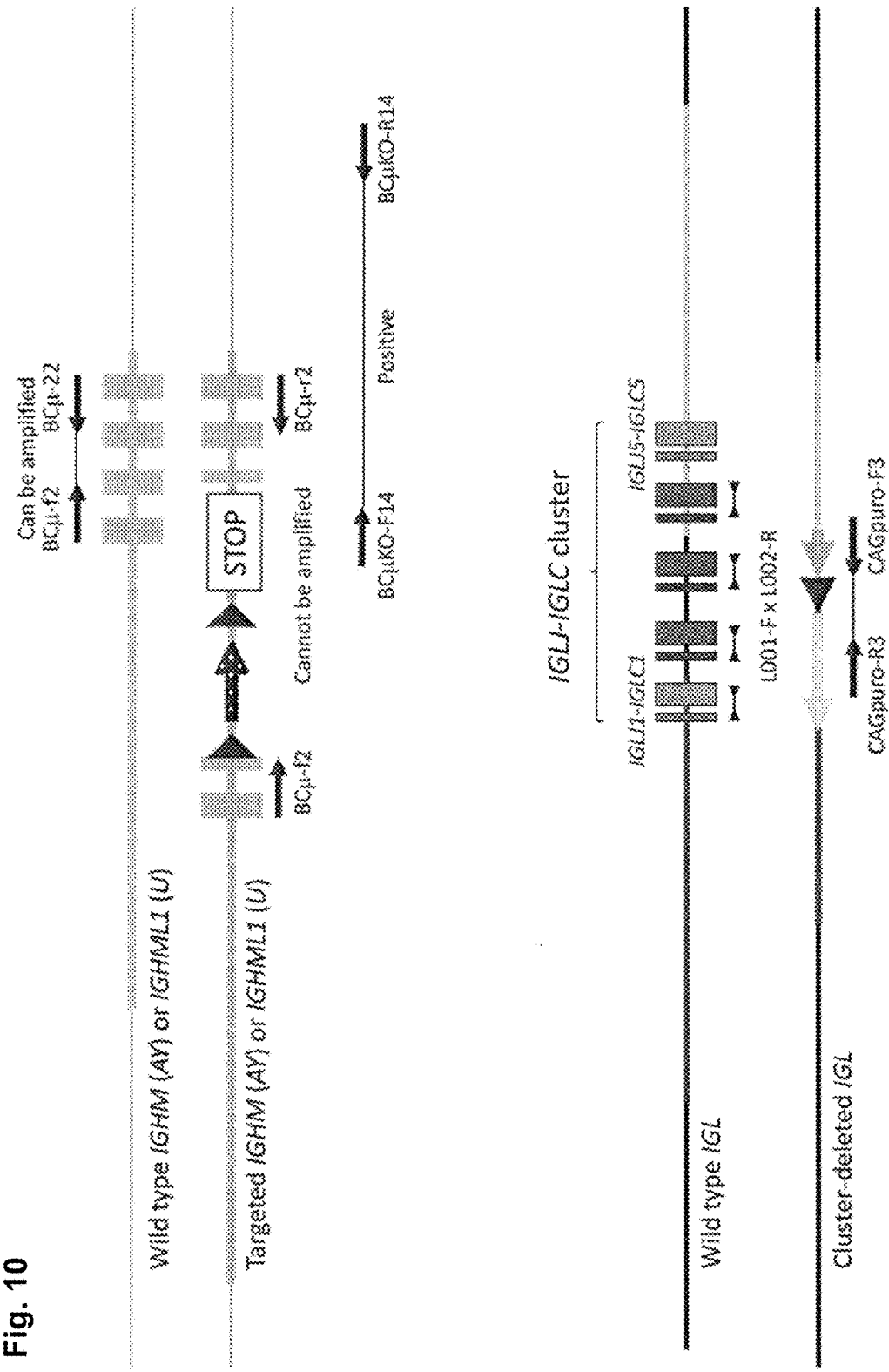
FIG. 10 shows genotyping of the IGHM$^{-/-}$IGHML1$^{-/-}$ IGL$^{-/-}$ (TKO) cell lines. To confirm the IGHM$^{-/-}$IG-HML1$^{-/-}$ (DKO) genotype, the negative PCR, BCμ-f2r2, was performed because the presence of KO cassettes inhibits the amplification. As a positive PCR, BCμKO-F14R14, was implemented. For the IGL$^{-/-}$ genotype, the negative PCR, L001-F×L002-R, was done to confirm the absence of the IGLC genes. At the same time, the positive PCR, CAGpuro-F3R3, specific to the cluster deletion was carried out.
Figure 11A:
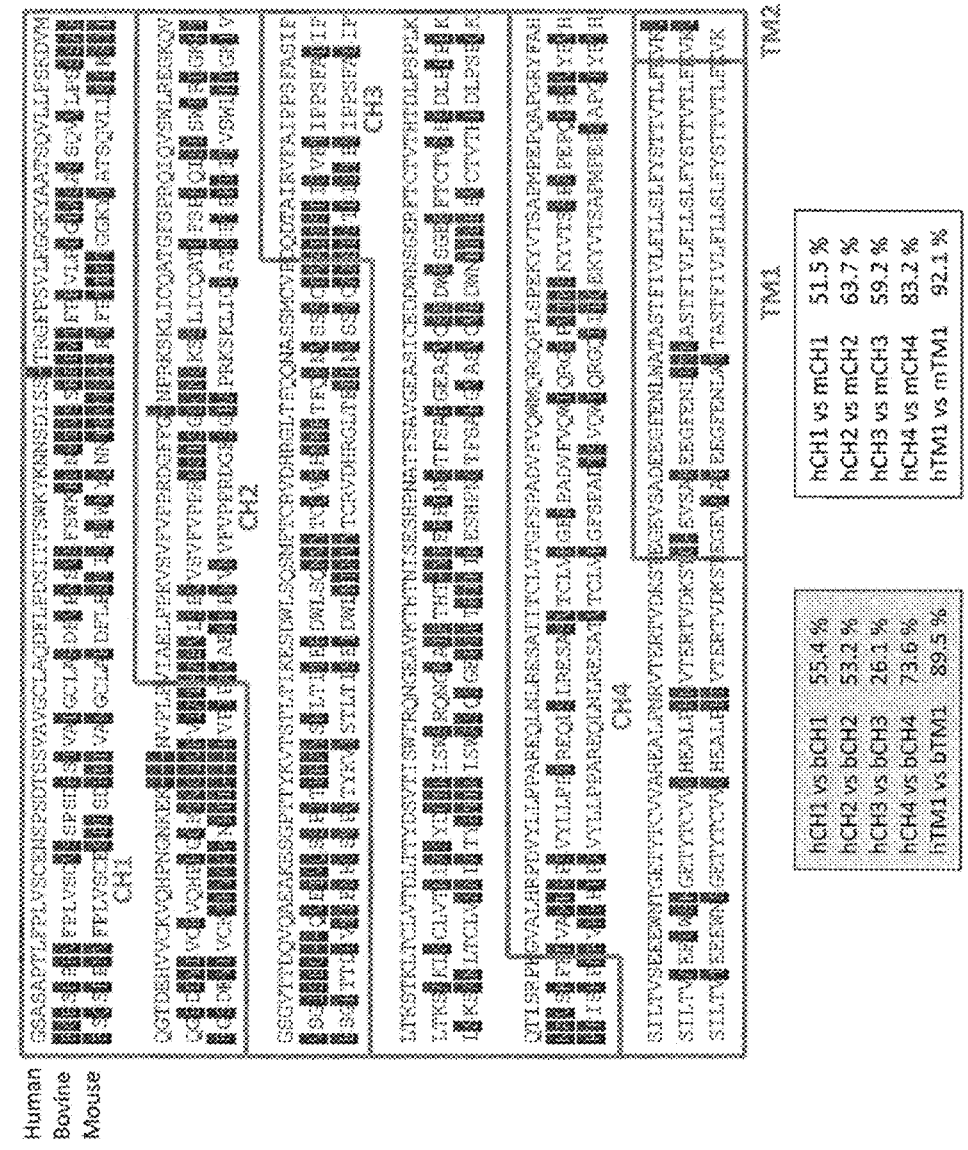
FIG. 11 shows the amino acid sequence alignment of human, bovine and mouse (A) IgM (human SEQ ID NO: 151, bovine SEQ ID NO: 152 and mouse SEQ ID NO: 153); (B) VpreB1 (human SEQ ID NO: 154, bovine SEQ ID NO: 155 and mouse SEQ ID NO: 156); (C) λ5 (human SEQ ID NO: 157, bovine SEQ ID NO: 158 and mouse SEQ ID NO: 159), (D) Ig-α (human SEQ ID NO: 160, bovine SEQ ID NO: 161 and mouse SEQ ID NO: 162) and (E) Ig-β (human SEQ ID NO: 163, bovine SEQ ID NO: 164 and mouse SEQ ID NO: 165) among human, bovine and mouse. Each percentage shows homology. h, human, b, bovine, m; mouse. Shaded amino acid depicts a different one from human.
Figure 11B:
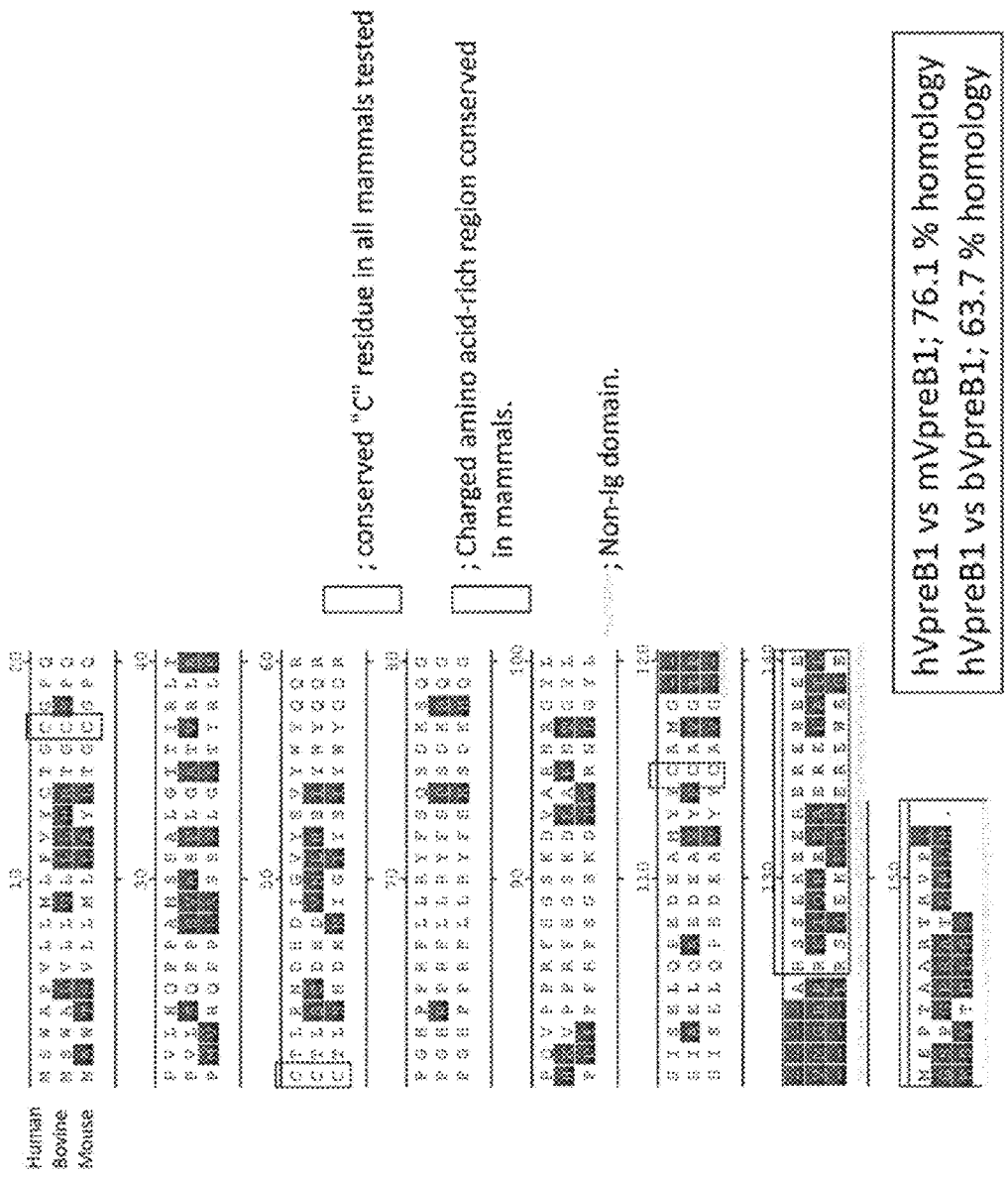
Figure 11C:
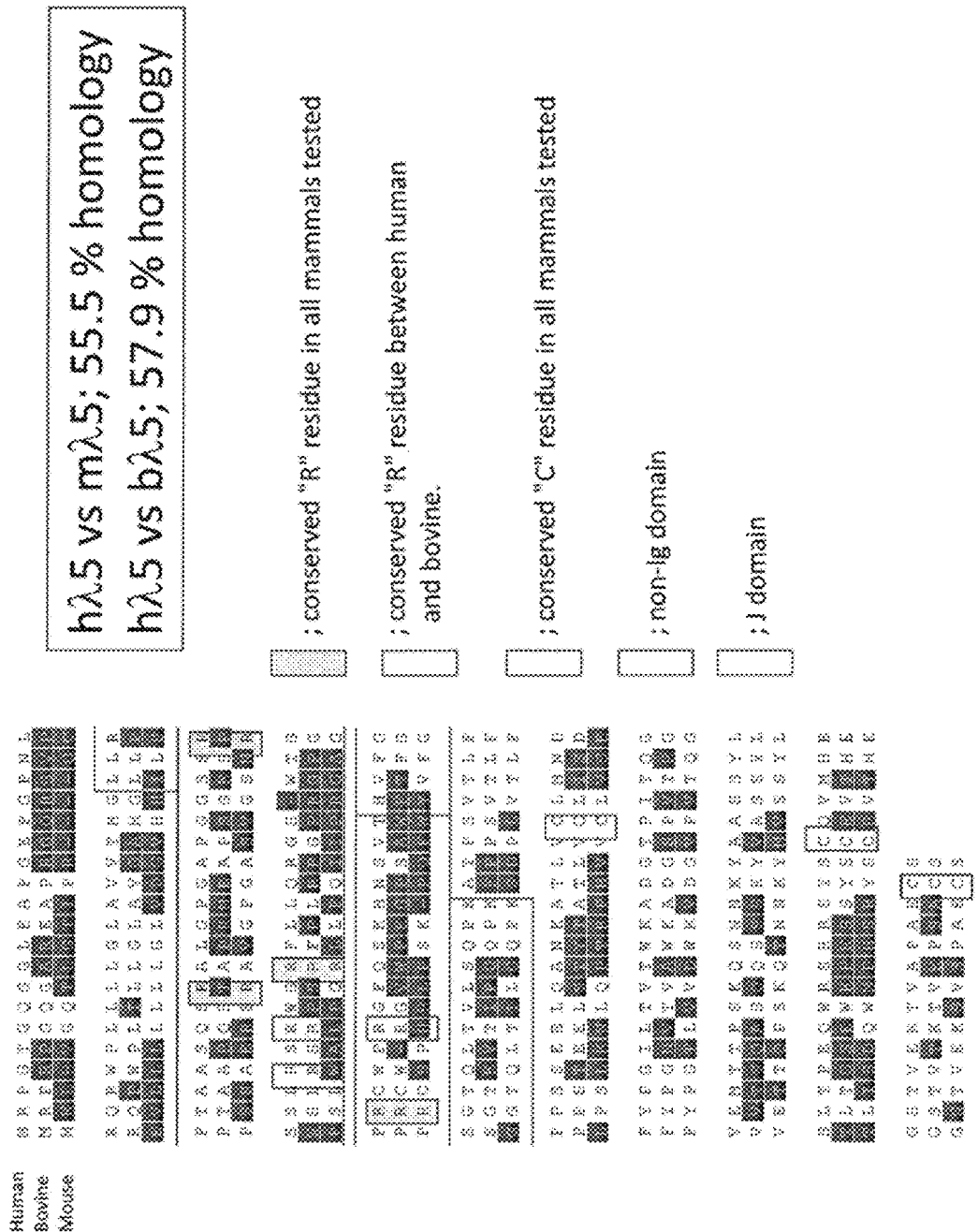

Subsequently, the cell line K655-1 was co-transfected with the pC$_{\lambda 5}$(A)CAG$^{loxP}$neoDT vector specific to the allele A and the Cre-expression plasmid to bring about the cluster deletion, which was selected by puromycin. Twenty-one puromycin-resistant colonies were obtained and subjected to two kinds of genomic PCRs, CL5CAG-F2R2 and CAG-puro-F3R3, as shown in FIG. 2D. The former was to identify the occurrence of the homologous recombination at the 3' side of the IGLC5 gene and the latter was to detect the incidence of the cluster deletion. All the PCR products were confirmed to be correct by sequencing analysis. The double positive colonies were used for cloning to establish a cell line G054 IGHM$^{-/-}$IGHML1$^{-/+}$IGL$^{-/+}$, which was further used to generate calves. Similarly, the female cell line H412 (IGHM$^{-/-}$IGHML1$^{-/+}$), in which the inventors designated the bIGL alleles as B and C, was subjected to the two-step cluster deletion on the allele B to generate calves. Finally, the male and female IGHM$^{-/-}$IGHML1$^{-/+}$IGL$^{-/+}$ animals were bred each other around 18-20 months of age. Around 40 days of gestation, 58 fetuses were collected and genotyped. Five fetuses (8.62%) were of the IGHM$^{-/-}$IGHML1$^{-/-}$IGL$^{-/-}$ genotype, and then five IGHM$^{-/-}$IGHML1$^{-/-}$IGL$^{-/-}$ triple knock out (TKO) cell lines were established (FIG. 2E and FIG. 10).

Example 3. cKSL-HACΔ and KcHACΔ Vector Construction

It is possible that there could be some species-incompatibilities between human and bovine that could hamper high production of fully hIgG in the bovine. As one of such species-incompatibilities, the IgM-based pre-BCR/BCR function was addressed. Among immunoglobulin heavy (IgH) chain classes, the IgM heavy chain is the first to be expressed, and is important for B cell development to eventually lead to secretion of IgG. In the Tc bovine condition, hIgM is expressed on the bovine B cell surface to interact with bovine surrogate light chain, followed by orthodox bovine light chain, and with bovine Ig-α/Ig-β molecules for the pre-BCR/BCR-mediated signaling, which is crucial for the subsequent B cell development. There may be species-incompatibilities in the hIgM protein interacting with bovine surrogate light chain, orthodox light chain and Ig-α/Ig-β molecules, due to the species-specific sequence differences (FIG. 11A-11D). To address this hypothesis, two HAC vectors were constructed, KcHACΔ and cKSL-HACΔ (FIG. 3A). In the KcHACΔ, part of the hIGHM constant region gene (the CH1 through TM2 domains) was bovinized so that such a chimeric IgM {cIgM (CH1)} protein could interact with bovine surrogate light chain, orthodox light chain and Ig-α/Ig-β molecules for better pre-BCR/BCR signaling. In the cKSL-HACΔ, part of the hIGHM constant region gene (the CH2 through TM2 domains) was differently bovinized and, additionally, the human surrogate light chain hVPREB1 and hIGLL1 (λ5 in the mouse) genes were introduced with the hChr22 fragment so that such a chimeric IgM ('cIgM (CH2)'; SEQ ID NO: 200) protein could pair with human surrogate light chain and could also interact with bovine Ig-α/Ig-β molecules for better pre-BCR/BCR signaling. Due to the species-specific distinct sequences of the variable region and constant region of hIgM, cIgM (CH1) and cIgM (CH2) proteins, pre-BCR/BCR function/signaling in each HAC vector (e.g., κHAC, KcHACΔ, cKSL-HACΔ, respectively) could affect B cell developmental fate, and eventually hIgG production profile, differently.

As a starting HAC vector onto which a defined human chromosome region can be cloned (chromosome cloning) by means of site-specific chromosome translocation, the hChr14 fragment SC20 was used. SC20 was a naturally occurring fragment during microcell-mediated chromosome transfer (MMCT), thus its structure was not defined. For the purpose of using a structure-defined hChr14 vector and of removing as many irrelevant human genes as possible, the intact hChr14 was modified, followed by the IgM bovinizations, which generated new hChr14-based vectors, CH1D2 and CH2D4, for the KcHACΔ and cKSL-HACΔ vector construction, respectively.

The cKSL-HACΔ vector was constructed in chicken DT40 cells as outlined in FIG. 3B (see also Methods). Clone SLKD18 which contains the SLKH fragment was created by translocating the hChr22 fragment, covering the entire hIGL and surrogate light chain hVPREB1/hIGLL1 loci, to the hChr2 fragment having the hIGK locus, and clone CH2D4 which contains the hChr14 fragment (14D) with the cIgM (CH2)-bovinized hIGH locus, were fused to generate DT40 hybrid clone cKSLD22. The Cre expression plasmid was introduced to mediate site-specific recombination between the two loxP sites, one at the cos138 locus on the SLKH fragment and another at the RNR2 locus on the CH2D fragment, and also to delete the floxed CAG promoter-zeo cassette within the cIgM (CH2) domain. Recombinants were enriched by sorting of GFP positive cells as GFP expression was conferred by reconstitution of the PGK promoter-loxP-GFP cassette at the translocation site. This is the first report of construction of an artificial chromosome composed of structurally defined, three different chromosome fragments (e.g., hChr2, hChr14 and hChr22).

Figure 3C:
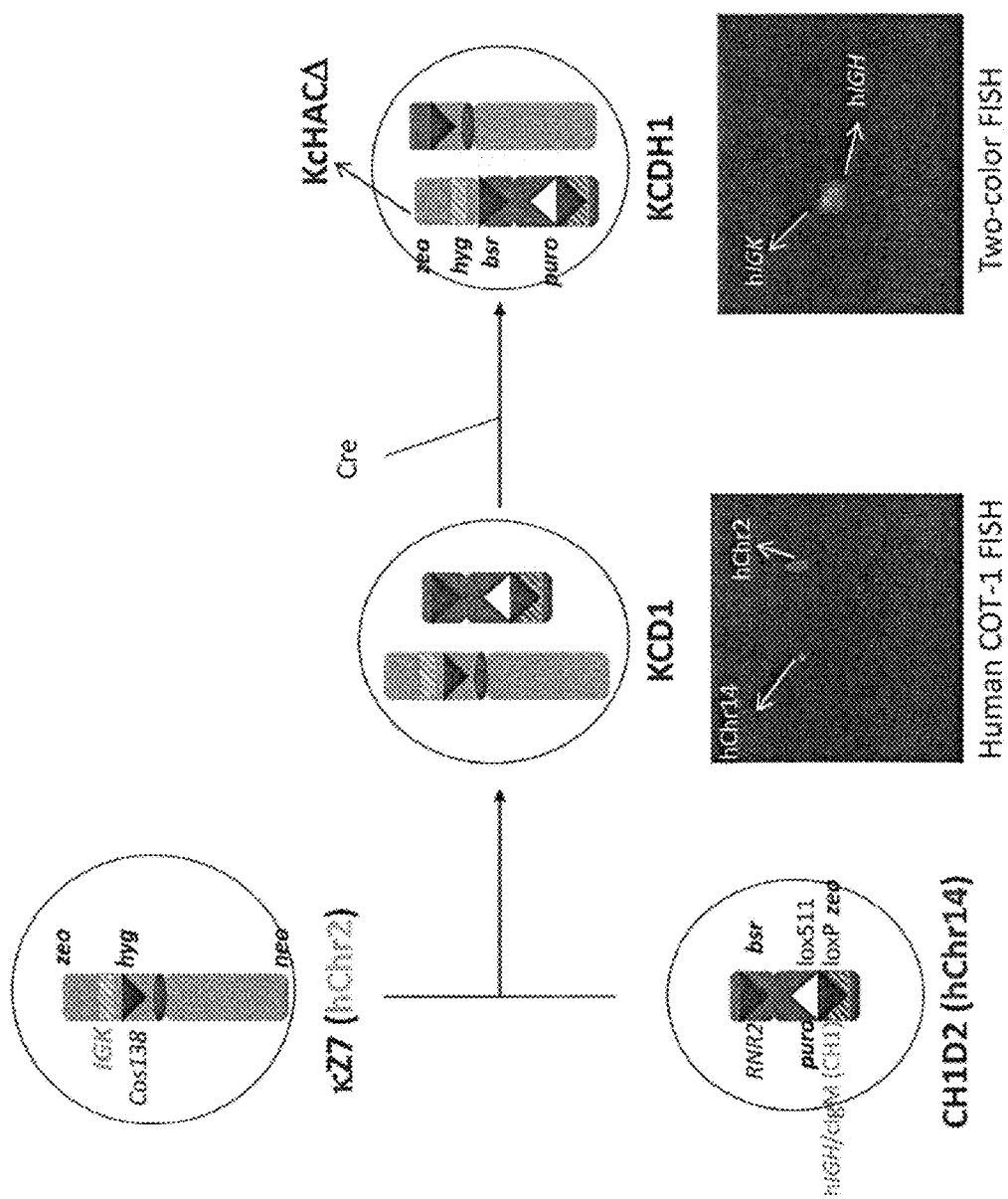

The KcHACΔ vector was similarly constructed in DT40 cells as outlined in FIG. 3C (see also Methods). Likewise, the KcHAC vector was constructed in which the hChr2 fragment (KTL1) was translocated to the SC20 fragment bearing the bovinized IgM {cIgM (CH1)} sequence.

Figure 4A:
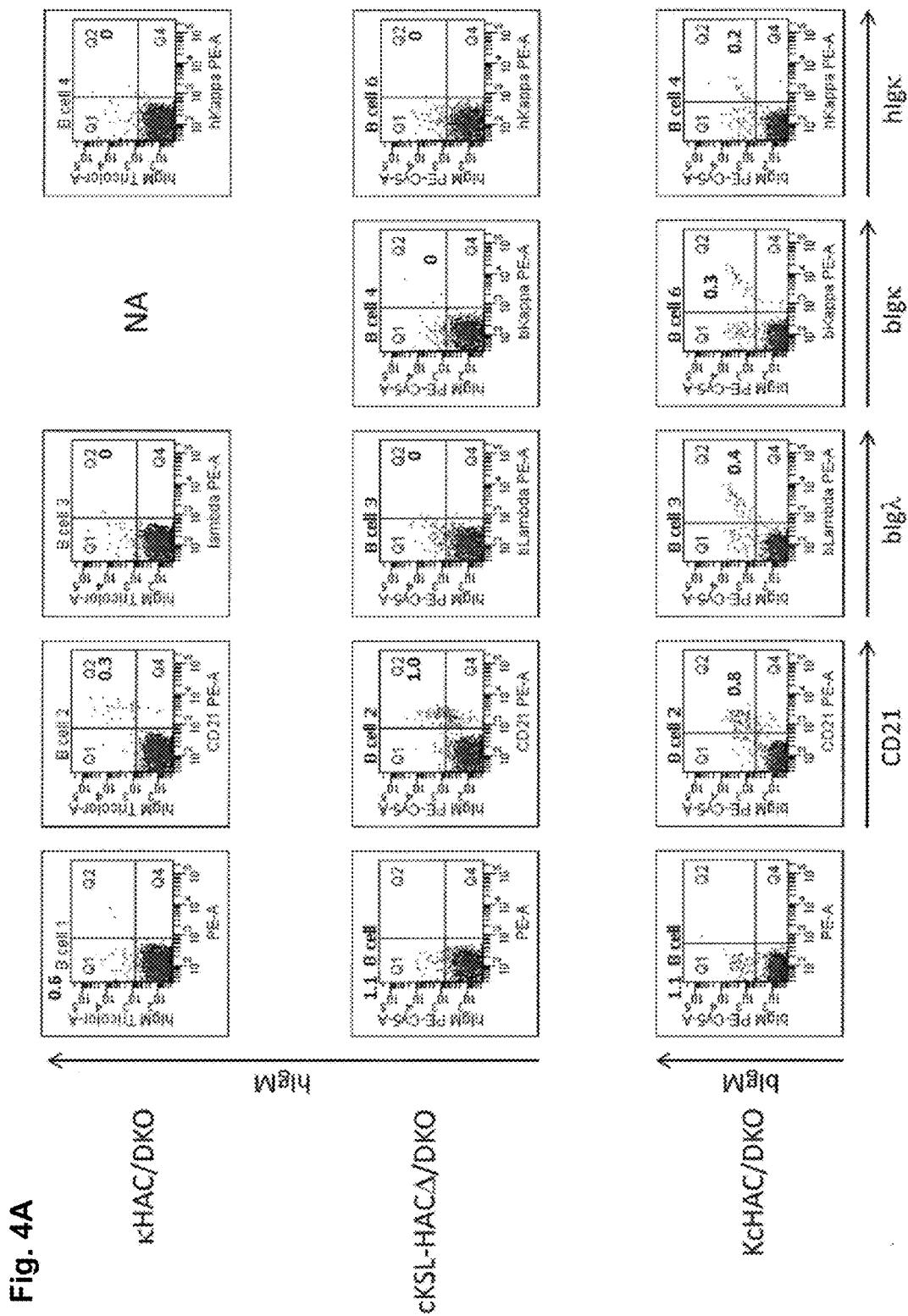
FIG. 4 shows the characterization of the κHAC, cKSL-HACΔ and KcHAC IGHM$^{-/-}$IGHML1$^{-/-}$ double knockout (DKO) calves. (A) Representative flow cytometry analysis of peripheral blood monocytes (PBMCs) from a series of HAC/DKO calves at newborn stage. For IgM detection, anti-hIgM or anti-bIgM antibody was used for the κHAC and cKSL-HACΔ/DKO calves or for the KcHAC/DKO calves, respectively. From left to right panels, PBMCs were stained for IgM alone, IgM/bCD21, IgM/bIgλ, IgM/bIgκ and IgM/hIgκ. Each bold number represents percentages of cells in Q1 (IgM alone) or Q2 (IgM/bCD21, IgM/bIgλ, IgM/bIgκ and IgM/hIgκ). NA; not applicable (because, at that time, the anti-bIgκ antibody was not available). (B,C) Serum concentrations of (B) total hIgG (μg/ml) and (C) fully hIgG/hIgκ (μg/ml) in a series of HAC/DKO calves at 5-6 months of age. n, number of animals analyzed for each genotype. For each genotype, values of minimum, first quartile, median, third quartile and maximum were calculated and plotted in each graph. The values of calf 468 were indicated in dashed circle. (D,E) Serum (D) fully hIgG/hIgκ (%)/total hIgG and (E) hIgG1/hIgG2 ratio in a series of HAC/DKO calves at 5-6 months of age. n, number of animals analyzed for each genotype. For each genotype, values of minimum, first quartile, median, third quartile and maximum were calculated and plotted in the left graph.
Figure 12C:
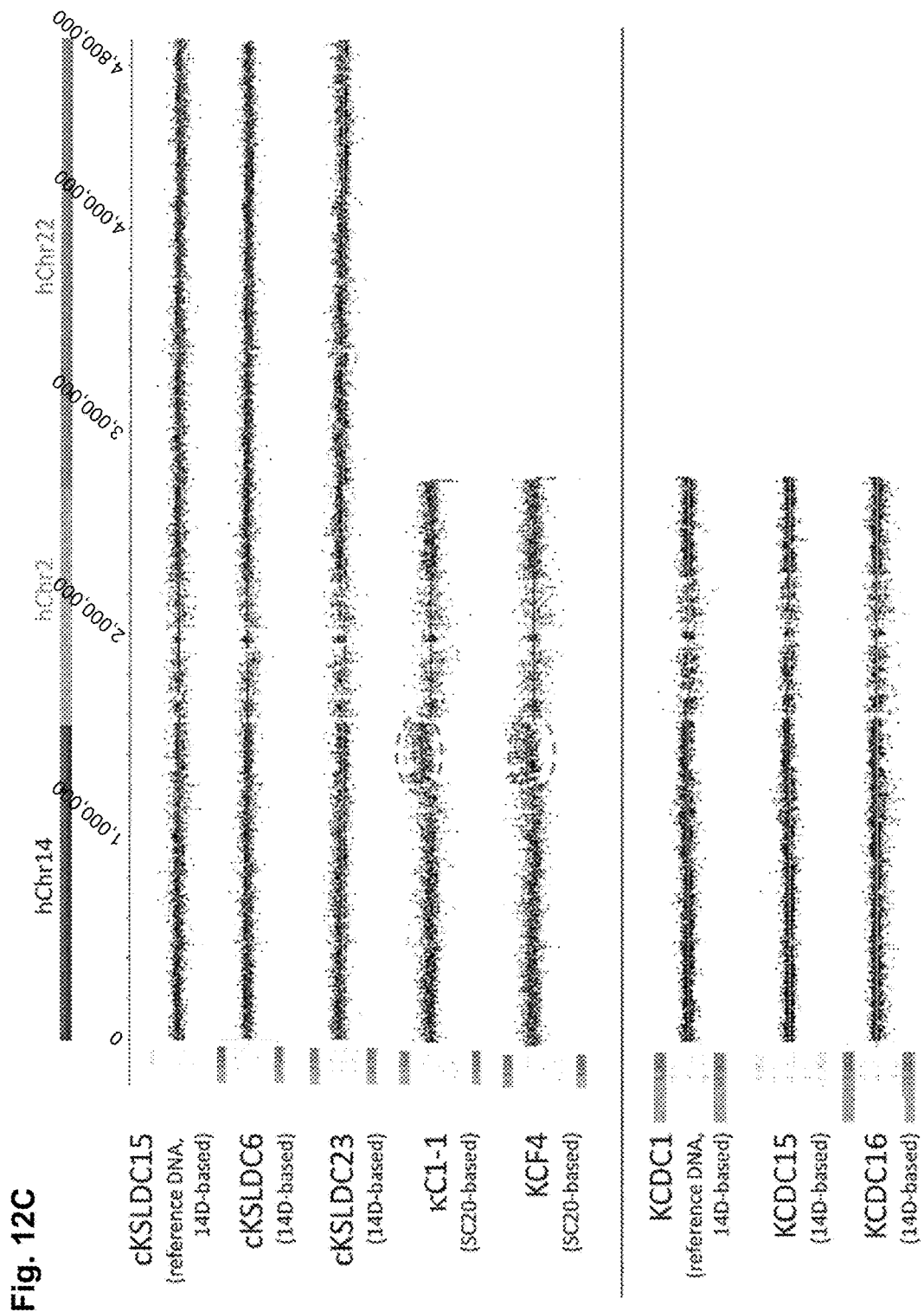
Figure 12D:
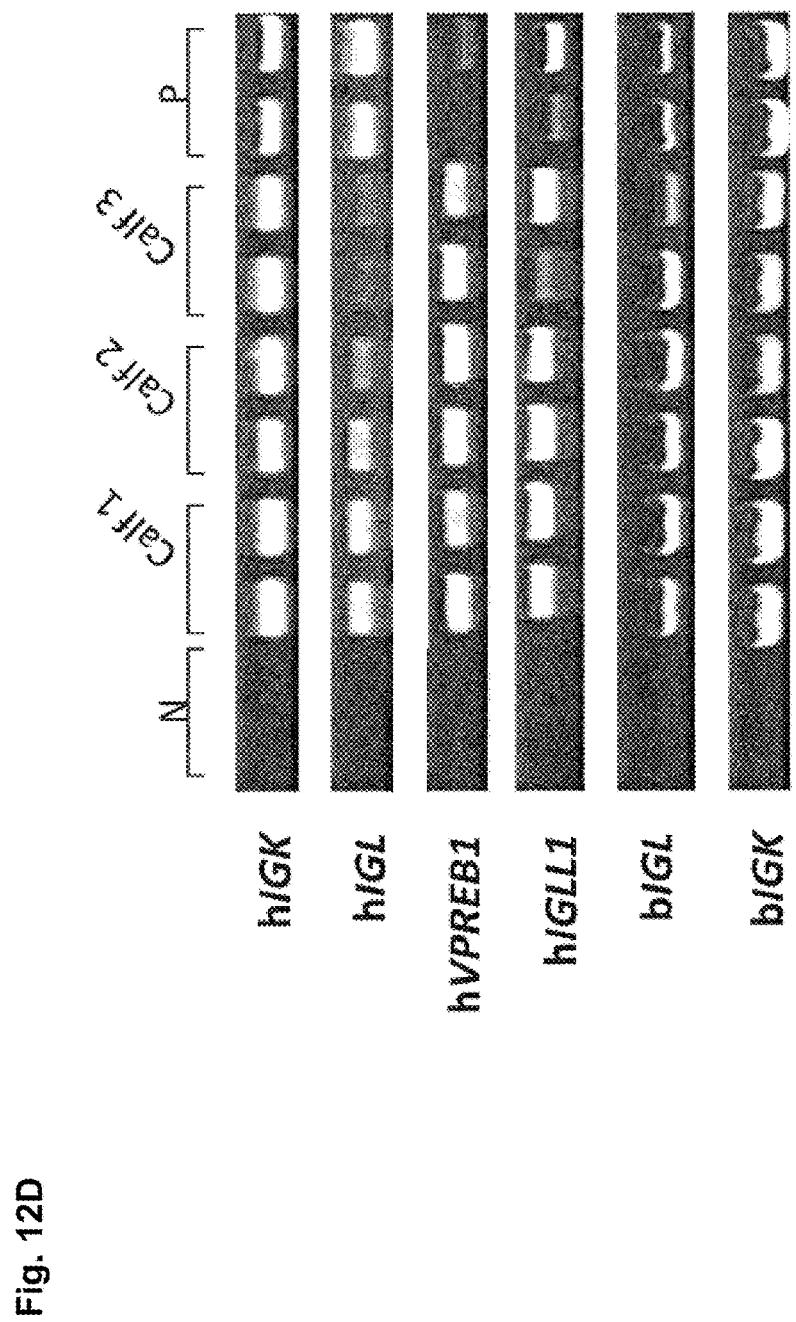

Example 4. Human IgG Production in a Series of HAC/IGHM$^{-/-}$IGHML1$^{-/-}$ (DKO) Cattle The cKSL-HACΔ, KcHACΔ and KcHAC vectors were transferred to Chinese hamster ovary (CHO) cells by means of MMCT to establish CHO-based master cell banks, cKSLDC6, 15, 23, KCDC15 and CKF4, respectively, which were confirmed by the extensive genomic PCR and CGH (FIG. 12A-12C). Three HAC vectors, cKSL-HACΔ, KcHAC and κHAC, were then transferred from the CHO cell lines to IGHM$^{-/-}$IGHML1$^{-/-}$ (DKO) cell lines obtained from breeding to generate cKSL-HACΔ/DKO, KcHAC/DKO and κHAC/DKO calves. An aim of the cKSL-HACΔ and KcHAC vectors was to address the species-incompatibility between human and bovine in the IgM-mediated pre-BCR/BCR function for B cell development, therefore B cell development profile was investigated in peripheral blood mononuclear cells (PBMCs) of these animals at newborn stage (FIG. 4A). For IgM detection in the KcHAC/DKO animals, anti-bIgM antibody was used because of its bovinized CH1 domain while anti-hIgM antibody can still recognize the cIgM (CH2) protein from the cKSL-HACΔ vector. In comparison with the κHAC/DKO animals, both the cKSL-HACΔ/DKO and KcHAC/DKO calves indicated higher percentages of IgM-single positive and IgM/CD21-double positive B cells. Surprisingly, IgM/bIgλ, IgM/bIgκ and even IgM/hIgκ-double positive B cells were only detected in the KcHAC/DKO animals. In the cKSL-HACΔ/DKO calves, either hIgM/bIgλ, hIgM/bIgκ, hIgM/hIgκ or hIgM/hIgλ-double positive B cells were undetectable by flow cytometry, despite the increased percentage of hIgM/CD21-double positive B cells, although these transcripts were detected by RT-PCR (FIG. 12D).

Figure 4B:
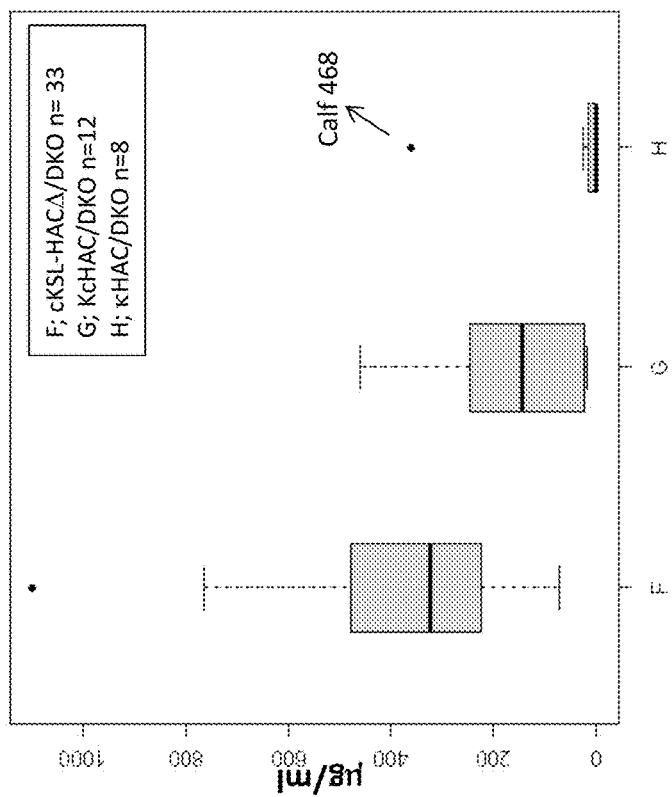
Figure 4C:
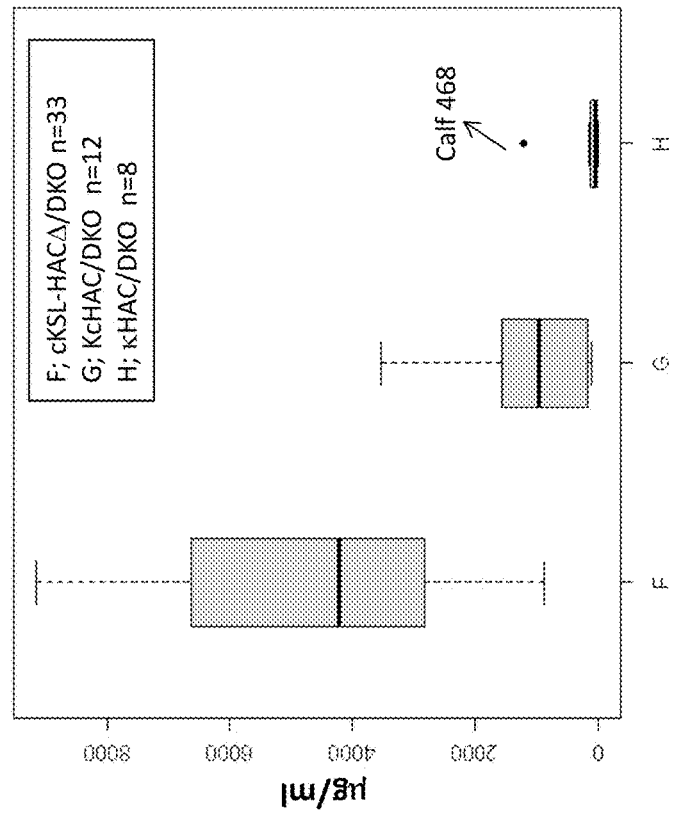
Figure 4E:
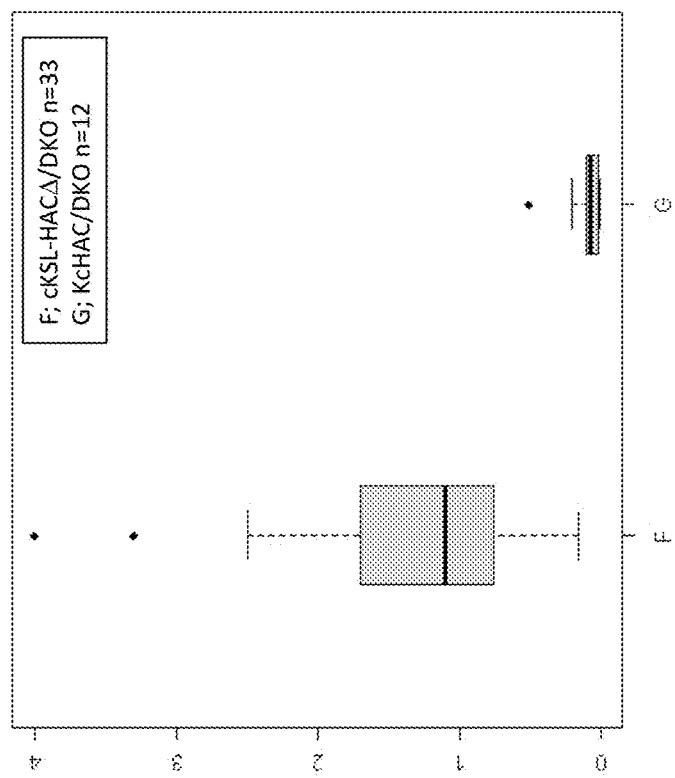
Figure 4D:
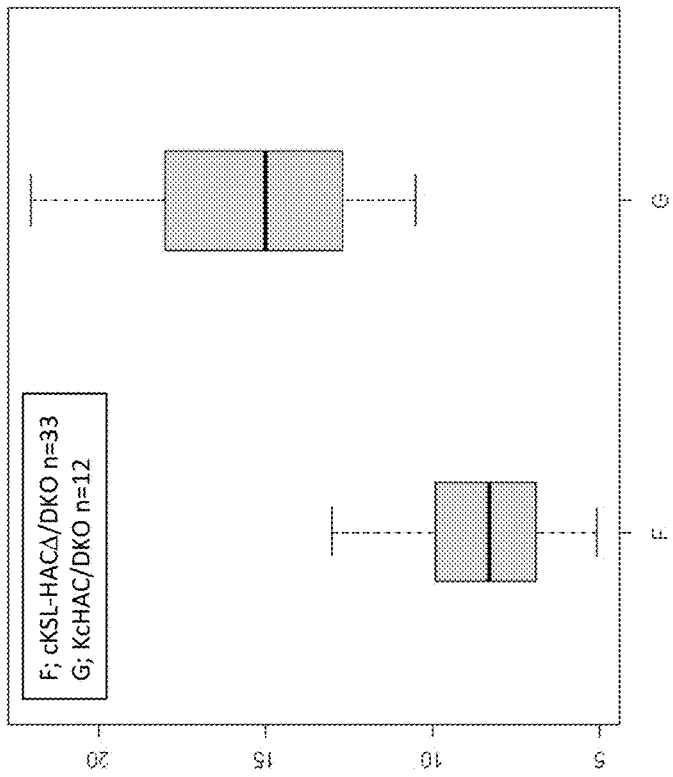

Around 5-6 months of age, concentrations of serum total hIgG, pairing either with hIgκ/λ or bIgλ/κ, and fully hIgG/hIgκ were measured (FIG. 4B). Compared with the κHAC/DKO animals excluding calf 468, serum concentrations of total hIgG drastically increased particularly with the cKSL-HACΔ vector with mostly hIgG1-dominance (hIgG1/hIgG2 ratio >1) while the KcHAC/DKO animals showed considerably high hIgG2 dominancy (FIG. 4C). Although the cKSL-HACΔ/DKO calves produced substantially higher amounts of total hIgG than the KcHAC/DKO ones, percentages of fully hIgG/hIgκ appeared to be lower (FIG. 4B, 4C), with fully hIgG/hIgλ being 5-10% of fully hIgG/hIgκ.

These data suggest potential species-incompatibilities in the IgM pre-BCR/BCR function, leading to the considerable differences in the B cell development and hIgG production profile between the differently bovinized cIgM (CH1) and cIgM (CH2) proteins without or with human surrogate light chain. This is novel evidence of the species-incompatibility in IgM pre-BCR/BCR function that eventually affects fully hIgG production profile.

Example 5. isHAC, istHAC and isKcHACΔ Vector Construction

The next strategy was to directly alter the efficiency of class switch to hIgG, especially to hIgG1, by direct bovinization of the hIGHG1 gene class switch regulatory element on the cKSL-HACΔ and KcHACΔ vectors. The transmembrane and cytoplasmic domains of the hIGHG1 gene were also bovinized for potentially better hIgG1 BCR-mediated signaling under the bovine environment.

Figure 13A:
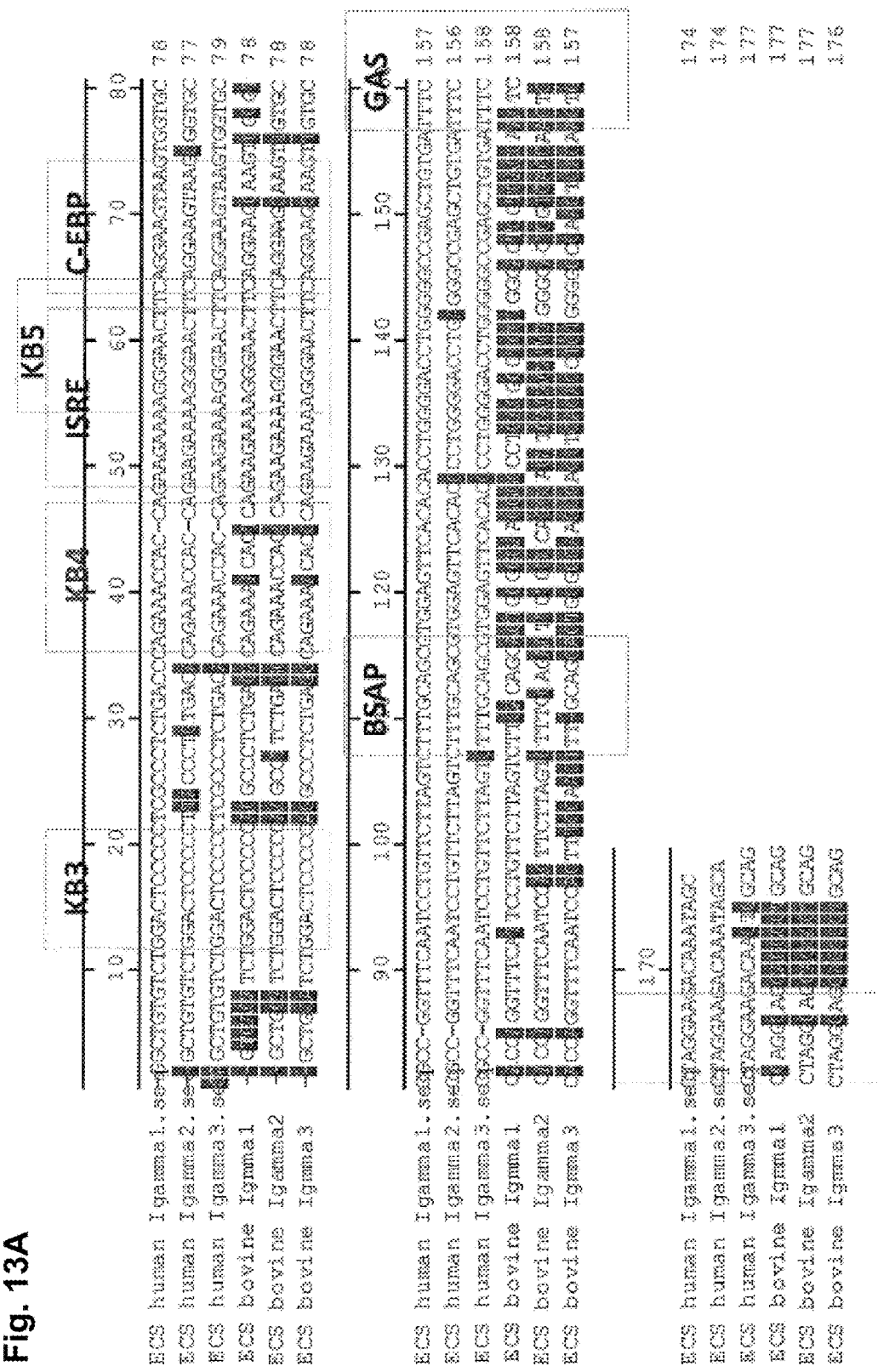
FIG. 13 shows the alignment of the sequence relevant to IgG1 class switch regulation and secretion between bovine and human. (A) Alignment of DNA sequence of the $I_{\gamma 1}$ (human Igamma1 SEQ ID NO: 166, bovine Igamma1 SEQ ID NO: 167), $I_{\gamma 2}$ (human Igamma 2 SEQ ID NO: 168, bovine Igamma2 SEQ ID NO: 169) and $I_{\gamma 3}$ (human Igamma 3 SEQ ID NO: 170, bovine Igamma3 SEQ ID NO: 171) ECS (evolutionary conserved sequence) elements between human and bovine. Shaded nucleotide base depicts a different one from the human $I_{\gamma 1}$ sequence. Binding sites of KB3 (kappa B3), KB4 (kappa B4), KB5 (kappa B5), ISRE (interferon stimulated response element), C-EBP (CCAAT-enhancer binding protein), BSAP (B-cell lineage specific activator protein) and GAS (Gamma interferon activation site) are indicated by line rectangle. (B) Dot plot alignment between the human and bovine $S_{\gamma 1}$ sequence. (C) Amino acid sequence alignment of the IgG1 transmembrane/cytoplasmic domains between human (SEQ ID NO: 172) and bovine (SEQ ID NO: 173). Shaded amino acid depicts a different one from human.
Figure 13B:
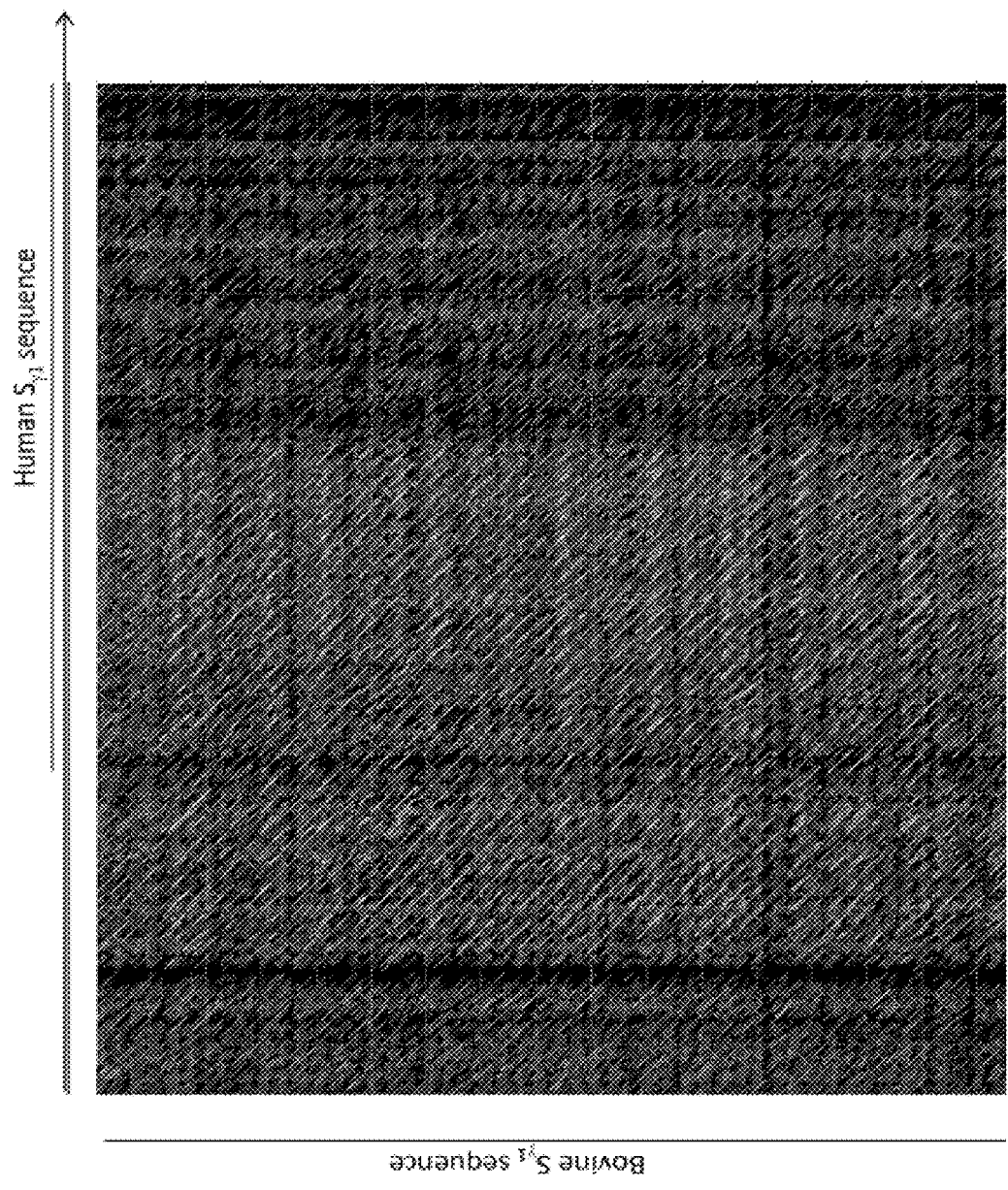
Figure 14:
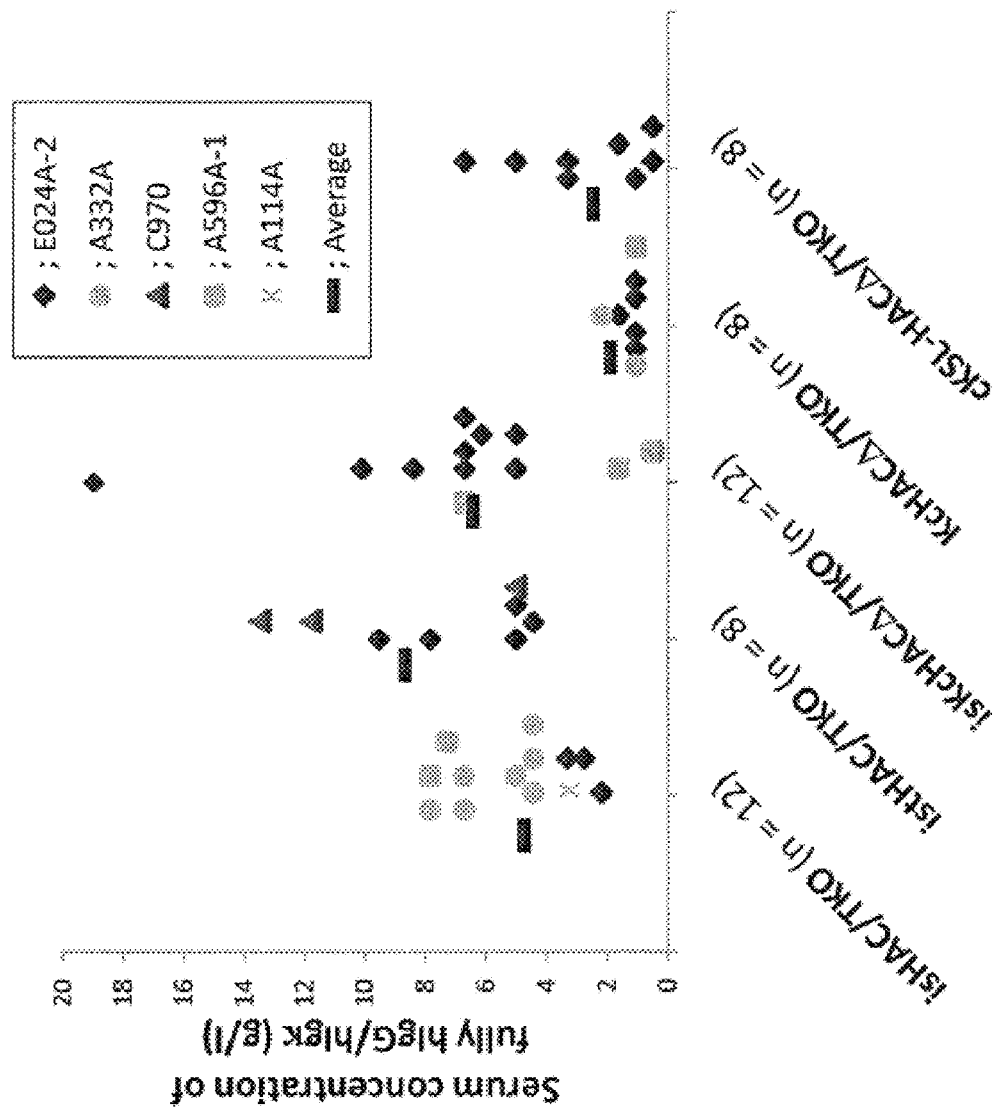
FIG. 14 shows serum concentrations of fully hIgG/hIgκ (g/L) in a series of HAC/TKO calves at 5-6 months of age. n, number of animals analyzed for each genotype. For each genotype, individual value was plotted, based on the TKO cell line used.

The determination on IgG subclass class switch recombination is preceded by transcription from each immunoglobulin heavy chain (IGH) locus-associated switch region ($S_H$), called germline transcript. Each IGH constant region ($C_H$) gene is linked with its own $S_H$ region which is also associated with its own $I_H$ exons. The germline transcript $I_H$-$S_H$-$C_H$ (eventually spliced to mature $I_H$-$C_H$) is driven by the promoter/enhancer elements located just 5' of the $I_H$ exons and those elements are cytokine or other activator-responsive. In a simple model of class switch, the specific activators and/or cytokines induce the germline transcript from its activator/cytokine-responsive $I_H$ promoter/enhancer. The 3'E$_\alpha$ element further enhances the transcription of $I_H$-$S_H$-$C_H$ sequence. This transcription causes the switch region to be relaxed so that it can be targeted by the enzyme, activation-induced cytidine deaminase (AID), which causes fusion with another $S_H$ region, leading to class switch. A hypothesis was that, for example, the hI$_{\gamma1}$-hS$_{\gamma1}$ regulatory element (from human IgG1) linked with the hIGHG1 gene was somehow incompatible with such bovine activators/cytokines-induced proteins to efficiently induce class switch to hIgG1, due to the species-specific sequence differences (FIG. 13A, 13B). This may be why many Tc bovines showed hIgG2-dominancy while hIgG1 is a major subclass in humans.

Figure 5:
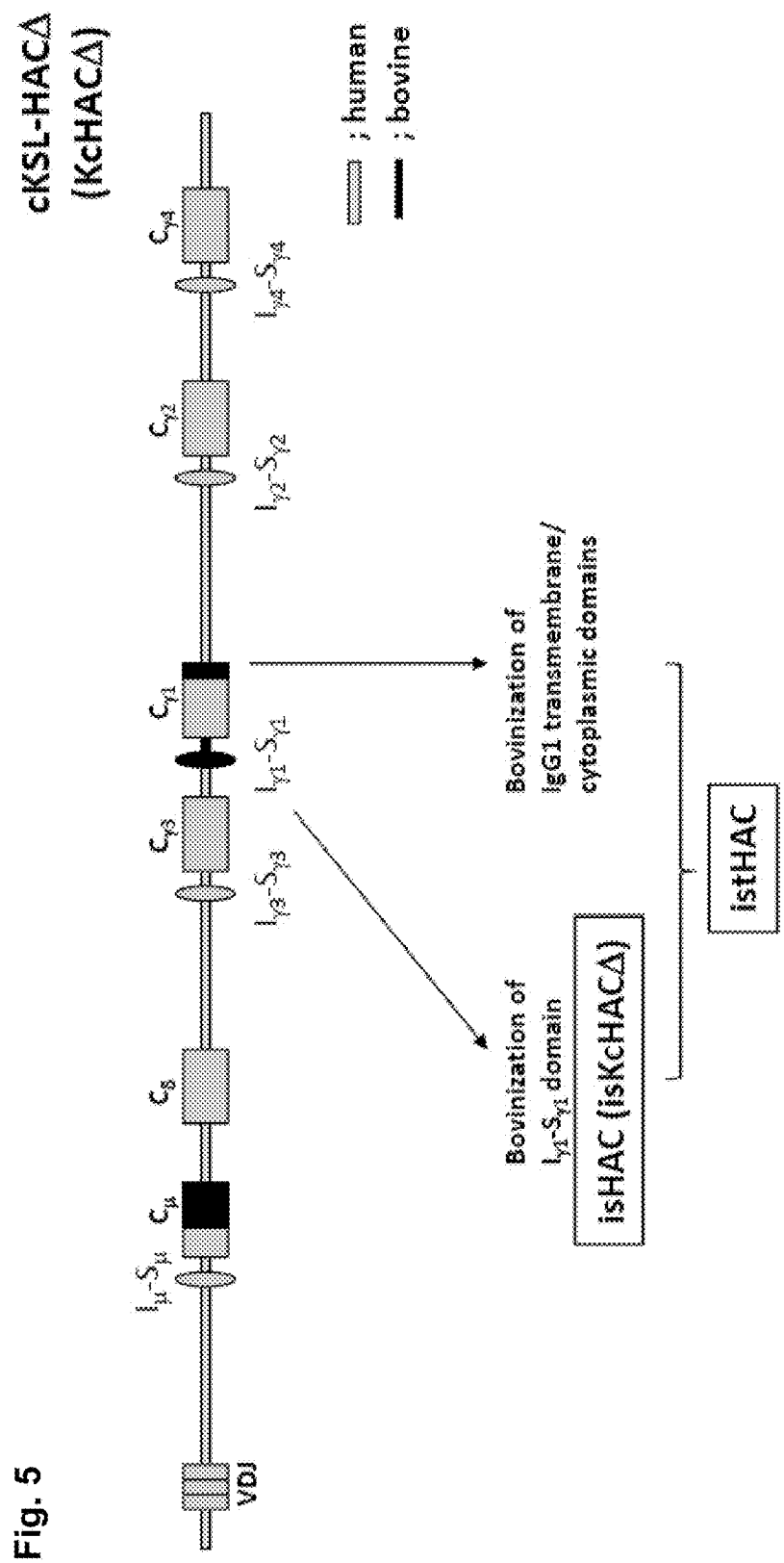
FIG. 5 shows the construction of the isHAC (isKcHACΔ) and istHAC. On either cKSL-HACΔ or KcHACΔ vector, the $hI_{\gamma 1}$-$hS_{\gamma 1}$ class switch regulatory element was bovinized to build the isHAC or isKcHACΔ vector, respectively. The istHAC vector is a derivative of the isHAC vector where the hIGHG1 gene transmembrane/cytoplasmic domains were also bovinized.

Based on the above hypothesis, the hI$_{\gamma1}$-hS$_{\gamma1}$ class switch regulatory element was bovinized with the class switch regulatory element of the bIGHG1 gene to construct the isHAC vector having the bI$_{\gamma1}$-bS$_{\gamma1}$ sequence upstream of the hC$_{\gamma1}$ (human heavy chain IgG1) region on the cKSL-HACΔ vector (FIG. 5, see also Methods). Moreover, the transmembrane and cytoplasmic domains of the hIGHG1 gene on the isHAC was further bovinized with the bIGHG1 gene transmembrane and cytoplasmic domains to generate the istHAC (FIG. 5, see also Methods), considering the species-specific sequence differences (FIG. 13C). Since the cKSL-HACΔ and KcHACΔ vectors might potentially have functional differences, as seen in the DKO background, and it was uncertain how these two HACs would behave in the TKO background lacking the bIGL expression, the KcHACΔ vector was also bovinized to build the isKcHACΔ vector having the bI$_{\gamma1}$-bS$_{\gamma1}$ sequence upstream of the hC$_{\gamma1}$ region on the KcHACΔ (FIG. 5, see also Methods).

Figure 6A:
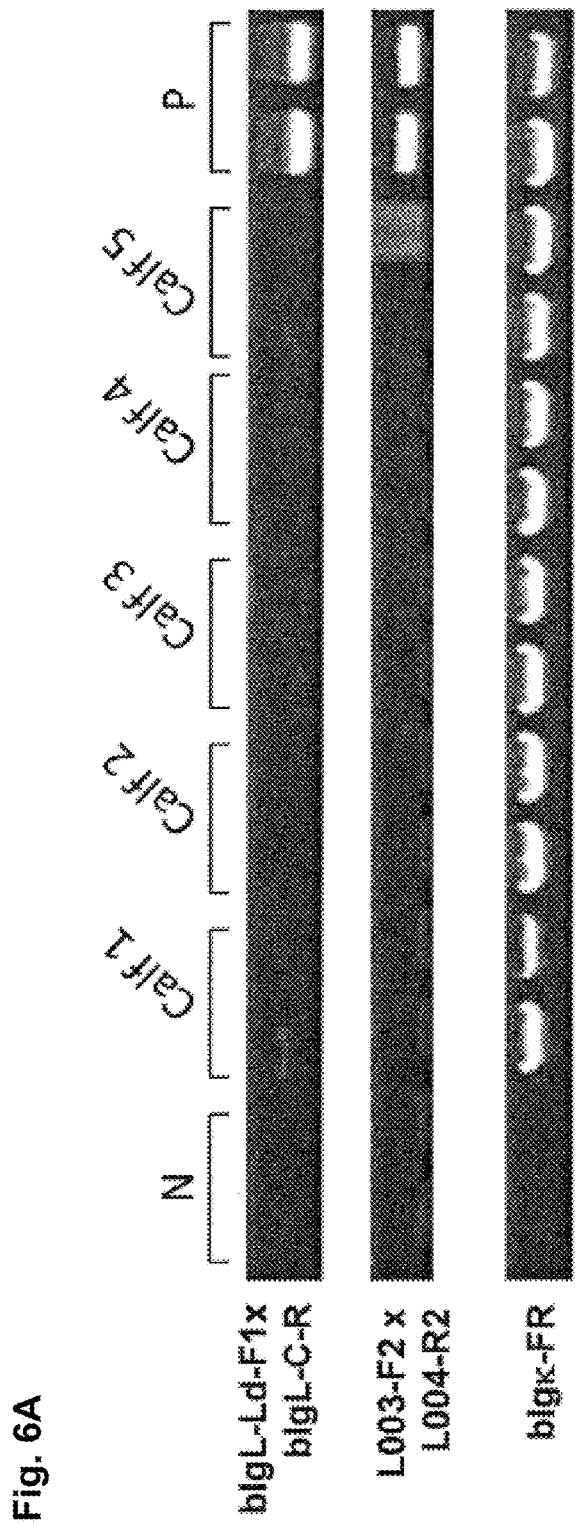
FIG. 6 shows the characterization of the isHAC/TKO, istHAC/TKO and isKcHACΔ/TKO calves. (A) Lack of the bIGL expression in the HAC/TKO calves. PBMCs from five KcHACΔ/TKO calves (Calf 1-5) at newborn stage were subjected to RT-PCR to confirm the lack of the bIGL expression. The primer pairs, bIgL-Ld-F1×bIgL-C-R and L003-F2×L004-R2, are to amplify the VJ-rearranged bIGL and constant region IGLC (bC$_\lambda$) genes, respectively. The primer pair, bIgκ-FR, is to amplify the VJ-rearranged bIGK gene. N, negative control; P, positive control. (B) Representative flow cytometry analysis of PBMCs from a series of HAC/TKO calves at newborn stage. For IgM detection, anti-hIgM or anti-bIgM antibody was used for the isHAC, istHAC and cKSL-HACΔ/TKO calves or for the isKcHACΔ and KcHACΔ/TKO calves, respectively. From left to right panels, PBMCs were stained for IgM alone, IgM/bCD21, IgM/bIgλ, IgM/bIgκ and IgM/hIgκ. Each bold number represents percentages of cells in Q1 (IgM alone) or Q2 (IgM/bCD21, IgM/bIgλ, IgM/bIgκ and IgM/hIgκ). (C) Box-whisker plots of serum concentrations of total hIgG (g/l) in a series of HAC/TKO and HAC/DKO calves at 5-6 months of age. A, cKSL-HACΔ/TKO (n=8); B, isHAC/TKO (n=12); C, istHAC/TKO (n=8); D, KcHACΔ/TKO (n=8); E, isKcHACΔ/TKO (n=12); F, cKSL-HACΔ/DKO (n=33); G, KcHAC/DKO (n=12); H, κHAC/DKO (n=8). Dots represent outliers. The value of calf 468 was indicated with an arrow. For each genotype, values of min, first quartile, median, third quartile and max were calculated and plotted in each graph. (D) Panel shows 95% family-wise confidence level in each pair comparison. (E) Box-whisker plots of serum concentrations of fully hIgG/hIgκ (g/l) in a series of HAC/TKO and HAC/DKO calves at 5-6 months of age. A, cKSL-HACΔ/TKO (n=8); B, isHAC/TKO (n=12); C, istHAC/TKO (n=8); D, KcHACΔ/TKO (n=8); E, isKcHACΔ/TKO (n=12); F, cKSL-HACΔ/DKO (n=33); G, KcHAC/DKO (n=12); H, κHAC/DKO (n=8). Dots represent outliers. The value of calf 468 was indicated with an arrow. For each genotype, values of min, first quartile, median, third quartile and max were calculated and plotted in each graph. (F) Panel shows 95% family-wise confidence level in each pair comparison. (G) Box-whisker plots of serum fully hIgG/hIgκ (%)/total hIgG in a series of HAC/TKO and HAC/DKO calves at 5-6 months of age. Dots represent outliers. The value of calf 468 was indicated with an arrow. For each genotype, values of min, first quartile, median, third quartile and max were calculated and plotted in each graph. (H) Panel shows 95% family-wise confidence level in each pair comparison. n, number of animals analyzed for each genotype. (I) Box-whisker plots of hIgG1/hIgG2 ratio in a series of HAC/TKO and HAC/DKO calves at 5-6 months of age. Dots represent outliers. A, cKSL-HACΔ/TKO (n=8); B, isHAC/TKO (n=12); C, istHAC/TKO (n=8); D, KcHACΔ/TKO (n=8); E, isKcHACΔ/TKO (n=12); F, cKSL-HACΔ/DKO (n=33); G, KcHAC/DKO (n=12); H, κHAC/DKO (n=8). For each genotype, values of min, first quartile, median, third quartile and max were calculated and plotted in the left graph. (J) Panel shows 95% family-wise confidence level in each pair comparison in difference in proportions of hIgG1-dominancy. (K) The table shows actual values for each genotype. (L) Anti-human carcinoma hIgG/hIgκ response in a series of HAC/TKO and HAC/DKO calves, following two times vaccinations (V2) of human oral squamous cell carcinoma. The percentages of bold rectangle area shows percentages of the human carcinoma cells doubly positive with hIgG and hIgκ derived from serum of each animal at day 9-10 after V2, where serum dilution factor is 1:1280. A separated panel labeled as "V1D0" is flow cytometry result of the human carcinoma cells stained with serum of the istHAC/TKO calf 2 at day 0 after V1 (V1D0), where serum dilution factor is 1:1280.
Figure 6B:
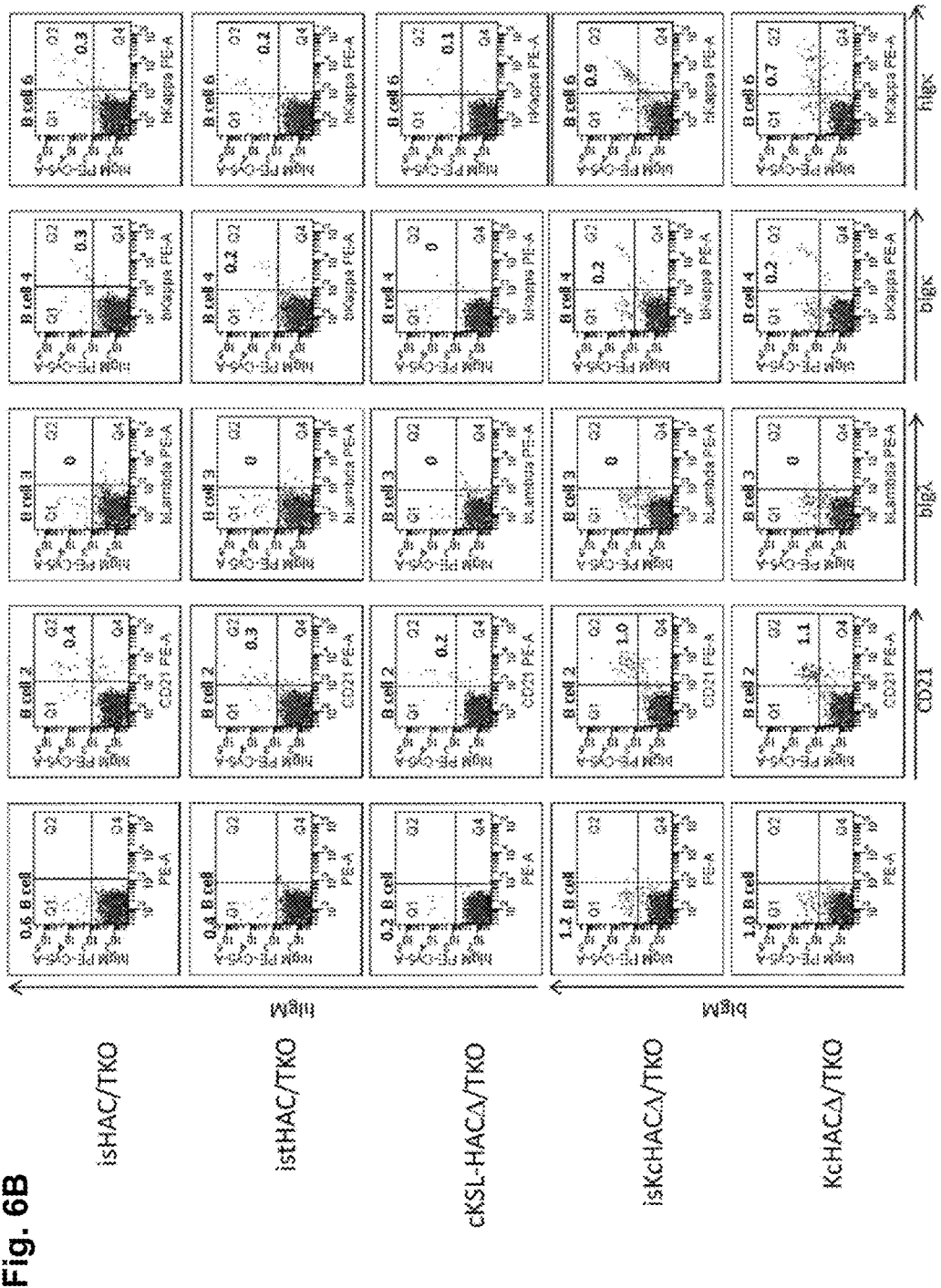
Figure 6H:
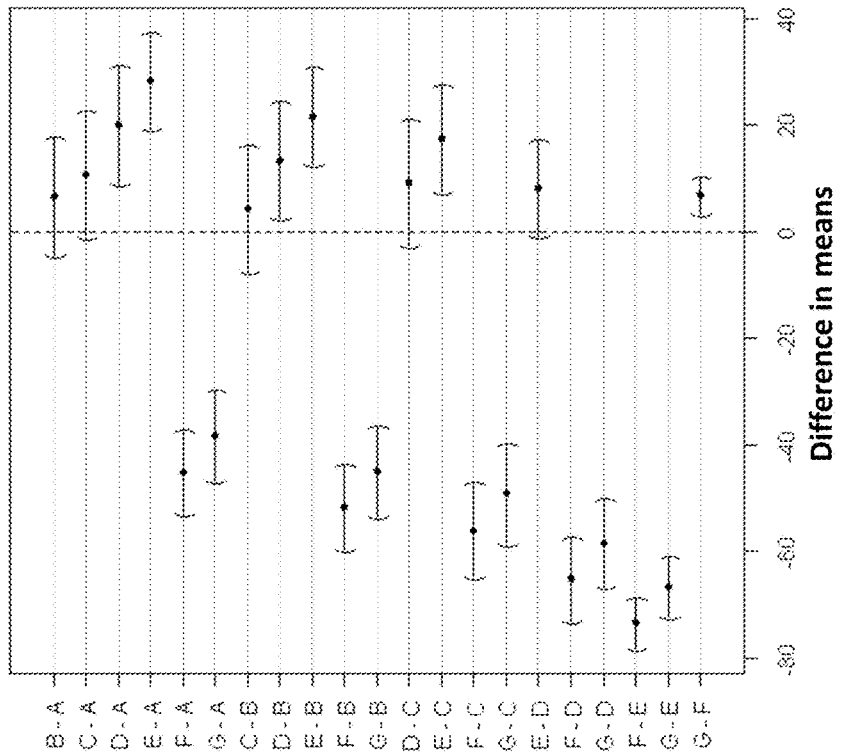
Figure 6G:
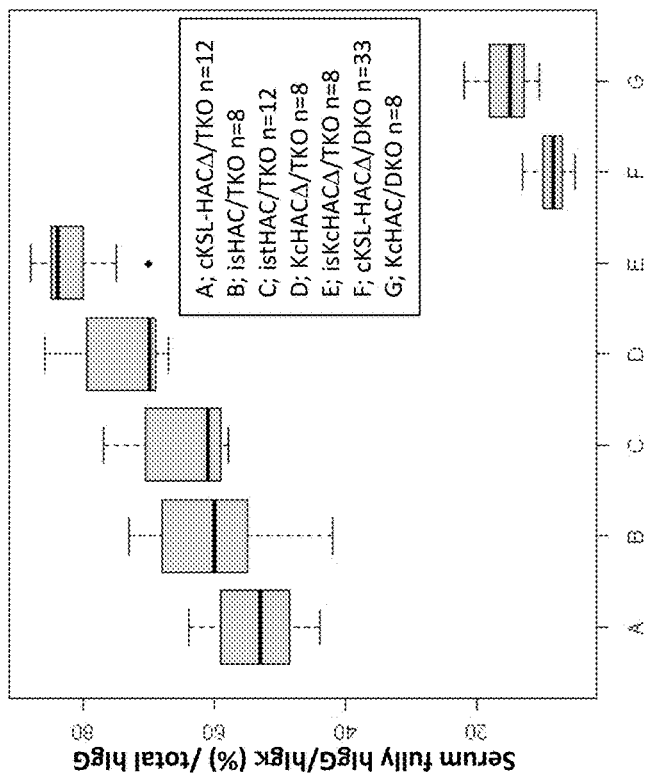

Example 6. Human IgG Production in a Series of HAC/IGHM$^{-/-}$IGHML1$^{-/-}$IGL$^{-/-}$ (TKO) Cattle The isHAC, istHAC, isKcHACΔ, KcHACΔ and cKSL-HACΔ vectors were transferred from the CHO master cell banks to the IGHM$^{-/-}$IGHML1$^{-/-}$IGL$^{-/-}$ (TKO) cell lines by MMCT to generate a series of HAC/TKO calves. Calving efficiency at 270 days of gestation was around 7% out of recipients implanted, 60-70% of which survived at least up to 5-6 months after birth (Table 2). First of all, the lack of the bIGL expression was confirmed by RT-PCR at newborn stage (FIG. 6A). Then, in order to address an impact of the ablation of the bIGL expression on B cell development, flow cytometry was performed on the five genotypes of HAC/TKO calves at newborn stage (FIG. 6B). In comparison with the DKO background, percentages of hIgM-single positive and hIgM/CD21-double positive B cells seemed lower, except that percentages of hIgM/hIgκ (or hIgM/bIgκ)-double positive B cells increased, in the cKSL-HACΔ series (e.g., isHAC, istHAC and cKSL-HACΔ itself) with hIgG/hIgλ-double positive B cells undetectable. On the contrary, percentages of bIgM-single positive and bIgM/CD21-double positive B cells appear to be considerably similar to that of the DKO background in the KcHACΔ series (e.g., isKcHACΔ and KcHACΔ itself), with percentages of bIgM/hIgκ (or bIgM/bIgκ)-double positive B cells substantially increased.

TABLE 3-continued p values for the comparison in serum concentration of total hIgG among the genotypes

| A | B | C | D | E | F | G | H |
|---|---|---|---|---|---|---|---|
| F |   |   |   |   |   | <0.001* | <0.001* |
| G |   |   |   |   |   |   | 0.1111 |

A, cKSL-HACΔ/TKO (n = 8);
B, isHAC/TKO (n = 12);
C, istHAC/TKO (n = 8);
D, KcHACΔ/TKO (n = 8);
E, isKcHACΔ/TKO (n = 12);
F, cKSL-HACΔ/DKO (n = 33);
G, KcHAC/DKO (n = 12);
H, κHAC/DKO (n = 8)
*shows a significant difference (p < 0.05).

TABLE 2

Production of cloned calves from genetically modified fibroblast cell lines

| TKO cell line ID | Genotype | Recipients | Pregnant at (%)$^a$ | | | | Calves survived up to 5-6 months (%)$^a$ |
|---|---|---|---|---|---|---|---|
| | | | 40 d | 120 d | 180 d | 270 d | |
| E024A-2 | KcHACΔ/TKO | 85 | 36 (42) | 17 (20) | 17 (20) | 6 (7) | 5 (6) |
| A596A-1 | | 85 | 22 (26) | 11 (13) | 10 (12) | 5 (6) | 1 (1) |
| A332A | | 80 | 28 (35) | 9 (11) | 9 (11) | 4 (5) | 2 (3) |
| Subtotal | | 250 | 86 (34) | 37 (15) | 36 (14) | 15 (6) | 8 (3.2) |
| E024A-2 | cKSL-HACΔ/TKO | 139 | 52 (37) | 27 (19) | 25 (18) | 13 (9) | 8 (6) |
| E024A-2 | isHAC/TKO | 81 | 19 (23) | 4 (5) | 4 (5) | 3 (4) | 3 (4) |
| A596A-1 | | 80 | 24 (30) | 10 (13) | 9 (11) | 3 (4) | 2 (3) |
| A332A | | 68 | 21 (31) | 13 (19) | 12 (18) | 6 (9) | 6 (9) |
| A114A | | 48 | 18 (38) | 8 (17) | 7 (15) | 2 (4) | 1 (2) |
| Subtotal | | 277 | 82 (30) | 35 (13) | 32 (12) | 14 (5.1) | 12 (4.3) |
| E024A-2 | istHAC/TKO | 80 | 29 (36) | 18 (23) | 16 (20) | 8 (10) | 5 (6) |
| C970 | | 46 | 20 (43) | 11 (24) | 9 (20) | 3 (7) | 3 (7) |
| Subtotal | | 126 | 49 (39) | 29 (23) | 25 (20) | 11 (8.7) | 8 (6.3) |
| E024A-2 | isKcHACΔ/TKO | 80 | 33 (41) | 24 (30) | 24 (30) | 11 (14) | 9 (11) |
| A596A-1 | | 80 | 41 (51) | 21 (26) | 19 (24) | 6 (8) | 3 (4) |
| Subtotal | | 160 | 74 (46) | 45 (28) | 43 (27) | 17 (11) | 12 (7.5) |
| Total | | 952 | 343 (36) | 173 (18) | 161 (17) | 70 (7.4) | 48 (5) |

$^a$Percentages were calculated by dividing the number of fetuses or calves by that of recipients implanted.

TABLE 3 p values for the comparison in serum concentration of total hIgG among the genotypes

| | A | B | C | D | E | F | G | H |
|---|---|---|---|---|---|---|---|---|
| A | | 0.8096 | 0.1742 | 0.5559 | 0.9495 | 0.9818 | 0.0832 | 0.0205* |
| B | | | 0.6456 | <0.001* | 1.0000 | 0.0013* | <0.001* | <0.001* |
| C | | | | <0.001* | 0.8141 | 0.0018* | <0.001* | <0.001* |
| D | | | | | 0.0328* | 0.0039* | <0.001* | <0.001* |
| E | | | | | | 0.2741 | 0.0018* | <0.001* |

TABLE 4 p values for the comparison in serum concentration of fully hIgG/hIgκ among the genotypes

| | A | B | C | D | E | F | G | H |
|---|---|---|---|---|---|---|---|---|
| A | | 0.5011 | 0.0369* | 0.9092 | 0.2341 | 0.0438* | 0.0241* | 0.0170* |
| B | | | 0.4092 | <0.001* | 0.9202 | <0.001* | <0.001* | <0.001* |
| C | | | | <0.001* | 0.9974 | <0.001* | <0.001* | <0.001* |
| D | | | | | 0.0055* | <0.001* | <0.001* | <0.001* |

TABLE 4-continued p values for the comparison in serum concentration
of fully hIgG/hIgκ among the genotypes

| A | B | C | D | E | F | G | H |
|---|---|---|---|---|---|---|---|
| E |   |   |   |   | <0.001* | <0.001* | <0.001* |
| F |   |   |   |   |   | 0.0039* | <0.001* |
| G |   |   |   |   |   |   | 0.5162 |

A, cKSL-HACΔ/TKO (n = 8);
B, isHAC/TKO (n = 12);
C, istHAC/TKO (n = 8);
D, KcHACΔ/TKO (n = 8);
E, isKcHACΔ/TKO (n = 12);
F, cKSL-HACΔ/DKO (n = 33);
G, KcHAC/DKO (n = 12);
H, κHAC/DKO (n = 8)
*shows a significant difference (p < 0.05).

TABLE 5 p values for the comparison in serum fully hIgG/hIgκ
(%)/total hIgG among the genotypes

| | A | B | C | D | E | F | G |
|---|---|---|---|---|---|---|---|
| A |   | 0.5344 | 0.0914 | <0.001* | <0.001* | <0.001* | <0.001* |
| B |   |   | 0.9248 | 0.0074* | <0.001* | <0.001* | <0.001* |
| C |   |   |   | 0.2155 | <0.001* | <0.001* | <0.001* |
| D |   |   |   |   | 0.0938* | <0.001* | <0.001* |
| E |   |   |   |   |   | <0.001* | <0.001* |
| F |   |   |   |   |   |   | <0.001* |

A, cKSL-HACΔ/TKO (n = 8);
B, isHAC/TKO (n = 12);
C, istHAC/TKO (n = 8);
D, KcHACΔ/TKO (n = 8);
E, isKcHACΔ/TKO (n = 12);
F, cKSL-HACΔ/DKO (n = 33);
G, KcHAC/DKO (n = 12)
*shows a significant difference (p < 0.05).

Figure 15:
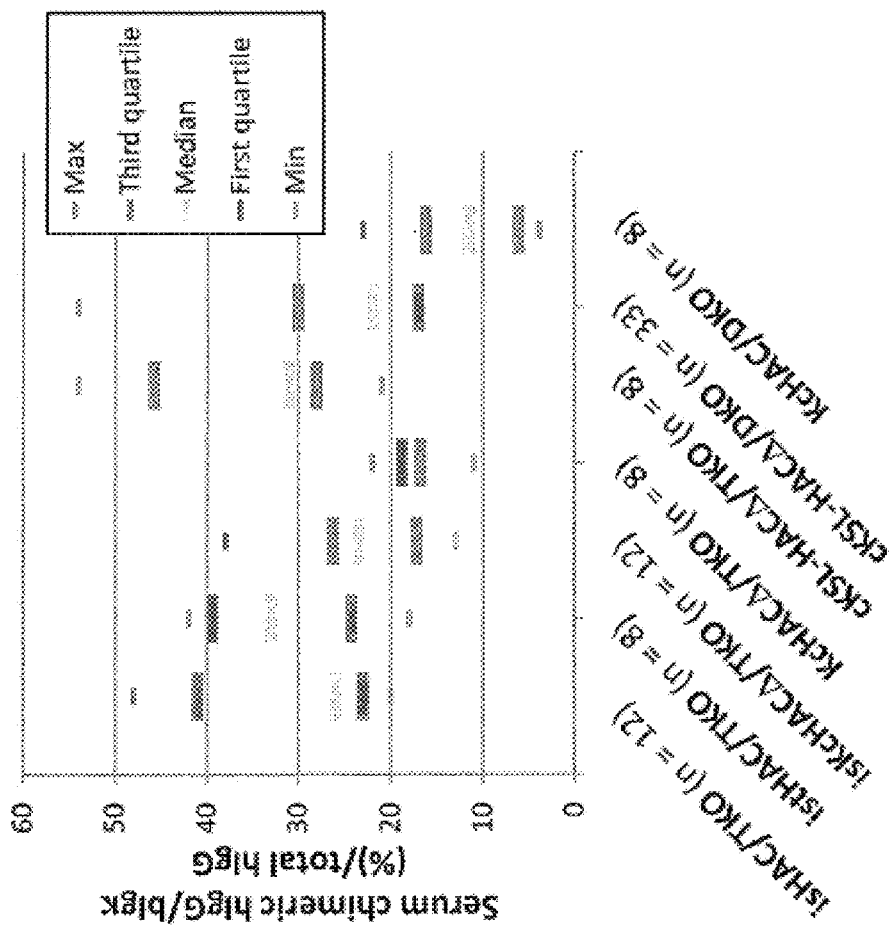
FIG. 15 shows serum fully hIgG/bIgκ (%)/total hIgG in a series of HAC/TKO and HAC/DKO calves at 5-6 months of age. n, number of animals analyzed for each genotype. For each genotype, values of min, first quartile, median, third quartile and max were calculated and plotted in the left graph.

Since the rationale for the isHAC, istHAC and isKcHACΔ vector construction was to directly alter the efficiency of class switch to hIgG, especially to hIgG1, under the bovine physiological condition, by bovinizing the hIGHG1 gene class switch regulatory element, serum concentrations of fully hIgG/hIgκ and hIgG subclass distribution were measured around 5-6 months of age in a series of HAC/TKO calves (FIG. 6C-6H, FIG. 14). Overall, in the five HAC/TKO genotypes, both concentrations and percentages of fully hIgG/hIgκ drastically increased when compared with those of the HAC/DKO animals including the previous unique calf 468, so the bIGL cluster deletion proved to be surprisingly effective for high productivity of fully hIgG/hIgκ. Fully hIgG/hIgλ was ~5% of hIgG/hIgκ and the rest was chimeric hIgG/bIgκ (FIG. 15). Surprisingly, the isHAC/TKO, particularly the istHAC/TKO calves, considerably raised both total hIgG and fully hIgG/hIgκ production when compared with their original cKSL-HACΔ/DKO and even cKSL-HACΔ/TKO animals (FIG. 6E and Table 4). Of particular note, hIgG1/hIgG2 ratio drastically arose both in the isHAC/TKO and istHAC/TKO calves while the cKSL-HACΔ/TKO animals turned hIgG2-dominant from hIgG1-dominancy in the cKSL-HACΔ/DKO ones (FIG. 6I). This observation was consistently seen also in comparison between the isKcHACΔ/TKO, KcHACΔ/TKO and KcHACΔ/DKO calves (FIG. 6C-6F), where fully hIgG/hIgκ production substantially increased with the switch to hIgG1-dominancy in the isKcHACΔ/TKO animals from hIgG2-dominancy in the original KcHACΔ/TKO and KcHAC/DKO calves.

These data demonstrated that the Iγ1-Sγ1 class switch regulatory element is controlled in a species-specific manner. The effect of the bovinized $I_{\gamma1}$-$S_{\gamma1}$ sequence is of a particular interest. It is reported that virtually all transcription factor-binding locations, landmarks of transcription initiation, and the resulting gene expression observed from the hChr21 in the human hepatocytes were recapitulated across the entire hChr21 in the mouse hepatocyte nucleus. This implies that the human-specific gene expression profile could be simply provided by the human DNA primary sequence even under the non-human species environment. Applying this view to the Tc bovine situation, the non-bovinized HAC would have been sufficient for providing the human-like hIgG expression profile, such as hIgG1-dominancy, in the bovine condition, which, however, was not the case. Thus, the finding that bovinization of the $hI_{\gamma1}$-$hS_{\gamma1}$ sequence surprisingly caused the sufficient switch from hIgG2-dominancy to hIgG1-dominancy in the Tc bovine condition strongly suggests the species-incompatibility in IgG1 class switch regulation between the two species. Since immunoglobulin gene organization and diversification including class switch are thought to be evolved distinctly among species, addressing such species-incompatibilities will be generally useful to express human antibodies in non-human species. The species-specific effect on fully hIgG serum concentration seems to be different between the differently bovinized cIgM proteins {cIgM (CH1) vs. cIgM (CH2)}; the bovinization of the Iγ1-Sγ1 element in the cIgM (CH1) background significantly improved it (i.e. isKcHACΔ vs KcHACΔ) while it did not in the cIgM (CH2) background (i.e. isHAC vs cKSL-HACΔ). In the cIgM (CH2) background, the bovinization of IgG1 transmembrane/cytoplasmic domains was additionally necessary to significantly improve fully hIgG/hIgκ production (i.e. istHAC vs cKSL-HACΔ). Both in the cIgM (CH1) and cIgM (CH2) backgrounds, the bovinized Iγ1-Sγ1 sequence drastically altered hIgG1 subclass-dominancy.

Figure 6L:
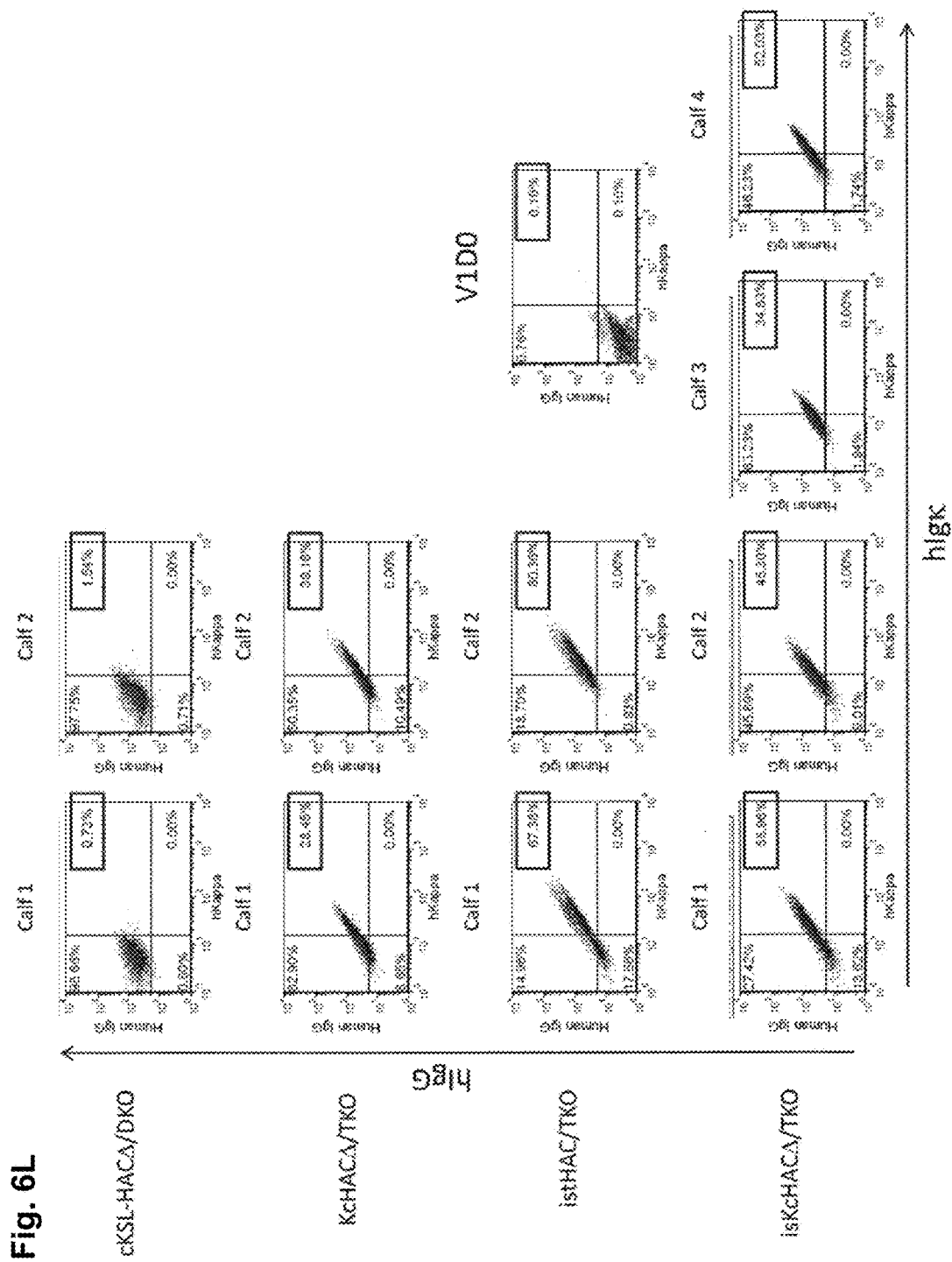
Figure 7:
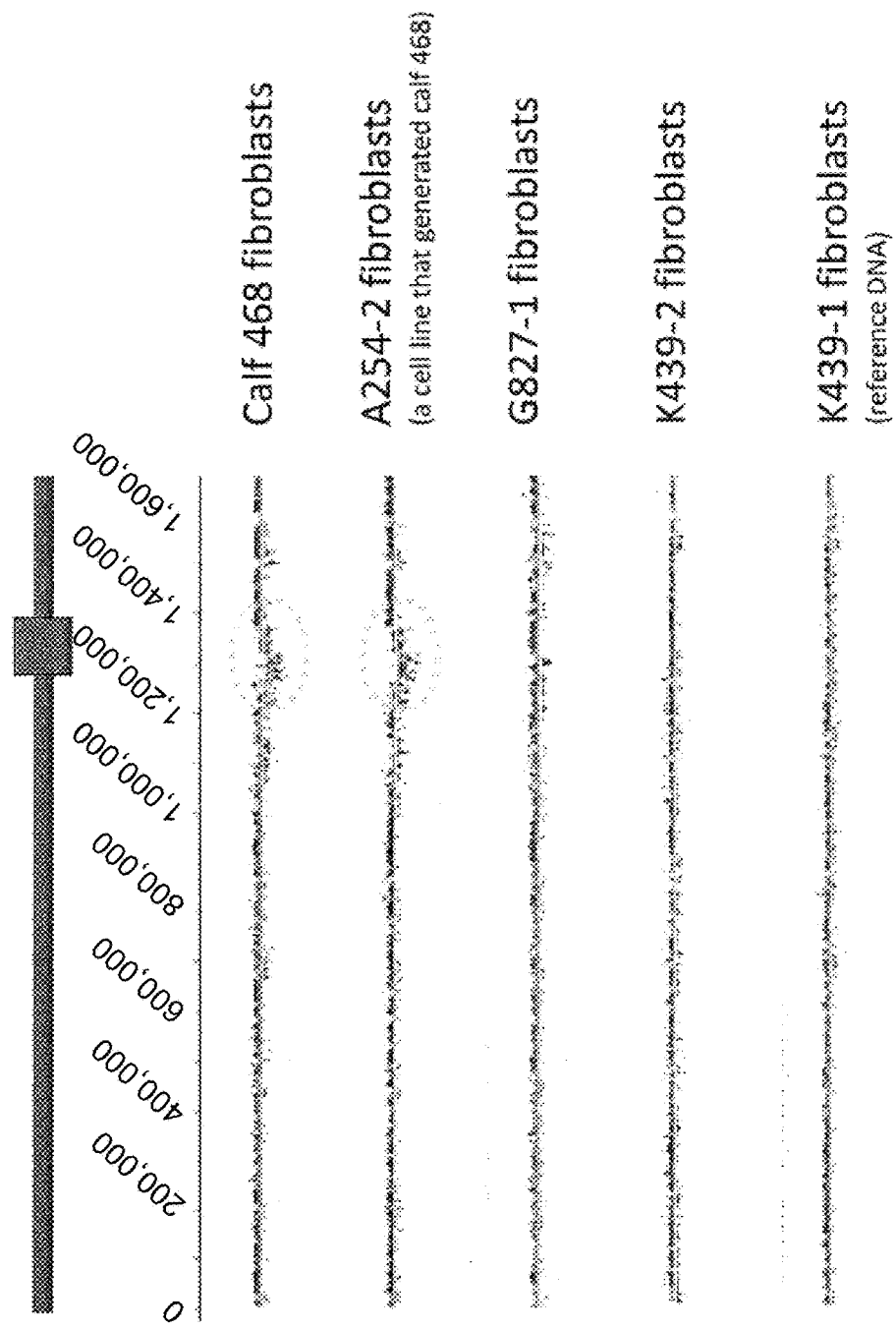
FIG. 7 shows comparative genomic hybridization (CGH) analysis on fibroblasts derived from the κHAC/IGHM$^{-/-}$ IGHML1$^{-/-}$ (DKO) fetuses and calf 468. More extensive analysis of calf 468 using CGH analysis on the κHAC vector present in the cell line that generated calf 468 showed some distinct structural alteration. A254-2 is the fetal fibroblast cell line that generated calf 468. A254-2, G827-1, K439-1 and K439-2 were generated through independent MMCT events of the κHAC vector from the CHO cell line κC1-1 to DKO cell lines. DNA from the fetal cell line K439-1 was used as a reference. Only A254-2 and the calf 468 showed the distinct CGH pattern around the 3' $E_{\alpha 2}$ region on the hChr14 (dashed circle).
Figure 16:
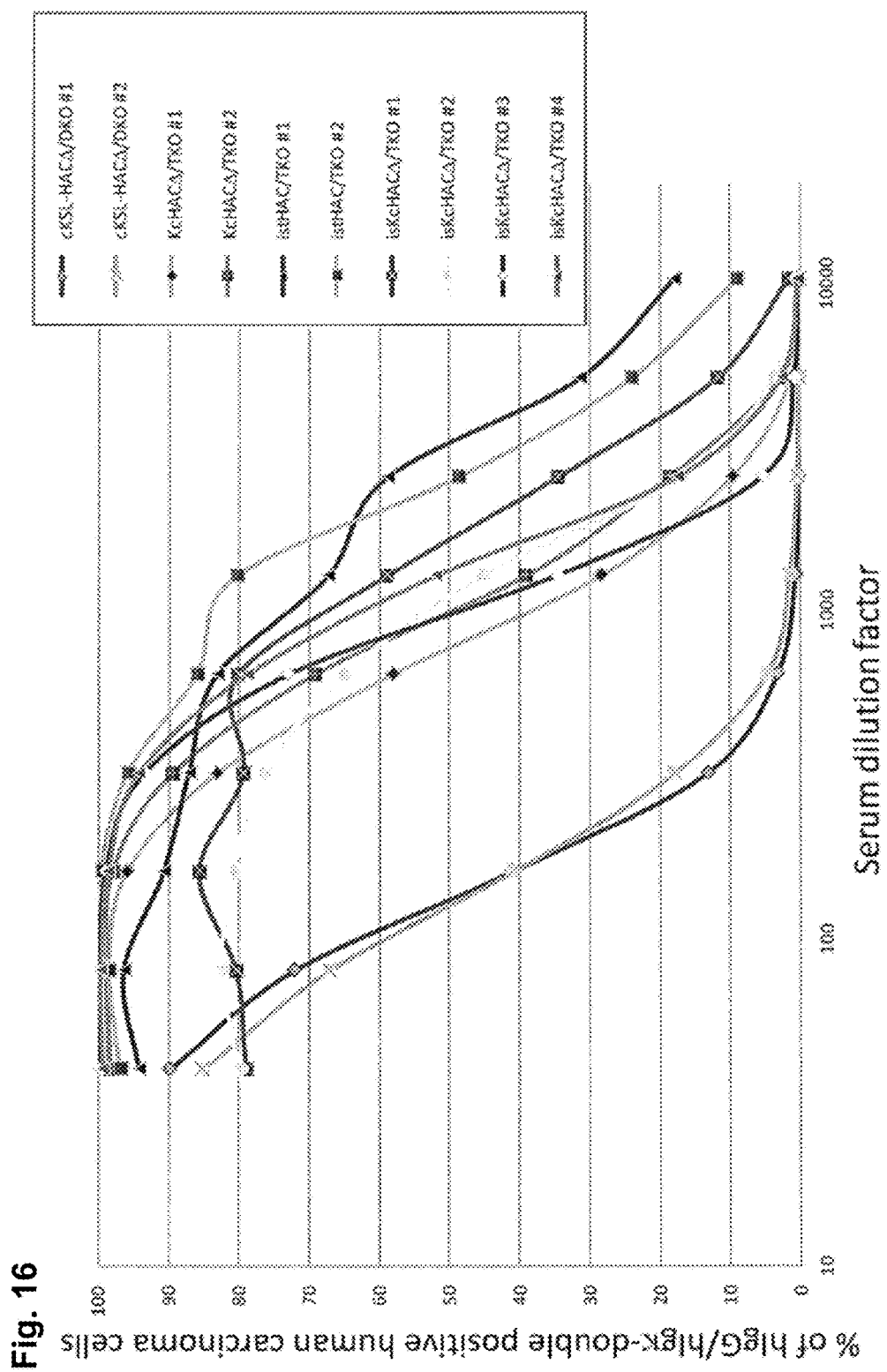
FIG. 16 shows anti-human carcinoma hIgG/hIgκ response in a series of HAC/TKO and HAC/DKO calves, following two times vaccinations (V2) of human oral squamous cell carcinoma. Percentages of hIgG/hIgκ-double positive human carcinoma cells was plotted from each animal immunized, at day 9-10 after V2 at indicated serum dilution factors.

Finally, to show that the HAC/TKO calves that underwent such complex chromosome engineering functionally generate fully hIgG/hIgκ polyclonal antibodies in response to antigen immunization, several HAC/TKO animals were hyperimmunized with human oral squamous cell carcinoma to see antigen-specific fully hIgG/hIgκ immune response in comparison with the HAC/DKO genotype, cKSL-HACΔ/DKO. All the HAC/TKO calves immunized mounted robust anti-human carcinoma fully hIgG/hIgκ response (28.45-80.36% positive for both hIgG and hIgκ), whereas the two cKSL-HACΔ/DKO animals had only 0.73-1.54% positive for both hIgG and hIgκ, and only showed hIgG-response (FIG. 6L, FIG. 16). The data indicates that HAC/TKO genotype is important for high productivity of antigen-specific fully hIgG/hIgκ polyclonal antibodies, which was further enhanced by the bovinized HAC vectors, istHAC and isKcHACΔ.

The invention is capable of producing a large quantity of fully hIgG/hIgκ (>5 g/l on average/median in the novel genotypes, i.e. isHAC/TKO, istHAC/TKO and isKcHACΔ/TKO) in sera of a large farm animal species. This serum concentration of fully hIgG/hIgκ is, to the inventors' knowledge, the highest of any other transgenic mouse systems producing fully hIgG (typically around 0.5 g/l) and is the closest to that in healthy humans. Moreover, hIgG subclass produced in the isHAC/TKO, istHAC/TKO and isKcHACΔ/TKO calves can be controlled to be hIgG I-dominant, which is the major subclass in healthy humans and is also that of therapeutic hIgG recombinant antibodies in development and on the market. Importantly, all the HAC/TKO calves tested functionally generated fully hIgG/hIgκ polyclonal antibodies against human-origin antigens immunized, which would be difficult to achieve by conventional human plasma-derived WIG, due to immune tolerance in humans. This was accomplished using a novel strategy of addressing potential species-incompatibilities in some key components (pre-BCR/BCR machinery and $I_{\gamma 1}$—$S_{\gamma 1}$ regulatory element) through complex human chromosome engineering, as well as endogenous bovine chromosome engineering (a site-specific, big DNA deletion). This new concept of species-incompatibilities may be also taken into consideration for high expression of complicatedly regulated human genes in transgenic animals if DNA sequences of some regulatory elements are considerably different from humans. Significantly, this complex chromosome engineering was done in somatic cells to alleviate a necessity of using ES cells.

REFERENCES

1. Lemieux, R., Bazin, R. and Neron, S. Therapeutic intravenous immunoglobulins. *Mol Immunol.* 42, 839-848 (2005).
2. Jolles, S., Sewell, W. A. C. and Misbah, S. A. Clinical uses of intravenous immunoglobulin. *Clini Exp Immunol.* 142, 1-11 (2005).
3. Newcombe, C. and Newcombe, A. R. Antibody production: polyclonal-derived biotherapeutics. *J Chromatogr B Analyt Technol Biomed Life Sci.* 848, 2-7 (2007).
4. Farrugia, A. & Poulis, P. Intravenous immunoglobulin: regulatory perspectives on use and supply. *Transfus. Med.* 11, 63-74 (2001).
5. Kuroiwa, Y. et al. Antigen-specific human polyclonal antibodies from hyperimmunized cattle. *Nat Biotechnol.* 27, 173-181 (2009).
6. Echelard, Y. Year of the ox. *Nat Biotechnol.* 27, 146-147 (2009).
7. Lonberg, N. Human antibodies from transgenic animals. *Nat Biotechnol.* 23, 1117-1125 (2005).
8. Aitken, R. et al. Structure and diversification of the bovine immunoglobulin repertoire. *Veterinary Immunol. Immunopathol.* 72, 21-29 (1999).
9. Chen, L. et al. Characterization of the bovine immunoglobulin lambda light chain constant IGLC genes. *Veterinary Immunol. Immunopathol.* 124, 284-294 (2008).
10. Ekman, A., Niku, M., Liljavirta, J. & Iivanainen, A. *Bos taurus* genome sequence reveals the assortment of immunoglobulin and surrogate light chain genes in domestic cattle. *BMC Immunol.* 10:22, (2009).
11. Hosseini, A., Campbell, G., Prorocic, M. and Aitken, R. Duplicated copies of the bovine $J_H$ locus contribute to the Ig repertoire. *Intern. Immunol.* 16, 843-852 (2004).
12. Kuroiwa, Y. et al. Sequential targeting of the genes encoding immunoglobulin-µ and prion protein in cattle. *Nat Genet.* 36, 775-780 (2004).
13. Kitamura, D., Roes, J., Kuhn, R. & Rajewsky, K. A. B cell-deficient mouse by targeted disruption of the membrane exon of the immunoglobulin chain gene. *Nature* 350, 423-426 (1991).
14. Tomizuka, K. et al. Double trans-chromosomic mice: Maintenance of two individual human chromosome fragments containing Ig heavy and κ loci and expression of fully human antibodies. *Proc. Natl. Acad. Sci. USA* 97, 722-727 (2000).
15. Yel, L et al. Mutations in the mu heavy chain gene in patients with agammaglobulinemia. *New Engl J Med* 335, 1486-1493 (1996).
16. Kitamura, D. et al. A critical role of 25 protein in B cell development. *Cell* 69, 823-831 (1992).
17. Mundt, C., Licence, S., Shimizu, T., Melchers, F. & Martensson, I-L. Loss of Precursor B Cell Expansion but Not Allelic Exclusion in VpreB1/VpreB2 double-deficient mice. *J Exp Med* 193, 435-445 (2001).
18. Zou, X. et al. Block in development at the pre-B-II to immature B cell stage in mice without IgK and Igλ light chain. *J Immunol* 170, 1354-1361 (2003).
19. Pelanda, R., Braun, U., Hobeika, E., Nussenzweig, M. C. & Reth, M. B cell progenitors are arrested in maturation but have intact VDJ recombination in the absence of Ig-α and Ig-β. *J Immunol* 169, 865-872 (2002).
20. Kuroiwa, Y. et al. Manipulation of human minichromosomes to carry greater than megabase-sized chromosome inserts. *Nat Biotechnol* 18, 1086-1090 (2000).
21. Kuroiwa, Y. et al. Cloned transchromosomic calves producing human immunoglobulin. *Nat Biotechnol.* 20, 889-894 (2002).
22. Chaudhuri, J. & Alt, F. W. Class switch recombination: interplay of transcription, DNA deamination and DNA repair. *Nat Review Immunol* 4, 541-552 (2004).
23. Tomizuka, K. et al. Double trans-chromosomic mice: Maintenance of two individual human chromosome fragments containing Ig heavy and κ loci and expression of fully human antibodies. *Proc. Natl. Acad. Sci. USA* 97, 722-727 (2000).
24. Stoop, J. W., Zegers, B. J. M., Sander, P. C. and Ballieux, R. E. Serum immunoglobulin levels in healthy children and adults. *Clin Exp Immunol.* 4, 101-112 (1969).
25. Kaisho, T., Schwenk, F. & Rajewsky, K. The roles of γ1 heavy chain membrane expression and cytoplasmic tail in IgG1 responses. *Science* 276, 412-415 (1997).
26. Wilson, M. D. et al. Species-specific transcription in mice carrying human chromosome 21. *Science* 322, 434-438 (2008).
27. Flajnik, M. F. Comparative analyses of immunoglobulin genes: surprises and portents. *Nat Rev Immunol* 2, 688-698 (2002).
28. Kawano, Y., Yoshikawa, S., Minegishi, Y. & Karasuyama, H. Pre-B Cell receptor assesses the quality of IgH chains and tunes the Pre-B cell repertoire by delivering differential signals. *J Immunol* 177, 2242-2249 (2006).
29. Casola, S. et al. B cell receptor signal strength determines B cell fate. *Nat Immunol* 5, 317-327 (2004).
30. Keenan, R. A. et al. Censoring of autoreactive B cell development by the pre-B cell receptor. *Science* 321, 696-699 (2008).
31. Martin, F. & Kearney, J. F. Marginal-zone B cells. *Nat Review Immunol* 2, 323-335 (2002).
32. Siber, G. R. et al. Correlation between serum IgG2 concentrations and the antibody response to bacterial polysaccharide antigens. *New Engl J Med* 303,178 (1990).
33. Shackelford, P. G. et al. Correlation of serum immunoglobulin subclass concentrations with antibody responses of children to immunization with *Haemophilus influenzae* type b polysaccharide-pertussis vaccine. *J Clin Immunol* 5, 390-395 (1985).

The invention claimed is:

1. A human artificial chromosome (HAC) vector comprising one or more human immunoglobulin heavy and light chain loci that are capable of undergoing rearrangement and expression in B-cells to produce a human immunoglobulin in response to exposure to one or more antigens, wherein said immunoglobulin loci comprise:
    (a) a gene encoding one or more human antibody heavy chains comprising at least a human IgG heavy chain, a human IgA heavy chain or both human IgG and IgA heavy chains, wherein each gene encoding an antibody heavy chain is operatively linked to its own class switch regulatory element upstream of the human antibody heavy chain;
    (b) a gene encoding one or more human antibody light chains; and
    (c) a gene encoding a human-ungulate chimeric IgM heavy chain constant region encoding constant heavy (CH) domains CH1, CH2, CH3 and CH4, and transmembrane domains (TM) TM1 and TM2, wherein the encoded CH1, CH2, and CH3 domains are human, and the encoded CH4, TM1 and TM2 domains are ungulate;
    wherein at least one class switch regulatory element of the genes encoding the one or more human antibody heavy chains is replaced with an ungulate class switch regulatory element selected from the group consisting of Imu-Smu (Iµ-Sµ), Igamma-Sgamma (Iγ-Sγ), Ialpha-Salpha (Iα-Sα), and Iepsilon-Sepsilon (Iε-Sε) ungulate class switch regulatory elements.

2. The HAC of claim 1, wherein the gene encoding the one or more human antibody heavy chains is a human IgG antibody heavy chain.

3. The HAC vector of claim 2, wherein the IgG heavy chain is an IgG1 antibody heavy chain.

4. The HAC vector of claim 1, wherein the gene encoding the one or more human antibody heavy chains is a human IgA antibody heavy chain.

5. The HAC vector of claim 1, wherein the gene encoding the one or more human antibody heavy chains further comprises a human IgM antibody heavy chain.

6. The HAC vector of claim 1, wherein the one or more human antibody heavy chains is selected from the group consisting of IgG1, IgG2, IgG3, IgG4, IgA1, and IgA2.

7. The HAC vector of claim 1, wherein the gene encoding the human-ungulate chimeric IgM heavy chain constant region is further modified so that:
    (a) the encoded CH1 domain is a human-ungulate chimeric CH1 domain, and the encoded CH2, CH3, CH4, and TM1 and TM2 domains are ungulate; or
    (b) the encoded CH1 domain is human, the encoded CH2 domain is a human-ungulate chimeric CH2 domain, and the encoded CH3, CH4, and TM1 and TM2 domains are ungulate.

8. The HAC vector of claim 7, wherein the encoded CH2, CH3, CH4, and TM1 and TM2 ungulate domains are bovine, the human-ungulate chimeric CH1 domain is a human-bovine chimeric CH1 domain and the human-ungulate chimeric CH2 domain is a human-bovine chimeric CH2 domain.

9. The HAC of claim 1, wherein the one or more human antibody heavy chains comprises a human IgG antibody heavy chain, wherein a transmembrane domain and an intracellular domain of a constant region of the human IgG heavy antibody chain are replaced with a transmembrane domain and an intracellular domain of an ungulate IgG antibody heavy chain constant region.

10. The HAC vector of claim 9, wherein the human IgG antibody heavy chain is a human IgG1 antibody heavy chain.

11. The HAC vector of claim 9, wherein the ungulate IgG antibody heavy chain constant region is a bovine IgG antibody heavy chain constant region.

12. The HAC vector of claim 1, wherein the ungulate class switch regulatory element is an Igamma-Sgamma (Iγ-Sγ) class switch regulatory element.

13. The HAC vector of claim 12, wherein the Iγ-Sγ class switch regulatory element is an Igamma1-Sgamma1 ($I_{γ1}$-$S_{γ1}$).

14. The HAC vector of claim 1, wherein each class switch regulatory element of the genes encoding the one or more human antibody heavy chains is replaced with an ungulate class switch regulatory element.

15. The HAC vector of claim 1, wherein the ungulate class switch regulatory element(s) are bovine class switch regulatory elements.

16. The HAC vector of claim 1, wherein the HAC vector comprises one or more genes encoding a human antibody surrogate light chain selected from the group consisting of pre-B lymphocyte 1 (VpreB1), pre-B lymphocyte 3(VpreB3) and lambda 5 (λ5) human antibody surrogate light chains.

17. The HAC vector of claim 1, further comprising an ungulate enhancer operatively linked to one or more genes encoding the one or more human antibody heavy chains.

18. The HAC vector of claim 17, wherein the enhancer is a 3'enhancer alpha (3'Ea enhancer).

19. A transgenic ungulate comprising the HAC vector of claim 1.

20. The transgenic ungulate of claim 19, wherein the transgenic ungulate is a transgenic bovine.

21. The HAC vector of claim 1, wherein the gene encoding the one or more human antibody light chains encodes at least a human kappa (κ) light chain, a human lambda (λ) light chain or both human kappa and lambda light chains.

22. The HAC vector of claim 6, further comprising one or more human antibody IgE and IgD human antibody heavy chains.

* * * * *

SEQUENCE LISTING

<160> NUMBER OF SEQ ID NOS: 200

<210> SEQ ID NO 1
<211> LENGTH: 41
<212> TYPE: DNA
<213> ORGANISM: Artificial Sequence
<220> FEATURE:
<223> OTHER INFORMATION: Artificially synthesized oligonucleotide

<400> SEQUENCE: 1
tcgaggatcc gccagggaga cagatgccaa gtacggttta g                          41

<210> SEQ ID NO 2
<211> LENGTH: 41
<212> TYPE: DNA
<213> ORGANISM: Artificial Sequence
<220> FEATURE:
<223> OTHER INFORMATION: Artificially synthesized oligonucleotide

<400> SEQUENCE: 2
tcgaggatcc aggatctttg ggggactgaa tggggtgtgc t                          41

<210> SEQ ID NO 3
<211> LENGTH: 46
<212> TYPE: DNA
<213> ORGANISM: Artificial Sequence
<220> FEATURE:
<223> OTHER INFORMATION: Artificially synthesized oligonucleotide

<400> SEQUENCE: 3
agcttggatc cataacttcg tataggatac tttatacgaa gttata                     46

<210> SEQ ID NO 4
<211> LENGTH: 46
<212> TYPE: DNA
<213> ORGANISM: Artificial Sequence
<220> FEATURE:
<223> OTHER INFORMATION: Artificially synthesized oligonucleotide

<400> SEQUENCE: 4
agcttataac ttcgtataaa gtatcctata cgaagttatg gatcca                     46

<210> SEQ ID NO 5
<211> LENGTH: 44
<212> TYPE: DNA
<213> ORGANISM: Artificial Sequence
<220> FEATURE:
<223> OTHER INFORMATION: Artificially synthesized oligonucleotide

<400> SEQUENCE: 5
tcgaggatcc ggcctcccaa aggattatag acgtgagcca ctgt                       44

<210> SEQ ID NO 6
<211> LENGTH: 45
<212> TYPE: DNA
<213> ORGANISM: Artificial Sequence
<220> FEATURE:
<223> OTHER INFORMATION: Artificially synthesized oligonucleotide

<400> SEQUENCE: 6
tcgaggatcc aaagaagggg cccgcctctg cctctaaatc ctgac                      45

<210> SEQ ID NO 7
<211> LENGTH: 29
<212> TYPE: DNA
<213> ORGANISM: Artificial Sequence

```
<220> FEATURE:
<223> OTHER INFORMATION: Artificially synthesized oligonucleotide

<400> SEQUENCE: 7
tgtagctgac tttagccacc cacaagtac                                          29

<210> SEQ ID NO 8
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 8
cttgctgatt atacctcatc tccttccctc                                         30

<210> SEQ ID NO 9
<211> LENGTH: 46
<212> TYPE: DNA
<213> ORGANISM: Artificial Sequence
<220> FEATURE:
<223> OTHER INFORMATION: Artificially synthesized oligonucleotide

<400> SEQUENCE: 9
gtacaataac ttcgtatagc atacattata cgaagttata gatctg                       46

<210> SEQ ID NO 10
<211> LENGTH: 46
<212> TYPE: DNA
<213> ORGANISM: Artificial Sequence
<220> FEATURE:
<223> OTHER INFORMATION: Artificially synthesized oligonucleotide

<400> SEQUENCE: 10
aattcagatc tataacttcg tataatgtat gctatacgaa gttatt                       46

<210> SEQ ID NO 11
<211> LENGTH: 40
<212> TYPE: DNA
<213> ORGANISM: Artificial Sequence
<220> FEATURE:
<223> OTHER INFORMATION: Artificially synthesized oligonucleotide

<400> SEQUENCE: 11
gatctataac ttcgtatagg atactttata cgaagttatg                              40

<210> SEQ ID NO 12
<211> LENGTH: 40
<212> TYPE: DNA
<213> ORGANISM: Artificial Sequence
<220> FEATURE:
<223> OTHER INFORMATION: Artificially synthesized oligonucleotide

<400> SEQUENCE: 12
ctagcataac ttcgtataaa gtatcctata cgaagttata                              40

<210> SEQ ID NO 13
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 13
gtacaatctt ggatcactac aacctctgcc tacca                                   35
```

```
<210> SEQ ID NO 14
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 14
tgctgtgtct aatcaggtgt tgaacccatc tacta                              35

<210> SEQ ID NO 15
<211> LENGTH: 40
<212> TYPE: DNA
<213> ORGANISM: Artificial Sequence
<220> FEATURE:
<223> OTHER INFORMATION: Artificially synthesized oligonucleotide

<400> SEQUENCE: 15
gatctataac ttcgtatagt atacattata cgaagttatg                         40

<210> SEQ ID NO 16
<211> LENGTH: 40
<212> TYPE: DNA
<213> ORGANISM: Artificial Sequence
<220> FEATURE:
<223> OTHER INFORMATION: Artificially synthesized oligonucleotide

<400> SEQUENCE: 16
ctagcataac ttcgtataat gtatactata cgaagttata                         40

<210> SEQ ID NO 17
<211> LENGTH: 40
<212> TYPE: DNA
<213> ORGANISM: Artificial Sequence
<220> FEATURE:
<223> OTHER INFORMATION: Artificially synthesized oligonucleotide

<400> SEQUENCE: 17
tcgaggatcc ttcgccaccc caaagatgat tacagattac                         40

<210> SEQ ID NO 18
<211> LENGTH: 43
<212> TYPE: DNA
<213> ORGANISM: Artificial Sequence
<220> FEATURE:
<223> OTHER INFORMATION: Artificially synthesized oligonucleotide

<400> SEQUENCE: 18
tcgaggatcc tacactagaa gcacaaaccc caccattaca cat                     43

<210> SEQ ID NO 19
<211> LENGTH: 46
<212> TYPE: DNA
<213> ORGANISM: Artificial Sequence
<220> FEATURE:
<223> OTHER INFORMATION: Artificially synthesized oligonucleotide

<400> SEQUENCE: 19
agcttggatc cataacttcg tatagtatac attatacgaa gttata                  46

<210> SEQ ID NO 20
<211> LENGTH: 46
<212> TYPE: DNA
<213> ORGANISM: Artificial Sequence
<220> FEATURE:
<223> OTHER INFORMATION: Artificially synthesized oligonucleotide
```

```
<400> SEQUENCE: 20
agcttataac ttcgtataat gtatactata cgaagttatg gatcca                    46

<210> SEQ ID NO 21
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 21
cagtccccgg cagattcagg tgtcc                                           25

<210> SEQ ID NO 22
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 22
gaaagtggca ttggggtggc tctcg                                           25

<210> SEQ ID NO 23
<211> LENGTH: 58
<212> TYPE: DNA
<213> ORGANISM: Artificial Sequence
<220> FEATURE:
<223> OTHER INFORMATION: Artificially synthesized oligonucleotide

<400> SEQUENCE: 23
ggaccaggtg gagactgtgc agtcctcacc cataactttc agggcctaca gcatgctg       58

<210> SEQ ID NO 24
<211> LENGTH: 58
<212> TYPE: DNA
<213> ORGANISM: Artificial Sequence
<220> FEATURE:
<223> OTHER INFORMATION: Artificially synthesized oligonucleotide

<400> SEQUENCE: 24
cagcatgctg taggccctga aagttatggg tgaggactgc acagtctcca cctggtcc       58

<210> SEQ ID NO 25
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 25
accccaaagg ccaaactctc cactc                                           25

<210> SEQ ID NO 26
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 26
cacttgtact ccttgccatt cagc                                            24

<210> SEQ ID NO 27
```

```
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 27
tcaacagcac ctaccgcgtg gtcag                                         25

<210> SEQ ID NO 28
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 28
gcggggtcgt gccgtacttg tcctc                                         25

<210> SEQ ID NO 29
<211> LENGTH: 73
<212> TYPE: DNA
<213> ORGANISM: Artificial Sequence
<220> FEATURE:
<223> OTHER INFORMATION: Artificially synthesized oligonucleotide

<400> SEQUENCE: 29
atgcatgagg ctctgcacaa ccactacaca cagaagagcc tctccctgtc tccgggtaaa   60
tgagcctcac gtc                                                      73

<210> SEQ ID NO 30
<211> LENGTH: 73
<212> TYPE: DNA
<213> ORGANISM: Artificial Sequence
<220> FEATURE:
<223> OTHER INFORMATION: Artificially synthesized oligonucleotide

<400> SEQUENCE: 30
gacgtgaggc tcatttaccc ggagacaggg agaggctctt ctgtgtgtag tggttgtgca   60
gagcctcatg cat                                                      73

<210> SEQ ID NO 31
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 31
tctgtctgtc caacagtggc                                               20

<210> SEQ ID NO 32
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 32
attatgggat gagtccaggc                                               20

<210> SEQ ID NO 33
<211> LENGTH: 20
<212> TYPE: DNA
<213> ORGANISM: Artificial Sequence
```

```
<220> FEATURE:
<223> OTHER INFORMATION: Artificially synthesized oligonucleotide

<400> SEQUENCE: 33
ttaactgcgg tacaaggtgc                                               20

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 34
caacctctcc aggattctgg                                               20

<210> SEQ ID NO 35
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 35
gacaagcgtg ctagggtcat g                                             21

<210> SEQ ID NO 36
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 36
gggatgggac cttgttagac ttg                                           23

<210> SEQ ID NO 37
<211> LENGTH: 26
<212> TYPE: DNA
<213> ORGANISM: Artificial Sequence
<220> FEATURE:
<223> OTHER INFORMATION: Artificially synthesized oligonucleotide

<400> SEQUENCE: 37
cgcgcatggc cgagttgagc ggttcc                                        26

<210> SEQ ID NO 38
<211> LENGTH: 28
<212> TYPE: DNA
<213> ORGANISM: Artificial Sequence
<220> FEATURE:
<223> OTHER INFORMATION: Artificially synthesized oligonucleotide

<400> SEQUENCE: 38
caggctcccg gctggcgctg gtaagtcc                                      28

<210> SEQ ID NO 39
<211> LENGTH: 29
<212> TYPE: DNA
<213> ORGANISM: Artificial Sequence
<220> FEATURE:
<223> OTHER INFORMATION: Artificially synthesized oligonucleotide

<400> SEQUENCE: 39
gcccggcccc agatggaacc cgagacagg                                     29
```

<210> SEQ ID NO 40
<211> LENGTH: 29
<212> TYPE: DNA
<213> ORGANISM: Artificial Sequence
<220> FEATURE:
<223> OTHER INFORMATION: Artificially synthesized oligonucleotide

<400> SEQUENCE: 40
atgccaggcg ggccatttac cgtcattga                              29

<210> SEQ ID NO 41
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 41
gcggcgccgg caggaaggaa atg                                    23

<210> SEQ ID NO 42
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 42
cgaggcgcac cgtgggcttg ta                                     22

<210> SEQ ID NO 43
<211> LENGTH: 18
<212> TYPE: DNA
<213> ORGANISM: Artificial Sequence
<220> FEATURE:
<223> OTHER INFORMATION: Artificially synthesized oligonucleotide

<400> SEQUENCE: 43
accctcggtc accctgtt                                          18

<210> SEQ ID NO 44
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 44
tgagaaggtc tttattcagg ag                                     22

<210> SEQ ID NO 45
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 45
tctctggtga cggcaatag                                         19

<210> SEQ ID NO 46
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 46
cttcgtgagg aagatgtcgg                                          20

<210> SEQ ID NO 47
<211> LENGTH: 29
<212> TYPE: DNA
<213> ORGANISM: Artificial Sequence
<220> FEATURE:
<223> OTHER INFORMATION: Artificially synthesized oligonucleotide

<400> SEQUENCE: 47
ccacaaagga aaaagctgca ctgctatac                                29

<210> SEQ ID NO 48
<211> LENGTH: 28
<212> TYPE: DNA
<213> ORGANISM: Artificial Sequence
<220> FEATURE:
<223> OTHER INFORMATION: Artificially synthesized oligonucleotide

<400> SEQUENCE: 48
tgtgggatca ggaggtcaga tagacatc                                 28

<210> SEQ ID NO 49
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 49
gtggggccac agaaggcagg ac                                       22

<210> SEQ ID NO 50
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 50
acccgggtag aagtcgctga tgaga                                    25

<210> SEQ ID NO 51
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 51
ccctcggtca ccctgttccc                                          20

<210> SEQ ID NO 52
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 52
ctggtgtgag gcgacctggg                                          20

<210> SEQ ID NO 53

```
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 53
cagctcctgg ggctcctcct g                                              21

<210> SEQ ID NO 54
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 54 tgcaatagggg gttgatctgt ggaca                                         25

<210> SEQ ID NO 55
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 55
gggcaacata gcaagacacc attc                                           24

<210> SEQ ID NO 56
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 56
tcctctcacc tcagcctcca tagta                                          25

<210> SEQ ID NO 57
<211> LENGTH: 27
<212> TYPE: DNA
<213> ORGANISM: Artificial Sequence
<220> FEATURE:
<223> OTHER INFORMATION: Artificially synthesized oligonucleotide

<400> SEQUENCE: 57
acggcgtgag gaccaaggag cgaaacc                                        27

<210> SEQ ID NO 58
<211> LENGTH: 28
<212> TYPE: DNA
<213> ORGANISM: Artificial Sequence
<220> FEATURE:
<223> OTHER INFORMATION: Artificially synthesized oligonucleotide

<400> SEQUENCE: 58
tgagcgacga attaaaacag gcgatgac                                       28

<210> SEQ ID NO 59
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 59
```
aacagttgaa tttatgggga gtc                                           23

<210> SEQ ID NO 60
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 60
tcaggcttta aacacagtat cacag                                         25

<210> SEQ ID NO 61
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 61
actgaaatat tttaaatgtt tgcccttccc actcc                              35

<210> SEQ ID NO 62
<211> LENGTH: 32
<212> TYPE: DNA
<213> ORGANISM: Artificial Sequence
<220> FEATURE:
<223> OTHER INFORMATION: Artificially synthesized oligonucleotide

<400> SEQUENCE: 62
agacctccgc gccccgcaac ctccccttct ac                                 32

<210> SEQ ID NO 63
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 63
caagcatgga gcccgcagta atag                                          24

<210> SEQ ID NO 64
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 64
aaggtgaccc gggcagttgt agg                                           23

<210> SEQ ID NO 65
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 65
ccgacaggca gggcacgagg ag                                            22

<210> SEQ ID NO 66
<211> LENGTH: 21
<212> TYPE: DNA

```
<213> ORGANISM: Artificial Sequence
<220> FEATURE:
<223> OTHER INFORMATION: Artificially synthesized oligonucleotide

<400> SEQUENCE: 66
tgcgaggcgg gacaaagaca c                                        21

<210> SEQ ID NO 67
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 67
tgcaggtgaa gtgacggcca gccaagaaca                               30

<210> SEQ ID NO 68
<211> LENGTH: 33
<212> TYPE: DNA
<213> ORGANISM: Artificial Sequence
<220> FEATURE:
<223> OTHER INFORMATION: Artificially synthesized oligonucleotide

<400> SEQUENCE: 68
tggcagcagg gtgacaggga aggcagggaa aag                           33

<210> SEQ ID NO 69
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 69
cagcacccca acggcaacaa agaaa                                    25

<210> SEQ ID NO 70
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 70
ccccagggct gcactcacca acat                                     24

<210> SEQ ID NO 71
<211> LENGTH: 32
<212> TYPE: DNA
<213> ORGANISM: Artificial Sequence
<220> FEATURE:
<223> OTHER INFORMATION: Artificially synthesized oligonucleotide

<400> SEQUENCE: 71
aaggccccca agctgatttc cgtgagacta ag                            32

<210> SEQ ID NO 72
<211> LENGTH: 27
<212> TYPE: DNA
<213> ORGANISM: Artificial Sequence
<220> FEATURE:
<223> OTHER INFORMATION: Artificially synthesized oligonucleotide

<400> SEQUENCE: 72
gcctggacga gctgtacgcc gagtggt                                  27
```

<210> SEQ ID NO 73
<211> LENGTH: 29
<212> TYPE: DNA
<213> ORGANISM: Artificial Sequence
<220> FEATURE:
<223> OTHER INFORMATION: Artificially synthesized oligonucleotide

<400> SEQUENCE: 73
gctaaggcac ttcggttctc tttgtgttc                                    29

<210> SEQ ID NO 74
<211> LENGTH: 29
<212> TYPE: DNA
<213> ORGANISM: Artificial Sequence
<220> FEATURE:
<223> OTHER INFORMATION: Artificially synthesized oligonucleotide

<400> SEQUENCE: 74
ggttgtcttt aaaagcaggg ataaggatg                                    29

<210> SEQ ID NO 75
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 75
gtcagccagg cgggccattt accgtaagtt atgta                             35

<210> SEQ ID NO 76
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 76
agggctgggt tagatggcac caaatgaaag gagaa                             35

<210> SEQ ID NO 77
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 77
actccacaca ggcatagagt gtc                                          23

<210> SEQ ID NO 78
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 78
gtgggcttgt actcggtcat                                              20

<210> SEQ ID NO 79
<211> LENGTH: 22
<212> TYPE: DNA
<213> ORGANISM: Artificial Sequence
<220> FEATURE:

<223> OTHER INFORMATION: Artificially synthesized oligonucleotide

<400> SEQUENCE: 79
tgaaggtagt gaccagtgtt gg                                              22

<210> SEQ ID NO 80
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 80
accagcgcgt catcatcaag                                                 20

<210> SEQ ID NO 81
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 81
atcgccagcc tcaccatttc                                                 20

<210> SEQ ID NO 82
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 82
cactgcctgc ccgctgctgg ta                                              22

<210> SEQ ID NO 83
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 83
gggcggggaa gtgggggaga g                                               21

<210> SEQ ID NO 84
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 84
agccccaaga acccagccga tgtga                                           25

<210> SEQ ID NO 85
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 85
ggcagaggga gtgtggggtg ttgtg                                           25

```
<210> SEQ ID NO 86
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 86
atcatctgct cgctctctcc                                          20

<210> SEQ ID NO 87
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 87
cacatctgta gtggctgtgg                                          20

<210> SEQ ID NO 88
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 88
ggagaccacc aaaccctcca aa                                       22

<210> SEQ ID NO 89
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 89
gagagttgca gaagggtga ct                                        22

<210> SEQ ID NO 90
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 90
tgtcctgggc tcctgtcctg ctcat                                    25

<210> SEQ ID NO 91
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 91
ggcggcggct ccaccctctt                                          20

<210> SEQ ID NO 92
<211> LENGTH: 25
<212> TYPE: DNA
<213> ORGANISM: Artificial Sequence
<220> FEATURE:
<223> OTHER INFORMATION: Artificially synthesized oligonucleotide
```

```
<400> SEQUENCE: 92
agatctcttg agcccagcag tttga                                          25

<210> SEQ ID NO 93
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 93
tgaagttagc cggggataca gacg                                           24

<210> SEQ ID NO 94
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 94
tatcaagggg gtgtcggaaa tcgtg                                          25

<210> SEQ ID NO 95
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 95
actgggcctg ggagaacctg agact                                          25

<210> SEQ ID NO 96
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 96
aggtgctgct gggtggtcaa gt                                             22

<210> SEQ ID NO 97
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 97
gctcctgcaa atgtctcctg tca                                            23

<210> SEQ ID NO 98
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 98
cttacccagg ctccaggctc tatt                                           24

<210> SEQ ID NO 99
<211> LENGTH: 25
```

```
<212> TYPE: DNA
<213> ORGANISM: Artificial Sequence
<220> FEATURE:
<223> OTHER INFORMATION: Artificially synthesized oligonucleotide

<400> SEQUENCE: 99
ctctacctcc ctaccccatc atcac                                          25

<210> SEQ ID NO 100
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 100
tggaaggtgg ataacgccct                                                20

<210> SEQ ID NO 101
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 101
tcattctcct ccaacattag ca                                             22

<210> SEQ ID NO 102
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 102
agtcagggca ttagcagtgc                                                20

<210> SEQ ID NO 103
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 103
gctgctgatg gtgagagtga                                                20

<210> SEQ ID NO 104
<211> LENGTH: 26
<212> TYPE: DNA
<213> ORGANISM: Artificial Sequence
<220> FEATURE:
<223> OTHER INFORMATION: Artificially synthesized oligonucleotide

<400> SEQUENCE: 104
tctttctctc acctaattgt cctggc                                         26

<210> SEQ ID NO 105
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 105
```

```
aggactggca ctcttgtcga tacc                                          24

<210> SEQ ID NO 106
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 106
gccattgtcg agcaggtagt                                               20

<210> SEQ ID NO 107
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 107
tccctcatca gccatcctaa                                               20

<210> SEQ ID NO 108
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 108
agcactttac gcatcccagc atgt                                          24

<210> SEQ ID NO 109
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 109
ccaagagagt agtcgtgccc ctca                                          24

<210> SEQ ID NO 110
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 110
cccactttac cgtgctcatt                                               20

<210> SEQ ID NO 111
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 111
atgaaggtcc gtgactttgg                                               20

<210> SEQ ID NO 112
<211> LENGTH: 29
<212> TYPE: DNA
<213> ORGANISM: Artificial Sequence
```

```
<220> FEATURE:
<223> OTHER INFORMATION: Artificially synthesized oligonucleotide

<400> SEQUENCE: 112
gccctcacct tgcagaccac ctccatcat                                    29

<210> SEQ ID NO 113
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 113
cctctcctgc tcagtcccct tccttccatc                                   30

<210> SEQ ID NO 114
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 114
agtgagataa gcagtggatg                                              20

<210> SEQ ID NO 115
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 115
cttgtgctac tcccatcact                                              20

<210> SEQ ID NO 116
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 116
ttgcaaaggg gcctggtgga ata                                          23

<210> SEQ ID NO 117
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 117
gcagggaacg ggatgaggat agagg                                        25

<210> SEQ ID NO 118
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 118
gggagagtga agcagaacgt                                              20
```

<210> SEQ ID NO 119
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 119
ttgctgacaa aggtccgtct a                                              21

<210> SEQ ID NO 120
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 120
gcttggcggc gaatgggctg ac                                             22

<210> SEQ ID NO 121
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 121
agagaagatg gggcccaaga gcgcagctgt ccaga                               35

<210> SEQ ID NO 122
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 122
gttcacgctg ttctcctgcc gcactccccg tatgg                               35

<210> SEQ ID NO 123
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 123
tttctcagga ggcagttaat gtggtctggt attcc                               35

<210> SEQ ID NO 124
<211> LENGTH: 36
<212> TYPE: DNA
<213> ORGANISM: Artificial Sequence
<220> FEATURE:
<223> OTHER INFORMATION: Artificially synthesized oligonucleotide

<400> SEQUENCE: 124
gcagggctgc cagggttag tgccgtgggg gtagat                               36

<210> SEQ ID NO 125
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 125
ccagggccac agttaacgga tacga        25

<210> SEQ ID NO 126
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 126
gggtcacttt ctcggtcctg gtct        24

<210> SEQ ID NO 127
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 127
ggcccctcca tttgtacttt ctat        24

<210> SEQ ID NO 128
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 128
ggggcaggag gagaagggga cgac        24

<210> SEQ ID NO 129
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 129
cctggtcctc acatggccat acctc        25

<210> SEQ ID NO 130
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 130
ggtccgggct ctggggattt cat        23

<210> SEQ ID NO 131
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 131
cctccctggt cctcacatgg ccata        25

<210> SEQ ID NO 132

<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 132
catggcacgg cagggtccgg gc                                              22

<210> SEQ ID NO 133
<211> LENGTH: 33
<212> TYPE: DNA
<213> ORGANISM: Artificial Sequence
<220> FEATURE:
<223> OTHER INFORMATION: Artificially synthesized oligonucleotide

<400> SEQUENCE: 133
ctctgcagag cccaaatctt gtgacaaaac tca                                  33

<210> SEQ ID NO 134
<211> LENGTH: 37
<212> TYPE: DNA
<213> ORGANISM: Artificial Sequence
<220> FEATURE:
<223> OTHER INFORMATION: Artificially synthesized oligonucleotide

<400> SEQUENCE: 134
cccccgggct gcaggaattc gatatcaagc ttaggac                              37

<210> SEQ ID NO 135
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 135
aagcgggaag ggactggctg ctattgggcg aagtg                                35

<210> SEQ ID NO 136
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 136
ggagcccggc accgtcctgg gtttcctttc cttat                                35

<210> SEQ ID NO 137
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 137
atggacggga tgacctggga gatcgtggca agttt                                35

<210> SEQ ID NO 138
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 138 ggggcccgg taccgaagtt cctattccga agttc         35

<210> SEQ ID NO 139
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 139
cactggtcag tgagaaggac                         20

<210> SEQ ID NO 140
<211> LENGTH: 28
<212> TYPE: DNA
<213> ORGANISM: Artificial Sequence
<220> FEATURE:
<223> OTHER INFORMATION: Artificially synthesized oligonucleotide

<400> SEQUENCE: 140
caccccaggc tttacacttt atgcttcc                28

<210> SEQ ID NO 141
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 141
gctcccccta ccacctccct ttac                    24

<210> SEQ ID NO 142
<211> LENGTH: 27
<212> TYPE: DNA
<213> ORGANISM: Artificial Sequence
<220> FEATURE:
<223> OTHER INFORMATION: Artificially synthesized oligonucleotide

<400> SEQUENCE: 142
ggcggggttc ggcttctggc gtgtgac                 27

<210> SEQ ID NO 143
<211> LENGTH: 28
<212> TYPE: DNA
<213> ORGANISM: Artificial Sequence
<220> FEATURE:
<223> OTHER INFORMATION: Artificially synthesized oligonucleotide

<400> SEQUENCE: 143
cttggccatg tagattgact tgaactcc                28

<210> SEQ ID NO 144
<211> LENGTH: 32
<212> TYPE: DNA
<213> ORGANISM: Artificial Sequence
<220> FEATURE:
<223> OTHER INFORMATION: Artificially synthesized oligonucleotide

<400> SEQUENCE: 144
ggcgccgctt aaaccacccc accaacccac aa           32

<210> SEQ ID NO 145
<211> LENGTH: 33
<212> TYPE: DNA

<213> ORGANISM: Artificial Sequence
<220> FEATURE:
<223> OTHER INFORMATION: Artificially synthesized oligonucleotide

<400> SEQUENCE: 145
acctgggcac ggtgggcatg tgtgagtttt gtc                          33

<210> SEQ ID NO 146
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 146
agacagcaaa gagaaagaac aggcccccac attag                        35

<210> SEQ ID NO 147
<211> LENGTH: 1303
<212> TYPE: DNA
<213> ORGANISM: Bos taurus

<400> SEQUENCE: 147
gtgagtctcc ctcctccctt ctctccctct tctttccccc aggtttagac acttttctgt     60
cactttgctc ttttctgtgc ccagtgtcag cctgtggtca agccttcacc cgggacccac    120
ctctggggcc ctgacctctt ccctttccct gatcccaggc ttctcctact ggcactgag     180
gtcccaccag agcctcccct ctgaccccag aggcagggga atgagcaggc tgacctaagg    240
acttgtctgt ctggctcccg atcctcgctc tcctctgtgc ccccaacccc caatctgggc    300
tctatgctga cccagctttg tctctgaggg tcacttgggt tccccatctc atggggaaga    360
gggaactgga ctgcagatga ggaaacatgg ggagacatca gagggacaca gaaccctcag    420
ggctggggac cgaagtcata gggccaggac actctgggac cttgggtcta gggatccggg    480
tcagggactc ggcagaggtg gaggggctcc cccaggcctc catggggctg ccgtgaagat    540
cctgggccgg ccagggaccc agggaaagtg caagggaag acggggagg agaaggtgct     600
gaactcagaa ctggggaaag agataggagg tcaggatgca ggggacacgg actcctgagt    660
ctgcaggaca cactcctcag aagcaggagt ccctgaagaa gcagagagac aggtaccagg    720
gcaggaaacc tccagaccca agaagaatca gagaggaacc tgagctcaga tctgcggatg    780
ggggaccga ggacaggcag acaggctccc cctcgaccag cacagaggct ccaagggaca     840
cagacttgga gaccaacgga cgccttcggg caacggctcg aacacacatg tcagctcaaa    900
atatacctgg actgacccac aggaggccag ggaggccaca tcatccactc aggggacaga    960
cagacagact gccagcccca ggcagacccc ggtcaaccat cagacgggca ggcaaggaga   1020
gtgagggtca ggtgtctgtg tgggaaacca agagccaggg ggtctcagga cagcgctggc   1080
aggggtccag gctcaggctt tccaggaag atggggaggt gcctgagaaa acccaccca     1140
ccttccctgg cacaggccct ctggctcaca gtggtgcctg gactcggggt cctgctgggc   1200
tctcaaagga tcctgtgtcc cctgtgaca cagactcagg ggctctcatg acgggcacca   1260
gacctctgat tgagtgatat tcttcccctc gcccactttg cag                    1303

<210> SEQ ID NO 148
<211> LENGTH: 1303
<212> TYPE: DNA
<213> ORGANISM: Bos taurus

<400> SEQUENCE: 148

```
gtgagtctcc ctcctcccctt ctctccctct tctttccccc aggtttagac acttttctgt    60
cactttgctc ttttctgtgc ccagtgtcag cctgtggtca agccttcacc cgggacccac   120
ctctggggcc ctgacctctt cccttcccct gatcccaggc ttctcctact tggcactgag   180
gtcccaccag agcctcccct ctgacccag aggcagggga atgagcaggc tgacctaagg    240
acttgtctgt ctggctcccg atcctcgctc tcctctgtgc ccccaaccc caatctgggc    300 tctatgctga cccagctttg tctctgaggg tcacttgggt tccccatctc atggggaaga   360
gggaactgga ctgcagatga ggaaacatgg ggagacatca gagggacaca gaaccctcag   420
ggctggggac cgaagtcata gggccaggac actctgggac cttgggtcta gggatccggg   480
tcagggactc ggcagaggtg gagggctcc cccaggcctc catgggctg ccgtgaagat    540 cctgggccgg ccaggaccc agggaaagtg caaggggaag acgggggagg agaaggtgct   600
gaactcagaa ctggggaaag agataggcgg tcaggatgca ggggacacgg actcctgagt   660
ctgcaggaca cactcctcag aagcaggagt ccctgaagaa gcagagagac aggtaccagg   720
gcaggaaacc tccagaccca agaagaatca gagaggaacc tgagctcaga tctgcggatg   780
gggggaccga ggacaggcag acaggctccc cctcgaccag cacagaggct ccaagggaca   840
cagacttgga gaccaacgga cgccttcggg caaaggctcg aacacacatg tcagctcaaa   900
atatacctgg actgactcac aggaggccag ggaggccaca tcatccactc agggagacaga 960 cagacagact gccagcccca ggcagacccc ggtcaaccat cagatgggca ggcaaggaga  1020
gtgaaggtca ggtgtctgtg tgggaaacca agagccaggg ggtctcagga cagcgctggc  1080
aggggtccag gctcaggctt tcccaggaag atggggaggt gcctgagaaa accccaccca  1140
ccttccctgg cacaggccct ctggctcaca gtggtgcctg gactcggggt cctgctgggc  1200
tctcaaagga tcctgtgtcc ccctgtgaca cagactcagg ggctctcatg acgggcacca  1260
gacctctgat tgagtgatat tcttcccctc gcccactttg cag                    1303

<210> SEQ ID NO 149
<211> LENGTH: 138
<212> TYPE: DNA
<213> ORGANISM: Bos taurus

<400> SEQUENCE: 149
ggccctggac ccccaccctc gggggccctc tggcccacac cccctccccc acctctccat    60 ggaccctga gccctgccc aggtcgcctc acaccagggg cctctcctcc ctccctgttc    120
ctgtttctcc tgaataaa                                                 138

<210> SEQ ID NO 150
<211> LENGTH: 137
<212> TYPE: DNA
<213> ORGANISM: Bos taurus

<400> SEQUENCE: 150
ggccctggac ccccaccctc gggggccctc tggcaacgcc ccctccccca gctctccatg    60 gaccctgag ccccgcccca ggtcgcctca caccagggc ctctcttccc tccctgttcc    120
tgcttctcct gaataaa                                                  137

<210> SEQ ID NO 151
<211> LENGTH: 474
<212> TYPE: PRT
<213> ORGANISM: Homo sapiens
```

<400> SEQUENCE: 151

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415
```

His Glu Ala Leu Pro Asn Arg Val Thr Glu Arg Thr Val Asp Lys Ser
420                     425                 430

Thr Glu Gly Glu Val Ser Ala Asp Glu Glu Gly Phe Glu Asn Leu Trp
    435                 440                 445

Ala Thr Ala Ser Thr Phe Ile Val Leu Phe Leu Leu Ser Leu Phe Tyr
450                 455                 460

Ser Thr Thr Val Thr Leu Phe Lys Val Lys
465                 470

<210> SEQ ID NO 152
<211> LENGTH: 476
<212> TYPE: PRT
<213> ORGANISM: Bos taurus

<400> SEQUENCE: 152

Glu Gly Glu Ser His Pro Arg Val Phe Pro Leu Val Ser Cys Val Ser
1               5                   10                  15

Ser Pro Ser Asp Glu Ser Thr Val Ala Leu Gly Cys Leu Ala Arg Asp
                20                  25                  30

Phe Val Pro Asn Ser Val Ser Phe Ser Trp Lys Phe Asn Asn Ser Thr
            35                  40                  45

Val Ser Ser Glu Arg Phe Trp Thr Phe Pro Glu Val Leu Arg Asp Gly
50                  55                  60

Leu Trp Ser Ala Ser Ser Gln Val Leu Pro Ser Ser Ser Ala Phe
65                  70                  75                  80

Gln Gly Pro Asp Asp Tyr Leu Val Cys Glu Val Gln His Pro Lys Gly
                85                  90                  95

Gly Lys Thr Val Gly Thr Val Arg Val Ile Ala Thr Lys Ala Glu Val
            100                 105                 110

Leu Ser Pro Val Val Ser Val Phe Val Pro Pro Arg Asn Ser Leu Ser
            115                 120                 125

Gly Asp Gly Asn Ser Lys Ser Ser Leu Ile Cys Gln Ala Thr Asp Phe
        130                 135                 140

Ser Pro Lys Gln Ile Ser Leu Ser Trp Phe Arg Asp Gly Lys Arg Ile
145                 150                 155                 160

Val Ser Gly Ile Ser Glu Gly Gln Val Glu Thr Val Gln Ser Ser Pro
                165                 170                 175

Ile Thr Phe Arg Ala Tyr Ser Met Leu Thr Ile Thr Glu Arg Asp Trp
            180                 185                 190

Leu Ser Gln Asn Val Tyr Thr Cys Gln Val Glu His Asn Lys Glu Thr
        195                 200                 205

Phe Gln Lys Asn Val Ser Ser Cys Asp Val Ala Pro Pro Ser Pro
    210                 215                 220

Ile Gly Val Phe Thr Ile Pro Pro Ser Phe Ala Asp Ile Phe Leu Thr
225                 230                 235                 240

Lys Ser Ala Lys Leu Ser Cys Leu Val Thr Asn Leu Ala Ser Tyr Asp
                245                 250                 255

Gly Leu Asn Ile Ser Trp Ser Arg Gln Asn Gly Lys Ala Leu Glu Thr
            260                 265                 270

His Thr Tyr Phe Glu Arg His Leu Asn Asp Thr Phe Ser Ala Arg Gly
        275                 280                 285

Glu Ala Ser Val Cys Ser Glu Asp Trp Glu Ser Gly Glu Glu Phe Thr
    290                 295                 300

Cys Thr Val Ala His Ser Asp Leu Pro Phe Pro Glu Lys Asn Ala Val

```
                305                 310                 315                 320
Ser Lys Pro Lys Asp Val Ala Met Lys Pro Pro Ser Val Tyr Leu Leu
                    325                 330                 335

Pro Pro Thr Arg Glu Gln Leu Ser Leu Arg Glu Ser Ala Ser Val Thr
                    340                 345                 350

Cys Leu Val Lys Gly Phe Ala Pro Ala Asp Val Phe Val Gln Trp Leu
                    355                 360                 365

Gln Arg Gly Glu Pro Val Thr Lys Ser Lys Tyr Val Thr Ser Ser Pro
                370                 375                 380

Ala Pro Glu Pro Gln Asp Pro Ser Val Tyr Phe Val His Ser Ile Leu
385                 390                 395                 400

Thr Val Ala Glu Glu Asp Trp Ser Lys Gly Glu Tyr Thr Cys Val
                    405                 410                 415

Val Gly His Glu Ala Leu Pro His Met Val Thr Glu Arg Thr Val Asp
                    420                 425                 430

Lys Ser Thr Glu Gly Glu Val Ser Ala Glu Glu Gly Phe Glu Asn
                    435                 440                 445

Leu Asn Thr Met Ala Ser Thr Phe Ile Val Leu Phe Leu Leu Ser Leu
                    450                 455                 460

Phe Tyr Ser Thr Thr Val Thr Leu Phe Lys Val Lys
465                 470                 475

<210> SEQ ID NO 153
<211> LENGTH: 476
<212> TYPE: PRT
<213> ORGANISM: Mus musculus

<400> SEQUENCE: 153

Glu Ser Gln Ser Phe Pro Asn Val Phe Pro Leu Val Ser Cys Glu Ser
1               5                   10                  15

Pro Leu Ser Asp Lys Asn Leu Val Ala Met Gly Cys Leu Ala Arg Asp
                20                  25                  30

Phe Leu Pro Ser Thr Ile Ser Phe Thr Trp Asn Tyr Gln Asn Asn Thr
            35                  40                  45

Glu Val Ile Gln Gly Ile Arg Thr Phe Pro Thr Leu Arg Thr Gly Gly
        50                  55                  60

Lys Tyr Leu Ala Thr Ser Gln Val Leu Leu Ser Pro Lys Ser Ile Leu
65                  70                  75                  80

Glu Gly Ser Asp Glu Tyr Leu Val Cys Lys Ile His Tyr Gly Gly Lys
                85                  90                  95

Asn Arg Asp Leu His Val Pro Ile Pro Ala Val Ala Glu Met Asn Pro
            100                 105                 110

Asn Val Asn Val Phe Val Pro Pro Arg Asp Gly Phe Ser Gly Pro Ala
        115                 120                 125

Pro Arg Lys Ser Lys Leu Ile Cys Glu Ala Thr Asn Phe Thr Pro Lys
130                 135                 140

Pro Ile Thr Val Ser Trp Leu Lys Asp Gly Lys Leu Val Glu Ser Gly
145                 150                 155                 160

Phe Thr Thr Asp Pro Val Thr Ile Glu Asn Lys Gly Ser Thr Pro Gln
                165                 170                 175

Thr Tyr Lys Val Ile Ser Thr Leu Thr Ile Ser Glu Ile Asp Trp Leu
            180                 185                 190

Asn Leu Asn Val Tyr Thr Cys Arg Val Asp His Arg Gly Leu Thr Phe
        195                 200                 205
```

```
Leu Lys Asn Val Ser Ser Thr Cys Ala Ala Ser Pro Ser Thr Asp Ile
210                 215                 220

Leu Thr Phe Thr Ile Pro Pro Ser Phe Ala Asp Ile Phe Leu Ser Lys
225                 230                 235                 240

Ser Ala Asn Leu Thr Cys Leu Val Ser Asn Leu Ala Thr Tyr Glu Thr
            245                 250                 255

Leu Asn Ile Ser Trp Ala Ser Gln Ser Gly Glu Pro Leu Glu Thr Lys
            260                 265                 270

Ile Lys Ile Met Glu Ser His Pro Asn Gly Thr Phe Ser Ala Lys Gly
                275                 280                 285

Val Ala Ser Val Cys Val Glu Asp Trp Asn Asn Arg Lys Glu Phe Val
290                 295                 300

Cys Thr Val Thr His Arg Asp Leu Pro Ser Pro Gln Lys Lys Phe Ile
305                 310                 315                 320

Ser Lys Pro Asn Glu Val His Lys His Pro Pro Ala Val Tyr Leu Leu
                325                 330                 335

Pro Pro Ala Arg Glu Gln Leu Asn Leu Arg Glu Ser Ala Thr Val Thr
            340                 345                 350

Cys Leu Val Lys Gly Phe Ser Pro Ala Asp Ile Ser Val Gln Trp Leu
            355                 360                 365

Gln Arg Gly Gln Leu Leu Pro Gln Glu Lys Tyr Val Thr Ser Ala Pro
370                 375                 380

Met Pro Glu Pro Gly Ala Pro Gly Phe Tyr Phe Thr His Ser Ile Leu
385                 390                 395                 400

Thr Val Thr Glu Glu Glu Trp Asn Ser Gly Glu Thr Tyr Thr Cys Val
                405                 410                 415

Val Gly His Glu Ala Leu Pro His Leu Val Thr Glu Arg Thr Val Asp
            420                 425                 430

Lys Ser Thr Glu Gly Glu Val Asn Ala Glu Glu Glu Gly Phe Glu Asn
            435                 440                 445

Leu Trp Thr Thr Ala Ser Thr Phe Ile Val Leu Phe Leu Leu Ser Leu
450                 455                 460

Phe Tyr Ser Thr Thr Val Thr Leu Phe Lys Val Lys
465                 470                 475

<210> SEQ ID NO 154
<211> LENGTH: 145
<212> TYPE: PRT
<213> ORGANISM: Homo sapiens

<400> SEQUENCE: 154

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
                20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
                100                 105                 110
```

Tyr Tyr Cys Ala Met Gly Ala Arg Ser Ser Glu Lys Glu Glu Arg Glu
            115                 120                 125

Arg Glu Trp Glu Glu Met Glu Pro Thr Ala Ala Arg Thr Arg Val
    130                 135                 140

Pro
145

<210> SEQ ID NO 155
<211> LENGTH: 152
<212> TYPE: PRT
<213> ORGANISM: Bos taurus

<400> SEQUENCE: 155

Met Ser Trp Ala Leu Val Leu Leu Gly Leu Leu Leu His Arg Thr Gly
1               5                   10                  15

Cys Ser Pro Gln Pro Val Leu Ser Gln Pro Ser Val Ala Ser Phe
            20                  25                  30

Leu Gly Ala Thr Val Arg Leu Ala Cys Thr Leu Ser Ser Asp His Asp
        35                  40                  45

Val Asn Leu His Ser Ile Tyr Trp Tyr Gln Gln Arg Pro Gly His Arg
50                  55                  60

Pro Arg Phe Leu Leu Arg Tyr Phe Ser Pro Ser Asp Lys Arg Gln Gly
65                  70                  75                  80

His Lys Val Pro Pro Arg Phe Ser Gly Ser Lys Asp Leu Ala Lys Asn
                85                  90                  95

Thr Gly Tyr Leu Ser Ile Ala Glu Leu Gln Ala Glu Asp Glu Ala Val
            100                 105                 110

Tyr Phe Cys Ala Val Gly Thr Pro Val Met Gly Arg Arg Lys Ile
        115                 120                 125

Gln Arg Glu Arg Ala Glu Arg Glu Leu Ala Thr Leu Gly Ser Pro Gly
130                 135                 140

Pro Arg Ala Thr Leu Pro Leu His
145                 150

<210> SEQ ID NO 156
<211> LENGTH: 142
<212> TYPE: PRT
<213> ORGANISM: Mus musculus

<400> SEQUENCE: 156

Met Ala Trp Thr Ser Val Leu Leu Met Leu Leu Ala Tyr Leu Thr Gly
1               5                   10                  15

Cys Gly Pro Gln Pro Met Val His Gln Pro Pro Leu Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Thr Arg Asn
                85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser Gln Glu Lys Lys Arg Met Glu
        115                 120                 125

Arg Glu Trp Glu Gly Glu Lys Ser Tyr Thr Asp Leu Gly Ser
            130                 135                 140

<210> SEQ ID NO 157
<211> LENGTH: 213
<212> TYPE: PRT
<213> ORGANISM: Homo sapiens

<400> SEQUENCE: 157

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
        50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210

<210> SEQ ID NO 158
<211> LENGTH: 213
<212> TYPE: PRT
<213> ORGANISM: Bos taurus

<400> SEQUENCE: 158

Met Arg Pro Arg Pro Gly Gln Gly Ala Arg Glu Ala Pro Arg Gly Gln
1               5                   10                  15

Arg Gly Val Pro Arg Gln Pro Trp Pro Leu Ile Leu Leu Gly Leu Ala
            20                  25                  30

Val Gly Ala His Gly Leu Leu Pro Pro Thr Ala Ala Pro Gln Ser Thr
            35                  40                  45

Ala Pro Arg Met Glu Ala Pro Ser Gly Lys Ser Pro Trp Ser Leu Arg
        50                  55                  60

Ser Arg Pro Ser Arg Phe Pro Leu Arg Pro Gly Pro Arg Gly Pro Gly
65                  70                  75                  80

Pro Arg Cys Trp Arg Gly Val Pro Glu Gly Pro Ser Ala Trp Phe
                85                  90                  95

```
Thr Phe Gly Ser Gly Thr Lys Val Thr Ile Pro Asp Gln Pro Lys Phe
                100                 105                 110

Pro Pro Ser Val Thr Leu Phe Pro Pro Ser Thr Glu Glu Leu Ser Thr
            115                 120                 125

Tyr Thr Ala Thr Leu Val Cys Leu Ile Ser Asp Phe Tyr Pro Gly Asn
        130                 135                 140

Val Thr Val Ala Trp Lys Ala Asp Gly Ser Pro Val Thr Arg Gly Val
145                 150                 155                 160

Val Thr Ser Gln Ala Ser Gln Ser Ser Lys Tyr Val Ala Ser
            165                 170                 175

Ser Tyr Leu Thr Leu Thr Gly Ser Glu Trp Lys Pro Lys Ser Ser Tyr
            180                 185                 190

Ser Cys Glu Val Thr His Glu Gly Ser Thr Val Thr Lys Thr Val Lys
            195                 200                 205

Pro Ser Ala Cys Ser
    210

<210> SEQ ID NO 159
<211> LENGTH: 209
<212> TYPE: PRT
<213> ORGANISM: Mus musculus

<400> SEQUENCE: 159

Met Lys Leu Arg Val Gly Gln Thr Leu Gly Thr Ile Pro Arg Gln Cys
1               5                   10                  15

Glu Val Leu Leu Leu Leu Leu Leu Gly Leu Val Asp Gly Val His
            20                  25                  30

His Ile Leu Ser Pro Ser Ser Ala Glu Arg Ser Arg Ala Val Gly Pro
        35                  40                  45

Gly Ala Ser Val Gly Ser Asn Arg Pro Ser Leu Trp Ala Leu Pro Gly
    50                  55                  60

Arg Leu Leu Phe Gln Ile Ile Pro Arg Gly Ala Gly Pro Arg Cys Ser
65                  70                  75                  80

Pro His Arg Leu Pro Ser Lys Pro Gln Phe Trp Tyr Val Phe Gly Gly
            85                  90                  95

Gly Thr Gln Leu Thr Ile Leu Gly Gln Pro Lys Ser Asp Pro Leu Val
            100                 105                 110

Thr Leu Phe Leu Pro Ser Leu Lys Asn Leu Gln Pro Thr Arg Pro His
            115                 120                 125

Val Val Cys Leu Val Ser Glu Phe Tyr Pro Gly Thr Leu Val Val Asp
        130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
            165                 170                 175

Leu Ile Ser Asp Gln Trp Met Pro His Ser Arg Tyr Ser Cys Arg Val
            180                 185                 190

Thr His Glu Gly Asn Thr Val Glu Lys Ser Val Ser Pro Ala Glu Cys
            195                 200                 205

Ser

<210> SEQ ID NO 160
<211> LENGTH: 226
<212> TYPE: PRT
<213> ORGANISM: Homo sapiens
```

<400> SEQUENCE: 160

```
Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225
```

<210> SEQ ID NO 161
<211> LENGTH: 223
<212> TYPE: PRT
<213> ORGANISM: Bos taurus

<400> SEQUENCE: 161

```
Met Pro Glu Gly Pro Gln Ala Leu Gln Ser Pro Pro Ala Thr Ile Phe
1               5                   10                  15

Leu Leu Leu Ile Ser Ala Ala Gly Leu Gly Pro Gly Cys Gln Ala Leu
            20                  25                  30

Trp Val Glu Trp Gly Pro Pro Ser Val Thr Val Ser Val Gly Glu Glu
        35                  40                  45

Val Arg Leu Gln Cys Thr His Asn Gly Ser Asn Thr Asn Val Thr Trp
    50                  55                  60

Trp His Val Leu Gln Ser Asn Ser Ser Trp Pro Pro Val Met Tyr Arg
65                  70                  75                  80

Gly Asp Val Gly Ala Gly Gly Glu Leu Ile Ile Lys Pro Val Asn Lys
                85                  90                  95

Thr His Arg Gly Met Tyr Arg Cys Gln Val Ser Asp Gly Lys Lys Ile
            100                 105                 110

Gln Arg Ser Cys Gly Thr Tyr Leu Arg Val Arg Asp Pro Leu Pro Arg
        115                 120                 125
```

```
Pro Phe Leu Asp Met Gly Glu Gly Thr Lys Asn Asn Ile Ile Thr Ala
        130                 135                 140

Glu Gly Ile Ile Leu Leu Ile Cys Ala Val Val Pro Gly Thr Leu Leu
145                 150                 155                 160

Leu Phe Arg Lys Arg Trp Gln Asn Met Lys Phe Gly Ala Asp Ile Gln
                165                 170                 175

Asp Asp Tyr Glu Asp Glu Asn Leu Tyr Glu Gly Leu Asn Leu Asp Asp
            180                 185                 190

Cys Ser Met Tyr Glu Asp Ile Ser Arg Gly Leu Gln Gly Thr Tyr Gln
        195                 200                 205

Asp Val Gly Ser Leu His Ile Gly Asp Ala Gln Leu Glu Lys Pro
    210                 215                 220
```

<210> SEQ ID NO 162
<211> LENGTH: 220
<212> TYPE: PRT
<213> ORGANISM: Mus musculus

<400> SEQUENCE: 162

```
Met Pro Gly Gly Leu Glu Ala Leu Arg Ala Leu Pro Leu Leu Leu Phe
1               5                   10                  15

Leu Ser Tyr Ala Cys Leu Gly Pro Gly Cys Gln Ala Leu Arg Val Glu
            20                  25                  30

Gly Gly Pro Pro Ser Leu Thr Val Asn Leu Gly Glu Glu Ala Arg Leu
        35                  40                  45

Thr Cys Glu Asn Asn Gly Arg Asn Pro Asn Ile Thr Trp Trp Phe Ser
    50                  55                  60

Leu Gln Ser Asn Ile Thr Trp Pro Pro Val Pro Leu Gly Pro Gly Gln
65                  70                  75                  80

Gly Thr Thr Gly Gln Leu Phe Phe Pro Glu Val Asn Lys Asn His Arg
                85                  90                  95

Gly Leu Tyr Trp Cys Gln Val Ile Glu Asn Asn Ile Leu Lys Arg Ser
            100                 105                 110

Cys Gly Thr Tyr Leu Arg Val Arg Asn Pro Val Pro Arg Pro Phe Leu
        115                 120                 125

Asp Met Gly Glu Gly Thr Lys Asn Arg Ile Ile Thr Ala Glu Gly Ile
    130                 135                 140

Ile Leu Leu Phe Cys Ala Val Val Pro Gly Thr Leu Leu Leu Phe Arg
145                 150                 155                 160

Lys Arg Trp Gln Asn Glu Lys Phe Gly Val Asp Met Pro Asp Asp Tyr
                165                 170                 175

Glu Asp Glu Asn Leu Tyr Glu Gly Leu Asn Leu Asp Asp Cys Ser Met
            180                 185                 190

Tyr Glu Asp Ile Ser Arg Gly Leu Gln Gly Thr Tyr Gln Asp Val Gly
        195                 200                 205

Asn Leu His Ile Gly Asp Ala Gln Leu Glu Lys Pro
    210                 215                 220
```

<210> SEQ ID NO 163
<211> LENGTH: 229
<212> TYPE: PRT
<213> ORGANISM: Homo sapiens

<400> SEQUENCE: 163

```
Met Ala Arg Leu Ala Leu Ser Pro Val Pro Ser His Trp Met Val Ala
1               5                   10                  15
```

```
Leu Leu Leu Leu Leu Ser Ala Glu Pro Val Pro Ala Ala Arg Ser Glu
                20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Gly Phe Thr Val Lys Met His
 50                  55                  60

Cys Tyr Met Asn Ser Ala Ser Gly Asn Val Ser Trp Leu Trp Lys Gln
 65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
            115                 120                 125

Thr Ser Glu Val Tyr Gln Gly Cys Gly Thr Glu Leu Arg Val Met Gly
130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
            180                 185                 190

Asp His Thr Tyr Glu Gly Leu Asp Ile Asp Gln Thr Ala Thr Tyr Glu
            195                 200                 205

Asp Ile Val Thr Leu Arg Thr Gly Glu Val Lys Trp Ser Val Gly Glu
210                 215                 220

His Pro Gly Gln Glu
225

<210> SEQ ID NO 164
<211> LENGTH: 229
<212> TYPE: PRT
<213> ORGANISM: Bos taurus

<400> SEQUENCE: 164

Met Ala Gly Ser Ala Leu Ile Pro Gly Leu Asn Asn Trp Leu Val Leu
 1               5                  10                  15

Gly Leu Leu Leu Leu Ser Gly Glu Lys Val Leu Ala Asp Lys Thr Asp
                20                  25                  30

Asp Leu Leu Arg Asp Pro Lys Gly Asn Thr Cys Ser Arg Ile Trp Gln
            35                  40                  45

His Pro Arg Phe Val Ala Lys Lys Arg Gly Ser Thr Val Glu Ile Arg
 50                  55                  60

Cys His Val Glu Asp Asp Gly Leu Val Ser Trp Phe Arg Lys Pro Lys
 65                  70                  75                  80

Pro Asp Ser Glu Pro Lys Thr Leu His Ala Glu Gln Gly Arg Ile Leu
                85                  90                  95

Gln Ser His Asn Lys Ser Glu Ala Val Leu Thr Ile Leu Ser Val Gln
            100                 105                 110

Phe Gln Asp Asn Gly Ile Tyr Phe Cys Lys Gln Glu Cys Ala Lys Gly
            115                 120                 125

Thr Gln Arg Thr Glu His Gly Cys Gly Thr Glu Leu Arg Val Met Gly
130                 135                 140

Phe Ser Thr Leu Ala Gln Leu Lys Arg Arg Asn Thr Leu Lys Asp Gly
```

```
            145                 150                 155                 160
Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
                195                 200                 205

Asp Ile Val Thr Leu Arg Thr Gly Glu Val Lys Trp Ser Val Gly Glu
                210                 215                 220

His Pro Gly Gln Glu
225

<210> SEQ ID NO 165
<211> LENGTH: 228
<212> TYPE: PRT
<213> ORGANISM: Mus musculus

<400> SEQUENCE: 165

Met Ala Thr Leu Val Leu Ser Ser Met Pro Cys His Trp Leu Leu Phe
  1               5                  10                  15

Leu Leu Leu Leu Phe Ser Gly Glu Pro Val Pro Ala Met Thr Ser Ser
                 20                  25                  30

Asp Leu Pro Leu Asn Phe Gln Gly Ser Pro Cys Ser Gln Ile Trp Gln
                 35                  40                  45

His Pro Arg Phe Ala Ala Lys Lys Arg Ser Ser Met Val Lys Phe His
             50                  55                  60

Cys Tyr Thr Asn His Ser Gly Ala Leu Thr Trp Phe Arg Lys Arg Gly
 65                  70                  75                  80

Ser Gln Gln Pro Gln Glu Leu Val Ser Glu Glu Gly Arg Ile Val Gln
                 85                  90                  95

Thr Gln Asn Gly Ser Val Tyr Thr Leu Thr Ile Gln Asn Ile Gln Tyr
                100                 105                 110

Glu Asp Asn Gly Ile Tyr Phe Cys Lys Gln Lys Cys Asp Ser Ala Asn
                115                 120                 125

His Asn Val Thr Asp Ser Cys Gly Thr Glu Leu Leu Val Leu Gly Phe
            130                 135                 140

Ser Thr Leu Asp Gln Leu Lys Arg Arg Asn Thr Leu Lys Asp Gly Ile
145                 150                 155                 160

Ile Leu Ile Gln Thr Leu Leu Ile Ile Leu Phe Ile Ile Val Pro Ile
                165                 170                 175

Phe Leu Leu Leu Asp Lys Asp Asp Gly Lys Ala Gly Met Glu Glu Asp
                180                 185                 190

His Thr Tyr Glu Gly Leu Asn Ile Asp Gln Thr Ala Thr Tyr Glu Asp
                195                 200                 205

Ile Val Thr Leu Arg Thr Gly Glu Val Lys Trp Ser Val Gly Glu His
            210                 215                 220

Pro Gly Gln Glu
225

<210> SEQ ID NO 166
<211> LENGTH: 174
<212> TYPE: DNA
<213> ORGANISM: Homo sapiens

<400> SEQUENCE: 166
ggctgtgtct ggactccccc tcgccctctg acccagaaac caccagaaga aaagggaact      60
```

```
tcaggaagta agtggtgccg ccggtttcaa tcctgttctt agtctttgca gcgtggagtt        120
cacacacctg gggacctggg ggccgagctg tgatttccta ggaagacaaa tagc              174

<210> SEQ ID NO 167
<211> LENGTH: 177
<212> TYPE: DNA
<213> ORGANISM: Bos taurus

<400> SEQUENCE: 167
gtcacatctg gactccccca ggccctctga gacagaaaac actcagaaga aagggaact         60 tcaggaagca agtcgcgtca ccaggtttca ttcctgttct tagtcttcac agcactgggg        120 gaagggcect cacgcctcct gggactggtg accaagtccc agggagcagg gctgcag           177

<210> SEQ ID NO 168
<211> LENGTH: 174
<212> TYPE: DNA
<213> ORGANISM: Homo sapiens

<400> SEQUENCE: 168
gctgtgtctg gactccccct taccctgtga cacagaaacc accagaagaa aagggaactt        60
caggaagtaa gcggtgccgc cggtttcaat cctgttctta gtctttgcag cgtggagttc        120
acacccctgg ggacctgagg gccgagctgt gatttcctag gaagacaaat agca              174

<210> SEQ ID NO 169
<211> LENGTH: 177
<212> TYPE: DNA
<213> ORGANISM: Bos taurus

<400> SEQUENCE: 169
gctgcatctg gactccccca ggccttctga ggcagaaacc acccagaaga aagggaact         60 tcaggaagca agttgtgcca ccaggtttca atccacttct tagtgtttgg agacttgtgg        120
gcagggagtt cacacatcag gggactggtg accaagtgct agggagcagg gctgcag           177

<210> SEQ ID NO 170
<211> LENGTH: 177
<212> TYPE: DNA
<213> ORGANISM: Homo sapiens

<400> SEQUENCE: 170
cagctgtgtc tggactcccc ctcgccctct gacacagaaa ccaccagaag aaaagggaac        60
ttcaggaagt aagtggtgcc gccggtttca atcctgttct tagtgtttgc agcgtggagt        120
tcacacccct ggggacctgg gggccgagct gtgatttcct aggaagacaa gtggcag           177

<210> SEQ ID NO 171
<211> LENGTH: 176
<212> TYPE: DNA
<213> ORGANISM: Bos taurus

<400> SEQUENCE: 171
gctgcatctg gactccccca ggccctctga ggcagaaaac acccagaaga aagggaact         60 tcaggaagca agttgtgcca ccaggtttca atccactttg caagtttgca ggactggggg        120
aagggagttc acacctctgg gggccaagtc acaagtgcta gggagcaggg ctgcag            176

<210> SEQ ID NO 172
<211> LENGTH: 70
<212> TYPE: PRT
```

<213> ORGANISM: Homo sapiens

<400> SEQUENCE: 172

Leu Gln Leu Glu Glu Ser Cys Ala Glu Ala Gln Asp Gly Glu Leu Asp
1               5                   10                  15

Gly Leu Trp Thr Thr Ile Thr Ile Phe Ile Thr Leu Phe Leu Leu Ser
                20                  25                  30

Val Cys Tyr Ser Ala Thr Val Thr Phe Phe Lys Val Lys Trp Ile Phe
            35                  40                  45

Ser Ser Val Val Asp Leu Lys Gln Thr Ile Ile Pro Asp Tyr Arg Asn
        50                  55                  60

Met Ile Gly Gln Gly Ala
65                  70

<210> SEQ ID NO 173
<211> LENGTH: 70
<212> TYPE: PRT
<213> ORGANISM: Bos taurus

<400> SEQUENCE: 173

Leu Leu Glu Glu Glu Ile Cys Ala Asp Ala Gln Asp Gly Glu Leu Asp
1               5                   10                  15

Gly Leu Trp Thr Thr Ile Ser Ile Phe Ile Thr Leu Phe Leu Leu Ser
                20                  25                  30

Val Cys Tyr Ser Ala Thr Val Thr Leu Phe Lys Val Lys Trp Ile Phe
            35                  40                  45

Ser Ser Val Val Glu Leu Lys Arg Thr Ile Val Pro Asp Tyr Arg Asn
        50                  55                  60

Met Ile Gly Gln Gly Ala
65                  70

<210> SEQ ID NO 174
<211> LENGTH: 476
<212> TYPE: PRT
<213> ORGANISM: Ovis aries

<400> SEQUENCE: 174

Glu Ser Glu Ser His Pro Lys Val Phe Pro Leu Val Ser Cys Val Ser
1               5                   10                  15

Ser Pro Ser Asp Glu Asn Thr Val Ala Leu Gly Cys Leu Ala Arg Asp
                20                  25                  30

Phe Val Pro Asn Ser Val Ser Phe Ser Trp Lys Phe Asn Asn Ser Thr
            35                  40                  45

Val Ser Ser Glu Arg Phe Trp Thr Phe Pro Glu Val Leu Arg Asp Gly
        50                  55                  60

Leu Trp Ser Ala Ser Gln Val Ala Leu His Ser Ser Ser Thr Phe
65                  70                  75                  80

Gln Gly Thr Asp Gly Tyr Leu Val Cys Glu Val Gln His Pro Lys Gly
                85                  90                  95

Gly Lys Thr Val Gly Thr Val Met Val Val Ala Pro Lys Val Glu Val
            100                 105                 110

Leu Ser Pro Val Ser Val Phe Val Pro Pro Cys Asn Ser Leu Ser
            115                 120                 125

Gly Asn Gly Asn Ser Lys Ser Ser Leu Ile Cys Gln Ala Thr Asp Phe
        130                 135                 140

Ser Pro Lys Gln Ile Ser Leu Ser Trp Phe Arg Asp Gly Lys Arg Ile
145                 150                 155                 160

Val Ser Asp Ile Ser Glu Gly Gln Val Glu Thr Val Gln Ser Ser Pro
        165                 170                 175

Thr Thr Tyr Arg Ala Tyr Ser Val Leu Thr Ile Thr Glu Arg Glu Trp
            180                 185                 190

Leu Ser Gln Ser Ala Tyr Thr Cys Gln Val Glu His Asn Lys Glu Thr
        195                 200                 205

Phe Gln Lys Asn Ala Ser Ser Cys Asp Ala Thr Pro Pro Ser Pro
        210                 215                 220

Ile Gly Val Phe Thr Ile Pro Pro Ser Phe Ala Asp Ile Phe Leu Thr
225                 230                 235                 240

Lys Ser Ala Lys Leu Ser Cys Leu Val Thr Asn Leu Ala Ser Tyr Asp
                245                 250                 255

Gly Leu Asn Ile Ser Trp Ser His Gln Asn Gly Lys Ala Leu Glu Thr
            260                 265                 270

His Thr Tyr Phe Glu Arg His Leu Asn Asp Thr Phe Ser Ala Arg Gly
        275                 280                 285

Glu Ala Ser Val Cys Ser Glu Asp Trp Glu Ser Gly Glu Glu Tyr Thr
    290                 295                 300

Cys Thr Val Ala His Leu Asp Leu Pro Phe Pro Glu Lys Ser Ala Ile
305                 310                 315                 320

Ser Lys Pro Lys Asp Val Ala Met Lys Pro Ser Val Tyr Val Leu
                325                 330                 335

Pro Pro Thr Arg Glu Gln Leu Ser Leu Arg Glu Ser Ala Ser Val Thr
            340                 345                 350

Cys Leu Val Lys Gly Phe Ala Pro Ala Asp Val Phe Val Gln Trp Leu
            355                 360                 365

Gln Lys Gly Glu Pro Val Ala Lys Ser Lys Tyr Val Thr Ser Ser Pro
370                 375                 380

Ala Pro Glu Pro Gln Asp Pro Ser Ala Tyr Phe Val His Ser Ile Leu
385                 390                 395                 400

Thr Val Thr Glu Glu Asp Trp Ser Lys Gly Glu Thr Tyr Thr Cys Val
            405                 410                 415

Val Gly His Glu Ala Leu Pro His Met Val Thr Glu Arg Thr Val Asp
            420                 425                 430

Lys Ser Thr Glu Gly Glu Val Ser Ala Glu Glu Gly Phe Glu Asn
        435                 440                 445

Leu Asn Thr Met Ala Ser Thr Phe Ile Val Leu Phe Leu Ser Leu
    450                 455                 460

Phe Tyr Ser Thr Thr Val Thr Leu Phe Lys Val Lys
465                 470                 475

```
<210> SEQ ID NO 175
<211> LENGTH: 477
<212> TYPE: PRT
<213> ORGANISM: Sus scrofa

<400> SEQUENCE: 175
```

Glu Ser Gln Ser Ala Pro Asn Leu Phe Pro Leu Val Ser Cys Val Ser
1               5                   10                  15

Pro Pro Ser Asp Glu Ser Leu Val Ala Leu Gly Cys Leu Ala Arg Asp
            20                  25                  30

Phe Leu Pro Ser Ser Val Thr Phe Ser Trp Asn Tyr Lys Asn Ser Ser
        35                  40                  45

Lys Val Ser Ser Gln Asn Ile Gln Asp Phe Pro Ser Val Leu Arg Gly

```
            50                  55                  60
Gly Lys Tyr Leu Ala Ser Ser Arg Val Leu Leu Pro Ser Val Ser Ile
 65                  70                  75                  80

Pro Gln Asp Pro Glu Ala Phe Leu Val Cys Glu Val Gln His Pro Ser
                 85                  90                  95

Gly Thr Lys Ser Val Ser Ile Ser Gly Pro Val Val Glu Glu Gln Pro
                100                 105                 110

Pro Val Leu Asn Ile Phe Val Pro Thr Arg Glu Ser Phe Ser Ser Thr
            115                 120                 125

Pro Gln Arg Thr Ser Lys Leu Ile Cys Gln Ala Ser Asp Phe Ser Pro
            130                 135                 140

Lys Gln Ile Ser Met Ala Trp Phe Arg Asp Gly Lys Arg Val Val Ser
145                 150                 155                 160

Gly Val Ser Thr Gly Pro Val Glu Thr Leu Gln Ser Ser Pro Val Thr
                165                 170                 175

Tyr Arg Leu His Ser Met Leu Thr Val Thr Glu Ser Glu Trp Leu Ser
            180                 185                 190

Gln Ser Val Phe Thr Cys Gln Val Glu His Lys Gly Leu Asn Tyr Glu
            195                 200                 205

Lys Asn Ala Ser Ser Leu Cys Thr Ser Asn Pro Asn Ser Pro Ile Thr
210                 215                 220

Val Phe Ala Ile Ala Pro Ser Phe Ala Gly Ile Phe Leu Thr Lys Ser
225                 230                 235                 240

Ala Lys Leu Ser Cys Leu Val Thr Gly Leu Val Thr Arg Glu Ser Leu
                245                 250                 255

Asn Ile Ser Trp Thr Arg Gln Asp Gly Glu Val Leu Lys Thr Ser Ile
                260                 265                 270

Val Phe Ser Glu Ile Tyr Ala Asn Gly Thr Phe Gly Ala Arg Gly Glu
                275                 280                 285

Ala Ser Val Cys Val Glu Asp Trp Glu Ser Gly Asp Arg Phe Thr Cys
            290                 295                 300

Thr Val Thr His Thr Asp Leu Pro Ser Pro Leu Lys Gln Ser Val Ser
305                 310                 315                 320

Lys Pro Arg Gly Ile Ala Arg His Met Pro Ser Val Tyr Val Leu Pro
                325                 330                 335

Pro Ala Pro Glu Glu Leu Ser Leu Gln Glu Trp Ala Ser Val Thr Cys
                340                 345                 350

Leu Val Lys Gly Phe Ser Pro Ala Asp Val Phe Val Gln Trp Leu Gln
            355                 360                 365

Lys Gly Glu Pro Val Ser Ala Asp Lys Tyr Val Thr Ser Ala Pro Val
            370                 375                 380

Pro Glu Pro Glu Pro Lys Ala Pro Ala Ser Tyr Phe Val Gln Ser Val
385                 390                 395                 400

Leu Thr Val Ser Ala Lys Asp Trp Ser Asp Gly Glu Thr Tyr Thr Cys
                405                 410                 415

Val Val Gly His Glu Ala Leu Pro His Thr Val Thr Glu Arg Thr Val
                420                 425                 430

Asp Lys Ser Thr Glu Gly Glu Val Ser Ala Glu Glu Gly Phe Glu
            435                 440                 445

Asn Leu Asn Thr Met Ala Ser Thr Phe Ile Val Leu Phe Leu Leu Ser
            450                 455                 460

Leu Phe Tyr Ser Thr Thr Val Thr Leu Phe Lys Val Lys
465                 470                 475
```

<210> SEQ ID NO 176
<211> LENGTH: 471
<212> TYPE: PRT
<213> ORGANISM: Equus caballus

<400> SEQUENCE: 176

```
Glu Ser Thr Lys Thr Pro Asp Leu Phe Pro Leu Val Ser Cys Gly Pro
1               5                   10                  15

Ser Leu Asp Glu Ser Leu Val Ala Val Gly Cys Leu Ala Arg Asp Phe
            20                  25                  30

Leu Pro Asn Val Ile Thr Phe Ser Trp Asn Tyr Gln Asn Asn Thr Val
        35                  40                  45

Val Arg Ser Gln Asp Ile Lys Asn Phe Pro Ser Val Leu Arg Glu Gly
    50                  55                  60

Lys Tyr Thr Ala Ser Ser Gln Val Leu Leu Pro Ser Gly Asp Val Pro
65                  70                  75                  80

Leu Val Cys Thr Val Asn His Ser Asn Gly Asn Lys Lys Val Glu Val
                85                  90                  95

Arg Pro Gln Val Leu Ile Gln Asp Glu Ser Pro Asn Val Thr Val Phe
            100                 105                 110

Ile Pro Pro Arg Asp Ala Phe Thr Gly Pro Gly Gln Arg Thr Ser Arg
        115                 120                 125

Leu Val Cys Gln Ala Thr Gly Phe Ser Pro Lys Glu Ile Ser Val Ser
    130                 135                 140

Trp Leu Arg Asp Gly Lys Pro Val Glu Ser Gly Phe Thr Thr Glu Glu
145                 150                 155                 160

Val Gln Pro Gln Asn Lys Glu Ser Trp Pro Val Thr Tyr Lys Val Thr
                165                 170                 175

Ser Met Leu Thr Ile Thr Glu Ser Asp Trp Leu Asn Gln Lys Val Phe
            180                 185                 190

Thr Cys His Val Glu His Gln Gln Gly Val Phe Gln Lys Asn Val Ser
        195                 200                 205

Ser Met Cys Ser Pro Asn Ser Pro Val Pro Ile Lys Ile Phe Ala Ile
    210                 215                 220

Pro Pro Ser Phe Ala Gly Ile Phe Leu Thr Lys Ser Ala Lys Leu Ser
225                 230                 235                 240

Cys Gln Val Thr Asn Leu Gly Thr Tyr Asp Ser Leu Ser Ile Ser Trp
                245                 250                 255

Thr Arg Gln Asn Gly Glu Ile Leu Lys Thr His Thr Asn Ile Ser Glu
            260                 265                 270

Ser His Pro Asn Gly Thr Phe Ser Ala Leu Gly Glu Ala Thr Ile Cys
        275                 280                 285

Val Glu Asp Trp Glu Ser Gly Asp Tyr Ile Cys Thr Val Thr His
    290                 295                 300

Thr Asp Leu Pro Phe Pro Leu Lys Gln Ala Ile Ser Arg Pro Asp Ala
305                 310                 315                 320

Val Ala Lys His Pro Ser Val Tyr Val Leu Pro Pro Thr Arg Glu
                325                 330                 335

Gln Leu Ser Leu Arg Glu Ser Ala Ser Val Thr Cys Leu Val Lys Gly
            340                 345                 350

Phe Ser Pro Pro Asp Val Phe Val Gln Trp Leu Gln Lys Gly Gln Pro
        355                 360                 365

Leu Ser Ser Asp Lys Tyr Val Thr Ser Ala Pro Met Pro Glu Pro Gln
```

```
            370                 375                 380
Ala Pro Gly Leu Tyr Phe Val His Ser Ile Leu Thr Val Ser Glu Glu
385                 390                 395                 400

Asp Trp Ser Ser Gly Glu Thr Tyr Thr Cys Val Val Gly His Glu Ala
                405                 410                 415

Leu Pro His Val Val Thr Glu Arg Thr Val Asp Lys Ser Thr Glu Gly
                420                 425                 430

Glu Val Ser Ala Glu Glu Gly Phe Glu Asn Leu Ser Ala Met Ala
                435                 440                 445

Ser Thr Phe Ile Val Leu Phe Leu Ser Leu Phe Tyr Ser Thr Thr
450                 455                 460

Val Thr Leu Phe Lys Val Lys
465                 470

<210> SEQ ID NO 177
<211> LENGTH: 213
<212> TYPE: PRT
<213> ORGANISM: Homo sapiens

<400> SEQUENCE: 177

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
                20                  25                  30

Val Val Thr His Gly Leu Leu Arg Pro Thr Ala Ala Ser Gln Ser Arg
                35                  40                  45

Ala Leu Gly Pro Gly Ala Pro Gly Gly Ser Ser Arg Ser Ser Leu Arg
50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
                100                 105                 110

Thr Pro Ser Val Thr Leu Phe Pro Pro Ser Ser Glu Glu Leu Gln Ala
                115                 120                 125

Asn Lys Ala Thr Leu Val Cys Leu Met Asn Asp Phe Tyr Pro Gly Ile
130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
                180                 185                 190

Ser Cys Gln Val Met His Glu Gly Ser Thr Val Glu Lys Thr Val Ala
                195                 200                 205

Pro Ala Glu Cys Ser
        210

<210> SEQ ID NO 178
<211> LENGTH: 123
<212> TYPE: PRT
<213> ORGANISM: Homo sapiens

<400> SEQUENCE: 178

Met Ala Cys Arg Cys Leu Ser Phe Leu Leu Met Gly Thr Phe Leu Ser
```

```
1               5                   10                  15
Val Ser Gln Thr Val Leu Ala Gln Leu Asp Ala Leu Val Phe Pro
                20                  25                  30

Gly Gln Val Ala Gln Leu Ser Cys Thr Leu Ser Pro Gln His Val Thr
                35                  40                  45

Ile Arg Asp Tyr Gly Val Ser Trp Tyr Gln Gln Arg Ala Gly Ser Ala
 50                  55                  60

Pro Arg Tyr Leu Leu Tyr Tyr Arg Ser Glu Glu Asp His His Arg Pro
 65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
                100                 105                 110

Tyr Tyr Cys Ser Val Gly Tyr Gly Phe Ser Pro
                115                 120
```

<210> SEQ ID NO 179
<211> LENGTH: 400
<212> TYPE: PRT
<213> ORGANISM: Bos taurus

<400> SEQUENCE: 179

```
Ala Ser Thr Thr Ala Pro Lys Val Tyr Pro Leu Ser Ser Cys Cys Gly
 1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
                35                  40                  45

Gly Val His Thr Phe Pro Ala Val Leu Gln Ser Ser Gly Leu Tyr Ser
                50                  55                  60

Leu Ser Ser Met Val Thr Val Pro Ala Ser Ser Gly Thr Gln Thr
 65                  70                  75                  80

Phe Thr Cys Asn Val Ala His Pro Ala Ser Ser Thr Lys Val Asp Lys
                85                  90                  95

Ala Val Asp Pro Thr Cys Lys Pro Ser Pro Cys Asp Cys Cys Pro Pro
                100                 105                 110

Pro Glu Leu Pro Gly Gly Pro Ser Val Phe Ile Phe Pro Pro Lys Pro
                115                 120                 125

Lys Asp Thr Leu Thr Ile Ser Gly Thr Pro Glu Val Thr Cys Val Val
                130                 135                 140

Val Asp Val Gly His Asp Asp Pro Glu Val Lys Phe Ser Trp Phe Val
 145                 150                 155                 160

Asp Asp Val Glu Val Asn Thr Ala Thr Thr Lys Pro Arg Glu Glu Gln
                165                 170                 175

Phe Asn Ser Thr Tyr Arg Val Val Ser Ala Leu Arg Ile Gln His Gln
                180                 185                 190

Asp Trp Thr Gly Gly Lys Glu Phe Lys Cys Lys Val His Asn Glu Gly
                195                 200                 205

Leu Pro Ala Pro Ile Val Arg Thr Ile Ser Arg Thr Lys Gly Pro Ala
                210                 215                 220

Arg Glu Pro Gln Val Tyr Val Leu Ala Pro Pro Gln Glu Glu Leu Ser
 225                 230                 235                 240

Lys Ser Thr Val Ser Leu Thr Cys Met Val Thr Ser Phe Tyr Pro Asp
                245                 250                 255
```

```
Tyr Ile Ala Val Glu Trp Gln Arg Asn Gly Gln Pro Glu Ser Glu Asp
                260                 265                 270

Lys Tyr Gly Thr Thr Pro Pro Gln Leu Asp Ala Asp Ser Ser Tyr Phe
            275                 280                 285

Leu Tyr Ser Lys Leu Arg Val Asp Arg Asn Ser Trp Gln Glu Gly Asp
        290                 295                 300

Thr Tyr Thr Cys Val Val Met His Glu Ala Leu His Asn His Tyr Thr
305                 310                 315                 320

Gln Lys Ser Thr Ser Lys Ser Ala Asp Leu Leu Glu Glu Ile
                325                 330                 335

Cys Ala Asp Ala Gln Asp Gly Glu Leu Asp Gly Leu Trp Thr Thr Ile
                340                 345                 350

Ser Ile Phe Ile Thr Leu Phe Leu Ser Val Cys Tyr Ser Ala Thr
            355                 360                 365

Val Thr Leu Phe Lys Val Lys Trp Ile Phe Ser Ser Val Val Glu Leu
        370                 375                 380

Lys Arg Thr Ile Val Pro Asp Tyr Arg Asn Met Ile Gly Gln Gly Ala
385                 390                 395                 400

<210> SEQ ID NO 180
<211> LENGTH: 72
<212> TYPE: PRT
<213> ORGANISM: Bos taurus

<400> SEQUENCE: 180

Asp Leu Leu Glu Glu Ile Cys Ala Asp Ala Gln Asp Gly Glu
1               5                   10                  15

Leu Asp Gly Leu Trp Thr Thr Ile Ser Ile Phe Ile Thr Leu Phe Leu
            20                  25                  30

Leu Ser Val Cys Tyr Ser Ala Thr Val Thr Leu Phe Lys Val Lys Trp
        35                  40                  45

Ile Phe Ser Ser Val Val Glu Leu Lys Arg Thr Ile Val Pro Asp Tyr
    50                  55                  60

Arg Asn Met Ile Gly Gln Gly Ala
65                  70

<210> SEQ ID NO 181
<211> LENGTH: 396
<212> TYPE: PRT
<213> ORGANISM: Bos taurus

<400> SEQUENCE: 181

Ala Ser Thr Thr Ala Pro Lys Val Tyr Pro Leu Thr Ser Cys Cys Gly
1               5                   10                  15

Asp Lys Ser Ser Ser Arg Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ser Asp Cys Ser Lys Pro Asn Asn Gln His Cys Val
            100                 105                 110
```

Arg Glu Pro Ser Val Phe Ile Phe Pro Pro Lys Pro Lys Asp Thr Leu
         115                 120                 125
Met Ile Thr Gly Thr Pro Glu Val Thr Cys Val Val Val Asn Val Gly
    130                 135                 140
His Asp Asn Pro Glu Val Gln Phe Ser Trp Phe Val Asp Asp Val Glu
145                 150                 155                 160
Val His Thr Ala Arg Thr Lys Pro Arg Glu Glu Gln Phe Asn Ser Thr
                165                 170                 175
Tyr Arg Val Val Ser Ala Leu Pro Ile Gln His Gln Asp Trp Thr Gly
            180                 185                 190
Gly Lys Glu Phe Lys Cys Lys Val Asn Ile Lys Gly Leu Ser Ala Ser
        195                 200                 205
Ile Val Arg Ile Ile Ser Arg Ser Lys Gly Pro Ala Arg Glu Pro Gln
    210                 215                 220
Val Tyr Val Leu Asp Pro Pro Lys Glu Glu Leu Ser Lys Ser Thr Val
225                 230                 235                 240
Ser Val Thr Cys Met Val Ile Gly Phe Tyr Pro Glu Asp Val Asp Val
                245                 250                 255
Glu Trp Gln Arg Asp Arg Gln Thr Glu Ser Glu Asp Lys Tyr Arg Thr
            260                 265                 270
Thr Pro Pro Gln Leu Asp Ala Asp Arg Ser Tyr Phe Leu Tyr Ser Lys
        275                 280                 285
Leu Arg Val Asp Arg Asn Ser Trp Gln Arg Gly Asp Thr Tyr Thr Cys
    290                 295                 300
Val Val Met His Glu Ala Leu His Asn His Tyr Met Gln Lys Ser Thr
305                 310                 315                 320
Ser Lys Ser Ala Asp Leu Leu Leu Glu Glu Ile Cys Ala Asp Ala
                325                 330                 335
Gln Asp Gly Glu Leu Asp Gly Leu Trp Thr Thr Ile Ser Ile Phe Ile
            340                 345                 350
Thr Leu Phe Leu Leu Ser Val Cys Tyr Ser Ala Thr Val Thr Leu Phe
        355                 360                 365
Lys Val Lys Trp Ile Leu Ser Ser Val Val Glu Leu Lys Gln Ser Ile
    370                 375                 380
Thr Pro Asn Tyr Arg Asn Met Ile Gly Gln Gly Ala
385                 390                 395

<210> SEQ ID NO 182
<211> LENGTH: 9483
<212> TYPE: DNA
<213> ORGANISM: Bos taurus

<400> SEQUENCE: 182
gatcaaacac tgtcaaacca acacaagaga gccccagtac cagatgtgag gctcccccca      60
gaccccagtc acagtgcagc ctgtagaggg aacaggccca gtcgggagac caggaccgag     120
aaagtgaccc ctgtcagtca gtccagctac tcagtcatgt ccgactcttt gcaaccccac     180
agactgcagc acgccaggcc tccctgccca tcaccaactc ccggagcttg ctcaaactca     240
agtccattga gtcggcgatg ccatccagcc atctcatcct ctgtcgtccc cttctcctcc     300
tgcccccaat ccctcccagc atcagagtct tttccaatga gtcaactctt cgcatgaggt     360
ggccaaagta ttggagtttc agcttcaacg tcagtccttc caatgaacac ccaggactga     420
tctcctttac aatggactga ttggatctca ttgtagtcca agggattctc aagagtcttt     480
tccaacagca cagttcaaaa gcattgattt tttactcagc tttctttatg gtccaactct     540

-continued

```
cacatccata catgactact ggaaaaacca tagctttgac tagacggacc tttgtcagca    600
aagtaatatc tctgctttct aatgtgctgt ctacgttggt catagctttt cttccaagga    660
acaagtgtct tttaatttca tggctgcagt caccatctgg agtgattttg gagcccaaga    720
aaatagtctg tcactgtttc cattgtttcc tcgtctattt tgccatgaat gccatgatct    780 tcattttcg aatgttgagt tttaagccag cttttcact ctcctctttc actttcatca    840
agagtctctc tagttcctct tcattttctg ccatgagagt ggtgtcatct gcatatctga    900
ggttattgct atttctcctg gtaatcttga ttccagcttg tgcttcctcc atccaggtat    960
gtcacatgat gtactctgca tagaagttaa ataagcaggg tcacaaaata caatcttgat   1020
gttctccttt tccaaatttt aaccagtccg ttgttcctta tctggttctg ttacttcttg   1080
acctgcatat aggtttctca ggaggcagtt aatgtggtct ggtattcccc tctctttaag   1140
aatgttccag tctgttgtga tccacccatt caaaggcttt agtgtagtca ataaagcaga   1200
agcagtaaaa tgctgccact ttctaggtgg agctcacata tggataccac acccaaacct   1260
tgaccaagcc agaacctcat gacaatcatg tgcagtgcta taaatgatct cagctgttac   1320
acagtcacta tttacaaaat gtggggcaag agagcctgaa catgccatct tggccaattt   1380
tctctctcct catgggttgt ttagcttttt ttctttttt tttttttaa ttaagctgta   1440 tgagttgctt gcacattttg gaagtttatt ctttagtggt cacgtgattt gcaaatatct   1500
tctctaattc tgcaggtagt cttgttttgt tgatggtttt ccatggtgta caaaagcctt   1560
ttagcttaat taggtcccat ttgtttattt ttctttttat ttctattact ctaggagatg   1620
gatggagaag gaaatggcag cccactccag tgttcttgcc tggagaatcc cagggacggg   1680
ggagcctggt gggctgccgt ctatgggtt gcactgagtc ggacatgact gaagtgatat   1740
agcattagca ttaggagata aatacaaaaa gacaccacct tgatttatgt caaagagtgt   1800
tctgcccatg tttccctctg ttttatagcc tcccatttca cacttttgtc tttaatccat   1860
tttgagttta ttttgtccca tggcactaga gaatttataa tttcatttat taacaggtag   1920
caatccagtt tttccagaac ttattcaaga gactgtcttt tctccatctt acactcttgc   1980
ctcctgggtc atacatgaat tgatcatagg tgggtgggat tgttcctggg ctgtctatcc   2040
tgtctcactg atcactgatc tataattgtg gttttgtgcc agcaccatag tgttttgatg   2100
gccgtagctt tgcagtatgc tctgaagtct gggagcctga tgcctccagc tccacttttg   2160
tttcttgaga ttgctttgac tatttggggt ctttatgtct cccaacaaat tttcaaaagt   2220
tttgttctgg gtctgtggaa attgccattg gtcatttgat aggtgttaca ctgaacctgt   2280
agattgcttt cggtagaagt gtcattggca caatattgat tcttctgatt taagagtatc   2340
ttttctaaat agacatttct ccaaaaaaga catacagatg gctaacaaac acatgaaaag   2400
atgctcaaca tcactcatta tcagagaaat gcaaatcaaa accactatga ggtaccattt   2460
cacaccagtc agaatggctg cgatccaaaa gtctacaagc aataaatgct ggagagggtg   2520
tggagaaaag ggaaccctct tacactgttg gtgggaatgc aaactagtac agccactatg   2580
gagaacagtg tggagattcc ttaaaaaact ggaaatagaa ctgccttatg atccagcaac   2640
cccactgctg ggcatacaca ctgaggaaac cagaagggaa agagacacgt gtaccccaat   2700
gttcatcgca gcactgttta taatagccaa gacatggaag caacctagat gtccatcagc   2760
agatgaatgg ataagaaagc tgtggtacat atacacaatg gagtattact cagccattaa   2820
aaagaataca tttgaatcag ttctaatgag gtggatgaaa ctggagccta ttatacagag   2880
```

| | |
|---|---|
| tgaagtaagc cagaaggaaa aacataaata cagtatacta acgcatatat atggaattta | 2940 |
| gaaagatggt aacaataacc cggtgtacga gacagcaaaa gagacactga tgtatagaac | 3000 |
| agtcttatgg actctgtggg agagggagag ggtgggaaga tttgggagaa tggcaatgaa | 3060 |
| acatgtaaaa tatcatgtag gaaacgagtt gccagtccag gttcgatgca cgatgctgga | 3120 |
| tgcttgggc tggtgcactg ggacggccca gagggatggt atggggaggg aggagggagg | 3180 |
| agggttcggg atggggaaca catgtatacc tgtggtggat tcattttgat atttggcaaa | 3240 |
| actaatacaa ttatgtaaag tttaaaaata aaataaaatt ggaagaataa aaaaaaaaa | 3300 |
| agagtatctt ttcatctgtt tgtgtcacct taatttcttt catcagtgtc ttagagcttt | 3360 |
| cagagcagag gaattttgcc tcctagggaa ggtttattcc taggtatttt attcttttg | 3420 |
| atgggatggt aagtgggatt cttccttaa attctcttta tggtatttca ttgctgccat | 3480 |
| acagaatgca acagattttt gtgtattaat tttgtatcca taaattttat ccaattcatt | 3540 |
| cctgagctct agggttttct gtaccttctt tagcattttg catgtgttaa atcatgtcac | 3600 |
| ctgcaaacag caggtgtttc ttacttggct tctggattcc ctgtgtccct ttctctcccc | 3660 |
| tgattcttac acttaggcct tcactgtgct gcactgtggg cccttgctgg ttacctacta | 3720 |
| tatacgcagt cgtgtggatg tattagcacc aaactcctaa tttatccctg ggatgtggtg | 3780 |
| ggtcaaccag gcgcagtgca tgaggaagag gaacaccgtg acggctagga ttcccactcc | 3840 |
| tcccctgggt gcaagggcgc cgcttaaacc accccaccaa cccacaagac atacctcagt | 3900 |
| cacatctgga ctcccccagg ccctctgaga cagaaaacac tcagaagaaa agggaacttc | 3960 |
| aggaagcaag tcgcgtcacc aggtttcatt cctgttctta gtcttcacag cactggggga | 4020 |
| agggccctca cacctcctgg gactggtgac caagtcccag ggagcagggc tgcagacaca | 4080 |
| gaacacaggg aacttcagga ggcagatgga gtcaccaggt ttcattcctg ttcttagtct | 4140 |
| tcacagcact gggggaaggg ccctcacgcc tcctgggact ggtgaccaag tcttagggag | 4200 |
| cagggctgca gaaacagcac gcagatccca ggagccacat gtgtctgtgg gccagagcag | 4260 |
| ggaaggggcc cggagcccca ggctgtgggg cagcccctc catggccccc accatgggtg | 4320 |
| agtggggacc ccgaggatga gcgcacaggg acaggaatga gagccctgga gggagaccgg | 4380 |
| cctcgggacg cccagagggg ctggagcagc cgagtgggcc cagggggaggc agctgcccct | 4440 |
| ggtcacagtg caggacgagc gtgtggacag aacccagaca gggtgcacca caccaagagc | 4500 |
| actgctgccc agggctggag agctcagggg gctgtgggcc gtggaggagc aggatgggct | 4560 |
| tggggcgg agggaaggga tgtgcatgac caggggctct ggaggccggg gctgggcagt | 4620 |
| catgaggacc agccaggacg gaaagagggt ctgacctgag gacgcaggga agggagagga | 4680 |
| ccccagagca gtgaagtctt ctggacaggc cagtggagcc agcgtcggtc ccagggcagg | 4740 |
| gccacatgca gggactgtgg gtcccgactg ggctggggcc gagggcagcg gcagacttgg | 4800 |
| gggcaaggct gcaggccag ccgggttcta tgtccacagc aggcaccacg gggctgaacc | 4860 |
| cacagccccc caggacacag ggggctgacc agagctcagg gcctgaggac cagcagtggg | 4920 |
| agccagagag aggcaggtga cccgaaaact ggaggcagca aggggccaga ggagggtgtg | 4980 |
| gatggaggga tagagaagag cagagagcaa aggcaggacc tctgccagga ggggcccggg | 5040 |
| tggacagagc tcctccaggg gagagttgcc tggaggccag tgggcacctg gcaagtccag | 5100 |
| ggatgagagc tgaacccagg aaataaagga gtgaggagtg gagatgggca ggggtgaggg | 5160 |
| cttccagagg ggccagaggg gcaagaaagg ctgagggggc ggcccaagga caggggcag | 5220 |
| caaggctgca ggtgagcagg ggctgggagg gcagggggc ccctagagat ctgggggagc | 5280 |

```
aggcacagct tgtgggtgaa aaggggttag gagggcaggg ggcccctggt gtttggggga    5340
gcagatagag cttttgtagg tgagcaggga gctgggaggg cggggagag ggtggcctgg    5400
tgctttgggg agcaggtaca gcctgtgagg gtgagcaggg gctgggaggg caggggtgt    5460
tcctggtgtt tggggtagaa ggcacagctt atgggtgagc aggggctggg agggcagggg   5520
gagcccccgg tgctttgggg gagcaggtac tggttatgag ggtgagcaag ggctgggagg   5580
acgggggag ccccagtgc tttgggggaa caggtacagg ttatgagggt tgagcagggg    5640
gctgagagta aggaggtgag cctagtgctt tgggggagca tgtacagcct gtgaaggtga   5700
gcaagggcta ggaggacagt gggatccct ggtgctttag gggagcaggt acagcttgtg    5760
agggtgagca agggactggg aggacaaggg gtgcccctgg tgtttggggg agcaggtact   5820
agttatgagg gtgagcaggg gctggaggga ctggggagc cctagtgct ttggggagc     5880
aggtacaggt tatgagggtg agcaggggct gggaggacag ggggtgttcc tggtgtttgg   5940
ggtagaaggc acagcttatg ggtgagcagg ggctggaggg acaggggggc ccctggagat   6000
atggggaagc aggtacagct tgttggtgag caggggctgg gaggacaggg ggagcccctg   6060
gtgctttggg ggaacaggta caggttatga gggtgagcag ggggctgaga gtaaggaggt   6120
gagcctagtg ctttggggga gcatgtacag cctgtgaagg tgagcaaggg ctaggaggac   6180
agtgggatcc cctggtgctt tgggggagca ggtacaggtt atgagggtga gcaaggggct   6240
gggaggacaa ggggtgcccc tggtgctttg ggggaacaag tacagcctgt gacggtgagc   6300
agggagctgg gagggcaggg ggtgcctctg gtgctttggg ggagcaggta cagcttgtga   6360
gtgtgagcaa gggctgggag aactgggggt gtccctggta tttggggag caggtactgg   6420
ttatgagggt gagcagggc tggaggact gggggagccc ccagtgcttt ggggagcag    6480
gtacaagtta tgagggtgag caggggctt agagtaaggg gggtgcacc tggtgctttg    6540
gggagcgtta cagcctctga gggtgagcat gggctgggag acagtgggga tcccctggtg   6600
cttttgggga gcaggtacag cctgtgaggg tgagcagggg ctgggaggac agggggagcc   6660
cttggtgttt ggggagcgt gtacagcctg tgagggtgag caggggctgg gaggaaagtg    6720
ggagcccctg gtgtttgggg gagcaggtac agcctgtgag ggtgagcagg ggctgggagg   6780
aaagtgggag cccctggtgt ttgggggagc gtgtacagcc tgtgagggtg agcagggct    6840
gggaggaaag taggagcccc tggtgtttgg ggagcgtgt acagcctgtg agggtgagca    6900
cgggctggga ggcagggggg agcccctggt gctttggggg agcaggtaca ggttatgagg   6960
gtgagcaagg ggctgggagg gcaggggag ccctggtgt ttgggggagc atgtacagcc     7020
tgtgagggtg agcaggggct ggagggcag ggggcgcccc tggtgttttg gggagcggta   7080
cagcttgaga gggtgaacag ggctgggag acaggggga gccctgatg ctttggggga     7140
gcaggtacag cttgtgagtg tgagcaaggg ctgggaaaac tgggggtgtc cctggtgttt   7200
gggggagcag gtactggtta tgagggtgag caggggctgg gaggactggg ggagcccgtg   7260
gtgctttggg ggagcaggta caggttatga gggtgagcag ggggctgaga gaaagggggg   7320
tgtgcctggt gctttgggga gcattacaat ctgtgagggt gagcagggc tgggagggca    7380
gggggagccc ctggtgcttt gggagaacag gtacagcctg tgaggtgag cagggggctgg   7440
gaggacaggg ggagcccctg gtgtttgggg gagtgtgtac agcctgtgag ggtgagcagg   7500
agctgggagg gcaggggag cccctggtgc tttgggggag caggtacagg ttatgagggt    7560
gagcaggggc tggaggact gggggtgtgc ctgatgcttt gggggagcag gtacagcttg    7620
```

| | |
|---|---|
| tgagggtgag caggggggccg ggaaagcagg gtgtatctca aaaactttag gggatcaggt | 7680 |
| agtgcttctg gggatgagca gaggtctggg aggacagggg gtgcccttgg agttggagag | 7740 |
| caggtacagt ctgtgaggtg agtagagggc tgggcaggca cagggagccc ctggtgcttt | 7800 |
| gggggaacag gtgcaggtcg tgagggtgag caggggctgg gaggacaggg agtgtccctg | 7860 |
| gtgtttgggg tagaaggcac agcttatggg tgagcagggc ctgggaggac aggggagcc | 7920 |
| cctgttgctt tggggagca gtacagcttt gtgaggtga gctgggtctg gaagacagg | 7980 |
| gggagcccct ggtgctttgg gggagcaggt acagcttgtg agggtgagct gggtctggga | 8040 |
| agacagggg agcccctggt gtttgggaga gcagatacag cctgtgaggg ttagcagggg | 8100 |
| ctgggaggac aggggtgcc cttggagttg gagagcaggt acagtctgtg aggtgagtag | 8160 |
| agggctgggt gggcagggg agccctggt gctttggggg aacaggtaaa ggttatgagg | 8220 |
| gtgagcaggg ggctgagagt aagggcgtgt gcctgttgct ttgggaagc atgtacagcc | 8280 |
| tgtgagggtg agcaggagct gggagggcag gggggagccc ctggtgcttt ggggagcag | 8340 |
| gtacagcctg tgagggtatc caggggctg ggaggacatg gggtgcccct ggagattttt | 8400 |
| ggaagcagta atagcttgtg ggtgagcagg aagctgcgag acaggaggt gcccctgttg | 8460 |
| ctttgggtga acaggtacaa cttggtgag caggggctgg gaggacaggg agtgcccttg | 8520 |
| gagatttggg ggagcaggtg cagcttctgg ggataagcag ggggctggga gttcagggta | 8580 |
| ttaggggagc agacaaagat cgcgcagctg agcaggcgct ggaatgtcac gccctgccg | 8640 |
| acgacctcag ttgaccatgt gtgtgctgag cacatcggta cgaaagggtc cgagggtgca | 8700 |
| aggggccatt tgtgctgtgg gccagatgca ggacacagg gcagtgtgag ccctgcagag | 8760 |
| aagatggggc ccaagagcgc agctgtccag agctgagtcc agagggctga gaccagtggt | 8820 |
| gtgggtgctg gacgagggtg aagggctggc gtgagggagc aagggcacag ggctgggaga | 8880 |
| gctcaggcca cagctggtga agcagagggc tgagacaagg ggtgtaggcc acccctcaag | 8940 |
| acaatggggg tgctgtttgg tggagggtct gcatgaagaa caaagcaagg aggagcgaag | 9000 |
| acccgagagg aagggctctg gggctgcagg gaaggggcgc cctgagggca ccgggtgggc | 9060 |
| tgcacttctg ggccgagggt ctgcctgtcc cagcagcctg tgtggctcag gagccaaagt | 9120 |
| ggggccagac ctgggacgct gtgcttgata gggcggtgca aggggccagg agctacaggg | 9180 |
| cgcccactgg cagtcagtcg ggctgcaggc ccagggagct gaccaggctg ggggagcagg | 9240 |
| ggccatggga agggccaggc gcccacagga gggaagggc cctgggctct gatccaggag | 9300 |
| gccacactca ccgacccaag ctgtgtccag acacccaac tgcagtacag agagccgggt | 9360 |
| ggccaccatg ccggccggtc atcagaccct ggaagcaggt ggtggctggg ctcggaggtg | 9420 |
| ccccaggcct gggcacctga ggtcctgctg gaccccgcat tcacccagcc tcctctctca | 9480 |
| cag | 9483 |

<210> SEQ ID NO 183
<211> LENGTH: 6802
<212> TYPE: DNA
<213> ORGANISM: Homo sapiens

<400> SEQUENCE: 183

| | |
|---|---|
| cagcagggtc acaagggcag gccgggtcct tgtggagagc acatttagtg ggagggacat | 60 |
| gatttccctt caaagtgccc attctggacg cttcccgttc catgctggac gcttcctctt | 120 |
| ccacgctgga tgcttcctgt tccacactgg atgcttcctg ttccacgctg atgtttcct | 180 |
| gttacactct ggatgcttcc tgttccacac tggatgcttc ctgttccatc ctggatgctt | 240 |

```
cctgttccat gctggacatt tcctgttcca ctctggatgc tccctgttcc atgctggatg    300
cttcctgttc catgctggat gcttcctgtt ccatgctgga catttcctgt tccactctgc    360
atgcttcctg ttccactctg gatgcttcct gttccatggt ggacgtttcc tgttccactc    420
tgcatgcttc ctgttccatg ctggatgctt ccttttccat tctggatgct tcctgttcca    480
tgttggatgt ttcttgttcc actctggatg cttcctattc cattctggat gcttcctgtt    540
ccatgctgga catttcctgt tccatgctgg atgctttctg ttacatcctg gatgcttcct    600
gttccatgct ggatgttttt tgtttgactc tggatgcttc cagttccatt ctggatgctt    660
cctgttccat gctggatgct tcctttccca ttccgcacaa ttcctattcc attctggaca    720
cttcctgtgc gacacctcct tgggttttct gtctgcccag tccctctatc ctcatcccgt    780
tccctgctac ctcccacctc acaatcgtc cttgcccagc tcctccctct ctctagagct    840
tcggcctggc aaggtccctc ctgatctcag tccaggctcc cccagcacag gtaggagcct    900
agcacctgcc cttggacctc cccacccctgc atggtgccag catcccccgg tccccaggga    960
ggccccattt ctctctctgc ttgtagtcca gtggccctgg agtcccactg caactcgggt   1020
gtgcccctga cctctgagga agttaagtgt cctgtcccta gccaggctat cccgtctgct   1080
cagccccagg gccctgcccc aaccccttc ccctcacctg caccacaggc tctggccaac   1140
tctgccaggg ccctgaatgg gccctctgg ctccctctg ctgctacact gccctgcacc   1200
acctccactc agcttcagtg tgttcatcca cctgtcccaa gtccctcgg ccccaggag   1260
cacagctggt ggccctggct cctggcagcc catcttgttc cttctggagc accagcctca   1320
gaggccttcc tgtgcagggt ccacttggcc agccctggga ccctcctggt ctcaagcaca   1380
cacgttctcc ctgcagccag acctgcccct gcctgtgagc tcagccctga gccttggaat   1440
gccttcccat ctccatccca gctcgccttt gccagctgct cagcaggatg aactcacact   1500
cccctccctg caccatgagt cagagccagc tggagacacg cccaggccaa agcagccacc   1560
agggcctagt gggggccaga agcttcagat gagaggccca ggtattgaga ggctgagatc   1620
acgggcagaa tggtcataat cgctgccagt atcagtccag ccccagggac tcagagacag   1680
agaaaagagc agcacacaag gtctgggctc cccaccttct cccgtgagta cgggggagta   1740
tgggggcagc caccacccc atccccacac acccatgagg cagcctcggc tgtgtctgga   1800
ctccccctcg ccctctgacc cagaaaccac cagaagaaaa gggaacttca ggaagtaagt   1860
ggtgccgccg gtttcaatcc tgttcttagt ctttgcagcg tggagttcac acacctgggg   1920
acctgggggc cgagctgtga tttcctagga agacaaatag cggctgacgg caggggcggg   1980
gctgcccaca tgtacctcgc agaacagga agggctgaga cccccacctc ggtgagtggg   2040
gtcagcacag gcaggggca caggctcggg aggaggacag agcctggggg cagccgtggg   2100
cgctcctgga cctgagatgc tgaacaggct ccaagaggct ggggagacat ggggtcgagg   2160
ccggccccac atggaggccc aagcggagcc agcacggggg aggtgggcag ccttcaggca   2220
ccgatgccca cccagtgcga gacgacgggg accgtgggca ggggcttcca agccaacagg   2280
gcaggacaca ccagaggctg actgaggcct ccaggacgac cgggctggga gcacgaggaa   2340
catgactgga tgcggcagag ccggccgtgg ggtgatgcca ggatgggcac gaccgacctg   2400
agctcaggag gcagcagagc gagggaggag gagaggcccc aggtgaacgg aggggcttgt   2460
ccaggccgga agcatcaccg gagcccaggg cagggtcagc agtgctggcc gtggggcct   2520
cctctcagcc aggaccaagg acagcaggtg agccgggagc agagcaggga gggtgagtgt   2580
```

```
ggcagcagga caggagggtg gaagccaagg agcccagagg cagaggcagg gacaggggag    2640
gcacaggggc tgggctcaga gccagctgat ggggttgggg cacctgctgg cggggagcag    2700
ggctgtggtc agcagtggag aggaggggag agctgtgctg agtgcacggg cgggagaagg    2760
gaagagtcca gggaggccca gaaaggccca gagtgcagca ggcctgggc gaggggaagg     2820 gctgaggctc cgtgcgttca gggaactgac ccagcagagc agaggccact gaggagctga    2880
ggttccagag aggcttccag agcaggagca gtgcagggac aggaggatcc gggagctcat    2940
tcaggagggg cacatgggca agggcaaggg gctctgttgg ggagacctga ctggacactg    3000
gggctgctcc acagcatagg gaacacgcca agtgctgcaa aatcaaaaat gagggcagaa    3060
aaacagccca aacctggaca gagggtgcca ggacaggcag gggggcaaca gtgacctgag    3120
tgacattgct gcccgggttg agggagggca gagtgagcag ggagcaggca ttggagctca    3180
gggaccagga ccaagcagcc acaggtgagc agggcaggtg ggggcagaag gagcagggg    3240 cacctcctgg agctcagggg accagggcag agcagcctca ggtgagcagg ggctggtggg    3300
cggcaggatg agcaggggga agaccctgga gctcagggga ccaggcaga gcatcagaag    3360 gtgagcatgg ctagtgggag atgggcaagc aggggcagc ccctggagct caggggacca    3420
ggacagagca tcaggaggtg agcatggcta gtggaggtg ggcgagcagg gggcagcccc    3480
tggaactcag ggaccagggg cagagcagcc gcaggtgagc acgggctggt gggaggcggg    3540
aggaacaggg ggcagctcct ggacttcagg ggaccaggga gggcatctga aggtgaacag    3600
gggccagtgg ggggcaggat gagcaggggg aagctcctgg agctcaggga gccaaggcag    3660
agcagccgca ggtcagcagg ggcaggtggg aagcatgggg agcaggtggg cagcccctgg    3720
agctcagaga gccagggcag atcatccaca ggagagcagg ggctggtagg aagcaggagg    3780
agcaagtggg cagcttttgg agctcagagc accagggcag aagagcctca ggtgagaagg    3840
ggcaggtggg aggcagaata gcaggggac agcccctgga cctcaggaga ccagggcaga    3900
gcatcacaac gtcagcatgg ctggtgggag gtgggcgagc aggggggcagc ccctggacct    3960 cagagagcca gggcagatct gcaggtgagc agggcaggt gggaggcagg aagagcagga    4020
ggcagctcct ggagctcagg ggatcagggc agagcagcca caggtgagca ggggcaggta    4080
ggaagcagaa agatcagggg tcagcccctg gagctcaggg gacaagggga gagcatcaga    4140
aggtgagcag gactgaggct cagcctcagg gagccagggc agagcagctg caggtgagca    4200
gggccggtgg gaagcaggag gagcaggtgg gcagccctg gagctcagag agccagggaa    4260
gatcatccgc aggtgagcag gggctggtgg gaagcaggag gagcaagggg cagctcctgg    4320
agctcagggg accagggcag agcagtcgca ggtgaacagg ggcaggtggg gggcaggagg    4380
agcaaggagc agctcctgga gctcagggga ccagggcaga gcagtcgcag gtgaacaggg    4440
gcaggaggag caagggggcag ctcctggagc tcaggggacc agggcagagc agccgcaggt    4500
gagcaggtgc agtgggggg caggaggagc aggggggcagc tcctggagct caggggacca    4560
gggcagagca gccgcaggtg agcaggggca ggtgggtgc aggaggagca gggggcaggc    4620
actggagctc aggggaccag ggcagagcag tcgcaggtga acagggggcag gtgggggca    4680 ggagtagcaa ggggcagctc ctggagctca ggggaccagg gcagagcagt cgcaggtgaa    4740
caggggcagg tgggggcag gaggagcagg gggcagctcc tggagctcag ggaccaggg     4800 cagagcagcc gcaggtgagc aggtgcaggt gggggcagg aggagcaggg gtcaggcact    4860
ggagctcagg gaccagggc agagcagccg caggtgagca ggggcaggtg gggggcagga    4920
ggagcagggg gcaggcactg gagctcaggg gaccagggca gagcagccgc aggtgagcag    4980
```

```
gggcaggtgg ggggcaggag gagcaggggg caggcactgg agctcagggg accagggcag      5040
agcagccgca ggtgagcagg ggcaggtggg gggcaggagg agcagggggc aggcactgga      5100
gctcagggga ccagggcaga gcagccgcag gtcagcaggg ccggtgggag gcaggacgag      5160
caggggacag gcactagagc tcagggcaag gcagccacag gtgagcaggg ctggtgggag      5220
gcatcactca gctcctagac tttggcagga gctgggtagt tgctggcaac agacagctga      5280
gggctggtga aagtgcagtg cagcctcctg gtgccgggaa gggagtgtga gtccatccca      5340
ctgagcagtt ggcaagggcg agctgggatg gagaagggaa ggcgttccag ggctcagggc      5400
tgagctctca ggcaggggca ggtgtggctg caggggaac gtgtgcttga gaccaggagg       5460
gtcccacggc tggtcccagc ggaccctggg caggaaggcc tctgaggctg gcgccccaga      5520
aggagcaaga tgggctgcca ggagccaggg ccaccagcac aatgaagctg agtgaggtg       5580 gtgcagggca gtgtagcagc agagggcagc cagaggggcc cattcagggc ctgggcagag      5640
tcagccagag cctgtggtgc aggtgagggg aaggggtggt gagcgggcc ctggggctga      5700 gcagagggga tggcctggct gagggcaggg cgcttagcct cctcagaggt cagggcaca       5760 ccccaccctgc agtgggactc cagggccact gggccagcgg cagagagaaa tggggcctcc    5820
ctgtggcctg ggggtcctgg caccatgcag ggtggggagg gccaagggca ggtgcaaggc     5880
tcctacctgt gctgggggc ctgggttgag cccagcaggg accttgccgg gggaagctct      5940
ggagagaggg aggaggtggg ctggtggccg agaaggccag gccagggctg ggagggtgac     6000
ggtgtggtga ctgagcctcc agaagtaatg caggacactg ggaggcaggg ggcatccagg     6060
cactcagggc cctgacctgg gctgctgcac actggggcta aggggaaagg aggggagagg     6120
ctgaggagga ggctccagga ggctattcca aggcaggggg ttccgggcc ctggggctga      6180 agggcgccga ccctatgcag tgtctggccc ctctgctgca cagaagaaaa gggccttgga    6240
gggcagaggg caggctatga ccagggccct gggcaagtca ggccaactca ctaggggagg     6300
gccacgctgg ggcggcaggg tcagggcctt caggggctc gggggaccca cgagaagcca     6360
tctgagaaca gtgtccactg gtcaagccag gcacccataa aaggctggag tggggccaat     6420
gggcatgagc cgtccctgag gtggcaccga tggccagagc tgaggccaag ctagaggccc     6480
tggactgtgc tgactcccgg cagacacaga gcgctgacct ggctgccgag ccccgcctcc    6540
taggctgcag gggtgcctgc agaagggcac cacagggcca ccggtcctgc aagctttctg     6600
gggcaggccg ggcctgacct tggctttggg gcaggggtg ggctaaggtg acgcaggtgg     6660
cgccagccag gcgcacaccc aatgcccgtg agcccagaca ctggacgctg aacctcgcgg     6720
acagttaaga acccaggggc ctctgcgccc tgggcccagc tctgtcccac accgcggtca     6780
catggcacca cctctcttgc ag                                              6802
```

<210> SEQ ID NO 184
<211> LENGTH: 6299
<212> TYPE: DNA
<213> ORGANISM: Homo sapiens

<400> SEQUENCE: 184

```
ggcaggccgg gtccttgtgg agagcacatt tagtgggagg gacatgattt cccttcaaag       60
tgcccattct ggacgcttcc cgttccatgc tggacgcttc ctcttccacg ctggatgctt      120
cctgttccac gctggatgct tcctgttcca cgctggatgt ttcctgttac actctggatg      180
cttcctgttc cacactggat gcttcctgtt ccatcctgga tgcttcctgt tccatgctgg      240
```

```
acatttcctg ttccactctg gatgctccct gttccatgct ggatgcttcc tgttccatgc    300
tggatgcttc ctgttccatg ctggacattt cctgttccac tctgcatgct tcctgttcca    360
ctctggatgc ttcctgttcc acactggacg cttcctgctc cacgctggac gcttcctgtt    420
ccatgctgga tgcttcccgt tacattctgg atgcttcccg ttccatgctg gacgcttcct    480
gttccacgct ggacgtttct tgttccactc tggatgcttc ctgttccacg ctggatgctt    540
cctttccac gctggacact tcctgttccg cgctggacac ttcctgctcc acactggacg    600
cttcctgctc caggctggac gcttcctgtt ccatgctgga tgcttcctgt tacattctgg    660
atgcttcccg ttccatgctg gacgcttcct gttccacgct ggacgtttct tgttccactc    720
tggatgcttc ctgttccacg ctggacgctt cccattccac tctggatgct tcctgttcca    780
tgctggacat ttcttgttcc actctggatg cttcctgttc catgctggat gcttcctgtt    840
ccatgctgga tgcttcctgt tccatgctgg acgtttcttg ttccactctg gatgcttcct    900
gttacatgct ggatgcttcc tgttccatgc tggacgtttc ttgttccact ctggatgctt    960
cctgttccat gctggatgct tcctgttaca ttctggatgc ttcctgttcc atgctggaca   1020
tttcctgttc cactctggat gcttcctgtt acattcttga tgcttcctgt tccatgctgg   1080
acatttcctg ttccactctg gatgcttcct gttacattct ggatgcttcc tgttccatgc   1140
tggacatttc ctgttccact ctggatgctt cctgttacat tctggatgct tcctgttcca   1200
tgctggacat ttcctgttcc actctggatg cttcctgtta cattcttgat gcttcctgtt   1260
ccatgctgga catttcctgt tccactctgg atgcttcctg ttacattctg gatgcttcct   1320
gttccactct ggacgcttcc cattccactc tggatgcttc cttttccatg ctggacctt    1380
cttgttccac tctggatgct tcctgttcca tgctggatgc ttcctttcc attccggaca   1440
cttcctattc cattctggac acttcctgtg cgacacctcc tcgggctttt ggtctgccca   1500
gtccctctgg cctcatacca tccccctta cctcccactt ccacgttcgt ccttcctcag   1560
ctcctcccte tctctagagc ttcggcctgg caaggtccct cctgatctca gtccaggctc   1620
ccccagcaca ggtaggagac ttgcacctgc ccttggacct ccccaccctg catgatgcca   1680
gcatccccca ggccccaggg aggccccatt tctctctctg cttgtagtcc agtggccctg   1740
gagtgccact gcaactcggg tgtgcccctc gcctctgagg aagctaagtg ccctaagcta   1800
agcagaggcc atccctctg ctcagccca gggccctgcc cctacccct tcccctcacc   1860
tgcaccacag gctctggcca actctgccca ggctctgaat gggcccctct ggctcccctc   1920
tgctgctaca ctgccctgca ccacctccac tcagcttcag tgtgttcatc cacctgtccc   1980
acgtcccctc ggcccccagg agcacagctg gtggccctgg ctcctggcag cccatcttgt   2040
tccttctgga gcaccagcct cagaagcctt cctgtgcagg gtccactcgg ccagccctgg   2100
gaccctcctg gtctcaagca cacacattct ccctgcagcc agacctgccc ctgcctgtga   2160
gctcagacct gagccttgga acgccttccc ttctccatcc cagctcgcct ttgccagctg   2220
ctcagcggga tgaactcaca ctcccctccc tgcaccatga gtgagagcca gctggagaga   2280
cgcccaggcc aaagcagcca ccagggccca gtggggtca aagcttcag gtgagaggcc   2340
caggtattga gaggctgaga ccacgggcag aatggtcata atcactgcca gtatcagtcc   2400
agccccaggg actcagagac agagaaaaga gcagtgaaca aggtccgggc tccccacctt   2460
ctcccacgag tatgggggca gccaccaccc ccatccccac acaccatga ggcagcctcg   2520
gctgtgtctg gactcccct acccctgtga cacagaaacc accagaagaa aagggaactt   2580
caggaagtaa gcggtgccgc cggtttcaat cctgttctta gtctttgcag cgtggagttc   2640
```

```
acacccctgg ggacctgagg gccgagctgt gatttcctag gaagacaaat agcagctgac    2700
ggcgtgggca agtctgccca catgtaccgc gccaaaacag gaagggctga gaccccacc     2760 tcggtgagta gggtcagcac agggcaaggg cacaggctcg ggaggagaag gacagagcct    2820
gggtgcagcc gtgggcgctc ctggacctca gctgctgaac aggctacaag aggctgggga    2880 gacgtgggg  caaggccagc cccacatgga gacccaagcg gagccagcac gggggaggtg    2940
ggcagccttc aggcaccaac gcccacccag tgcaagatga cggggaccgt gggcaggggc    3000
ttccaagcca acagggcagg acacaccaga ggctgactga ggcctccatg acgaccaggc    3060
tgggagcacg aggaacctga cgggatgcgg cagagccggc cgtggggtga tgccagcatg    3120
ggcaggaccc acctgagctg aggaggcagt agaacgaggg aggaggagag gccccaggtg    3180
aacggagggg cttgtccagg ccagcagcat cactggagcc cagggcaggg tcagcagtgc    3240
tggccgtggg gccctctctc agccaggacc aaggacagca ggtgagccgg gagcagagca    3300
gggagggtga gtgtgcagc  aggacaggag ggtggaagcc aaggagccca gaggcagagg    3360
cagggacagg ggaggcacag gggctaggct cagagccacc tgatggcgct ggggcacctg    3420
ctggcgggga gcagggctgt ggtcagcagc ggagtggagg ggagagctgt gctgagtgca    3480
cagatgggag gagggaagag tccagggagg cccagaaagg cccagagtgc agcaggcctg    3540
gggcgagggg aggggtgagg ctccgtgcgt tcagggagct gacccagcag agcagaggcc    3600
actgaggagc tgaggttctg gagaggcttc cagagcagga gcagtgcagg gacgggagga    3660
tctgggagct cacccaggag gggcacatgg gcaaggcaa  gggctctgt  tggggagacc    3720 tgactggaca ctggggctgc tccacagcat agggaacaag ccaagtgctg caaaaacaaa    3780
aatgaggcca gaaaaacagc ccaaacctgg acagagggtg ccaggacagg cagggggca    3840 acagtgacct gagtgacatt gctgcccggg ttgagggagg gcagagtgag caggggggcag    3900 gcattggagt tcagggtacc aggaccgagc agccacaggt gagcagggca ggtgggggca    3960
gaaggagcag ggggcacctc ctggagctca gcagaccagg gcagagcaac tgaaggtgaa    4020
caagggcagg tgggaggcag gatgagcagg gggaagaccc tggagctcag ggaccaggg    4080 cagagcagcc tcaggtgcct caggtgagca ggggctggtg ggtggcagga cgagtagggg    4140
acagctcctg gagctcaggg gaccaggaca gagcatcaag agctgagcat ggctagtggg    4200
aggtgggcga cagggtgca  gcccctggaa ctcgggacca gggcagagca gcggcaggtg    4260
agcacgggct ggtgggaggc aggaggaaca ggggcagct  ctgggacttc aggggaccag    4320
gggagggcat ctgaaggtga acaggggctg gtggggggcag gaagagcagg gggaagcccc    4380
tggagctcag ggaccaggg  cagagcagcc acaggtgagc aggggctggt aggaagcagg    4440
aggagcaggg gacagcccct ggagctcaga gcaccagggc agagcaccct caggtaagca    4500
ggggcaggta ggaggcagga cgagcagggg acagcccctg gagctcaggg gacagaggag    4560
agcatcagaa ggtgagcagg actgaggctt agcctcaggg aatcagagca gagcagccac    4620
aggtgagcag ggccggtggg aggcaggacg agcagggac  aggcactaga gctcagggca    4680
aggcaaccac aggtgagcag ggccggtggg aggcatcact cagctcctag attttggcag    4740
gagctgggta gttgctggca gcagacagct gagggctggt gaaagtgcag tgcagcctcc    4800
tggtgccagg aagggagtgt gagcccatcc cactgagcag ttggcaaggg tgagctggga    4860
tggagaaggg aaggcattcc agggctcggg gctgagctct caggcagggg caggtgtggc    4920
tgcaggggga atgtgtgctt gagaccagga gggtcccagg gctggcccca gcggacccta    4980
```

| | | | | |
|---|---|---|---|---|
| ggcaggaagg | cctctgaggc | tggcgcccca | gaaggagcaa | gatgggctgc caggagccag | 5040 |
| ggccaccagc | acaatgaagc | tgagtggagg | tggtgcaggg | cagtgtagca gcagagggct | 5100 |
| gccagagggg | cccattcagg | gcctgggcag | agtcagccag | agcctgtggt gcaggtgagg | 5160 |
| ggaaggggtg | gtgagcgggg | ccctgggggct | gagcagaggg | gatggcctgg ctgagggcag | 5220 |
| ggcacttagc | ctcctcagag | gtcaggggca | caccccacct | gcagtgggac tccagggcca | 5280 |
| ctgggccagc | ggcagagaga | aatgggggcct | ccctgtggcc | tgggggtcct ggcaccacgc | 5340 |
| agggtgggga | gggccaaggg | caggtgcaag | gctcctacct | gtgctggggg gcctgggttg | 5400 |
| agcccagcag | ggaccttgcc | gggggaagct | ctggagagag | ggaggaggtg ggctggtggc | 5460 |
| cgagaaggcc | aggccagggc | tgggagggtg | aggttgtggt | gactgagcct ccagaagtaa | 5520 |
| tgcaggacac | tgggaggcag | ggggcatcca | ggcactcagg | gccctgacct gggctgctgc | 5580 |
| acactggggc | taagggggaaa | ggaggggaga | ggctgaggag | gaggctccag gaggctattc | 5640 |
| caaggcaggg | ggttccgggg | ccctgggggct | gaagggcgcc | gaccctatgc agtgtctggc | 5700 |
| ccctctgctg | cacagaagaa | aagggccttg | gagggcagag | ggcaggctat gaccagggcc | 5760 |
| ctgggcaagt | caggcccact | cactagcgga | gggccacgct | ggggcggcag ggtcaggagc | 5820 |
| ttcaggggac | tcgggggacc | cacgagaagc | catctgagaa | cagtgtccac tggtcaagcc | 5880 |
| aggcacccat | aaaaggctgg | agtgggggcca | atgggcatga | gccgtccctg aggtggcacc | 5940 |
| gatggccaga | gctgaggcca | agctagaggc | cctggactgt | gctgactccc ggcaggcaca | 6000 |
| gagcgctgac | ctggctgccg | agccccgcct | cctaggctgc | aggggtgcct gcagaagggc | 6060 |
| accacagggc | caccggtcct | gcaagctttc | tggggcaggc | cgggcctgac tttggctttg | 6120 |
| gggcagggag | ggggctaagg | tgacgcaggt | ggcgccagcc | aggtgcacac ccaatgcccg | 6180 |
| tgagcccaga | cactggaccc | tgcctggacc | ctcgcagata | gacaagaacc gaggggcctc | 6240 |
| tgcgccctgg | gcccagctct | gtcccacacc | gcggtcacat | ggcaccacct ctcttgcag | 6299 |

```
<210> SEQ ID NO 185
<211> LENGTH: 10298
<212> TYPE: DNA
<213> ORGANISM: Equus caballus
<220> FEATURE:
<221> NAME/KEY: misc_feature
<222> LOCATION: (6918)..(8037)
<223> OTHER INFORMATION: n is a, c, g, or t

<400> SEQUENCE: 185
```

| | | | | |
|---|---|---|---|---|
| agatatcccc | caagtcatgt | cacaatacta | ccatgttcaa | agtacatgaa tgctttgaaa | 60 |
| cagactggtc | tcagtggctg | ggtgttcctt | gggtggctcc | taatggaact cagtggttgt | 120 |
| gtggaacaaa | cctctagtct | tggctcctgc | ctggatggct | gggacactgc acctggact | 180 |
| tcctttggag | gcagggaagg | agtcgccctg | agctaacagc | tggtctcaat gttcctccca | 240 |
| gtaaggccag | atggactcca | tcagtgttca | ctggtatgac | caccagcggc tatatttgct | 300 |
| gcttccttgg | gctacaagat | gtcatatcac | atagaggctc | taactaaatt tactcaaact | 360 |
| gccctcaatg | aaagtcaggt | aggaatatccc | ttattaaata | ctcaaatgtc tttagtgggg | 420 |
| agggctgtct | cccatcaga | atggcctag | atagtctaac | agcatcccaa ggtgggacat | 480 |
| gtgcactcat | tcaaactgaa | cgctgcgttt | ttagacctga | tgagtcttcc aatgtgtcct | 540 |
| ctctgctaaa | gcacttggaa | aagcaggtaa | atgcctaag | cgatcctgca tccaggcttg | 600 |
| atttgcgtgg | ttggctccct | tcaggtgtgg | ctgccctctt | gaaatctgaa ttgcaattcc | 660 |
| tgtgtctgtt | actccttgga | attcttctat | taatcataat | atgcaaacta attactcttt | 720 |

```
cctttactca gtgttgtaag actggcatgc aggctagaat aatggttgct cagccacttg    780
aggtgattga ttgatcttac aaccctggat gaatttcctt ctcataagac tatgcctaag    840
aactcatttt tcaaataatc ctttcaagtt ttgaattatc agcactgtta gtgtagctgt    900
tctataatta ggcacatgca gcatcatgag tcagatcaaa gcataggtac aacgtttgtg    960
tgacaatcta aagttactga aaacttacat aacctatgga atgcttcccc tgtaattgta   1020
tacctctatg ctcatccact atatccaact atttcctgcc attgggcata actgagcacg   1080
tcaatgagat aaaagcccag cactgatggc catcatggac cagggcaggc aacaatcacc   1140
atagcaccaa gggacaatat ttagatcatc agtgctttct ataaaaacat tatcgatcaa   1200
aggtgggaaa ataatgaatc aatgaaagca ataagaaaag ttaaaatgtt gaggtatatg   1260
aggaagccat ttggtttaga ctaattaggc ctcatctagt ttttctggaa agtcctgatg   1320
tgcctgtcga atatgcattg tacatctgct gcatttacaa tgtcccaaag caagaatgat   1380
gcccttgaaa ttatcctgcc ccttttggc atttctttat agatgagcac ttcttcccag   1440
aatgcaagga ttcgttactg acctactgtg tcatcttgtg atcactcacc cgcaatacta   1500
gcaaagcatc ttgtgactgt agtaaaagag atactcctgt catatgtgat gtacgtccct   1560
tgttccaaga cggtatataa ccacgctgca cacccggctt cttcacaaca cttccttcct   1620
tggtgaaggt tattgtcccg ggctatgtag tcctcaaatt ggctcaaata ataaactcac   1680
cccaattttg attaacagat tgattatagt ttattgcctc aacatttcct gaccagaaat   1740
tacatagatg aacgtgcttc ttatgtaacg gcagcgatgc tcacagcctg cggagcacat   1800
gactgaggga ggctgccttc cgtgggagag atggcaaaac tgcgtgggcg ccatggagag   1860
gaggccgggc cagagccgcc gggagtgtgc agtggattat catgaattca tcccggaggg   1920
accagagggc actcccttca ccaaggctgc tgctgacggc gttttctggg tgtccacagc   1980
aacattccca ggaccacagg ctcctccatc acctggtcct gccccatgca gaggttcact   2040
tccctcacca gaccccaggg tacccatgcg actgactcca tggggacagg gccactgagg   2100
gaccactgct gggtctctga gagcaggacc taaggagaca gggctcctcc tgggagtcag   2160
gcccgggcac cactcagcgt gggcaatccc catggaaaga tcacagagac agagggaaca   2220
cgggcgcccg cccagcccag cgccagact ccaggtggag ccttccagcc cctcgctgat   2280
gcgagtggag cagagaggag cgccccccgcc cacagaagcc ggcactgcct gcaggccacc   2340
aacgcagaag caaatcagca gaagagctgc agaggccact ctctgtgggg cggtccacag   2400
cacacccatg aaccgccgga cacgatatgg gacccgcacg tgggcgctgc tctgagaaac   2460
ctcaactcta gaaagtaagc acgaggacca gagagcaggg gaggcagagg gacccagagt   2520
agaccgttgg gggatgtgga gtggctctgg gacacccga ggccaaaggg tgctgcaaat   2580
agcaacaggt gggagggccg actcccctcg tacatctcag gtcacctcct agaaggttcg   2640
ctttggactt tgctcttggc ccacctaagc ggccacagcg tacgccctg cccaccaacc   2700 attggaagga gccaggcctg ccttcacgtc cagtcaccta cctggccccc ggcaattcca   2760
gggtggggac catggtgccg cccagggatc cccgatccaa ggcctaacgt gcaagagacg   2820
ggatggccca ggtttgtaca cggggccttg ggtgtgccga ggcactgcaa gtcatgagac   2880
actgagggtc cgtgtcccc cacagacaaa aagctgggtc ctggcccaca cacgggagga   2940
caggaacagc atgctgtctc tcagacagag gagacctttg gccccagtg accaccgtgg   3000 actctgtcct tgtacataga cttctttctg tccccagagg acagctgtgg atgggagaat   3060
```

| | |
|---|---|
| atcttccctg ggaccctggg tgctaccacc cttcagtcag agatccagcc atggatggag | 3120 |
| ccagagaggg atggagggaa gaggcaggga cccagaggaa gacggctttg tacttagggg | 3180 |
| gctggcctgg caggaggaca ggatgaggcc ctgggctgag ctgcgggctg tgagcaggac | 3240 |
| agcctgtgtc cacaatggac gctgactagg gcaggggag gtgtcctctg ggctgtgggt | 3300 |
| accagagggc tcaggtgaga ggcctgggtg ccctggcctt tggtggggcc atcgggcata | 3360 |
| atccttgtgg gagggagaga gcaaagagag gcatgtgagc ccggacttcc tgcactctcc | 3420 |
| ccagagtcct gggcgccaga ccccctccac tcccacacac ccacgtgtgg cagcctctgc | 3480 |
| ctcacgtctg tactccccc ggctctctaa gacagaaacc acccagaaga aaagggaact | 3540 |
| tcagggagca agcggtgccc ctgctttcag tcccgttctt agtctttgca gggtcgtgga | 3600 |
| gagtgggttc ccacctccgg gaaccagcta ccacctccgg gaaccagcta ccaactccta | 3660 |
| ggaagcaggg cagagggcaa caagcccggg gccgcgagga gccacatgtg cccggggcca | 3720 |
| gagcaggggc gtggggggag ctcctcggaa gccctggctt ccaccacctc cacagccccc | 3780 |
| acccttggtg agtggggtcc ccacggagca ggggaaggg agtggagtca gggcagtgga | 3840 |
| aacggttgca gagctacggg gagcccaggc acccagggac gactccgagg ggctcaagca | 3900 |
| gctgagccag cacgggggag ggcaggctgc ccacgagcca cggtgccaac cggacgcagg | 3960 |
| caccaggcag ccatgggcag ggcacgccca cgccaacaga gctggacaca ccagaggccc | 4020 |
| atgaaagtta accttgagga aattgatgac cttgaggcca gaagcctgag ggctgcattt | 4080 |
| ggccagctgt gctgagggca ggaccagcca ggagctgagc tgctgcagca cggacgccag | 4140 |
| gatgcacaga tgggtttgag cacagagagg gggctggctc agagcagggg aggaagagga | 4200 |
| cctccaggtg gcctaagggt cctgtccacg ccaatgagcc agctcaagcc ccagggcagg | 4260 |
| gtcagaggtg gccgccatgg tgtcctaggc tgtagccagg accgagggca gcaggtgagc | 4320 |
| caggtgcaga gcccaaaggg ccggcggatg cacccatgtg ctcagaactc agactgcaca | 4380 |
| gggctgggca ggagctcagt ggctacaggc agacgttggg agccaggcag tgagggtcca | 4440 |
| gagcaggtgc tggggttgca gtgttgggag ctgggtggca aggggagctg acccagcaat | 4500 |
| ggagggagca cagtcccgag gggccttcca gatgggcttc tgagcgccgt gaggggcaca | 4560 |
| gagacggtga agcccagctg gccaggagc tcctccagga ggagaccacg gcaggcaggg | 4620 |
| gctctgccag gggagagtta gccagagaga gggtgggcat ctggtggctc caggaggcaa | 4680 |
| aggccagtga tgggaaagga atgagcccag gatggagggt gaacctgggc tgagggtgct | 4740 |
| gggagaggca ggaggggcaa aggcagcccc ggcagaccc agcagcctgg ggctgagctt | 4800 |
| agggacctga gctgtgtgga ggggatcgta ggacaggagg acagagggc tgctgtggac | 4860 |
| ctggagttcc agggacaacg ggaagaacag ctacggatga gcaggggaag gtgggagggc | 4920 |
| acaaaaggac aggagcctac accaagagat gcatggggc aggcagagca gctacaggtg | 4980 |
| agcagaggcc agtgggaggg ctggaggaa aggggctgc ccaggggctc tggaagggg | 5040 |
| caggtagagc agctacaggt gagcagagga atggagacc aggagggaca ggtcacagcc | 5100 |
| caggagcccc atgggtgtgg agagcagagc ttggcatgta agtaggaagc aggaagggct | 5160 |
| gaaggggcag ggctacccca gcagctccac aggagcaggc agagaagcta caggtgagca | 5220 |
| ggggccggtg ggagggctgc aggggcaggg ggctgcccag gagctccggg gagcaggcag | 5280 |
| agcagctaca ggtgagcagg ggccgatggg agggctgcag gggcagggg ctgcccagga | 5340 |
| gctccgggga gcaggcagag cagctacagg tgagcagggg ccgatgggag ggctgcaggg | 5400 |
| acctgcccag gagctctggc ggagtagtca gagcagctac aggtgagcag gggccagtgg | 5460 |

```
gagggctgga ggggcagggt cctgcccagg agttccaggg gagcaggcag agcagctata    5520
ggtgagcaga cgctggtgag aggtctggag gggcaggggg ctgcccagga gctctagcgg    5580
gagcaggcag agaagctata ggtgagcagg ggccggtggg agggctgcag gggccggggc    5640
ctgccgagga gctccggcgg ggtagtcagg gcagctatag gtgagcaggg gccggtggga    5700
gggctggagg ggcagtggga tacccaggag ctccgccagg gtagtcagag cagctacagg    5760
tgagcagggg caagcaggag ggctggaggg gcaggaggct gcccaggagc tccggcgggg    5820
tagtcagagc agctacaggt gagcaggtgc cagcgggagg gctggagggg caggggctg     5880 cccaggagct ctgggaggag caggctgaga agctgtagtt gagcagggc cagtgggagg     5940 gctggagggg caggcggctg cccaggagct ccggggagc aagcagagca gctataggtg     6000
agcaggggca ggtgggggg ctggaggggc agggcaatgc ccaggagctc cggcggggta    6060
gtcagagcag ctacagtgga gcaggtgcca gcgggagggc tggaggggca ggggctgcc    6120 caggagctcc gggggagcag gcagagcagc tacaggtgag caggagcaag tgggagggct    6180
ggaggggcag aggactgctc aggagctccg ggggagcagg cagagcagct acaggtgagc    6240
aggagcaagt gggagggctg gaggggcaga ggactgctca ggagctccag gggagcaggc    6300
agaacagcta ctggtgagca ggggtcagcg ggagcgctgg aggggcaggg ggctgcccag    6360
gagctccggg ggagcaggca gagcagctat aggtgagcag gggcaggtgg gagggctgga    6420
ggggcagggc aatgcccagg agctccggcg gggtagtcag agcagctaca gtggagcagg    6480
tgccagcggg agggctggag gggcaggggg ctgcccagga gctccggggg agcaggcaga    6540
gcagctacag gtgagcaggg gccggtggga gggctgcagg ggcagggtcc tgcccaggag    6600
ctccacagga gcagacagag aagctatagg taagcagggc cggtgggaga gctgaggggg    6660
cagggtccgg cccaggagtt ccgggggagc aggcagagca ggtacaggtg agcaggcgct    6720
ggtgagaggt ctggagcggc aggtggctgc ccatgagctc tgggggagc aggcagagca     6780 gctataggtt agcagtggcc agcaggaggg ctggaggggc agggagcagt tcaaggagct    6840
ccagcggaat aatcagagca gctataggtg agcatgggcc agcgggaggg actgggacgg    6900
ggcagggagc tgccaggnnn nnnnnnnnn nnnnnnnnnn nnnnnnnnnn nnnnnnnnn      6960 nnnnnnnnnn nnnnnnnnnn nnnnnnnnnn nnnnnnnnnn nnnnnnnnnn nnnnnnnnnn    7020
nnnnnnnnnn nnnnnnnnnn nnnnnnnnnn nnnnnnnnnn nnnnnnnnnn nnnnnnnnnn    7080
nnnnnnnnnn nnnnnnnnnn nnnnnnnnnn nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnnnnnn    7260
nnnnnnnnnn nnnnnnnnnn nnnnnnnnnn nnnnnnnnnn nnnnnnnnnn nnnnnnnnnn    7320
nnnnnnnnnn nnnnnnnnnn nnnnnnnnnn nnnnnnnnnn nnnnnnnnnn nnnnnnnnnn    7380
nnnnnnnnnn nnnnnnnnnn nnnnnnnnnn nnnnnnnnnn nnnnnnnnnn nnnnnnnnnn    7440
nnnnnnnnnn nnnnnnnnnn nnnnnnnnnn nnnnnnnnnn nnnnnnnnnn nnnnnnnnnn    7500
nnnnnnnnnn nnnnnnnnnn nnnnnnnnnn nnnnnnnnnn nnnnnnnnnn nnnnnnnnnn    7560
nnnnnnnnnn nnnnnnnnnn nnnnnnnnnn nnnnnnnnnn nnnnnnnnnn nnnnnnnnnn    7620
nnnnnnnnnn nnnnnnnnnn nnnnnnnnnn nnnnnnnnnn nnnnnnnnnn nnnnnnnnnn    7680
nnnnnnnnnn nnnnnnnnnn nnnnnnnnnn nnnnnnnnnn nnnnnnnnnn nnnnnnnnnn    7740
nnnnnnnnnn nnnnnnnnnn nnnnnnnnnn nnnnnnnnnn nnnnnnnnnn nnnnnnnnnn    7800
```

| | |
|---|---|
| nnnnnnnnnn nnnnnnnnnn nnnnnnnnnn nnnnnnnnnn nnnnnnnnnn nnnnnnnnnn | 7860 |
| nnnnnnnnnn nnnnnnnnnn nnnnnnnnnn nnnnnnnnnn nnnnnnnnnn nnnnnnnnnn | 7920 |
| nnnnnnnnnn nnnnnnnnnn nnnnnnnnnn nnnnnnnnnn nnnnnnnnnn nnnnnnnnnn | 7980 |
| nnnnnnnnnn nnnnnnnnnn nnnnnnnnnn nnnnnnnnnn nnnnnnnnnn nnnnnnngtt | 8040 |
| ccagggaatc ttctacaggg agctagatag agaaagttta taggtaaagc aggtgccggt | 8100 |
| cgggagaagt tgaaggggca gggtcctgcc ccaggaagtt cccgggggga gccaggcaga | 8160 |
| gcaggttaca ggtgagcagg cgattgtgag aagtctggaa gcggcaggtg tcttcccatg | 8220 |
| agctcttggg gggagcaggc agagcagcta taggttagca gtggccagca ggaggggctg | 8280 |
| gaggggcagg gggcagccaa ggagctccag cggggtagtc agagcagcta taggtgagca | 8340 |
| ggggccagcg ggagggctgg aggggcaggg gacttccaag gagctccatg ggtgcagaca | 8400 |
| gagcagaaac tggtgagcag gggccggtga gagatctgga gttgcagggg gctgcccagg | 8460 |
| agctccgggg gagcaggcag agcagctact ggttgcaggg gcaggtggga gggctggagg | 8520 |
| ggcaggggcc tgcccaggat ctccagggag caggcagagc agctataggt gagcaggggc | 8580 |
| aggtgagagg gctggagggg cagcgggctg cccaggagct caggggagc aggcagagca | 8640 |
| gctactggtt gcagggcagg tgggagagct ggaggggcag cgtcctgccc aggagctcca | 8700 |
| caggagcaga cagagaagct ataggtaagc aggggccggt gggagagctg gggggggcagg | 8760 |
| gtcctgccca ggagttccgg gggagcaggc agagcaggta caggtgagca ggtgctggtg | 8820 |
| agaggtctgg agaggcaggg ggctgcccac gactttaggg gatgaagggc actgggcctg | 8880 |
| agttaaacag agccctcaac tggtgggacc tgaggggta cagggagcag gacagctgg | 8940 |
| aggctcccag ggctcaggtc aggctggctg ggcagggagg agagttgagc tggttgagtt | 9000 |
| gccaggtgcc tgttgagttg gatggagggg ggccctggg atggaaggag tctagggctg | 9060 |
| aagggtcgg gggcatccct gagaggacca gatcggatgc agttcttggg tccaggcaca | 9120 |
| ccggccctgt tctggggttt gtggggacat gggacaggag ggatagacat tcggactcag | 9180 |
| tgtgggtgg cacagcgcag tgggctcagt gcatggaaga gtaagagtcc ccttggggcc | 9240 |
| tgagcccagg ctaccagcat ggggagaggc caggcaaggc cctgcggctg agcagacagg | 9300 |
| actcagggga ggaggggaca gggtgggcct ggctgttggg ggtggaggct gcaccctggc | 9360 |
| ccacacgggg gcctggggag gctggcaccg agaggagagg agtgccgagc gcagcgcatg | 9420 |
| gctcccgccc gcgcccaggg gccggctgtg ctggggaagg accacagctg gaggagggct | 9480 |
| ctgcagtgag caaggagctg gacaggccca agagcaggga gggcagaggg caggcggcgc | 9540 |
| tggcagggag gggccggagg tgagctcagg aagccgggcc aggaggacct gagcgggtag | 9600 |
| ggggcccaga ggcacatgca ggaggctggg ctgggacac acaggatgg gaggggaggg | 9660 |
| ggacaagaag actcccaggg atgggtcca gtacacggat ggagtccagg gaagggacgg | 9720 |
| ggtccaggac agggaaggga tgggttcagg acagggatgg ggtcgagggc aaggacaaag | 9780 |
| cccaaggcat gaacagggtt caagacagga tcaggatcag gggagcgttg gggacaagta | 9840 |
| ctcctggtgc tgtggctgtg gagctgactc agatgacacg tggcctggcg agcagagaca | 9900 |
| ggccatggca aagtcactga gctgagggc cgggagacaa caggacagt gcggcgcaga | 9960 |
| ggcccaccac acctgaagag atgcccaatc gcccagggct gggccaggct ggggccacag | 10020 |
| gacagcagat tagggtccat cagaagccga ccagaagcac aggtctctgg tccgggctca | 10080 |
| gactggggac tcagtcaggc gggccacctg caggaggcct gagcagggac aaggggcagg | 10140 |
| ggccccaggg ggctctaatc taggttctct gagcctgtgg ctgcagaggc accagccctg | 10200 |

| atgacaggca gccacaaggg gcatctaggc ctcagactct ctggaaacac acgggcgcag | 10260 |
| gggcaggccc tggtggtcac acgcctcctc tcttgcag | 10298 |

<210> SEQ ID NO 186
<211> LENGTH: 9313
<212> TYPE: DNA
<213> ORGANISM: Sus scrofa

<400> SEQUENCE: 186

| ggtatatata cacactagaa taccactcgg ccgtaaaaac gaaccaaata atgccattgg | 60 |
| cagcaacacg gatggaacca gagactctca tactaagtga agtaagtcag aaagaccaat | 120 |
| accatacgct atcacgtaca tctggaatct aatatatggc acaaataaac ctttccacag | 180 |
| aaaagaaacc catggacttg gagaaaatac ttgtggtcgc caagggtgag gtagtggggt | 240 |
| agactgggag tttggggtta gtagatgcaa catattgcat ttggcataga taaactatga | 300 |
| gatcctgctg gagagcacag ggagctgtat ctagtcccct tgtgatggaac atgttggagg | 360 |
| ataaagtgag aaaagaaaca tataaatata tacaccacac gcacacacac acacatatat | 420 |
| gaatgactgg gtcactttgc cgtagagtag aaattgacag aacacagtaa atcaactata | 480 |
| acggaaaaaa ataaaaaaca ttaaaaaaaa aaaaacagat gctcatctcc atggattctg | 540 |
| aacacatttt tgacagaatt caacacccaa cttttcttg atgattttta tttttccac | 600 |
| tgcaggtggt ttaccctgct ctgttgattc cactgtacag aaaagtgaca aagtcacaca | 660 |
| catatatata tgtagacatt cttttctca cattatcctc catcatgccc catcataggt | 720 |
| gactagatag agggaaacta caccaacata ctaaaagcca tatgacaa acccacaact | 780 |
| atcatcattc tcaatggtga aaacctgaaa gcatttccgc taagatcagg aacaagacaa | 840 |
| ggatgtctgc tctcaccact ctccttccac ggagttttgg aagtcctagc cagggcaatt | 900 |
| agagaagaaa aggaatccaa atcggaaacg gagaagtaac actaccgctc tttacaggtg | 960 |
| acgtgctgcg ataccctagag aatcctcaag gcactaccag aaacctctta gagctcgcca | 1020 |
| atgaatttgg tcaagctgca ggatacaaaa ttaacacaca gaaattggct gccttgctct | 1080 |
| acgttaacaa tgaaagagca gcgagagaaa ctagggaaac catcccactg agcagtgcct | 1140 |
| cgaaatgaat gaaatgccca ggaataaacc tacccaaaga cacaaagacc tggactctga | 1200 |
| aaaccataag gcactgctgg aagcaaccaa agacgacaca aaccggtgga aagctagacc | 1260 |
| atgctcctgc cctggaagaa ttaatactgg caaaagggcc ataccaccta aggccaccct | 1320 |
| cactctcagt gcaatccctc tcaaatctcc aatggcattt tccacagaac tagaacaaaa | 1380 |
| aacctcaaaa atttgcatgg aaacacaaat acctcactga cctgggctat actacaaagc | 1440 |
| tgcagtcatc aaaacggtat ggcactgaca ctcccccca aaaagacat acatatcagt | 1500 |
| ggaacagaac agaaagccca gcaataaacc caagcaccta tgctcaatcc atccatgaca | 1560 |
| taggaggcaa gactattcaa cagagaaggg agagtcactt cactaagtgg tgctggggag | 1620 |
| ctggacagct ccatgtaaag aatgaaacca gaacactccc aaacgccaaa cacaccaaaa | 1680 |
| aaaaacaaaa aacaaaaaaa aaaaaataaa aaaaccctca aaacaaatga aactcctaaa | 1740 |
| cgtaagactg gatacctata actcacagag gaaacaggag agaacgttct ttgacataaa | 1800 |
| tcacagcaac atcttatttg atccacctcc tggaataact acaataaaga caaaagtgga | 1860 |
| gttcccgtca cggctcagtg gtaaccaaat ctgactagga accatgaggt tgcgggttca | 1920 |
| atccctggcc ttgatcagtg ggttaaggat ccggcgttgc cgtcagctgt ggtgtaggtt | 1980 |

```
gcagacgcgg ctcggatccc acgttgctgt ggctctggtg taggccgaca gctacagctc    2040
caattcgacc cctagcctgg gaacctccac atgccatggg tgcggccctg gaaaagacaa    2100
aaagacgggg aaaaaatgaa agaaagaaag aaggaaagaa ggaaaggagg aaagaagaaa    2160
gaaagaaaga aagaaagaaa gaaagaaaga aagaaagaca gacagacaaa agtaaaccaa    2220
tgagatctaa ttaaactcaa aagcttttga aaagcaaaag aaaccatttt aaaagagaaa    2280
aacaggagtt cccgtcctgg ctcaggggtt aacgaatctg actagcatcc atgaggaggc    2340
agatttgatc cctggcctca ctcagcaggt taaggatccg gcattgccat gagctgtgag    2400
ctgtggtgta ggccagcagc cgtagctcca attcaacccc tagcccggga acctccatat    2460
gccacaggtg gggccctaaa accaaaaaa  gacaaaggaa aacaacccac agaatgggac    2520
aaaatctttg caaacaatgc agcccaccaa ggctcaatcc ccaaaatata caaacactct    2580
acaactcaac aacaacaaaa aacaaaccaa caaacaaccc aatcgataaa tgggcagaag    2640
acctaaatag acatttctcc aaagaagaca tacagatggc cagaagacac atgaaaaaat    2700
cctcaacagc actaattttt agggaaatgc aaatcaaaac tgcaatgagg caccacctca    2760
cactggtcag aatggccatc attaagagtc aactaacagc aaatgctgga gagggtgagg    2820
agaagaggga acccgccttc actgttggtg ggaatgcaac ttggtacaag cactgtggaa    2880
aacagtatgg aggaacctca gaaaactgaa cgtaaaacca cgattgaacc cagaaatctc    2940 accccctaggc ctgtatctcg atacgacttt cagtcaaaaa cttacatgca caactatgga    3000
ctttgcagaa gggttcaaaa tgggcaggac atgaaaacac tcaaacgccc atcaacagac    3060
gaacggatta agatgtggtt ctcacacaaa gtaagaacta cgtctcagcc gtaaaaaagg    3120
accaagtcac gccatttgca gcaacgtgga tggaactaga gactctcaca ctgagtgaag    3180
taagtcagaa agagaaagac agagaccaca tgataccact tatatgtgga atctaaaata    3240
cggcgcgatt gatcctgtgg acaaaacaga gacagagcat ggtcatggag agcagacttt    3300
gctttccagg gggagggaga gaagagattg acagggggtt tggagctggt agatgcaact    3360
gatcacattg aaaacgagta agtgatgggt cctactgggc agcacacgga acagtgcccg    3420
gcctcttgcg ttagaacgtg agagaggaag gagagtgtga aaagaaaaag aaggtaaatg    3480
tatgtacagc tgtacaaggg taattgaagg aacgttgtaa atcaactctg gttttaaaaa    3540
aaaaaaaaaa aatttaaaga aagaaaacgt tctccagagg cagaacgaga aggtggaacg    3600
gccgacaggt ctctgtcctg cagcggccgc tgacacgacc ccaggacagc ggaaatgaga    3660
cccaggctgc ctgtcgggca cacggcggcc gccccggcac cctggtgatc ctgtgcagca    3720
cgaggtgccc agtagagggg tgggcagggc agggcagggc agggcaggac ctggggacgc    3780
ggccgcagca ggtgggctcc agccaggaag gagccacgag tggggtgggg tctgctcgct    3840
gggctggagg caggagggc  acctcggctc caacatccca gccggggacc cggccagagg    3900 aagggctgc  gaggatgtct tccaagcatc tctttgctct tggaaccacg tggcgaagct    3960
ttctgaaagc agaccagact gcagcaccac ggtttctatt gtgaagggat ttttccagaa    4020
ggagtgggac cttgcgaacg gggatgtgga cacagggtgg cttctgatca gcccagggc    4080 cctgtgcagc caagtctcat ggtcacgccg tccggccgg  accagcctgc cccccacgcg    4140
gacccgggga aggcagggg  cccatgacca gcacgagaac gactgactcg ccttgacctc    4200
aagccacctc caggaccagg ggcagacggc ccggcaccac gaggaggagg cagagccccg    4260
ggcagggccc acttgccact tcacctcgcc agagagccgg gcagatgccg gcacgcgact    4320
cttggggcct gacggccccg agcccagacg ctctcggggc tttggccaga ctcgcagggc    4380
```

```
tgctgagcca agcagaggct acaaagctcc acgggcttcc aggcaaccgc tagagacacg    4440
tgggcacagc tcgcagagcc ggtgacccac gggccagatg gaacctccc tcctgtgccc     4500 cctcaaggcg tctcccggaa cggtggcctc ccacggcgct ggacggggct cggggcaggc    4560
ccgaggcagc acggcgccca caccgtccac tggccgcttg gaaggattca gccaacacca    4620
ccccaggccc gctgcacagc cggggtgggg gctgagacgt ccctcagggg tccccagtcc    4680
cagcctgatg ctgaagttac aggacggccc aggggcgccc aggggacagg gggagctgcg    4740
gccctccacg aatgaggaca gagggtccct gaccccacg cacggccggc aggtctcggt     4800
ccacgcagag cagtgagcgg ctgcccgcca gcccgctctc ggcccgggcac caccttcaca   4860 accctggga actctgtccc cacgtgggca gcacgggcct gggtctgggc agcaggctgg     4920
gcccagccac acacgcgggg gtcacaagag gtgcccggtg gggtcgggca accaagggct    4980
cacactaggg gcctggcacc cgggctgcag taggccaggc ggcataatcc ccgtgggaca    5040
tagagaacca cgacgtcctg agttcccgca ccctccccac cgctcaccca ccccacacac    5100
ccacatgagc cgccagggca ctgtctggac tccccaggc cctctgggac agaaagcaac     5160
cagaagaaaa gggaacttca ggaagcagcc gggccacccg gtttcaatcc cattcttagt    5220
gtgcagggct gtgggcagga aggtcgtgcc tccagggacc agacacccac ccgaggaagc    5280
agggctgcag gcacagagca cagacacaaa gagccacatg cacctggggc cagagcagga    5340
ggggcccgga gcccggggca gcaggggagc cacctcctcg gcccccacac tcggtgcgtg    5400
gggttcacga agaccagggg cagggcagc ggaggggga cgaggagggg agacccaca      5460 gcagggctgc agccgaccca gcccagggaa cacagcctgc acgcgggtca tgtcgcccgc    5520
ccagcacagg gaccagggag ccctggcagg ggcacgccca cgccaacaga ggtggtgccc    5580
cagaggccag aggaggtcgg tggggccgcc aggcctctgc ggaacatgat gggctggggt    5640
cagaggcctg agggatctgc tcggccaggt tgctggaggc acagggctgg gcaggggctg    5700
aggacgaggc caggatggac aggtgggtct ggcggagga ctcagggaag agacggacac     5760
agcgcagggg acaaagaggt cacctggggt tgcagggtcc tgtcccggct gccggagccc    5820
gcttgagccc cagggcaggt atgaaagcag taactgtcgg gtcccgggga aggagccagg    5880
gccacgggca gcaggtgagc cgggagcaga gcaggcaggg cgggccgggc tcctgtgtgc    5940
ccagagctgg cagcacaggg actgagccta aagctccaca ggccgcagga gggctgacgg    6000
gagccagggg cctgagggca ggagcgggag ccagggggctg ggagctgggc gccagtgcag   6060
ctgagccagc aactagaggg agccaggac cagacaggct ccaagggtgg tcgcggcgag     6120
aagagggtga gctcagaagg gtcaggagcc cctccgggag gggaccaggt gggacagagg    6180
ctctgccagg gggacgctac ccagagaggg tgggcaccca gggctccggg aacaaaggcc    6240
agccctggga aagaaaggaa gccaggagtg gagctagaca aggctgaggg ttcgggggca    6300
ggaagagggg tggtgacact gaggcccagg agccccaggg aaaggggcag gtaggctgca    6360
ggtgagcagg gaaccgggag ggcggaaaag ctgtccttag agctgctggg aacacataga    6420
gctggtgcag gtgaggaggg gttgggaggg caagggggct gaacctgaag ctcctcggaa    6480
ctggtagagc ttgtgcagat gagcagggc tgggagggca ggggcagcc ctgggaccac      6540 ctgagagctg tagatcttgg gcaggtgagc acaaactggt agggcagggg aagaacctgc    6600
agttcctggg agcaggagga gcttgtgcag gtgagcaggg gctggagggc agggggctaa    6660
acctggagct attgggaaga ggttaggctt gtgcaggcga gcaggggtg ggagggcgag     6720
```

```
ggtcagtcct gggagccctt tcgagccaat agagcccagg caggtgagca ggggcttggc    6780
gggcagggag catccctggg atgagtttgt gcaggtgagc aggggtggg agtgtaggga     6840
gcagtcctag caactcctgg gagctggtag agcttgggca ggtgaacagg ggctggaagt    6900
gcaggggca catctgggag gccctgggag caattagcgc tctggcaggt gagtaggggc     6960
tcggagggca gggagcagcc ctgggagctc cttggagcag gtagagcttg gcaggtgag    7020
caggggtgg gagggcaggg ggcagtccta gcaactcctg ggagcttgta gagcttgggc    7080
aggtgagaac gagctggtag ggcaggggaa tgaacctgga gttactgggt caggaggagc    7140
atgtgcaggt gagcagggc tggagggcag ggggctaaac ctggagctat gggaagagg     7200
ttaggcttgt gcaggcaagc aggggtggg agagcaaggg tcagtcctgg gagcccttgc    7260
gagccggtag agcccaggca ggtgagcagg ggctgggcgg gcaggagca gtcctagcaa    7320
ctcctgggag caggtagagc ttgtgcaggt gagcagggg tgggagggta gggagcagtc    7380
ctgggaactc ctgcgagcag gtagagcttg tgcaggtggg caggggtggg agggcagggg    7440
gctgaacctg gagctcctca gaactggtag agcttgtgca gatgagcagt ggctgggagg    7500
gcagggggca gccctgggag caatagacct tgggcaggtg agaacgagct ggtagggcag    7560
tggaatgaac ctgagttac tgggtcaaga agagcttgtg caggcaagca ggggctgaag    7620
ggcagggggc taaacctgga gctattggga agaggttagg cttgtgcagg cgagcagggg    7680
gtgggagggc aagggtcagt cctggagcc cttgcgagcc ggtagagccc aggcaggtga    7740
gcagggctg ggagggcagg gagcatccct gggacctctt gggagcaggt agagcttgtg    7800
caggtgagca ggggtggga gggtaggag ccgtcctagc aactcctgaa tctggtagag    7860
cttgcggagg tgaacagggg ctgggagtgc aggggcagt cctgggagcc cctgggagta    7920
attagagctt gggcaggtga gcaggagctt ggagtctagg gggctaaact ggagctattg    7980
ggaagagttt aggcttgttc aggtgagcaa ggggtgggag tagagggggc attcctagga    8040
gctcccgcga gttggtcaat ctcgggcagg taagcagggg ctcagaggcc tggagcagcc    8100
ctgggaccat ctgggagcag ggcgagcttg gcaggtgag ccgggccagg ggggatgcag    8160
gacagggcag gggcaacaga gtgggggtga gctcagggga gccccaggct cgagggaggg    8220
gccgatatag ggctagccag gctggaaagt gggctcctgg ggggaaggtc cccaggactg    8280
cggggggcagg gcagggctg aacagacgcc atgggtcaca gggatcgggc caacgggcca    8340
taccctgttc cagcaaagtg agtggacatg gacagagca gctggagtcc taagtgagaa    8400
cagcggcaca gggcagtgca catggtcggg gggtcgaggg gctcatctgg gcctgagctg    8460
gggaagcagg caatggctga acagaacagg ggggagagga ccggcccaac cgggcagggg    8520
cgcatgggt gctggcgccc cgtgggagag aaggccagg ggcagggctc ggctgcagca    8580
gtgctgccag gcaggctggc agcgggaagg gcaggagcag agggagggct ctggcctcag    8640
caggcagctg ggaggcccag agctgggctg caggggccgg ggctctgggg aaagctgcct    8700
cgggtgagct cagggccaag ccaggagccc cgtggagga gggaccggtg ggcccagagg    8760
cccagatttg gagcctgggc cagggccgga gggatggcag gggagggcc tcggaggaga    8820
ctacctgccc tcgcccaggg aaaggggcat gttggtgcca gggaccaacg cgcacgggcc    8880
ttgactgcag agctgaccca gaggaacggg gcctggagag caaacagcag gccaggacca    8940
ggggccagga gcagagcatg ggcagtgggt ggcagtgggt ggcagtgtcc ctgccaggct    9000
ggggaagcag gacggtggcc tcaggggacc agcagaagct ggccaggaac acaggccacc    9060
cgctggtcgg gccaggcacc cacagggggct ctgggccctg gcgggctctc atccaggcgg    9120
```

```
tcacccagct ctgaccaggc agctgcgccc agaacctgca gctgcaatgg cagcgagctg      9180
ggcggctggt ctgccgactt tctggaagca agtgggtgct gggcgcagcg gccccgctgt      9240
tctgagggcc cgattcgctg cccgccccac aaggaacaag gccctggcgg tcacgcagcc      9300
tcctctcttc cag                                                         9313

<210> SEQ ID NO 187
<211> LENGTH: 178
<212> TYPE: DNA
<213> ORGANISM: Bos taurus

<400> SEQUENCE: 187
cagtcacatc tggactcccc caggccctct gagacagaaa acactcagaa gaaaagggaa        60
cttcaggaag caagtcgcgt caccaggttt cattcctgtt cttagtcttc acagcactgg       120
gggaagggcc ctcacacctc ctgggactgg tgaccaagtc ccagggagca gggctgca        178

<210> SEQ ID NO 188
<211> LENGTH: 201
<212> TYPE: DNA
<213> ORGANISM: Equus caballus

<400> SEQUENCE: 188
gcctcacgtc tgtactcccc ccggctctct aagacagaaa ccacccagaa gaaaagggaa        60
cttcagggag caagcggtgc ccctgctttc agtcccgttc ttagtctttg cagggtcgtg       120
gagagtgggt tcccacctcc gggaaccagc taccacctcc gggaaccagc taccaactcc       180
taggaagcag ggcagagggc a                                                201

<210> SEQ ID NO 189
<211> LENGTH: 165
<212> TYPE: DNA
<213> ORGANISM: Sus scrofa

<400> SEQUENCE: 189
tggactcccc caggccctct gggacagaaa gcaaccagaa gaaaagggaa cttcaggaag        60
cagccgggcc acccggtttc aatcccattc ttagtgtgca gggctgtggg caggaaggtc       120
gtgcctccag ggaccagaca cccacccgag gaagcagggc tgcag                      165

<210> SEQ ID NO 190
<211> LENGTH: 337
<212> TYPE: DNA
<213> ORGANISM: Bos taurus

<400> SEQUENCE: 190
tccactaggg tggccaggca cagtcaccag aggggagggg ctcgggtgca ggggtgcggg        60
agggtggggg aggcagcggt gtttgtgtcc tcttgttttt ctctttcttc tcaagccccc       120
tgcacctcat cacctgctga acatccaaa atagctctag gtggctactg agtcattgcg       180
agcacagccc aacccaggtg tcccagccag gctgctcttc tgagaatcgg gccccaaaac       240
cgagacctgg ccaggtgggc ctggggcctg ggcccgggc caaagcccag gggagtccta       300
cgggggcagt gagttcccca aggcctggag agggccc                               337

<210> SEQ ID NO 191
<211> LENGTH: 246
<212> TYPE: DNA
<213> ORGANISM: Bos taurus
```

-continued

<400> SEQUENCE: 191

```
ccccaccccc taggcaggtg cgaggccctc tcagtttccc ccaggttact catttggggc      60
acactcagcc ttgcagggca tgcaaatggc tgtttgttcc acactgaaaa acatgtctaa     120
gcctctgtgg ttatttccag aaatagccta cgcccacgcc ccacctgcag ccccagctct     180
gaccctccag agtgccaggc tggcctggag ctcaggattc gggggaccct gcaccccctg     240
ccccag                                                                246
```

<210> SEQ ID NO 192
<211> LENGTH: 14
<212> TYPE: DNA
<213> ORGANISM: Bos taurus

<400> SEQUENCE: 192

```
tcctcagcgc tcac                                                        14
```

<210> SEQ ID NO 193
<211> LENGTH: 27
<212> TYPE: DNA
<213> ORGANISM: Bos taurus

<400> SEQUENCE: 193

```
acgggatgct cctgctggtt accccaa                                          27
```

<210> SEQ ID NO 194
<211> LENGTH: 27
<212> TYPE: DNA
<213> ORGANISM: Bos taurus

<400> SEQUENCE: 194

```
acgggatgct cctgctggtt accccaa                                          27
```

<210> SEQ ID NO 195
<211> LENGTH: 27
<212> TYPE: DNA
<213> ORGANISM: Bos taurus

<400> SEQUENCE: 195

```
actggatgct cctgctggtt accccaa                                          27
```

<210> SEQ ID NO 196
<211> LENGTH: 400
<212> TYPE: PRT
<213> ORGANISM: Bos taurus

<400> SEQUENCE: 196

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Thr Gln Thr
65                  70                  75                  80

Phe Thr Cys Asn Val Ala His Pro Ala Ser Ser Thr Lys Val Asp Lys
                85                  90                  95

Ala Val Asp Pro Thr Cys Lys Pro Ser Pro Cys Asp Cys Cys Pro Pro
```

```
                100                 105                 110
Pro Glu Leu Pro Gly Gly Pro Ser Val Phe Ile Phe Pro Lys Pro
            115                 120                 125
Lys Asp Thr Leu Thr Ile Ser Gly Thr Pro Glu Val Thr Cys Val Val
130                 135                 140
Val Asp Val Gly His Asp Asp Pro Glu Val Lys Phe Ser Trp Phe Val
145                 150                 155                 160
Asp Asp Val Glu Val Asn Thr Ala Thr Thr Lys Pro Arg Glu Glu Gln
                165                 170                 175
Phe Asn Ser Thr Tyr Arg Val Val Ser Ala Leu Arg Ile Gln His Gln
            180                 185                 190
Asp Trp Thr Gly Gly Lys Glu Phe Lys Cys Lys Val His Asn Glu Gly
        195                 200                 205
Leu Pro Ala Pro Ile Val Arg Thr Ile Ser Arg Thr Lys Gly Pro Ala
210                 215                 220
Arg Glu Pro Gln Val Tyr Val Leu Ala Pro Pro Gln Glu Glu Leu Ser
225                 230                 235                 240
Lys Ser Thr Val Ser Leu Thr Cys Met Val Thr Ser Phe Tyr Pro Asp
                245                 250                 255
Tyr Ile Ala Val Glu Trp Gln Arg Asn Gly Gln Pro Glu Ser Glu Asp
            260                 265                 270
Lys Tyr Gly Thr Thr Pro Pro Gln Leu Asp Ala Asp Ser Ser Tyr Phe
        275                 280                 285
Leu Tyr Ser Lys Leu Arg Val Asp Arg Asn Ser Trp Gln Glu Gly Asp
        290                 295                 300
Thr Tyr Thr Cys Val Val Met His Glu Ala Leu His Asn His Tyr Thr
305                 310                 315                 320
Gln Lys Ser Thr Ser Lys Ser Ala Asp Leu Leu Leu Glu Glu Glu Ile
                325                 330                 335
Cys Ala Asp Ala Gln Asp Gly Glu Leu Asp Gly Leu Trp Thr Thr Ile
            340                 345                 350
Ser Ile Phe Ile Thr Leu Phe Leu Leu Ser Val Cys Tyr Ser Ala Thr
        355                 360                 365
Val Thr Leu Phe Lys Val Lys Trp Ile Phe Ser Ser Val Val Glu Leu
370                 375                 380
Lys Arg Thr Ile Val Pro Asp Tyr Arg Asn Met Ile Gly Gln Gly Ala
385                 390                 395                 400

<210> SEQ ID NO 197
<211> LENGTH: 406
<212> TYPE: PRT
<213> ORGANISM: Equus caballus

<400> SEQUENCE: 197

Ala Ser Thr Thr Ala Pro Lys Val Phe Ala Leu Ala Pro Gly Cys Gly
1               5                   10                  15
Thr Thr Ser Asp Ser Thr Val Ala Leu Gly Cys Leu Val Ser Gly Tyr
                20                  25                  30
Phe Pro Glu Pro Val Lys Val Ser Trp Asn Ser Gly Ser Leu Thr Ser
            35                  40                  45
Gly Val His Thr Phe Pro Ser Val Leu Gln Ser Ser Gly Phe Tyr Ser
        50                  55                  60
Leu Ser Ser Met Val Thr Val Pro Ala Ser Thr Trp Thr Ser Glu Thr
65                  70                  75                  80
```

```
Tyr Ile Cys Asn Val His Ala Ala Ser Asn Phe Lys Val Asp Lys
                85                  90                  95

Arg Ile Glu Pro Ile Pro Asn Asn His Gln Lys Val Cys Asp Met Ser
            100                 105                 110

Lys Cys Pro Lys Cys Pro Ala Pro Glu Leu Leu Gly Gly Pro Ser Val
        115                 120                 125

Phe Ile Phe Pro Pro Asn Pro Lys Asp Thr Leu Met Ile Thr Arg Thr
    130                 135                 140

Pro Glu Val Thr Cys Val Val Asp Val Ser Gln Glu Asn Pro Asp
145                 150                 155                 160

Val Lys Phe Asn Trp Tyr Met Asp Gly Val Glu Val Arg Thr Ala Thr
                165                 170                 175

Thr Arg Pro Lys Glu Glu Gln Phe Asn Ser Thr Tyr Arg Val Val Ser
            180                 185                 190

Val Leu Arg Ile Gln His Gln Asp Trp Leu Ser Gly Lys Glu Phe Lys
        195                 200                 205

Cys Lys Val Asn Asn Gln Ala Leu Pro Gln Pro Ile Glu Arg Thr Ile
    210                 215                 220

Thr Lys Thr Lys Gly Arg Ser Gln Glu Pro Gln Val Tyr Val Leu Ala
225                 230                 235                 240

Pro His Pro Asp Glu Leu Ser Lys Ser Lys Val Ser Val Thr Cys Leu
                245                 250                 255

Val Lys Asp Phe Tyr Pro Pro Glu Ile Asn Ile Glu Trp Gln Ser Asn
            260                 265                 270

Gly Gln Pro Glu Leu Glu Thr Lys Tyr Ser Thr Thr Gln Ala Gln Gln
        275                 280                 285

Asp Ser Asp Gly Ser Tyr Phe Leu Tyr Ser Lys Leu Ser Val Asp Arg
    290                 295                 300

Asn Arg Trp Gln Gln Gly Thr Thr Phe Thr Cys Gly Val Met His Glu
305                 310                 315                 320

Ala Leu His Asn His Tyr Thr Gln Lys Asn Val Ser Lys Asn Pro Glu
                325                 330                 335

Met Val Leu Asp Glu Ser Cys Ala Glu Thr Gln Asp Gly Glu Leu Asp
            340                 345                 350

Gly Leu Trp Thr Thr Ile Ser Ile Phe Ile Thr Leu Phe Leu Leu Ser
        355                 360                 365

Val Cys Tyr Ser Ala Thr Val Thr Leu Phe Lys Val Lys Trp Ile Phe
    370                 375                 380

Ser Ser Val Val Glu Leu Lys Arg Thr Ile Val Pro Asp Tyr Arg Asn
385                 390                 395                 400

Met Ile Gly Gln Gly Ala
                405

<210> SEQ ID NO 198
<211> LENGTH: 397
<212> TYPE: PRT
<213> ORGANISM: Sus scrofa

<400> SEQUENCE: 198

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Met Thr Trp Asn Ser Gly Ala Leu Thr Ser
        35                  40                  45
```

Gly Val His Thr Phe Pro Ser Val Leu Gln Pro Ser Gly Leu Tyr Ser
            50                  55                  60

Leu Ser Ser Met Val Thr Val Pro Ala Ser Ser Leu Ser Ser Lys Ser
 65                  70                  75                  80

Tyr Thr Cys Asn Val Asn His Pro Ala Thr Thr Lys Val Asp Lys
                 85                  90                  95

Arg Val Gly Thr Lys Thr Lys Pro Pro Cys Pro Ile Cys Pro Gly Cys
            100                 105                 110

Glu Val Ala Gly Pro Ser Val Phe Ile Phe Pro Pro Lys Pro Lys Asp
            115                 120                 125

Thr Leu Met Ile Ser Gln Thr Pro Glu Val Thr Cys Val Val Val Asp
            130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
            195                 200                 205

Ala Pro Ile Thr Arg Thr Ile Ser Lys Ala Ile Gly Gln Ser Arg Glu
210                 215                 220

Pro Gln Val Tyr Thr Leu Pro Pro Pro Ala Glu Glu Leu Ser Arg Ser
225                 230                 235                 240

Lys Val Thr Val Thr Cys Leu Val Ile Gly Phe Tyr Pro Pro Asp Ile
                245                 250                 255

His Val Glu Trp Lys Ser Asn Gly Gln Pro Glu Pro Gly Asn Tyr
                260                 265                 270

Arg Thr Thr Pro Pro Gln Gln Asp Val Asp Gly Thr Phe Phe Leu Tyr
            275                 280                 285

Ser Lys Leu Ala Val Asp Lys Ala Arg Trp Asp His Gly Glu Thr Phe
            290                 295                 300

Glu Cys Ala Val Met His Glu Ala Leu His Asn His Tyr Thr Gln Lys
305                 310                 315                 320

Ser Ile Ser Lys Thr Gln Glu Leu Leu Leu Glu Glu Ser Cys Ala Asp
                325                 330                 335

Ala Gln Asp Gly Glu Leu Asp Gly Leu Trp Thr Thr Ile Ser Ile Phe
            340                 345                 350

Ile Thr Leu Phe Leu Leu Ser Val Cys Tyr Ser Ala Thr Val Thr Leu
            355                 360                 365

Phe Lys Val Lys Trp Ile Phe Ser Ser Val Val Glu Leu Lys Arg Thr
            370                 375                 380

Ile Val Pro Asp Tyr Arg Asn Met Ile Gly Gln Gly Ala
385                 390                 395

<210> SEQ ID NO 199
<211> LENGTH: 399
<212> TYPE: PRT
<213> ORGANISM: Homo sapiens

<400> SEQUENCE: 199

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr

-continued

```
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Glu Leu Gln Leu Glu Glu Ser Cys
                325                 330                 335
Ala Glu Ala Gln Asp Gly Glu Leu Asp Gly Leu Trp Thr Thr Ile Thr
            340                 345                 350
Ile Phe Ile Thr Leu Phe Leu Leu Ser Val Cys Tyr Ser Ala Thr Val
        355                 360                 365
Thr Phe Phe Lys Val Lys Trp Ile Phe Ser Ser Val Val Asp Leu Lys
        370                 375                 380
Gln Thr Ile Ile Pro Asp Tyr Arg Asn Met Ile Gly Gln Gly Ala
385                 390                 395

<210> SEQ ID NO 200
<211> LENGTH: 471
<212> TYPE: PRT
<213> ORGANISM: Artificial Sequence
<220> FEATURE:
<223> OTHER INFORMATION: Human-Bovine Chimeric IgM
```

-continued

```
<400> SEQUENCE: 200

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Glu Thr Val Gln Ser Ser Pro Ile Thr Phe Arg Ala
                165                 170                 175

Tyr Ser Met Leu Thr Ile Thr Glu Arg Asp Trp Leu Ser Gln Asn Val
            180                 185                 190

Tyr Thr Cys Gln Val Glu His Asn Lys Glu Thr Phe Gln Lys Asn Val
        195                 200                 205

Ser Ser Ser Cys Asp Val Ala Pro Pro Ser Pro Ile Gly Val Phe Thr
210                 215                 220

Ile Pro Pro Ser Phe Ala Asp Ile Phe Leu Thr Lys Ser Ala Lys Leu
225                 230                 235                 240

Ser Cys Leu Val Thr Asn Leu Ala Ser Tyr Asp Gly Leu Asn Ile Ser
                245                 250                 255

Trp Ser Arg Gln Asn Gly Lys Ala Leu Glu Thr His Thr Tyr Phe Glu
            260                 265                 270

Arg His Leu Asn Asp Thr Phe Ser Ala Arg Gly Glu Ala Ser Val Cys
        275                 280                 285

Ser Glu Asp Trp Glu Ser Gly Glu Glu Phe Thr Cys Thr Val Ala His
290                 295                 300

Ser Asp Leu Pro Phe Pro Glu Lys Asn Ala Val Ser Lys Pro Lys Asp
305                 310                 315                 320

Val Ala Met Lys Pro Pro Ser Val Tyr Leu Leu Pro Pro Thr Arg Glu
                325                 330                 335

Gln Leu Ser Leu Arg Glu Ser Ala Ser Val Thr Cys Leu Val Lys Gly
            340                 345                 350

Phe Ala Pro Ala Asp Val Phe Val Gln Trp Leu Gln Arg Gly Glu Pro
        355                 360                 365

Val Thr Lys Ser Lys Tyr Val Thr Ser Ser Pro Ala Pro Glu Pro Gln
370                 375                 380
```

-continued

```
Asp Pro Ser Val Tyr Phe Val His Ser Ile Leu Thr Val Ala Glu Glu
385                 390                 395                 400

Asp Trp Ser Lys Gly Glu Thr Tyr Thr Cys Val Val Gly His Glu Ala
                405                 410                 415

Leu Pro His Met Val Thr Glu Arg Thr Val Asp Lys Ser Thr Glu Gly
            420                 425                 430

Glu Val Ser Ala Glu Glu Gly Phe Glu Asn Leu Asn Thr Met Ala
        435                 440                 445

Ser Thr Phe Ile Val Leu Phe Leu Leu Ser Leu Phe Tyr Ser Thr Thr
    450                 455                 460

Val Thr Leu Phe Lys Val Lys
465                 470
```